United States Patent
Meier et al.

(10) Patent No.: US 9,636,106 B2
(45) Date of Patent: May 2, 2017

(54) TERMINATION DEVICES AND RELATED METHODS

(71) Applicant: Ancora Heart, Inc., Santa Clara, CA (US)

(72) Inventors: Stephen C. Meier, San Francisco, CA (US); Eugene Serina, Fremont, CA (US); Charles J. Adam, San Jose, CA (US); Mariel Fabro, San Francisco, CA (US); Tammy Y. Tam, San Francisco, CA (US); John P. Lunsford, San Carlos, CA (US); Tenny C. Calhoun, Sunnyvale, CA (US); Brian Tang, Fremont, CA (US); Stephen Olson, Los Altos, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 0 days.

(21) Appl. No.: 14/033,369

(22) Filed: Sep. 20, 2013

(65) Prior Publication Data
US 2014/0188140 A1  Jul. 3, 2014

Related U.S. Application Data

(63) Continuation of application No. 12/577,044, filed on Oct. 9, 2009, now abandoned.
(Continued)

(51) Int. Cl.
*A61B 17/10* (2006.01)
*A61B 17/04* (2006.01)
(Continued)

(52) U.S. Cl.
CPC ...... *A61B 17/0487* (2013.01); *A61B 17/0467* (2013.01); *A61B 17/0485* (2013.01);
(Continued)

(58) Field of Classification Search
CPC ... A61B 17/0487; A61B 17/083; A61B 17/10; A61B 2017/045; A61B 2017/0451; A61B 2017/0488; A61B 2017/0496
(Continued)

(56) References Cited

U.S. PATENT DOCUMENTS 2,618,137 A   11/1952   White
3,537,666 A   11/1970   Lewis
(Continued)

FOREIGN PATENT DOCUMENTS

EP    0 669 101 A1    8/1995
WO    WO-94/03227 A1    2/1994
(Continued)

OTHER PUBLICATIONS

Australian First Examination Report mailed May 9, 2014, for Australian Patent Application No. 2009302169, filed on Oct. 9, 2009, 3 pages.
(Continued)

*Primary Examiner* — Gregory Anderson

(57) ABSTRACT

Devices and methods for locking and/or cutting tethers during a tissue modification procedure are described. In some variations, a tether may be used to tighten tissue by bringing two pieces or sections of the tissue together. The tether, which may be under tension, may be locked to maintain the tension, and excess tether may be severed, using one or more of the devices and/or methods. The devices and/or methods may be used, for example, in minimally invasive procedures.

20 Claims, 92 Drawing Sheets

Related U.S. Application Data

(60) Provisional application No. 61/104,681, filed on Oct. 10, 2008.

(51) Int. Cl.
*A61B 17/064* (2006.01)
*A61B 17/068* (2006.01)
*A61B 17/08* (2006.01)
*A61B 17/00* (2006.01)
*A61B 17/32* (2006.01)

(52) U.S. Cl.
CPC ......... *A61B 17/068* (2013.01); *A61B 17/0644* (2013.01); *A61B 17/083* (2013.01); *A61B 17/10* (2013.01); *A61B 2017/00243* (2013.01); *A61B 2017/00783* (2013.01); *A61B 2017/045* (2013.01); *A61B 2017/0451* (2013.01); *A61B 2017/0488* (2013.01); *A61B 2017/0496* (2013.01); *A61B 2017/320052* (2013.01)

(58) Field of Classification Search
USPC ....................................................... 606/232
See application file for complete search history.

(56) References Cited

U.S. PATENT DOCUMENTS

| | | |
|---|---|---|
| 3,656,185 A | 4/1972 | Carpentier |
| 3,727,614 A | 4/1973 | Kniazuk |
| 3,773,034 A | 11/1973 | Burns et al. |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,290,151 A | 9/1981 | Massana |
| 4,373,923 A | 2/1983 | Kilwin |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,510,934 A | 4/1985 | Batra |
| 4,549,545 A | 10/1985 | Levy |
| 4,619,247 A | 10/1986 | Inoue et al. |
| 4,700,250 A | 10/1987 | Kuriyama |
| 4,705,040 A | 11/1987 | Mueller et al. |
| 4,726,371 A | 2/1988 | Gibbens |
| 4,750,492 A | 6/1988 | Jacobs |
| 4,758,221 A | 7/1988 | Jureidini |
| 4,784,133 A | 11/1988 | Mackin |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,035,701 A | 7/1991 | Kabbara |
| 5,053,047 A | 10/1991 | Yoon |
| 5,064,431 A | 11/1991 | Gilbertson et al. |
| 5,078,731 A | 1/1992 | Hayhurst |
| 5,084,058 A | 1/1992 | Li |
| 5,087,263 A | 2/1992 | Li |
| 5,103,804 A | 4/1992 | Abele et al. |
| 5,133,723 A | 7/1992 | Li et al. |
| RE34,021 E | 8/1992 | Mueller et al. |
| 5,221,255 A | 6/1993 | Mahurkar et al. |
| 5,242,456 A | 9/1993 | Nash et al. |
| 5,242,457 A | 9/1993 | Akopov et al. |
| 5,242,459 A | 9/1993 | Buelna |
| 5,257,975 A | 11/1993 | Foshee |
| 5,282,832 A | 2/1994 | Toso et al. |
| 5,312,341 A | 5/1994 | Turi |
| 5,312,423 A | 5/1994 | Rosenbluth et al. |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,383,905 A | 1/1995 | Golds et al. |
| 5,409,483 A | 4/1995 | Campbell et al. |
| 5,409,499 A | 4/1995 | Yi |
| 5,417,700 A | 5/1995 | Egan |
| 5,423,837 A | 6/1995 | Mericle et al. |
| 5,431,659 A | 7/1995 | Ross, Jr. et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,531,763 A | 7/1996 | Mastri et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,584,835 A | 12/1996 | Greenfield |
| 5,591,194 A | 1/1997 | Berthiaume |
| 5,626,590 A | 5/1997 | Wilk |
| 5,626,614 A | 5/1997 | Hart |
| 5,630,824 A | 5/1997 | Hart |
| 5,643,289 A | 7/1997 | Sauer et al. |
| 5,665,109 A | 9/1997 | Yoon |
| 5,669,917 A | 9/1997 | Sauer et al. |
| 5,674,279 A | 10/1997 | Wright et al. |
| 5,690,655 A | 11/1997 | Hart et al. |
| 5,702,397 A * | 12/1997 | Goble ............... A61B 17/0401 606/232 |
| 5,709,695 A | 1/1998 | Northrup, III |
| 5,716,370 A | 2/1998 | Williamson, IV et al. |
| 5,718,725 A | 2/1998 | Sterman et al. |
| 5,725,542 A | 3/1998 | Yoon |
| 5,733,308 A | 3/1998 | Daugherty et al. |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,861,003 A | 1/1999 | Latson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,989,284 A | 11/1999 | Laufer |
| 5,991,650 A | 11/1999 | Swanson et al. |

(56) References Cited

U.S. PATENT DOCUMENTS

| | | |
|---|---|---|
| 6,010,531 A | 1/2000 | Donlon et al. |
| 6,015,428 A | 1/2000 | Pagedas |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,989 A | 6/2000 | Kandel et al. |
| 6,080,182 A | 6/2000 | Shaw et al. |
| 6,086,608 A | 7/2000 | Ek et al. |
| 6,099,553 A | 8/2000 | Hart et al. |
| 6,125,852 A | 10/2000 | Stevens et al. |
| 6,149,658 A | 11/2000 | Gardiner et al. |
| 6,152,934 A | 11/2000 | Harper et al. |
| 6,162,168 A | 12/2000 | Schweich, Jr. et al. |
| 6,165,183 A | 12/2000 | Kuehn et al. |
| 6,171,317 B1 | 1/2001 | Jackson et al. |
| 6,197,017 B1 | 3/2001 | Brock et al. |
| 6,200,329 B1 | 3/2001 | Fung et al. |
| 6,221,084 B1 | 4/2001 | Fleenor |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,471,715 B1 | 10/2002 | Weiss |
| 6,514,265 B2 | 2/2003 | Ho et al. |
| 6,524,328 B2 | 2/2003 | Levinson |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,575,987 B2 | 6/2003 | Gellman et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,616,667 B1 | 9/2003 | Steiger et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,652,562 B2 | 11/2003 | Collier et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,094,246 B2 | 8/2006 | Anderson et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,326,231 B2 | 2/2008 | Phillips et al. |
| 7,374,530 B2 | 5/2008 | Schaller |
| 7,381,210 B2 | 6/2008 | Zarbatany et al. |
| 7,390,329 B2 | 6/2008 | Westra et al. |
| 7,452,325 B2 | 11/2008 | Schaller |
| 7,588,582 B2 | 9/2009 | Starksen et al. |
| 7,618,449 B2 | 11/2009 | Tremulis et al. |
| 7,666,193 B2 | 2/2010 | Starksen et al. |
| 7,699,892 B2 | 4/2010 | Rafiee et al. |
| 7,727,247 B2 | 6/2010 | Kimura et al. |
| 7,753,922 B2 | 7/2010 | Starksen |
| 7,758,637 B2 | 7/2010 | Starksen et al. |
| 7,815,659 B2 | 10/2010 | Conlon et al. |
| 7,883,538 B2 | 2/2011 | To et al. |
| 7,922,762 B2 | 4/2011 | Starksen |
| 7,993,368 B2 | 8/2011 | Gambale et al. |
| 8,066,766 B2 | 11/2011 | To et al. |
| 8,287,555 B2 | 10/2012 | Starksen et al. |
| 8,287,557 B2 | 10/2012 | To et al. |
| 8,641,727 B2 | 2/2014 | Starksen et al. |
| 8,795,298 B2 | 8/2014 | Hernlund et al. |
| 9,072,513 B2 | 7/2015 | To et al. |
| 9,226,825 B2 | 1/2016 | Starksen et al. |
| 9,468,528 B2 | 10/2016 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0041821 A1 | 11/2001 | Wilk |
| 2002/0013621 A1 | 1/2002 | Stobie et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0095180 A1 | 7/2002 | West, Jr. et al. |
| 2002/0116012 A1 | 8/2002 | May et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183835 A1 | 12/2002 | Taylor et al. |
| 2002/0193815 A1 | 12/2002 | Foerster et al. |
| 2003/0009196 A1 | 1/2003 | Peterson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |

(56) References Cited

U.S. PATENT DOCUMENTS

| | | |
|---|---|---|
| 2003/0130731 A1 | 7/2003 | Vidlund et al. |
| 2003/0144673 A1 | 7/2003 | Onuki et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0181800 A1 | 9/2003 | Bonutti |
| 2003/0181926 A1 | 9/2003 | Dana et al. |
| 2003/0191497 A1 | 10/2003 | Cope |
| 2003/0195562 A1 | 10/2003 | Collier et al. |
| 2003/0199974 A1 | 10/2003 | Lee et al. |
| 2003/0204205 A1 | 10/2003 | Sauer et al. |
| 2003/0220659 A1 | 11/2003 | Schmieding et al. |
| 2003/0220685 A1 | 11/2003 | Hlavka et al. |
| 2003/0225420 A1 | 12/2003 | Wardle |
| 2003/0229361 A1 | 12/2003 | Jackson |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0044365 A1 | 3/2004 | Bachman |
| 2004/0092962 A1 | 5/2004 | Thornton et al. |
| 2004/0093023 A1 | 5/2004 | Allen et al. |
| 2004/0097788 A1 | 5/2004 | Mourlas et al. |
| 2004/0097865 A1 | 5/2004 | Anderson et al. |
| 2004/0122450 A1 | 6/2004 | Oren et al. |
| 2004/0133274 A1 | 7/2004 | Webler et al. |
| 2004/0148020 A1 | 7/2004 | Vidlund et al. |
| 2004/0152947 A1 | 8/2004 | Schroeder et al. |
| 2004/0162465 A1 | 8/2004 | Carrillo |
| 2004/0172046 A1 | 9/2004 | Hlavka et al. |
| 2004/0181238 A1 | 9/2004 | Zarbatany et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0225300 A1 | 11/2004 | Goldfarb et al. |
| 2004/0236354 A1 | 11/2004 | Seguin |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0033325 A1 | 2/2005 | May et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0119735 A1 | 6/2005 | Spence et al. |
| 2005/0125011 A1 | 6/2005 | Spence et al. |
| 2005/0137689 A1 | 6/2005 | Salahieh et al. |
| 2005/0143762 A1 | 6/2005 | Paraschac et al. |
| 2005/0165424 A1 | 7/2005 | Gallagher et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0004409 A1 | 1/2006 | Nobis et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0106422 A1 | 5/2006 | Del Rio et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0200199 A1* | 9/2006 | Bonutti .............. A61B 17/0487 606/232 |
| 2006/0207606 A1 | 9/2006 | Roue et al. |
| 2006/0235413 A1 | 10/2006 | Denham et al. |
| 2006/0241656 A1 | 10/2006 | Starksen et al. |
| 2006/0264975 A1 | 11/2006 | Pipenhagen et al. |
| 2006/0265010 A1 | 11/2006 | Paraschac et al. |
| 2006/0271060 A1 | 11/2006 | Gordon |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0066994 A1 | 3/2007 | Blaeser et al. |
| 2007/0106310 A1 | 5/2007 | Goldin et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2007/0156172 A1 | 7/2007 | Alvarado |
| 2007/0213746 A1 | 9/2007 | Hahn et al. |
| 2007/0276437 A1 | 11/2007 | Call et al. |
| 2008/0004622 A1 | 1/2008 | Coe et al. |
| 2008/0033460 A1 | 2/2008 | Ziniti et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058868 A1 | 3/2008 | To et al. |
| 2008/0065156 A1 | 3/2008 | Hauser et al. |
| 2008/0097484 A1 | 4/2008 | Lim et al. |
| 2008/0172035 A1 | 7/2008 | Starksen et al. |
| 2008/0177304 A1 | 7/2008 | Westra et al. |
| 2008/0177380 A1 | 7/2008 | Starksen et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0234701 A1 | 9/2008 | Morales et al. |
| 2008/0234702 A1 | 9/2008 | Morales et al. |
| 2008/0234728 A1 | 9/2008 | Starksen et al. |
| 2008/0234815 A1 | 9/2008 | Starksen |
| 2008/0294177 A1 | 11/2008 | To et al. |
| 2009/0182417 A1 | 7/2009 | Tremulis et al. |
| 2009/0204125 A1 | 8/2009 | Onishi et al. |
| 2009/0234318 A1 | 9/2009 | Loulmet et al. |
| 2009/0276038 A1 | 11/2009 | Tremulis et al. |
| 2009/0292353 A1 | 11/2009 | Yoganathan et al. |
| 2010/0049213 A1 | 2/2010 | Serina et al. |
| 2010/0076408 A1 | 3/2010 | Krever et al. |
| 2010/0076548 A1 | 3/2010 | Konno |
| 2010/0121349 A1 | 5/2010 | Meier et al. |
| 2012/0271331 A1 | 10/2012 | To et al. |

(56) References Cited

U.S. PATENT DOCUMENTS

| | | | |
|---|---|---|---|
| 2013/0304093 | A1 | 11/2013 | Serina et al. |
| 2015/0164639 | A1 | 6/2015 | Starksen et al. |

FOREIGN PATENT DOCUMENTS

| | | | |
|---|---|---|---|
| WO | WO-95/15715 | A1 | 6/1995 |
| WO | WO-96/08208 | A1 | 3/1996 |
| WO | WO-96/39942 | A1 | 12/1996 |
| WO | WO-97/27799 | A1 | 8/1997 |
| WO | WO-97/27807 | A1 | 8/1997 |
| WO | WO-97/30639 | A1 | 8/1997 |
| WO | WO-98/07375 | A1 | 2/1998 |
| WO | WO-00/60995 | A2 | 10/2000 |
| WO | WO-00/60995 | A3 | 10/2000 |
| WO | WO-00/67640 | A2 | 11/2000 |
| WO | WO-00/67640 | A3 | 11/2000 |
| WO | WO-01/26586 | A1 | 4/2001 |
| WO | WO-01/54618 | A1 | 8/2001 |
| WO | WO-02/03892 | A1 | 1/2002 |
| WO | WO-02/051329 | A1 | 7/2002 |
| WO | WO-02/074178 | A2 | 9/2002 |
| WO | WO-02/074178 | A3 | 9/2002 |
| WO | WO-02/085251 | A1 | 10/2002 |
| WO | WO-02/085252 | A1 | 10/2002 |
| WO | WO-03/049648 | A2 | 6/2003 |
| WO | WO-03/049648 | A3 | 6/2003 |
| WO | WO-03/073913 | A2 | 9/2003 |
| WO | WO-03/088875 | A1 | 10/2003 |
| WO | WO-03/105667 | A2 | 12/2003 |
| WO | WO-03/105667 | A3 | 12/2003 |
| WO | WO-03/105670 | A2 | 12/2003 |
| WO | WO-03/105670 | A3 | 12/2003 |
| WO | WO-2004/037317 | A2 | 5/2004 |
| WO | WO-2004/037317 | A3 | 5/2004 |
| WO | WO-2004/045367 | A2 | 6/2004 |
| WO | WO-2004/045367 | A3 | 6/2004 |
| WO | WO-2004/082523 | A2 | 9/2004 |
| WO | WO-2004/082523 | A3 | 9/2004 |
| WO | WO-2004/082538 | A2 | 9/2004 |
| WO | WO-2004/082538 | A3 | 9/2004 |
| WO | WO-2005/025644 | A2 | 3/2005 |
| WO | WO-2005/025644 | A3 | 3/2005 |
| WO | WO-2005/062931 | A2 | 7/2005 |
| WO | WO-2005/062931 | A3 | 7/2005 |
| WO | WO-2005/102181 | A1 | 11/2005 |
| WO | WO-2005/110241 | A1 | 11/2005 |
| WO | WO-2006/037073 | A2 | 4/2006 |
| WO | WO-2006/039296 | A2 | 4/2006 |
| WO | WO-2006/097931 | A2 | 9/2006 |
| WO | WO-2006/097931 | A3 | 9/2006 |
| WO | WO-2006/116558 | A2 | 11/2006 |
| WO | WO-2006/116558 | A3 | 11/2006 |
| WO | WO-2006/116558 | C2 | 11/2006 |
| WO | WO-2006/128092 | A2 | 11/2006 |
| WO | WO-2006/128092 | A3 | 11/2006 |
| WO | WO-2007/001936 | A2 | 1/2007 |
| WO | WO-2007/001936 | A3 | 1/2007 |
| WO | WO-2007/005495 | A1 | 1/2007 |
| WO | WO-2007/021564 | A1 | 2/2007 |
| WO | WO-2007/021834 | A1 | 2/2007 |
| WO | WO-2007/035449 | A2 | 3/2007 |
| WO | WO-2007/056502 | A1 | 5/2007 |
| WO | WO-2007/100409 | A2 | 9/2007 |
| WO | WO-2008/028135 | A2 | 3/2008 |
| WO | WO-2008/028135 | A3 | 3/2008 |
| WO | WO-2008/112740 | A2 | 9/2008 |
| WO | WO-2008/112740 | A3 | 9/2008 |
| WO | WO-2009/052438 | A2 | 4/2009 |
| WO | WO-2009/052438 | A3 | 4/2009 |
| WO | WO-2009/061611 | A1 | 5/2009 |
| WO | WO-2010/042845 | A1 | 4/2010 |
| WO | WO-2010/042857 | A1 | 4/2010 |

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Carl.* 71:926-931.

De Simone, R. et al. (Apr. 1, 1994). "Adjustable Annuloplasty for Tricuspid Insufficiency with External Control," *Reader's Comments and Reply, Am. J. Cardiol.* 73(9):721-722.

Downing, S.W. et al. (2002). "Feasibility of Off-Pump ASD Closure Using Real-Time 3-D Echocardiography," *The Heart Surgery Forum* 5(2):96-99, Abstract 7025.

European Examination Communication mailed on Dec. 8, 2009, for EP Application No. 06 837 222.6 filed on Nov. 8, 2006, three pages.

Final Office Action mailed on Aug. 30, 2007, for U.S. Appl. No. 11/232,190, filed Sep. 20, 2005, 9 pages.

Final Office Action mailed on May 28, 2008, for U.S. Appl. No. 11/270,034, filed Nov. 8, 2005, 10 pages.

Final Office Action mailed on Aug. 1, 2008, for U.S. Appl. No. 11/232,190, filed Sep. 20, 2005, 8 pages.

Final Office Action mailed on Jul. 21, 2009, for U.S. Appl. No. 11/270,034, filed Nov. 8, 2005, 8 pages.

Final Office Action mailed on Sep. 2, 2009, for U.S. Appl. No. 11/232,190, filed Sep. 20, 2005, 8 pages.

Final Office Action mailed on Jul. 26, 2010, for U.S. Appl. No. 11/270,034, filed Nov. 8, 2005, 8 pages.

Final Office Action mailed on Sep. 15, 2010, for U.S. Appl. No. 11/894,401, filed Aug. 20, 2007, 6 pages.

Final Office Action mailed on Jun. 11, 2012, for U.S. Appl. No. 12/187,331, filed Aug. 6, 2008, 7 pages.

Final Office Action mailed on Oct. 23, 2012, for U.S. Appl. No. 12/576,955, filed Oct. 9, 2009, 8 pages.

Final Office Action mailed on Jan. 22, 2013, for U.S. Appl. No. 12/480,568, filed Jun. 8, 2009, 6 pages.

Final Office Action mailed on Mar. 20, 2013, for U.S. Appl. No. 12/577,044, filed Oct. 9, 2009, 7 pages.

International Search Report mailed on Dec. 10, 2009, for PCT Patent Application No. PCT/US2009/060202, filed on Oct. 9, 2009, 3 pages.

Nagy, Z.L. et al. (Dec. 2000). "Mitral Annuloplasty with a Suture Technique," *European Journal of Cardio-thoracic Surgery* 18(6):739-740.

Non-Final Office Action mailed on Dec. 27, 2006, for U.S. Appl. No. 11/270,034, filed Nov. 8, 2005, 8 pages.

Non-Final Office Action mailed on Mar. 12, 2007, for U.S. Appl. No. 11/232,190, filed Sep. 20, 2005, 11 pages.

Non-Final Office Action mailed on Aug. 30, 2007, for U.S. Appl. No. 11/270,034, filed Nov. 8, 2005, 10 pages.

Non-Final Office Action mailed Jan. 9, 2008, for U.S. Appl. No. 11/232,190, filed Sep. 20, 2005, 8 pages.

Non-Final Office Action mailed on Jan. 23, 2009, for U.S. Appl. No. 11/270,034, filed Nov. 8, 2005, 8 pages.

Non-Final Office Action mailed on Jan. 23, 2009, for U.S. Appl. No. 11/232,190, filed Sep. 20, 2005, 8 pages.

Non-Final Office Action mailed on Jan. 19, 2010, for U.S. Appl. No. 11/270,034, filed Nov. 8, 2005, 10 pages.

Non-Final Office Action mailed on Feb. 18, 2010, for U.S. Appl. No. 11/894,401, filed Aug. 20, 2007, 6 pages.

Non-Final Office Action mailed on Oct. 29, 2010, for U.S. Appl. No. 11/894,530, filed Aug. 20, 2007, 11 pages.

Non-Final Office Action mailed on Feb. 11, 2011, for U.S. Appl. No. 12/132,328, filed Jun. 3, 2008, 9 pages.

Non-Final Office Action mailed on Oct. 13, 2011, for U.S. Appl. No. 12/187,331, filed Aug. 6, 2008, 5 pages.

Non-Final Office Action mailed on Dec. 22, 2011, for U.S. Appl. No. 11/270,034, filed Nov. 8, 2005, 8 pages.

Non-Final Office Action mailed on Jan. 27, 2012, for U.S. Appl. No. 12/480,568, filed Jun. 8, 2009, 5 pages.

Non-Final Office Action mailed on Mar. 14, 2012, for U.S. Appl. No. 12/576,955, filed Oct. 9, 2009, 7 pages.

Non-Final Office Action mailed on Jun. 28, 2012, for U.S. Appl. No. 12/577,044, filed Oct. 9, 2009, 7 pages.

Notice of Allowance mailed on Nov. 17, 2010, for U.S. Appl. No. 11/232,190, filed Sep. 20, 2005, 11 pages.

(56) References Cited

OTHER PUBLICATIONS

Notice of Allowance mailed on Jul. 26, 2011, for U.S. Appl. No. 11/894,530, filed Aug. 20, 2007, 10 pages.
Notice of Allowance mailed on Jun. 8, 2012, for U.S. Appl. No. 11/894,401, filed Aug. 20, 2007, 9 pages.
Notice of Allowance mailed on Mar. 31, 2014, for U.S. Appl. No. 12/576,955, filed Oct. 9, 2009, 8 pages.
Shumway, S.J. et al. (Dec. 1988). "A 'Designer' Annuloplasty Ring for Patients with Massive Mitral Annular Dilatation," *Ann. Thorac. Surg.* 46(6):695-696.
Notice of Allowance mailed on Mar. 2, 2015, for U.S. Appl. No. 12/187,331, filed Aug. 6, 2008, 5 pages.
Final Office Action mailed Feb. 5, 2015, for U.S. Appl. No. 13/540,499, filed Jul. 2, 2012, 10 pages.
Final Office Action mailed May 18, 2015, for U.S. Appl. No. 10/901,554, filed Jul. 27, 2004, 17 pages.
Australian Notice of Acceptance mailed on Jan. 4, 2016, for Australian Patent Application No. 2009302169, Internationally filed on Oct. 9, 2009, 3 pages.
Canadian Office Action mailed on Sep. 23, 2015, for Canadian Application No. 2,740,233, Internationally filed on Oct. 9, 2009, 3 pages.
Canadian Office Action mailed on Oct. 5, 2015, for Canadian Patent Application No. 2,702,466, Internationally filed on Oct. 17, 2008, 4 pages.
European Extended Search Report mailed on May 17, 2016, for EP Application No. 09 819 970.6, filed on May 4, 2011, 8 pages.
European Extended Search Report mailed on May 17, 2016, for EP Application No. 09 819 978.9 filed on Oct. 9, 2009, 9 pages.
Final Office Action mailed Feb. 24, 2016, for U.S. Appl. No. 13/948,009, filed Jul. 22, 2013, 13 pages.
International Search Report mailed on May 19, 2009, for PCT Patent Application No. PCT/US2008/080381, filed on Oct. 17, 2008, 5 pages.
International Search Report mailed on Jan. 12, 2010, for PCT Patent Application No. PCT/US2009/60227, filed on Oct. 9, 2009, 2 pages.
International Search Report mailed on Mar. 7, 2007, for PCT Patent Application No. PCT/US2004/028431, filed on Sep. 1, 2004, 1 page.
International Search Report mailed Dec. 19, 2006, for PCT Application No. PCT/US2006/031190, filed on Aug. 10, 2006, 3 pages.
International Search Report mailed on Apr. 2, 2007, for PCT Application No. PCT/US2006/043597, filed on Nov. 8, 2006, 4 pages.
Non-Final Office Action mailed Jun. 18, 2015, for U.S. Appl. No. 13/948,009, filed Jul. 22, 2013, 20 pages.
Non-Final Office Action mailed Nov. 17, 2016, for U.S. Appl. No. 13/948,009, filed Jul. 22, 2013, 22 pages.
Non-Final Office Action mailed Apr. 21, 2016, for U.S. Appl. No. 13/540,499, filed Jul. 2, 2012, 13 pages.
Notice of Allowance mailed on Apr. 28, 2010, for U.S. Appl. No. 10/901,019, filed Jul. 27, 2004, 7 pages.
Notice of Allowance mailed on Oct. 29, 2015, for U.S. Appl. No. 10/901,554, filed Jul. 27, 2004, 8 pages.
Notice of Allowance mailed on Jun. 15, 2016, for U.S. Appl. No. 14/156,347, filed Jan. 15, 2014, 7 pages.
Written Opinion of the International Searching Authority mailed on May 19, 2009, for PCT Patent Application No. PCT/US2008/080381, filed on Oct. 17, 2008, 10 pages.
Written Opinion of the International Searching Authority mailed on Dec. 10, 2009, for PCT Patent Application No. PCT/US2009/060202, filed on Oct. 9, 2009, 10 pages.
Written Opinion of the International Searching Authority mailed on Jan. 12, 2010, for PCT Patent Application No. PCT/US2009/60227, filed on Oct. 9, 2009, 5 pages.
Written Opinion of the International Searching Authority mailed on Mar. 7, 2007, for PCT Patent Application No. PCT/US2004/028431, filed on Sep. 1, 2004, 4 pages.
Written Opinion of the International Searching Authority mailed Dec. 19, 2006, for PCT Application No. PCT/US2006/031190, filed on Aug. 10, 2006, 6 pages.
Written Opinion of the International Searching Authority mailed on Apr. 2, 2007, for PCT Application No. PCT/US2006/043597, filed on Nov. 8, 2006, 7 pages.
Written Opinion of the International Searching Authority mailed on Feb. 15, 2007, for PCT Application No. PCT/US2006/035933, filed on Sep. 15, 2006, 4 pages.
U.S. Appl. No. 15/265,781, filed Sep. 14, 2016, by Starksen et al.

\* cited by examiner

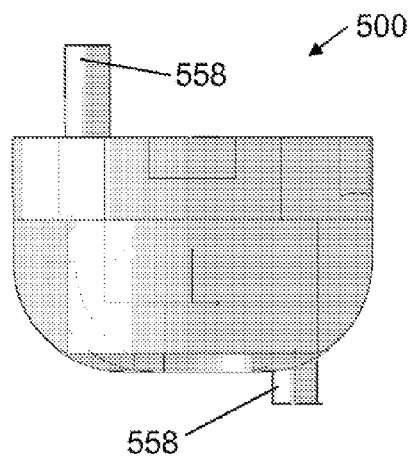
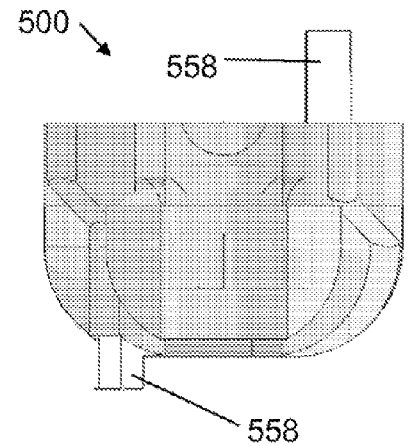
FIG. 5M  FIG. 5N
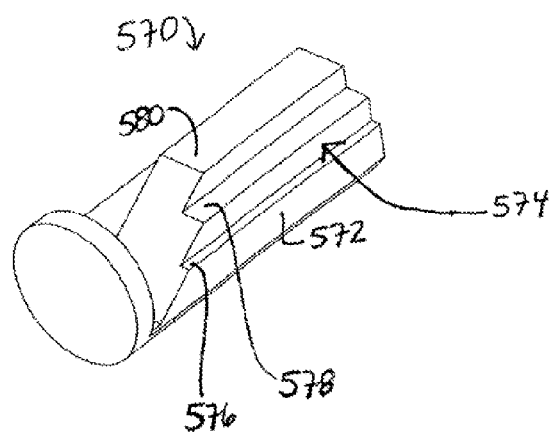
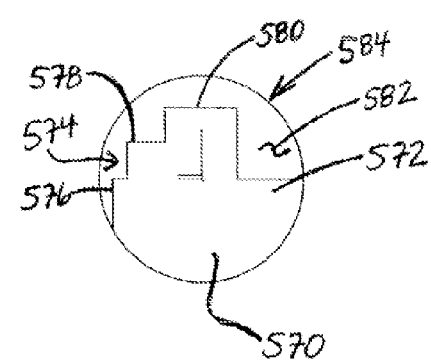
FIG. 5O  FIG. 5P

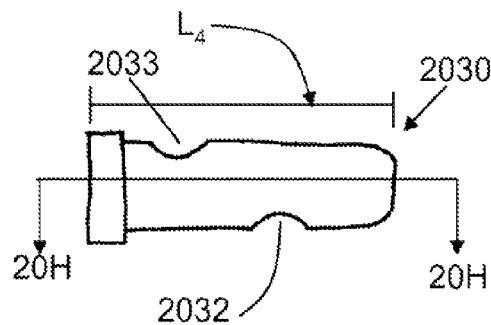
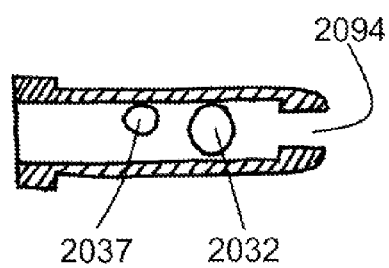
FIG. 20G
FIG. 20H
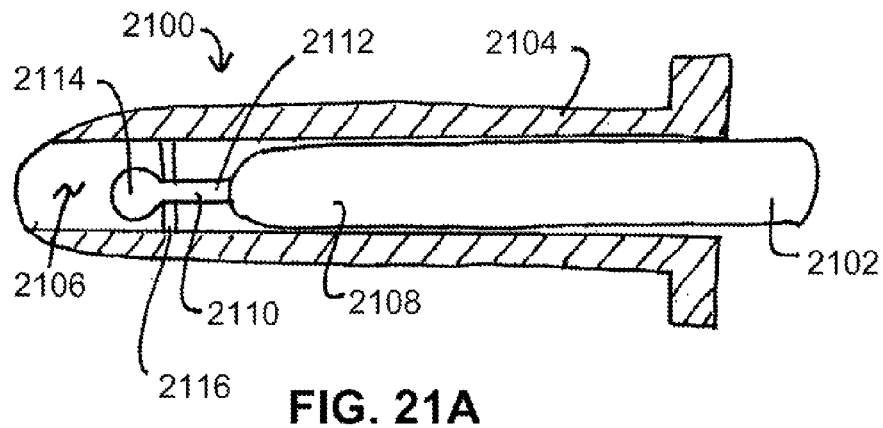
FIG. 21A
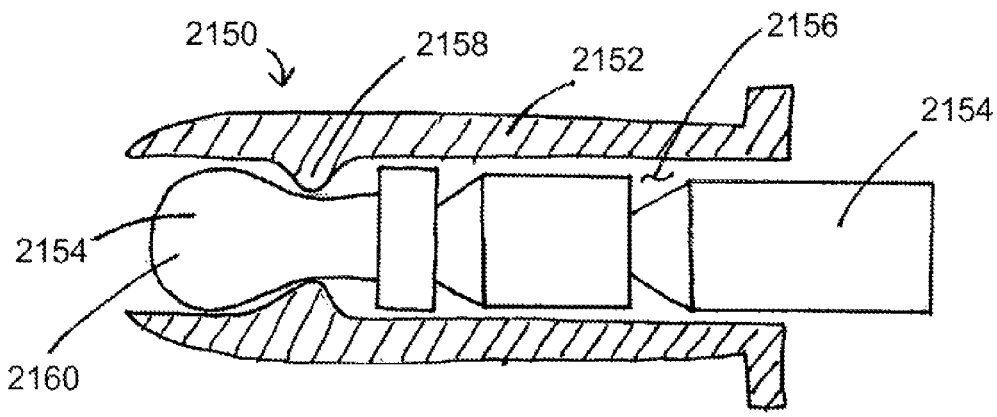
FIG. 21B

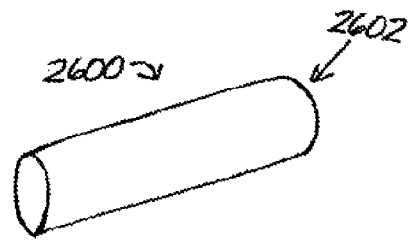
FIG. 26A  FIG. 26B
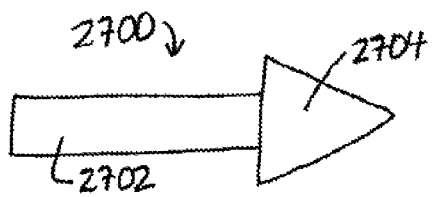
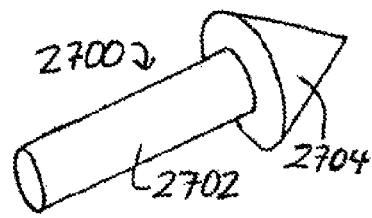
FIG. 27A  FIG. 27B
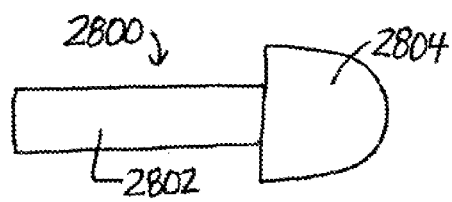
FIG. 28A  FIG. 28B
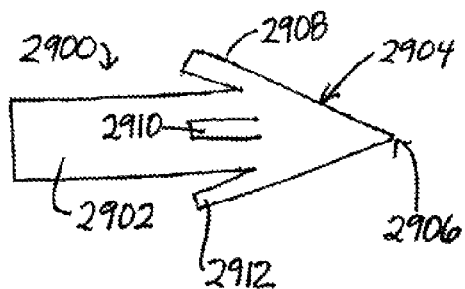
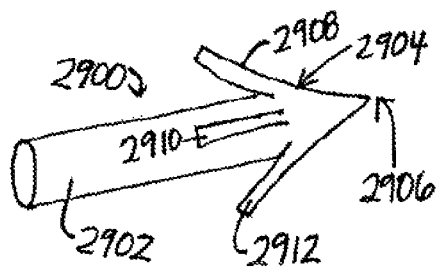
FIG. 29A  FIG. 29B

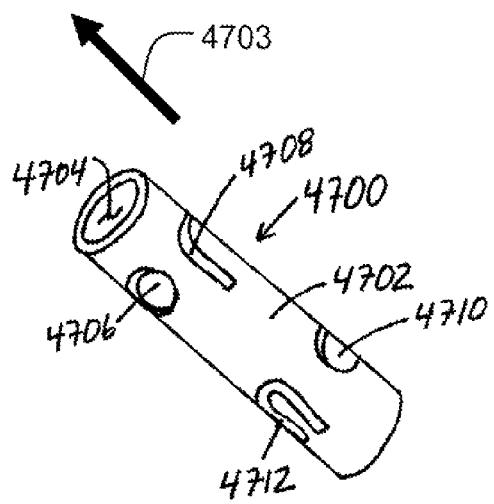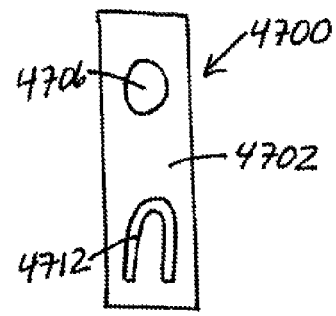
FIG. 47A  FIG. 47B
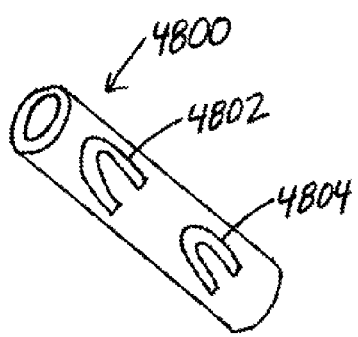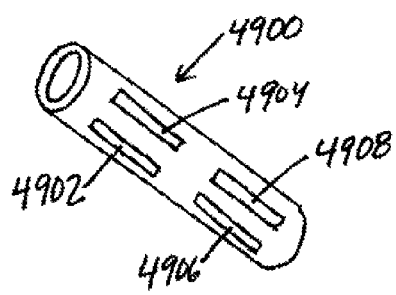
FIG. 48  FIG. 49

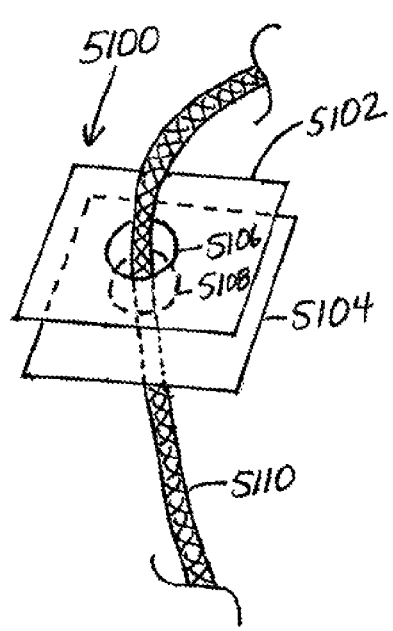
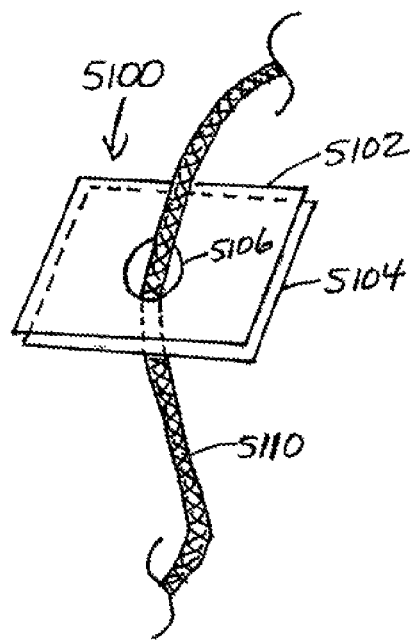
FIG. 51A  FIG. 51B
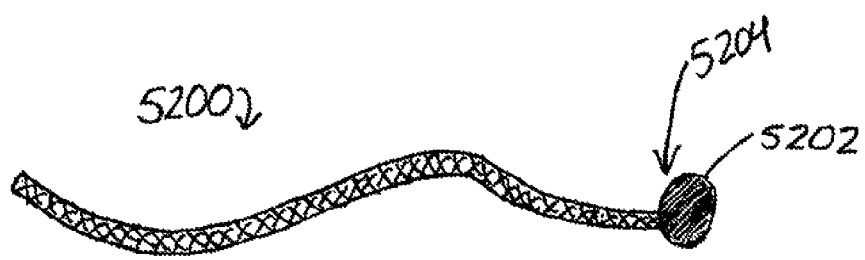
FIG. 52

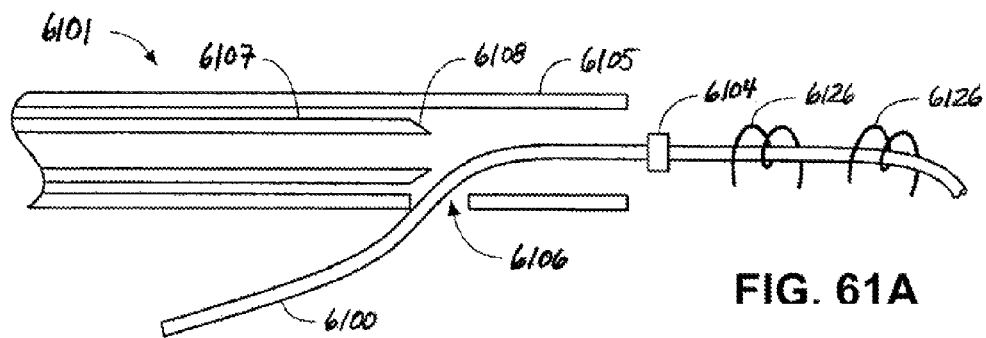
FIG. 61A
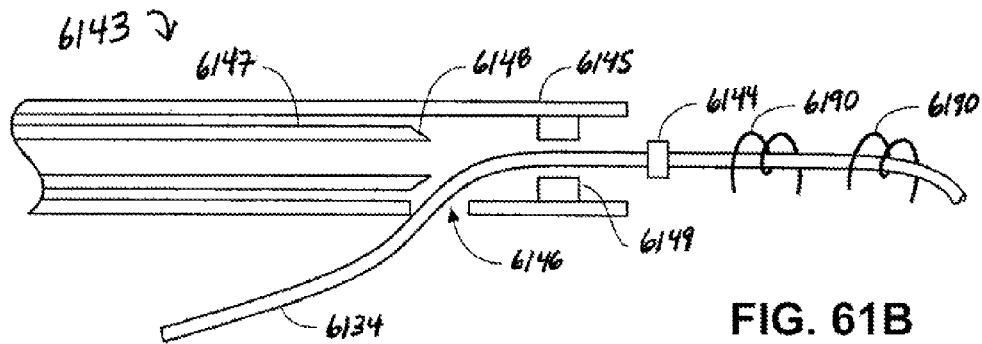
FIG. 61B
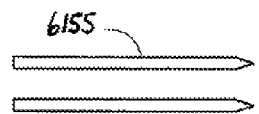   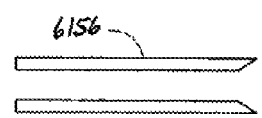   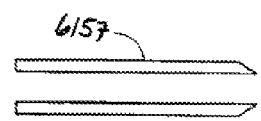
FIG. 61C    FIG. 61D    FIG. 61E
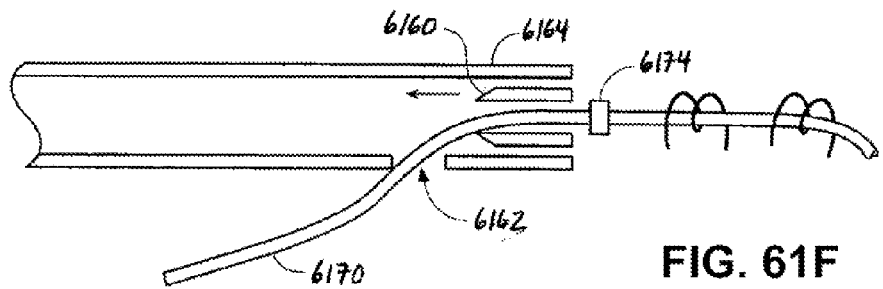
FIG. 61F

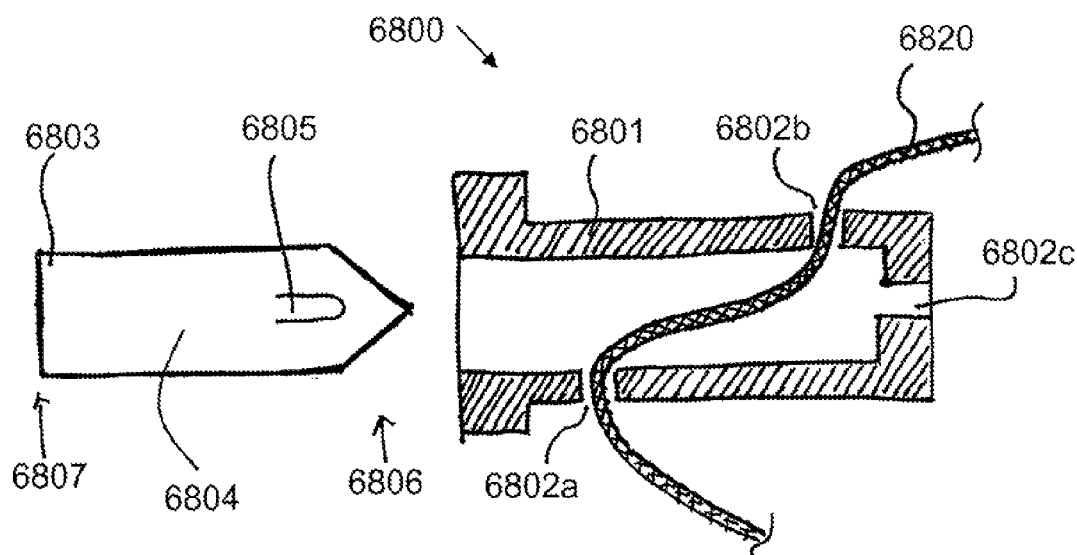
FIG. 68A
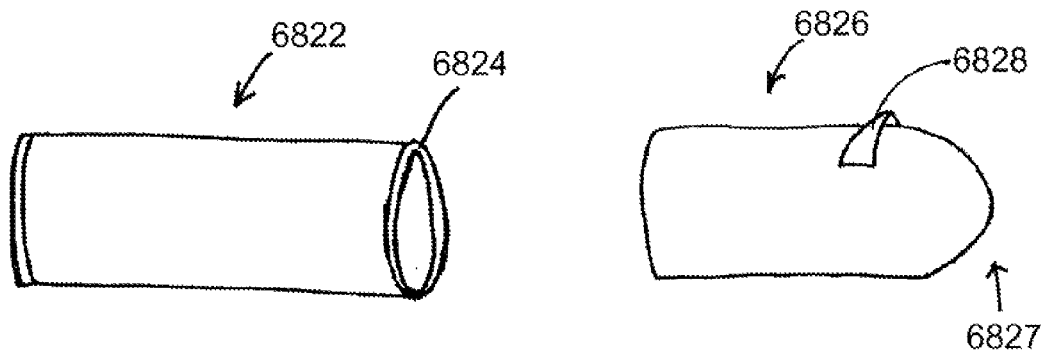
FIG. 68B  FIG. 68C

TERMINATION DEVICES AND RELATED METHODS

CROSS-REFERENCE TO RELATED APPLICATIONS

This application is a continuation of U.S. patent application Ser. No. 12/577,044, filed Oct. 9, 2009, which claims the benefit of U.S. Provisional Application No. 61/104,681, filed Oct. 10, 2008, the disclosures of both of which are incorporated herein by reference in their entirety.

FIELD

The devices and methods described herein relate generally to termination of tethers that have been deployed to a target site in a body of a subject. More specifically, the devices and methods described herein relate to locking and/or cutting such tethers after they have been deployed to the target site.

BACKGROUND

Many different types of medical procedures involve the use of tethers. For example, tethers may be used to tighten or compress tissue (e.g., by bringing two pieces or sections of tissue together). The tissue may be, for example, soft tissue, such as muscle tissue or fat tissue. As an example, in some tissue tightening procedures, anchors coupled to a tether are embedded in tissue, and the tether is then pulled upon to provide a cinching effect that tightens or compresses the tissue via the anchors. Examples of devices and methods for such procedures applied to heart valve repair are described, for example, in U.S. Patent Application Publication Nos. US 2006/0122633 A1, US 2006/0190030 A1, and US 2008/0172035 A1, all of which are hereby incorporated by reference in their entirety.

Some methods of tissue tightening or compression include threading a tether through two pieces of tissue, applying tension to the tether, and tying off or knotting the tether to maintain the tension. Extra tether material may then be cut and removed. However, the manipulation required when knotting, tying, and/or cutting a tether can be difficult (e.g., because of restricted space). Moreover, certain methods may not adequately maintain tension in a tether. Additionally, some methods of knotting, tying, and/or cutting a tether may be unduly complicated and/or time-consuming.

Accordingly, it would be desirable to provide methods and devices for effectively locking and/or cutting a tether to help maintain tension in the tether. It would further be desirable for such methods and devices to be relatively easy and/or efficient to use.

SUMMARY

Described here are devices and methods for locking and/or cutting tethers, such as tethers that have been used to tighten or compress tissue (e.g., by pulling two or more pieces or sections of the tissue together).

Certain variations of the devices described here comprise a locking member (e.g., a tubular member) configured to receive a plug within a lumen, and a plug rotatable within the lumen of the locking member to secure a portion of a tether within the lumen. The exterior surface of the plug may have at least one contour (e.g., a curvature) alignable with the interior surface of a wall portion of the locking member when the plug is at least partially disposed within the lumen of the locking member.

The wall portion of the locking member may comprise first and second apertures alignable for passage of a tether therethrough. The first and second apertures may be located such that a tether passing therethrough would not cross the center of the lumen of the locking member. The plug may be rotatable within the lumen of the locking member by tensioning a tether passing through the lumen of the locking member. The plug may be rotatable by at least about 1° (e.g., at least about 10°, at least about 20°, at least about 45°, at least about 90°, at least about 135°) and/or at most about 180° (e.g., at most about 135°, at most about 90°, at most about 45°, at most about 20°, at most about 10°) to secure a portion of a tether within the lumen of the locking member. The devices may further comprise a pullwire for rotating the plug within the lumen of the locking member. The plug may comprise at least one protrusion (e.g., in the form of at least one ridge) configured to engage a portion of a tether within the lumen of the locking member. In certain variations, the plug may comprise multiple protrusions. For example, the plug may comprise multiple protrusions that form a stepped configuration. In some variations, the plug may comprise a gear-shaped portion, such as a gear-shaped portion comprising a plurality of teeth, with each tooth being progressively longer than the previous tooth.

Certain variations of the methods described here may comprise tensioning a tether when at least a portion of the tether is disposed within the lumen of the locking member. Tensioning the tether may rotate the plug when the plug is at least partially disposed within the lumen of the locking member. In some variations, the methods may comprise rotating the plug when the tether passes through first and second apertures in the wall portion of the locking member. Rotating the plug may secure the portion of the tether between the exterior surface of the plug and the interior surface of the wall portion of the locking member. The methods may further comprise advancing the plug at least partially into the lumen of the locking member.

Some variations of the devices described here may comprise a locking member (e.g., a tubular member) configured to receive a plug and comprising a wall portion comprising first and second apertures and a lumen. The devices may further comprise a plug comprising a third aperture alignable with the first and second apertures for passage of a tether therethrough. The third aperture may be capable of being misaligned from at least one of the first and second apertures to secure a tether passing therethrough. The tether may be secured, for example, between the plug and the wall portion of the locking member. The plug may comprise at least two apertures.

Certain variations of the methods described here may comprise adjusting the relative position of the locking member and the plug when the plug is at least partially disposed within the lumen of the locking member. This may secure a tether passing through the first and second apertures in the wall portion of the locking member and the third aperture in the plug. The methods may further comprise advancing the plug at least partially into the lumen of the locking member. In some variations, the methods may further comprise advancing the tether through the first aperture in the wall portion of the locking member, through the second aperture in the plug, and/or through the third aperture in the wall portion of the locking member. The tether may be secured between the plug and the locking member.

Some variations of the devices described here may comprise a locking member (e.g., a tubular member) comprising a wall portion and a lumen, and a plug comprising first and second apertures. The plug may be configured to at least partially fit within the lumen of the locking member, and the first and second apertures may be configured such that a tether routed therethrough will be secured between the plug and the locking member. In certain variations, the plug may be secured within the locking member prior to securing the tether.

Some variations of the methods described here may comprise advancing the plug at least partially into the lumen of the locking member when the tether has been routed through the first and second apertures to secure the tether between the plug and the locking member. The plug may be secured to the locking member prior to being used to secure a tether. The methods may further comprise advancing the tether through the first and/or second apertures (e.g., while the plug is at least partially disposed within the lumen of the locking member and/or while the plug is secured with the locking member).

Certain variations of the devices described here may comprise a locking member (e.g., a tubular member) comprising a wall portion and a lumen, and a plug comprising at least one protrusion configured to engage a groove or first aperture in the wall portion of the locking member when the plug is at least partially disposed within the lumen of the locking member, where the plug and the locking member are configured to secure a tether therebetween. The protrusion on the plug may be configured to form a snap-fit with the groove or first aperture in the wall portion of the locking member. At least a portion of the plug may be configured to be compressed to fit within the locking member, and then released to form a snap-fit with the locking member. The device may further comprise a pushing member configured to push the plug toward the locking member. In some variations, the plug may comprise a second aperture. The wall portion of the locking member may comprise a third aperture that is alignable with the second aperture of the plug for routing of a tether therethrough.

Some variations of the methods described here may comprise advancing the plug into the lumen of the locking member while a portion of a tether is disposed within the lumen of the locking member, until at least one protrusion on the plug engages the groove or first aperture in the wall portion of the locking member. Advancing the plug into the lumen of the locking member may secure the portion of the tether between the plug and the locking member. The protrusion on the plug may form a snap-fit with the groove or first aperture in the wall portion of the locking member. The methods may further comprise advancing the tether through a second aperture in the plug after the protrusion has engaged the groove or first aperture in the wall portion of the locking member. In certain variations, the methods may comprise advancing the plug into the lumen of the locking member until the plug is entirely disposed within the lumen of the locking member.

Some variations of the devices described here may comprise an elongated member and a tubular member coupled to a distal portion of the elongated member, the tubular member comprising a lumen. The tubular member may further comprise a wall portion comprising at least one non-circular aperture sized and shaped for passage of a tether therethrough, and/or at least one circular aperture sized and shaped for passage of a tether therethrough. The non-circular aperture may be horseshoe-shaped, for example.

Certain variations of the methods described here may comprise routing the tether through the non-circular aperture in the wall portion of the tubular member when the tubular member is coupled to a distal portion of an elongated member. Routing the tether through the non-circular aperture may compress the tether.

Some variations of the devices described here may comprise a locking member (e.g., a tubular member) comprising a wall portion and a lumen, and a plug configured to at least partially fit within the lumen of the locking member. The interior surface of the wall portion may comprise at least one protrusion configured to engage a groove or first aperture in the plug when the plug is at least partially disposed within the lumen of the locking member. Additionally, the plug and the locking member are configured to secure a tether therebetween. The protrusion on the interior surface of the wall portion of the locking member may be configured to form a snap-fit with the groove or first aperture in the plug. The devices may further comprise a pushing member configured to push the plug toward the locking member. In certain variations, the plug may further comprise a second aperture. The wall portion of the locking member may comprise a third aperture that is alignable with the second aperture of the plug for passage of a tether therethrough.

Some variations of the methods described here may comprise at least partially fitting the plug within the lumen of the locking member and engaging the groove or first aperture in the plug with the protrusion on the interior surface of the wall portion of the locking member while a portion of the tether is disposed within the lumen of the locking member. This may, for example, secure the tether between the plug and the locking member. The protrusion may form a snap-fit with the groove or first aperture in the plug. The protrusion may comprise a lip or rim on the interior surface of the locking member. The methods may further comprise advancing the plug into the lumen of the locking member until the plug is entirely disposed within the lumen of the locking member.

Certain variations of the devices described here may comprise a locking member (e.g., a tubular member) comprising a wall portion and a lumen, and a plug comprising a body portion and a head portion comprising a one-way feature. The one-way feature may allow translation of the head portion in a first direction once within the lumen of the locking member, but not in a second direction opposite the first direction. The plug and the locking member may be configured to secure a tether therebetween when the plug is at least partially disposed within the lumen of the locking member. The devices may further comprise a pushing member configured to push the plug in the first direction. The plug may comprise at least one aperture configured for passage of a tether therethrough.

Some variations of the methods described here may comprise advancing the plug into the lumen of the locking member until the plug is at least partially disposed within the lumen of the locking member, to secure the tether between the plug and the locking member.

Certain variations of the devices described here may comprise a locking member configured to receive a plug and comprising a wall portion and a lumen, and a plug comprising a body portion and an anchor portion extending from the body portion, where the plug and the locking member are configured to secure a tether therebetween. The devices may further comprise a pushing member configured to push the plug into the lumen of the locking member.

Certain variations of the methods described here may comprise advancing the plug into the lumen of the locking member until the plug is at least partially disposed within the lumen, to secure a tether between the plug and the locking member. The methods may further comprise advancing the anchor portion into tissue so that the anchor portion engages the tissue.

Some variations of the devices described here may comprise a locking member comprising a first portion having a first surface and a second portion having a second surface, the first and second portions coupled to each other by a hinge (e.g., a living hinge). The locking member may have an open configuration in which the first surface does not contact the second surface and a closed configuration in which the first surface contacts the second surface, and may be configured to secure a tether between the first and second surfaces in the closed configuration. The first and second surfaces may be configured to couple to each other upon contacting each other. For example, the first surface may comprise a groove or aperture and the second surface may comprise at least one protrusion configured to engage the groove or aperture when the first surface contacts the second surface. At least one of the first and second surfaces may be textured. The first and second surfaces may be mirror images of each other.

Certain variations of the methods described here may comprise positioning a tether on one or both of the first and second surfaces when the first surface is not in contact with the second surface, and contacting the first surface with the second surface to secure a portion of the tether between the first and second portions of the locking member. The methods may further comprise coupling the first surface to the second surface, and/or cutting the tether.

Some variations of the devices described here may comprise a plug, a locking member (e.g., a tubular member) comprising a lumen configured to receive a plug, and a coupling member extending between the plug and the locking member to couple the plug to the locking member. The coupling member may be integral with the locking member and/or the plug. The coupling member may comprise a tether. Some variations of the methods described here may comprise advancing the plug at least partially into the lumen of the locking member when a portion of a tether is disposed within the lumen of the locking member to secure the portion of the tether between the plug and the wall portion of the locking member. The tether may pass through at least one aperture in the wall portion of the locking member.

Some of the devices described here may comprise a locking member (e.g., a tubular member) comprising a lumen and a clamping member slidably disposed within the lumen of the locking member. The clamping member may be configured to be advanced from, and withdrawn into, the lumen of the locking member, and may also be configured to clamp a tether when withdrawn into the locking member. In some variations, the clamping member may comprise jaws. Certain variations of the methods described here may comprise clamping a tether with the clamping member, and withdrawing the clamping member into the lumen of the locking member.

Some variations of the devices described here may comprise a locking member (e.g., a tubular member) comprising a lumen, and a plug comprising at least two coupling portions configured to couple the plug to the locking member, and to advance the plug into the lumen of the locking member. Certain variations of the methods described here may comprise coupling the plug to the locking member and advancing the plug into the lumen of the locking member to thereby secure a tether between the plug and the wall portion of the locking member. The tether may pass through at least one aperture in the wall portion of the locking member. The methods may further comprise cutting the tether.

Some variations of the devices described here may comprise a locking member (e.g., a tubular member) comprising a wall portion and a lumen, and a plug configured to at least partially fit within the lumen of the locking member. The plug may comprise at least one hook configured to engage a groove or aperture in an exterior surface of the wall portion of the locking member. The plug may also be configured to secure a tether against the interior surface of the wall portion of the locking member when the plug is at least partially disposed within the lumen of the locking member.

Certain method variations may comprise advancing the plug at least partially into the lumen of the locking member to secure a tether between the plug and the wall portion of the locking member, and engaging the hook of the plug with the groove or aperture in the exterior surface of the wall portion of the locking member to secure the plug to the locking member. The tether may pass through at least one aperture in the wall portion of the locking member.

Some device variations may comprise a locking member (e.g., a tubular member) comprising a wall portion and a lumen, and a plug configured to at least partially fit within the lumen of the locking member to secure a tether between the plug and the wall portion of the locking member. The plug may comprise a first ring portion configured for passage of a tether therethrough, and at least a portion of the first ring portion may be external to the lumen of the locking member when the plug is at least partially disposed within the lumen of the locking member. The locking member may further comprise a second ring portion configured for passage of a tether therethrough.

Some of the method variations may comprise advancing the plug at least partially into the lumen of the locking member to secure a first tether between the plug and the wall portion of the locking member, passing a second tether through the first ring portion, and securing the second tether to tissue of a subject. The locking member may further comprise a second ring portion, and the method may further comprise passing the second tether through the second ring portion. The plug may further comprise a second ring portion, and the method may further comprise passing the second tether through the second ring portion. The method may also comprise securing the second tether to tissue of the subject. The first and second tethers may be the same tether. The first tether may pass through at least one aperture in the wall portion of the locking member.

Some variations of the devices may comprise a locking member (e.g., a tubular member) comprising a wall portion and a lumen, and a plug configured to at least partially fit within the lumen of the locking member to secure a tether between the plug and the wall portion of the locking member. The locking member may further comprise a first ring portion configured for passage of a tether therethrough. The first ring portion may extend from the wall portion of the locking member. The locking member may further comprise a second ring portion configured for passage of a tether therethrough.

Some variations of the methods described here may comprise advancing the plug at least partially into the lumen of the locking member to secure a first tether between the plug and the wall portion of the locking member, passing a second tether through the first ring portion, and securing the second tether to tissue of a subject. The locking member may further comprise a second ring portion, and the method may further comprise passing the second tether through the second ring portion. The method may also comprise securing the second tether to tissue of the subject. The first and second tethers may be the same tether. The first tether may pass through at least one aperture in the wall portion of the locking member.

Some variations of the devices may comprise a tubular member and a locking member comprising a first clamping portion, a second clamping portion, and a hollow region therebetween. The hollow region may be configured to receive at least a portion of the tubular member when the locking member is in an open configuration. The locking member may also have a closed configuration in which the hollow region is not configured to receive any portion of the tubular member and in which the first clamping portion clamps against the second clamping portion. The first clamping portion may comprise a first plurality of teeth and the second clamping portion may comprise a second plurality of teeth that contact the first plurality of teeth when the locking member is in the closed configuration.

Some method variations may comprise advancing a tether through the tubular member while the tubular member is at least partially disposed within the hollow region of the locking member in an open configuration, and withdrawing the tubular member from the hollow region without also withdrawing the tether from the hollow region. The locking member may assume a closed configuration when the tubular member has been withdrawn from the hollow region, such that the locking member clamps down on the tether and thereby secures the tether.

Certain device variations may comprise a tubular member comprising a lumen, and a coil having a primary configuration when at least partially disposed within the lumen of the tubular member. The coil may be configured to assume a secondary configuration when not disposed within the lumen of the tubular member. Additionally, the coil may be configured for advancement of a tether therethrough when the coil is in its primary configuration, and may be configured to secure the tether when the coil assumes its secondary configuration. Some method variations may comprise advancing a tether through the coil while the coil is in a primary configuration and at least partially disposed within the lumen of the tubular member, and translating the coil relative to the tubular member so that the coil exits the lumen of the tubular member and assumes a secondary configuration in which the coil secures the tether.

Certain variations of the devices described herein may comprise an elongated member (e.g., a catheter). Moreover, in some variations of devices comprising a locking member, the locking member may be releasably coupled to a distal portion of the elongated member. Certain method variations may comprise decoupling the locking member from the distal portion of the elongated member (e.g., by applying force to the locking member with a pushing member). Some variations of the devices described herein may comprise a cutting member configured to cut a tether. Methods may comprise cutting one or more tethers.

Certain device variations may comprise a plug comprising a body with a proximal portion and a distal portion, a locking member comprising a proximal portion and a distal portion, and a cutting member that is coupled to or integral with the plug body. The locking member may further comprise a lumen extending at least partially therethrough, where the lumen is sized and shaped to receive the plug. In some variations, the plug may form a friction fit with the lumen of the locking member. The locking member may also comprise a wall portion with at least one aperture that is sized and shaped for passage of a tether therethrough. In some cases, the locking member may alternatively or additionally comprise a stop shoulder in the distal portion of the lumen. The cutting member may be located in the proximal or distal portion of the plug, and/or may surround at least a portion of the external surface of the plug body. In certain variations, the plug may comprise a collet comprising a cutting member. Some variations of devices may further comprise a pushing member that may be configured to push the plug into the lumen of the locking member. In certain variations, the pushing member may comprise a cutting member. In some such variations, the pushing member may be used both to push a plug and to cut a tether.

Certain device variations may comprise a plug comprising a body with a proximal portion and a distal portion, and a locking member comprising a proximal portion, a distal portion, and a lumen extending at least partially therethrough, where the locking member may be configured to receive the plug and form a friction-fit with the plug within the lumen. In some variations, the locking member may comprise a first cutting member. The locking member may further comprise a wall portion comprising at least one aperture sized and shaped for passage of a tether therethrough. In some variations, the first cutting member may be located in the distal portion of the locking member, and may have an aperture sized and shaped for passage of a tether therethrough. In certain variations, the first cutting member may surround at least a portion of an internal surface of the lumen of the locking member.

In certain device variations, the plug may further comprise a second cutting member that may be coupled to or integral with the plug body. The second cutting member may substantially contact the first cutting member when the plug is received within the lumen of the locking member. The device may also include a tether guide that may be configured to draw a tether passing through the lumen of the locking member transversely with respect to a longitudinal axis of the lumen.

Some variations of devices may comprise a plug comprising a body having proximal and distal portions, a locking member comprising proximal and distal portions and a lumen extending at least partially therethrough, and a pushing member comprising a plug-contacting portion and a cutting member. The locking member lumen may be configured to receive and form a friction-fit with the plug, and the pushing member may be configured to push the plug into the lumen of the locking member. The locking member may further comprise a wall portion comprising at least one aperture sized and shaped for passage of a tether therethrough. In some variations, the cutting member may be in the form of at least one shear edge on the body of the pushing member, and/or may be arranged symmetrically with respect to the plug-contacting portion of the pushing member. The shear edge or edges may also surround at least a portion of the external perimeter of the pushing member. The pushing member may have a first configuration in which the cutting member is covered and a second configuration in which the cutting member is uncovered or exposed.

Some variations of methods described here may comprise advancing a plug comprising a cutting member partially into a lumen of a locking member to secure a tether passing through the lumen, and advancing the plug further into the lumen to cut the tether. The tether may be secured between a wall of the plug and a wall of the lumen.

Certain variations of the methods described here may comprise advancing a plug partially into a lumen of a locking member to secure a tether passing through the lumen, and advancing the plug further into the lumen of the locking member to cut the tether. The tether may be cut, for example, by coming into contact with a cutting member disposed in the lumen of the locking member.

Some method variations may comprise advancing a plug comprising a first cutting member partially into a lumen of a locking member to secure a tether between a wall of the plug and a wall of the lumen, and advancing the plug further into the lumen of the locking member, such that the first cutting member contacts a second cutting member disposed within the lumen of the locking member, and thereby cuts the tether.

Some method variations may comprise using a pushing member to advance a plug partially into a lumen of a locking member to secure a tether passing through the lumen, where the pushing member comprises a cutting member. The tether may be secured, for example, between a wall of the plug and a wall of the lumen. The methods may also comprise advancing the pushing member until the cutting member contacts a portion of the locking member (e.g., the distal or proximal portion) and cuts the tether. In certain variations, the cutting member may contact and cut the tether as it exits at a shoulder of the proximal portion of the locking member.

Some method variations may comprise using a pushing member coupled to a plug to advance the plug partially into a lumen of a locking member to thereby secure a tether passing through the lumen. The tether may be secured, for example, between a wall of the plug and a wall of the lumen. In certain variations, the pushing member may comprise a cutting member. In such variations, the methods may, for example, further comprise advancing the pushing member until the cutting member contacts a portion of the locking member and cuts it. In some variations, the cutting member may cut the tether at a side aperture of the lumen of the locking member where the tether exits. In certain variations, the cutting member may contact and cut the tether as it exits at a shoulder in the lumen of the locking member.

Certain method variations described here may comprise using a pushing member to advance a plug partially into a lumen of a locking member and to thereby secure a tether passing through the lumen of the locking member. The tether may be secured, for example, between a wall of the plug and a wall of the lumen. In some variations, the locking member may comprise at least two apertures sized and shaped for passage of a tether therethrough. In certain variations, a cutting member may be coupled to the plug, and the methods may further comprise pushing the plug to advance the cutting member to contact a shoulder of the locking member and cut the tether.

Some method variations may comprise using a first pushing member to advance a plug partially into a lumen of a locking member to secure a tether passing through the lumen, where a proximal portion of the plug is coupled to an extendable cutting member. In some such variations, a second pushing member may be used to advance the extendable cutting member and thereby cut the tether.

BRIEF DESCRIPTION OF THE DRAWINGS

FIGS. 5I-5P show variations of components of devices for locking a tether.

FIG. 20G is a side view of a variation of a device that may be used to cut a tether, and FIG. 20H is a cross-sectional view of the device of FIG. 20G, taken along line 20H-20H.

FIGS. 21A, 21B, and 22-25 are side views in partial cross-section of variations of devices for locking a tether.

FIG. 26A is a side view of a variation of a device for locking a tether, and FIG. 26B is a perspective view of the device of FIG. 26A.

FIG. 27A is a side view of another variation of a device for locking a tether, and FIG. 27B is a perspective view of the device of FIG. 27A.

FIG. 28A is a side view of an additional variation of a device for locking a tether, and FIG. 28B is a perspective view of the device of FIG. 28A.

FIG. 29A is a side view of another variation of a device for locking a tether, and FIG. 29B is a perspective view of the device of FIG. 29A.

FIG. 47A is a perspective view of a variation of a device for locking a tether, and FIG. 47B is a side view of the device of FIG. 47A.

FIGS. 48 and 49 are perspective views of variations of devices for locking a tether.

FIGS. 51A and 51B illustrate variations of a device and a method for locking a tether.

FIG. 52 shows a variation of a tether comprising an integral locking feature.

FIGS. 61A-61F illustrate various examples of devices that may be used to cut a tether.

FIG. 68A is a side view in partial cross-section of one variation of a device and method that may be used to lock and cut a tether, FIGS. 68B and 68C are side perspective views of different variations of devices that may be used to lock and cut a tether.

DETAILED DESCRIPTION

Described here are methods and devices for locking and/or cutting a tether (e.g., after the tether has been tensioned to tighten or compress tissue). The devices and methods described here may be used in any appropriate procedure and location for which such tether locking and/or cutting is desired. While not so limited, the devices and methods described here may be used, for example, in Natural Orifice Transluminal Endoscopic Surgery ("NOTES") procedures, heart valve repair procedures (e.g., mitral valve annulus repair procedures), and/or endoscopic procedures (e.g., laparoscopy and/or arthroscopy). The devices and methods described here may be used in non-invasive or minimally invasive procedures (e.g., minimally invasive percutaneous procedures), or in invasive procedures, such as invasive surgeries (e.g., open-heart surgeries), as appropriate. Some of the devices described here may be used to lock or cut a tether, while other devices described here may be used to both lock and cut a tether. Specific examples of methods and devices will now be described in further detail below.

Figure 1A:
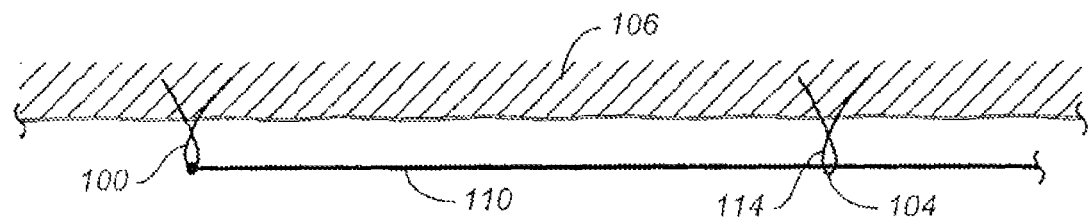
FIGS. 1A and 1B illustrate the tightening or compression of tissue of a subject using a tether.
Figure 1B:
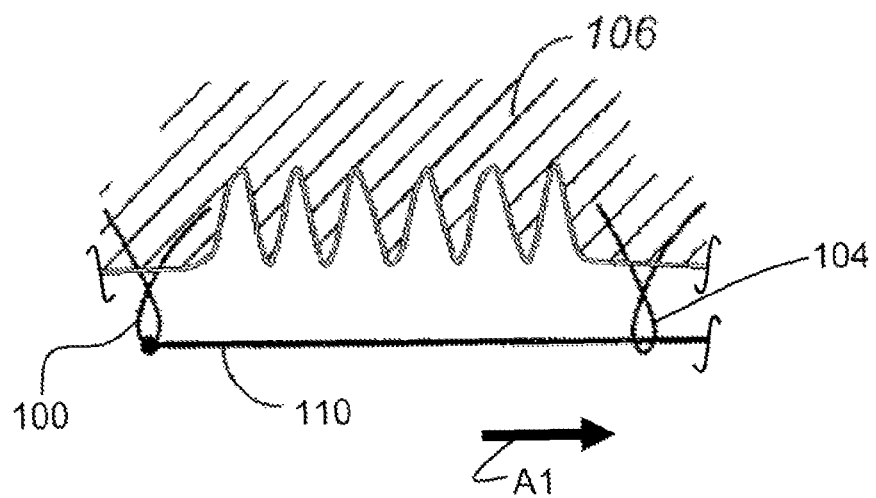

Turning now to the figures, FIG. 1A shows two anchors (100) and (104) anchored into tissue (106) of a subject. A tether (110) is fixedly attached to anchor (100), and is threaded through a loop region (114) of anchor (104). As shown in FIG. 1B, when tether (110) is pulled upon in the direction of arrow (A1), a cinching effect results, such that anchors (100) and (104) are brought closer together, and the tissue length between anchors (100) and (104) is reduced. In this way, tissue (106) may be gathered and/or compressed. While two anchors are shown in FIGS. 1A and 1B, in some cases multiple anchors may be used. Additionally, the anchors may all have the same size and shape, or may have different sizes and/or shapes. After tether (110) has been tensioned by a desired amount, tether (110) may be locked to maintain the tension, and in some cases, excess portions of tether (110) may be cut and removed.

The above-described process may be used in a wide variety of tissues. For example, in some variations, anchors that are connected to each other by a tether may be deployed into tissue in the region of a mitral valve annulus. The tether may then be pulled upon to provide a cinching effect, which restructures the mitral valve annulus (e.g., to reduce mitral valve regurgitation). Thereafter, a locking device may be used to lock the tether in place, thereby maintaining the cinching effect. Finally, a cutting device may be used to remove excess portions of the tether. Mitral valve repair is described, for example, in U.S. Patent Application Publication Nos. US 2006/0122633 A1, US 2006/0190030 A1, US 2008/0172035 A1, and US 2008/0177380 A1, all of which are hereby incorporated by reference in their entirety.

In certain variations, the above-described process may be used in a heart reshaping procedure, such as a ventricular remodeling procedure that is used to repair a heart experiencing valve dysfunction. Heart repair procedures, including heart reshaping procedures, are described, for example, in U.S. patent application Ser. No. 12/253,792, filed on Oct. 17, 2008, which is hereby incorporated by reference in its entirety.

As discussed above, the devices and methods described herein may be used, as appropriate, in any of a number of different sites within the body and/or to assist with any of a number of different types of procedures. As an example, the devices and methods described herein may be used in NOTES procedures. As another example, the devices and methods described herein may be used in heart procedures other than those involving mitral valve repair. For example, they may be used to repair an aortic valve or a tricuspid valve, or to secure a prosthetic heart valve, or they may be used in heart ports. As another example, the devices and methods may be employed in a procedure in which one or more tethers are used to reinforce an annuloplasty ring. Additionally, the devices and methods described herein may be used, for example, in a variety of open surgical procedures.

Anchors for use with the methods and devices described here may be any suitable anchor. The anchors may be made of any suitable material, may be any suitable size, and may be of any suitable shape. The anchors may be made of one material or more than one material. Examples of anchor materials include super-elastic or shape memory materials, such as nickel-titanium alloys and spring stainless steel. Examples of anchor shapes include T-tags, rivets, staples, hooks (e.g., C-shaped or semicircular hooks, curved hooks of other shapes, straight hooks, barbed hooks), multiple looped anchors, clips, and the like. The anchors may be configured to self-expand and self-secure into tissue, but need not be configured in such a fashion. Multiple anchors of the same shape may be used, or multiple anchors having different shapes may be used. Similarly, multiple anchors of the same size may be used, or multiple anchors having different sizes may be used. Illustrative examples of suitable anchors are described in more detail, for example, in U.S. Patent Application Publication Nos. US 2005/0273138 A1, US 2008/0045982 A1, US 2008/0045983 A1, US 2008/0051810 A1, and US 2008/0051832 A1, and US 2008/0058868 A1, all of which are hereby incorporated by reference in their entirety. Moreover, while anchors have been described, any other type of suitable fasteners or implants (e.g., leads, electrodes, etc.) may be used with one or more of the devices and/or methods described here. Additionally, some procedures employing the devices and methods described herein may not involve any anchors or other types of fasteners. As an example, certain variations of the devices and methods described here may be used to lock and/or cut a suture that has been sewn through tissue.

Tethers may be one long piece of material or two or more pieces, and may comprise any suitable material, such as suture, suture-like material, a DACRON® polyester strip, high-density polyethylene (HDPE), or the like. In some variations, tethers may be in the form of monofilament or multifilament textile yarns or fibers. Tethers may also have various braided textile configurations. While a procedure for tightening or compressing tissue using one tether has been described, other procedures for modifying tissue may involve the use of multiple tethers, such as two, three, four, five, or ten tethers. When multiple tethers are used, at least some of the tethers may be associated with (e.g., fixedly attached to) different anchors, and/or at least some of the tethers may be associated with (e.g., fixedly attached to) the same anchor. The devices and methods described herein may apply to single tether procedures, or to multiple tether procedures. As an example, a locking and/or cutting device may be used to lock and/or cut more than one tether, either simultaneously, or at different times.

As described above, after one or more anchors have been secured and the tether has been tensioned, the tether may then be locked or secured into place to maintain the tension (and, therefore, the cinching effect). Different variations of locking devices are described in further detail below.

Figure 2:
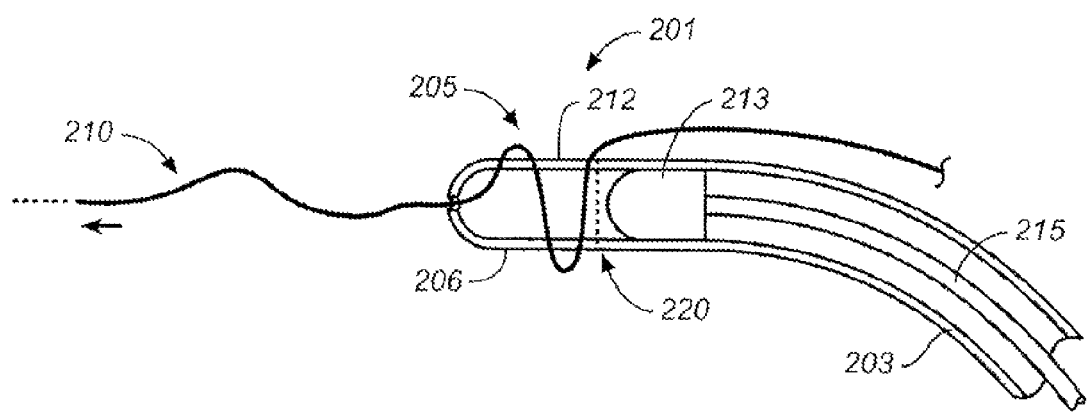
FIG. 2 shows a variation of a device for locking a tether.

For example, FIG. 2 shows a locking device (201) including a locking element (205) comprising a plug (213) and a hollow locking member (206). Hollow locking member (206) is releasably coupled to a tubular elongated member (203) in a distal region of the device. Elongated member (203) may be flexible over all or a portion of its length. As shown in FIG. 2, hollow locking member (206) is in the form of a distal extension of elongated member (203) (i.e., hollow locking member (206) extends beyond the distal end of elongated member (203)). However, in some variations, a locking device may comprise an elongated member and a locking member that is coupled to the elongated member, but that does not form a distal extension of the elongated member. Referring again to FIG. 2, hollow locking member (206) maintains the profile of elongated member (203), and may share a common wall with the elongated member. In some cases, though, a locking device may comprise an elongated member and a locking member that is smaller or larger than the elongated member in profile. Alternatively or additionally, the elongated member and the locking member may not share a common wall.

While the device shown in FIG. 2 is configured as a catheter, other configurations may be used. Moreover, the device may be scaled up (e.g., for use in a surgical procedure) or down (e.g., for use in a minimally invasive procedure), depending, for example, on the requirements of the particular procedure in which the device is to be used.

As shown in FIG. 2, a tether (210) is threaded through the distal region of locking device (201), particularly through hollow locking member (206). Although any suitable locking element may be included as part of a locking device, locking element (205) locks a tether when plug (213) is advanced into hollow locking member (206) such that the tether is secured between the plug and a wall of the locking member. As shown, tether (210) is threaded through multiple apertures in the wall (212) of hollow locking member (206). However, in some variations, a tether may be threaded through only one aperture in a wall of a locking member. Alternatively or additionally, a tether may pass through one or more apertures (e.g., passages or holes) in one or more other locations of a locking device (e.g., distally of the locking element). In certain variations, one or more apertures through which a tether is routed may be radiused (e.g., to enhance passage of the tether through the aperture or apertures).

Until the locking element is secured, the device may be moved along the tether (e.g., by sliding), or the tether may be pulled through the device. Thus, the tether may be used to provide a cinching effect by sliding the device distally down the tether. The apertures through the device shown in FIG. 2 may be positioned such that the device can still easily slide along the tether. In some variations, the tether may be threaded into the locking element in such a way that it winds in and out of the locking element, as suggested by FIG. 2.

The tether may be threaded or coupled to the device during manufacturing or by the user. For example, and as described further below, a lasso may be threaded through the apertures in the device. The lasso may then be used to engage the tether and to thread the tether through the apertures (e.g., by pulling on the opposite end of the lasso).

In some variations, the device may be slid along the tether until the tether has been pulled by the desired amount through the anchors, at which point the tether may be secured into position using the locking element. For example, and as described above, tether (210) of FIG. 2 may be secured into position by pushing plug (213) into hollow locking member (206) of locking element (205) (e.g., as a result of an interference fit between the plug and the locking member). In the variation shown in FIG. 2, plug (213) secures tether (210) by compressing at least a portion of the tether between the plug and the inner walls of hollow locking member (206).

In some variations, a device may comprise a plug and a hollow locking member, at least one of which comprises one or more features that limit the likelihood of the plug being released from the hollow locking member. For example, the plug and/or hollow locking member may include adhesive, glue, or cement, and/or may be at least partially deformable so that once the plug has been inserted into the hollow locking member, the plug is retained within the locking member. As an example, the plug may comprise a material which is compressible or elastic to aid in locking the plug into the locking member. In certain variations, the plug may have polygonal (e.g., hexagonal) sides that interact with the inner surface of the locking member. The plug may be solid or hollow. The plug may have bumps, dimples, ribs, grooves, or holes on its surface to increase friction with the tether. The locking member may also include or comprise one or more structures (e.g., rims, brackets, etc.) to help hold the plug in the locked configuration. In some variations, the locking member itself may alternatively or additionally be polygonal in cross-section. In certain variations, the plug and the locking member may have corresponding geometries, as described below. In some variations of devices, the plug and the locking member may each include different features that enhance the retention of the plug in the locking member.

The device shown in FIG. 2 further includes a pushing member (215) for pushing plug (213) into position to secure tether (210) within hollow locking member (206). The pushing member (shown in FIG. 2 as a rod, although other suitable forms of pushing members may be used) may be slidable within the lumen of the device. In some variations, the pushing member may include one or more guides (e.g., that guide the pushing member's direction) and/or one or more stops (e.g., that limit the distance traveled by the pushing member and/or the force applied by the pushing member). Thus, there may be motion-limiting features on the device and/or pushing member to prevent the pushing member from being pushed too far forward, or from applying too much force, which could disturb either the locking element or the tissue (e.g., after separation of the locking element from the rest of the device).

As described above, a locking element may be releasably coupled to the rest of a device. Any appropriate method may be used to provide such a releasable coupling. In some variations, the locking element (or a portion thereof) may include a releasable coupling region, such as a region that can be separated or broken to release the locking element from the rest of the device. As an example, a locking element may be frangibly connected to the rest of a device, and may be decoupled from the device by breaking the frangible connection. For example, a locking element may be fused to another portion of the device (e.g., a distal portion of an elongated member). The fused region may later be broken to decouple the locking element from the other portion of the device. The amount of heat and/or pressure that is applied during the fusion process, as well as the number of fused regions and their locations, may be selected so that a specific amount of force can be applied to the fused regions to break them.

Different regions of a locking device may comprise different materials, or may comprise the same material. In some variations, a locking device may comprise a locking element formed of a first material, another portion formed of a second material, and a fused region between the locking element and the other portion that is formed of a third material (or combination of materials). Using different materials for different regions of a locking device may be advantageous if the different regions have different material requirements. For example, a more distal region of the device may be formed of one or more materials that provide relative flexibility, while a more proximal region may be formed of one or more materials that provide relative stiffness, or vice-versa. Moreover, while locking devices comprising one or more fused regions and multiple different materials have been described, some variations of locking devices may comprise fused regions and may be formed entirely of one material or combination of materials, and other variations of locking devices may comprise multiple different materials (e.g., two, three, four, or five different materials) without comprising any fused regions.

In certain variations, a locking device may comprise a detachable locking element that is coupled to the rest of the device by a structurally weakened region. The structurally weakened region may, for example, be scored, etched, perforated, fractured, creased, slotted, and/or dimpled. An example of a perforated region (220) is shown in FIG. 2. The locking element may be made of the same material as the rest of the device, or the locking element and the rest of the device may be made of different materials. When a sufficient amount of force is applied to the structurally weakened region, the locking element may become separated from the rest of the device. Force may be applied to the structurally weakened region using, for example, a pushing member or any other suitable mechanism.

In some variations, a locking element may be releasably coupled to another portion of a locking device via at least one adhesive and/or a friction fit, so that the application of a certain amount of force causes the locking element to decouple from the other portion of the locking device. Additional non-limiting methods of releasably coupling a locking element to another portion of a locking device include fusing, brazing, soldering, and snap-locking. In some variations of locking devices, two or more different releasable coupling methods may be used in conjunction with each other.

As described above, in certain variations, a locking element may be controllably decoupled from the rest of a device by applying a force. Force may be applied in any appropriate manner (e.g., pushing on a pushing member, hydraulic force (using saline, water, or the like), magnetic force, pressurized gas, etc.). For example, the same pushing member (215) of FIG. 2, used to push plug (213) and secure the locking element, may also be used to decouple the locking element from the rest of the device (e.g., by pushing the pushing member with additional force). In some variations, one force applicator (e.g., a pushing member) may be used to secure the locking element and another force applicator (e.g., a second pushing member) may be used to decouple the locking element from the rest of the device.

The amount of force required to decouple a locking element from the rest of a device may be predetermined. In variations where the same force applicator (e.g., a pushing member, fluid line, magnet, etc.) is used both to lock the tether and to decouple the locking element, the force required to decouple the locking element may be greater than the force required to secure the locking element and thereby lock the tether. For example, a device may be configured for its locking element to decouple after the application of greater than about 2 lbs of force, greater than about 3 lbs of force, greater than about 4 lbs of force, greater than about 5 lbs of force, greater than about 10 lbs of force, greater than about 20 lbs of force, or between about 2 lbs and about 5 lbs of force. The amount of force that is needed to decouple a locking element from the rest of a locking device can depend on any of a number of different factors. Such factors may include, for example, the thickness of the coupling region, the material or materials that form the coupling region, and/or the location of scoring, perforations, or other weakened points in the coupling region. In some cases, the amount of force that is required to decouple a locking element from the rest of a locking device, as well as the way in which the force is applied to decouple the locking element, may be controlled to prevent damage to the locking element, the tether, the anchors, and/or the surrounding tissue.

While the application of force to decouple a locking element from the rest of a locking device has been described, other decoupling methods may alternatively or additionally be employed. As an example, a locking element may be decoupled by cutting a joint between the locking element and the rest of the device using, for example, a cutter. In some variations, the cutter may be in the form of a shearing blade that slides to shear the joint between the locking element and the rest of the device. In certain variations, a cutter that cuts the connection between a locking element and the rest of a locking device may also be used to cut a tether being secured by the locking device. For example, the cutter may cut both the tether and the joint in a combined manner, thus completely releasing the locking element with the tether severed.

It should be understood that any of the methods and device components described here for actuating a locking device (e.g., threading a tether through the locking device, advancing a plug into a locking member of the locking device, etc.) and/or decoupling one or more components of the locking device from the rest of the locking device may be employed with any of the other locking devices described here, if suitable to do so.

Figure 3A:
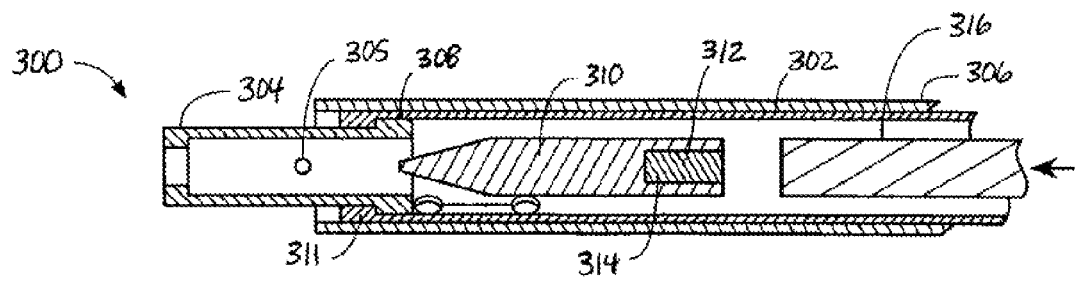
FIGS. 3A-3D show variations of a device and a method for locking a tether.

While certain methods and devices have been described above, other methods and/or devices may be used to couple and/or decouple a locking element or locking member and another portion of a locking device. For example, FIGS. 3A-3D illustrate a method of locking a tether using another variation of a locking device comprising a plug. Referring first to FIG. 3A, a locking device (300) includes a coupling tube (302) having a distal portion that is coupled to a locking member (304). As shown, locking member (304) is in the form of a locking tube having an aperture (305) configured for passage of a tether therethrough. While a locking tube is shown, other suitable configurations may be used for a locking member. Locking member (304) may be formed of, for example, one or more metals, metal alloys, polymers, and/or polymer composites. As an example, in some variations, locking member (304) may be formed of a nylon and bismuth trioxide composite, and may include a layer comprising one or more PEBAX® polymers.

A sheath (306) surrounds coupling tube (302), as well as a portion of locking member (304). However, in some variations, a sheath may cover the entirety of a locking member, and may even extend distally beyond the locking member. Moreover, in certain variations, a sheath may surround only a portion of a coupling tube. Sheath (306) helps to couple coupling tube (302) to locking member (304) by compressing the coupling tube to the locking member. Additionally, locking member (304) includes a shoulder (308), and coupling tube (302) is configured to latch onto shoulder (308) when sheath (306) compresses coupling tube (302) to locking member (304). As shown, coupling tube (302) comprises a shoulder (311) that latches to shoulder (308). While shoulders (308) and (311) are shown as generally angular, in some variations, a locking member shoulder and/or a coupling tube shoulder may be ramp-shaped, or may have any other suitable shape. A ramp-shaped coupling tube shoulder may, for example, provide for relatively easy decoupling of the coupling tube from the locking member when such decoupling is desired.

Locking device (300) is configured such that if sheath (306) is proximally retracted, locking member (304) is decoupled from coupling tube (302). However, in certain variations, a sheath may be proximally retracted, while a coupling tube and locking member are distally pushed upon, in order to decouple the locking member from the coupling tube. Alternatively or additionally, the coupling element and locking tube may be distally pushed upon before and/or after the sheath is proximally retracted. Any other suitable methods for decoupling the locking member from the coupling tube may also be employed.

As shown in FIG. 3A, a plug (310) is disposed within coupling tube (302), and has a generally missile-shaped configuration, although other appropriate configurations (e.g., a plug having any appropriate geometry, such as a plug in the shape of a cylinder or a plug having a hexagonal cross-section) may also be used. The plug may be formed of any appropriate materials, such as one or more polymers, and may in some variations be relatively rigid. In other variations, a plug may be relatively flexible. In certain variations, plug (310) may be formed of a nylon and bismuth trioxide composite. As shown in FIG. 3A, plug (310) includes a bore (312) containing a radiopaque marker (314). This may allow for ready viewing of the plug via X-ray fluoroscopy. A pushing member (316) is also disposed within coupling tube (302), and may be used to push plug (310) into locking member (304).

Figure 3B:
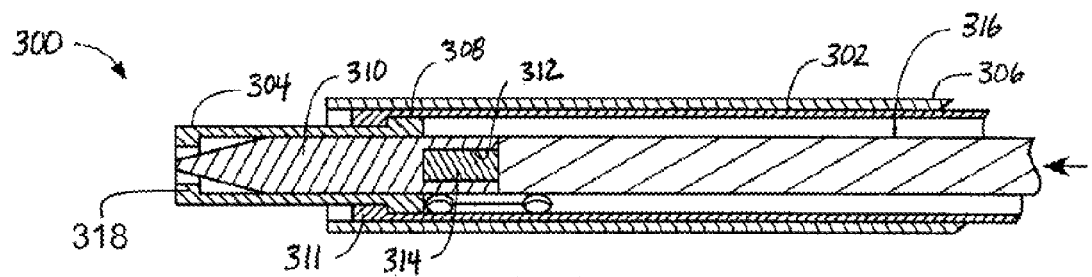

During use of locking device (300), a tether (not shown) may be threaded through locking member (304) and coupling tube (302). Any appropriate method may be used to thread the tether including, for example, one or more of the methods described below. As an example, a lasso may be used to capture the distal end of the tether, and to thread the tether first through aperture (305), and then through coupling tube (302). In some methods, the locking device may be advanced along the tether to a desired position. As shown in FIG. 3B, once the tether has been threaded through locking member (304) and coupling tube (302), pushing member (316) may be advanced toward the distal end of the locking device. This advancement of pushing member (316) pushes plug (310) into locking member (304), compressing the tether between plug (310) and the inner walls of locking member (304) (e.g., as a result of an interference fit between the plug and the locking member). Because coupling tube (302) engages shoulder (308) of locking member (304), a resistive force is provided during plug advancement. This resistive force may help to limit the likelihood of locking member (304) becoming prematurely decoupled from coupling tube (302), as a result of the advancement of pushing member (316). A step (318) (FIG. 3B) at the distal end of the locking member prevents the plug from exiting the locking member.

Figure 3C:
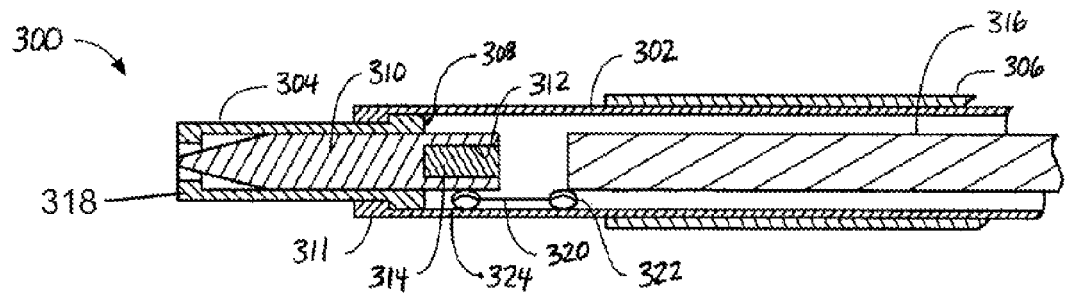

Referring now to FIG. 3C, after plug (310) has been pushed into locking member (304), sheath (306) is proximally retracted. Prior to being proximally retracted, sheath (306) compresses coupling tube (302) to locking member (304), thereby engaging coupling tube (302) with the shoulder (308) of locking member (304) and coupling the coupling tube to the locking member. However, once sheath (306) has been proximally retracted, this compressing force is no longer present. Coupling tube (302) is configured such that in the absence of this compressing force, coupling tube (302) no longer forms a tight fit around locking member (304). Rather, the removal of the compressing force allows coupling tube (302) to assume a more relaxed configuration, essentially opening up and thereby disengaging coupling tube (302) from shoulder (308) of locking member (304). As a result, coupling tube (302) and locking member (304) are decoupled from each other. This assumption of a more relaxed configuration by coupling tube (302) may be enhanced by the presence of a slit (320) in the distal portion of the coupling tube, as well as two apertures (322) and (324) along the slit that provide stress relief. While not shown, in some variations, a coupling tube may include more than one slit in its distal portion and/or may include a different number of apertures (e.g., two, three, four, five, etc.). Moreover, while apertures (322) and (324) are circular, in certain variations, a coupling tube may alternatively or additionally include one or more non-circular (e.g., rectangular, triangular, etc.) apertures.

Figure 3D:
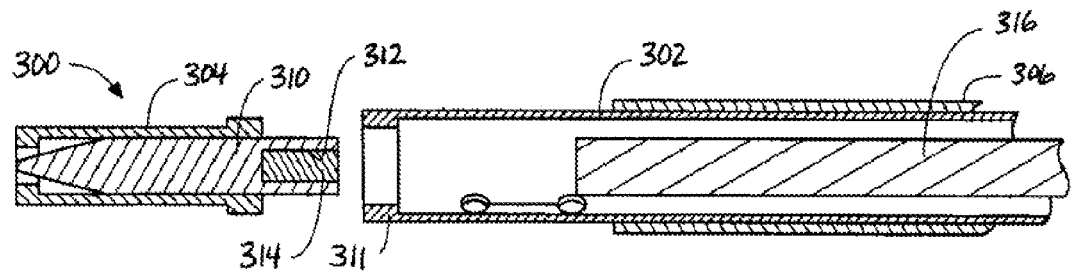

Referring finally to FIG. 3D, and as discussed above, the proximal retraction of sheath (306) causes locking member (304) to be released from coupling tube (302). Plug (310), which was previously pushed into locking member (304), is released along with locking member (304). The locking member and plug, now separated from the other components of the locking device, remain within the body, securing the tether, while the other components of the locking device are removed from the body. In this way, sheath (306) can function as a safety mechanism, preventing locking member (304) from being released prematurely, and providing the user with enhanced control over the release of locking member (304).

Although only a few of the ways in which a locking member or locking element may be releasably coupled to a device have been described, it should be understood that any appropriate coupling may be used, including snap-fits and other coupling mechanisms (e.g., threads, etc.). Additionally, the couplings described herein may be readily scaled in size for use even with applications that may require very small locking members or locking elements (e.g., for use in percutaneous applications and/or surgical applications, such as microsurgical applications). Locking members or locking elements that are releasably coupled to devices are described, for example, in U.S. Patent Application Publication No. US 2008/0172035 A1, and in U.S. patent application Ser. No. 12/253,885, filed on Oct. 17, 2008, and U.S. patent application Ser. No. 12/480,568, filed on Jun. 8, 2009, each of which is hereby incorporated by reference in its entirety.

Figure 4A:
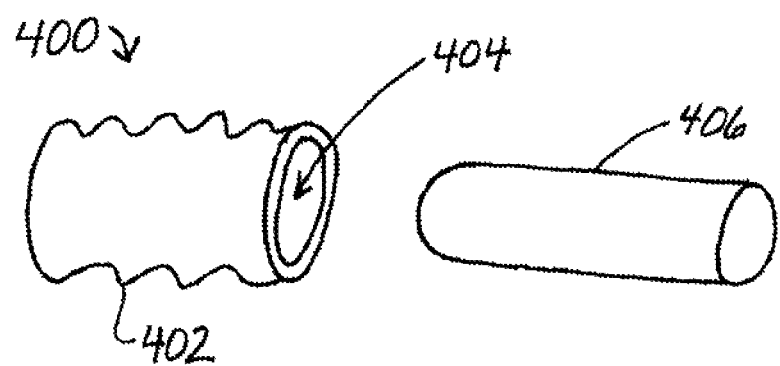
FIGS. 4A and 4B show another variation of a device for locking a tether.
Figure 4B:
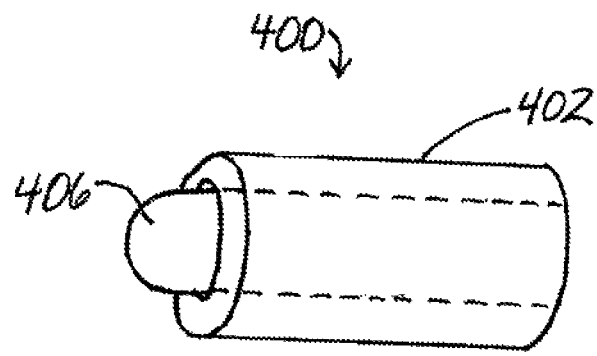

Locking devices including plugs and tubular components having a relatively fixed shape or configuration have been shown. However, in some variations, a locking device may include a plug and another component that does not have a relatively fixed shape or configuration. For example, a locking device may include a plug and an adjustable sleeve configured to be fitted over the plug to secure a tether therebetween. As an example, FIG. 4A shows a locking device (400) comprising a plug (406) and a sleeve (402) having a lumen (404). Referring to FIG. 4B, sleeve (402) may be fitted over plug (406) to secure one or more tethers (not shown) therebetween. For example, sleeve (402) may be stretched over plug (406). In some variations, sleeve (402) may have a larger inner diameter when in a compressed state and may be retained in a compressed state (e.g., in a catheter) to allow the sleeve to receive the plug and the tether. Once released from its compressed state (e.g., by an element or feature in the catheter), the inner diameter would collapse, thereby capturing the tether between the plug and the sleeve in a tight friction fit.

Sleeve (402) may be formed of, for example, one or more elastomeric materials and/or metal alloys (e.g., Nitinol foil). Alternatively or additionally, plug (406) may be formed of, for example, one or more polymers, such as nylon, polycarbonate, polyetheretherketone (PEEK), and/or one or more other polymers suitable for implantation in a body of a subject. The sleeve may be configured to fit over a portion of the plug, or to fit over the entire plug. Additionally, in some variations, multiple sleeves may be used with a single plug. For example, a first sleeve may be fitted over a plug to secure a tether therebetween, and then a second sleeve may be fitted over a second sleeve to secure the same tether (or a different tether) therebetween.

In some variations, a sleeve may comprise a wall portion having one or more apertures sized and shaped for passage of a tether therethrough. The sleeve may be maintained in a straight or taut configuration as a tether is routed through the apertures and a plug is pushed into the sleeve to secure the tether therebetween. In certain variations, the sleeve may be maintained in a straight or taut configuration using a sheath (e.g., as described above with reference to FIGS. 3A-3D).

Figure 5A:
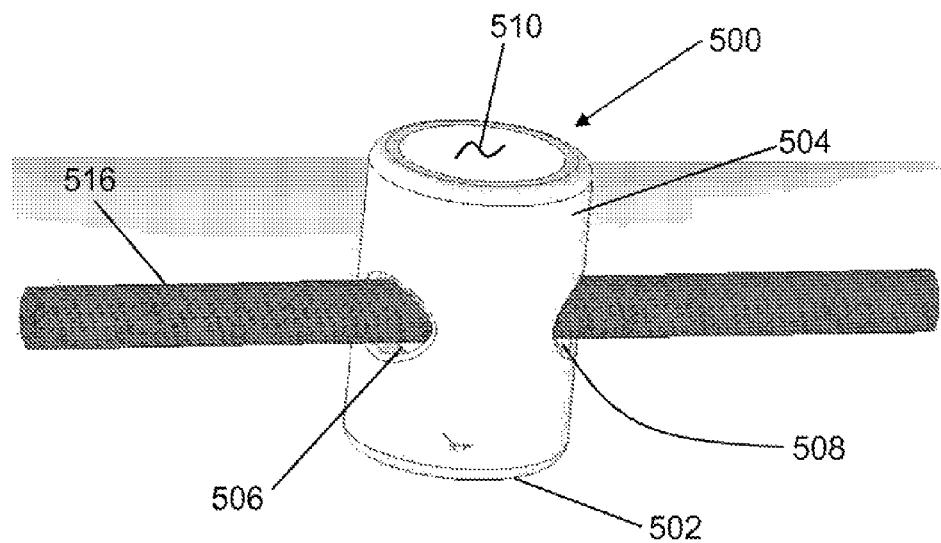
FIGS. 5A-5H depict variations of a device and method for locking a tether.
Figure 5B:
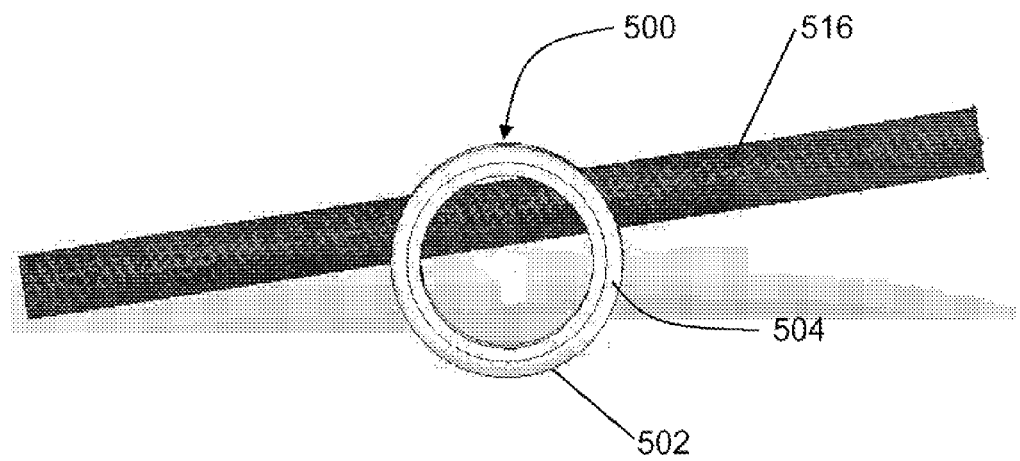
Figure 5C:
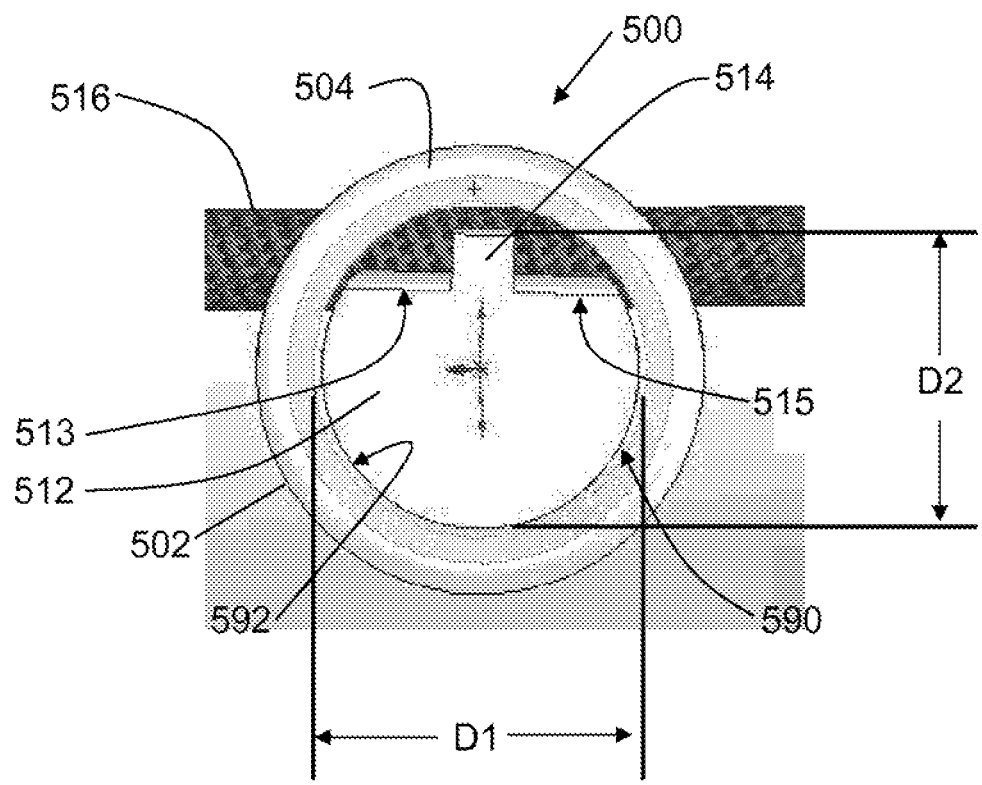

Locking device plugs may be configured to be fixedly positioned within a hollow portion of a locking member, or to be movably positioned within a hollow portion of a locking member. For example, in some variations, a locking device may comprise a hollow locking member and a rotatable plug configured to rotate within the hollow locking member. As shown in FIGS. 5A-5C, a locking device (500) comprises a locking tube (502) comprising a wall portion (504) with two apertures (506) and (508) therethrough. Locking tube (502) has a lumen (510), within which is disposed a rotatable plug (512) (shown in FIG. 5C, while FIGS. 5A and 5B depict the locking device without the rotatable plug). Plug (512) has a protrusion (514) located between two flat surfaces (513) and (515). In some variations, protrusion (514) may protrude from flat surfaces (513) and (515) by a distance of 0.003 inch to 0.005 inch. As shown in FIG. 5C, plug (512) has a dimension (D1) and a dimension (D2) that is smaller than dimension (D1). With the exception of the portion of plug (512) comprising protrusion (514) and flat surfaces (513) and (515), the remainder of plug (512) is generally cylindrical in shape. However, any other suitable rotatable plug configurations may be used. When plug (512) is disposed within lumen (510) and a tether (516) is threaded through apertures (506) and (508), thereby crossing the lumen, protrusion (514) contacts the tether.

Figure 5D:
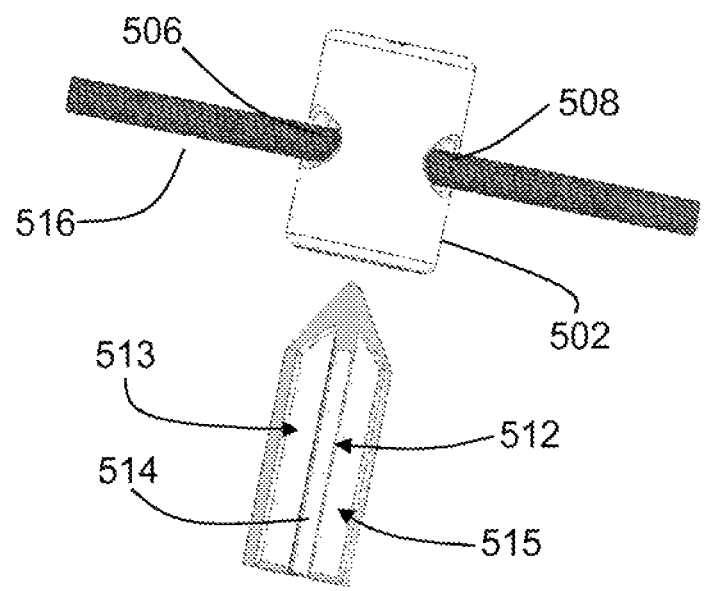
Figure 5E:
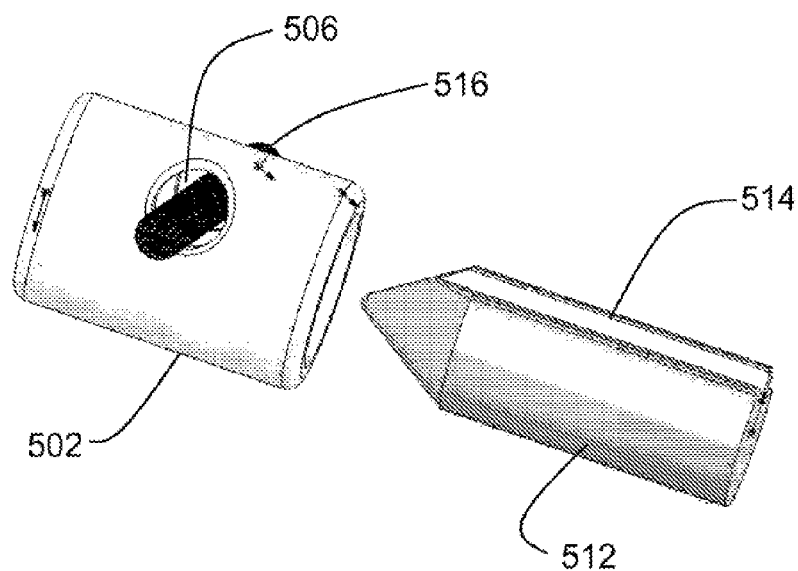

Referring now to FIGS. 5D and 5E, plug (512) may, in some variations, be a separate component from locking tube (502). Alternatively, a plug may be coupled to a locking member during manufacturing, or may be integrally formed with the locking member. As shown in FIGS. 5D and 5E, tether (516) may be threaded through apertures (506) and (508) in wall portion (504) when the plug is not yet disposed within the lumen of the locking tube. Of course, in certain variations, a tether may be threaded through the apertures during and/or after advancement of the plug into the locking tube. As shown, the tether crosses the lumen of the locking tube such that the tether is off-center with respect to the lumen. However, in some variations, the apertures may be positioned so that a tether passing through them crosses the center of the lumen.

Figure 5F:
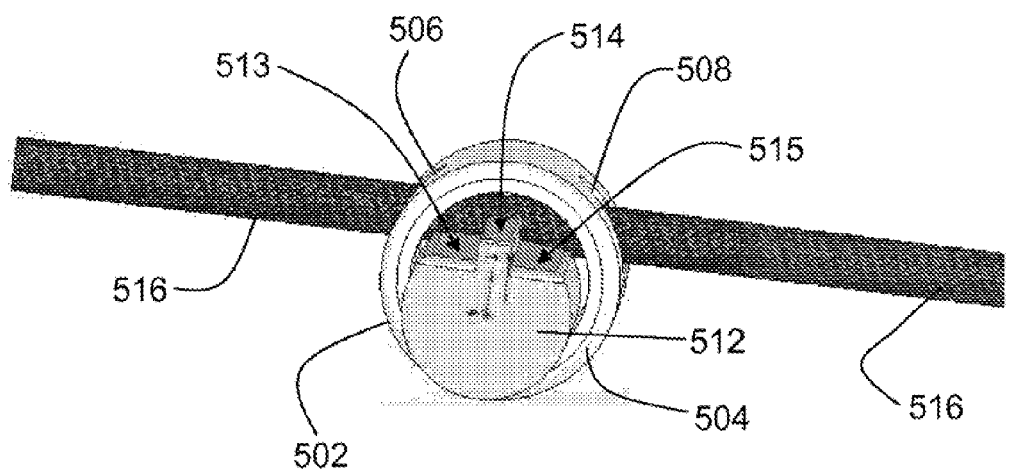
Figure 5G:
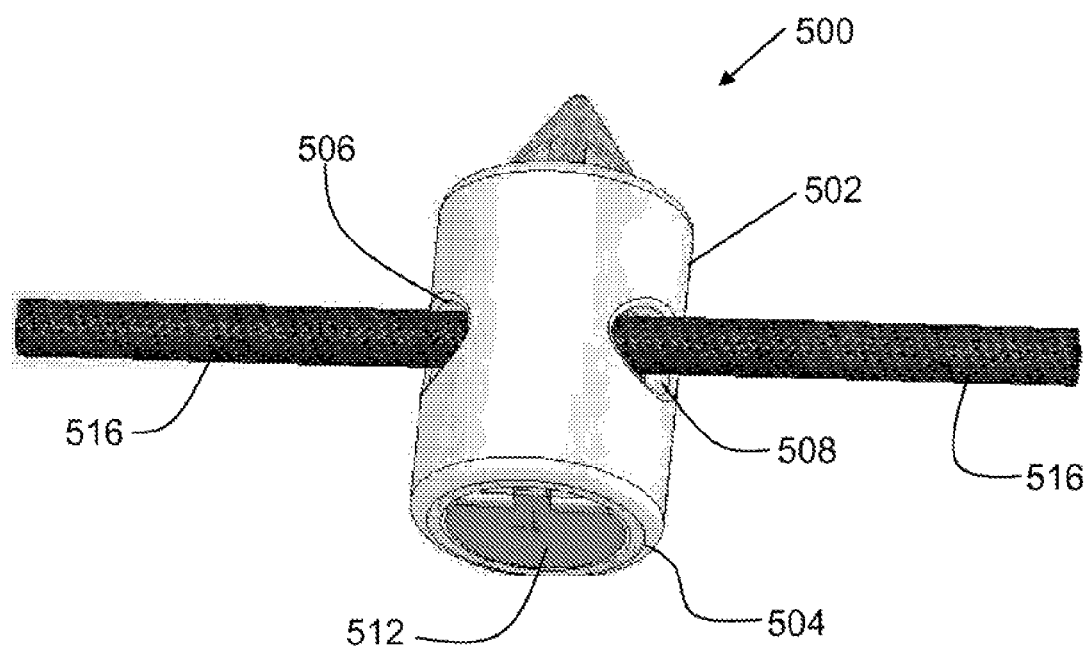
Figure 5H:
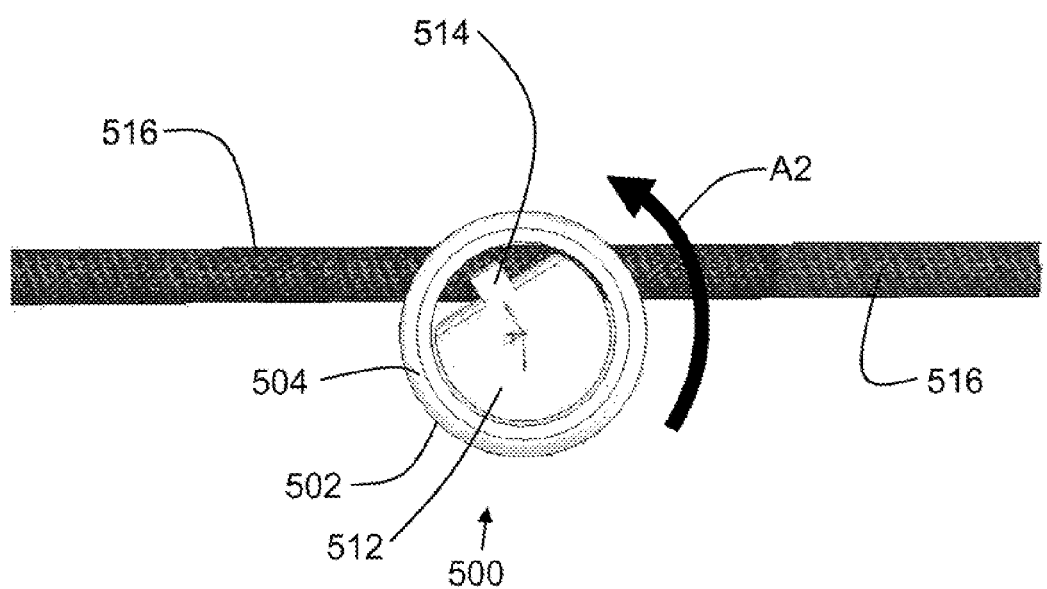

As shown in FIG. 5F, after tether (516) has been threaded through apertures (506) and (508) in locking tube (502), plug (512) may be advanced into the lumen of the locking tube (e.g., using a pushing member), such that protrusion (514) on plug (512) contacts the tether. Typically, this advancement of the plug into the locking tube may take place at least partially within a sheath or other elongated member that may later be withdrawn or otherwise removed from the plug and the locking tube. When the plug is fitted into the locking tube such that the protrusion contacts the tether, the contact between the protrusion and the tether provides friction that helps to hold the plug and the tether in place with respect to each other (i.e., minimizing relative motion between the plug and the tether). FIG. 5G shows plug (512) when it is disposed within locking tube (502). Referring back to FIG. 5C, which also shows the plug disposed within the locking tube, plug (512) has an exterior surface (590) with a contour (as shown, a curvature) alignable with an interior surface (592) of the locking tube. Referring now to FIG. 5H, tether (516) may be tensioned, thereby causing the plug to rotate within the lumen of the locking tube (e.g., in the direction of arrow A2) because of the contact between the tether and the protrusion on the plug. The tensioning of the tether will generally cause the plug to rotate toward the direction in which the tether is being tensioned. This rotation may, in turn, result in more contact between the plug and the tether, such that the tether may become further secured. In some variations, plug (512) may be rotated by at least about 1° (e.g., at least about 10°, at least about 20°, at least about 45°, at least about 90°, at least about 135°) and/or at most about 180° (e.g., at most about 135°, at most about 90°, at most about 45°, at most about 20°, at most about 10°).

In some variations, a relatively low plug force may be used to plug locking tube (502) with plug (512). Even though a relatively low plug force may be used, the resulting lock force may be relatively high. Thus, in certain variations, a tether may be locked very securely by applying minimal force to a locking device that locks the tether.

Figure 5I:
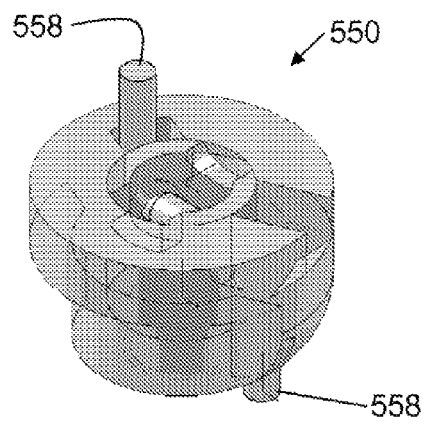
Figure 5J:
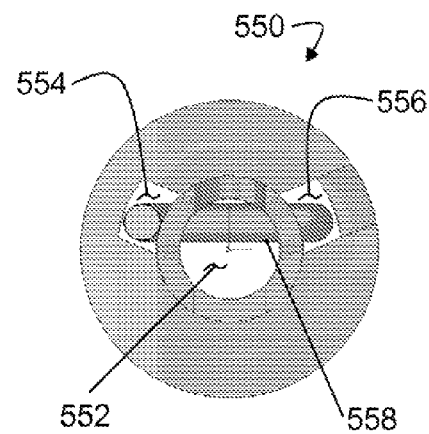
Figure 5K:
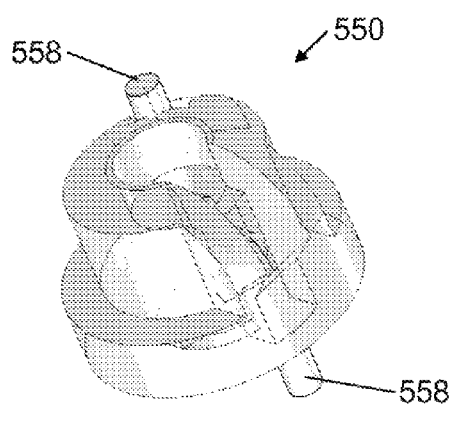
Figure 5L:
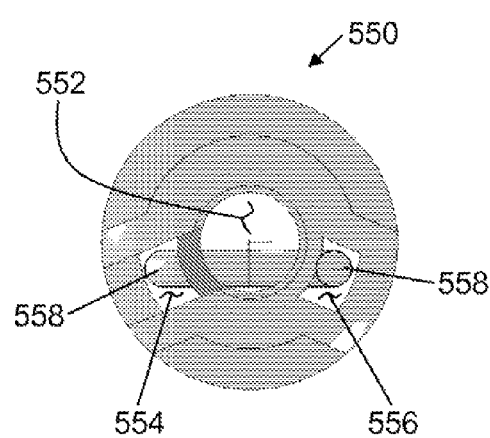

Other variations of plugs and/or locking members may also be used. As an example, FIGS. 5I-5N show different views of another variation of a locking member configured to receive a plug (e.g., a rotatable plug) to secure a tether therebetween. FIG. 5I shows a bottom angled perspective view of the locking member (550), while FIG. 5J shows a bottom view of locking member (550), FIG. 5K shows a top angled perspective view of locking member (550), FIG. 5L shows a top view of locking member (550), FIG. 5M shows a front view of locking member (550), and FIG. 5N shows a back view of locking member (550). As most clearly shown in FIGS. 5J and 5L, locking member (550) has a lumen (552) configured to receive a plug, as well as two apertures (554) and (556) configured for passage of a tether (558) therethrough. The configuration of locking member (550) may, for example, provide for relatively controlled tether routing through the locking member. This, in turn, may help to control the way in which locking member (550) lies against body tissue and/or one or more anchors during use.

FIGS. 5O and 5P show another variation of a plug that may be used to secure a tether. In some variations, the plug may be rotatable (e.g., within a lumen of a locking tube). As shown in FIGS. 5O and 5P, a plug (570) comprises a body (572) and a plurality of protrusions (as shown, three protrusions, although a greater or lesser number of protrusions may also be used) in the form of a stepped configuration (574) extending from the body. The radial length for each protrusion (576), (578), and (580) is longer than the previous protrusion. During use, plug (570) may be fitted into a lumen (582) of a locking tube (584) (FIG. 5P) or other locking member (e.g., by advancing the plug into the lumen with a pushing member). As the plug is rotated, the progressively longer protrusions may contact a tether crossing the lumen, and may secure the tether within the lumen. Other configurations may also be used. For example, in some variations, a rotatable plug may comprise a gear-shaped portion comprising a plurality of teeth of different lengths (e.g., with each tooth progressively longer than the previous tooth).

In certain variations, a locking device may lock a tether using one or more methods that are different from those described above. The method or methods may be used in addition to, or as an alternative to, tensioning a tether to rotate a rotatable plug and thereby lock the tether.

Figure 5Q:
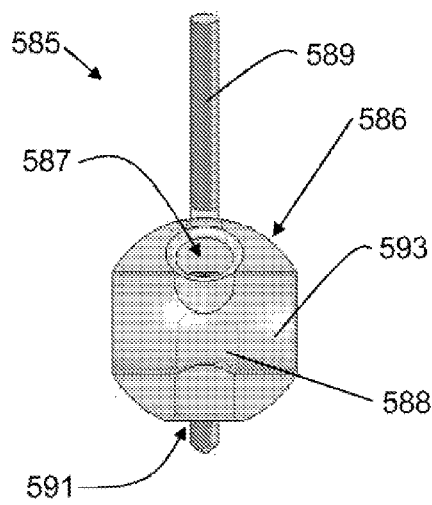
FIGS. 5Q-5X depict additional variations of a device and method for locking a tether.
Figure 5R:
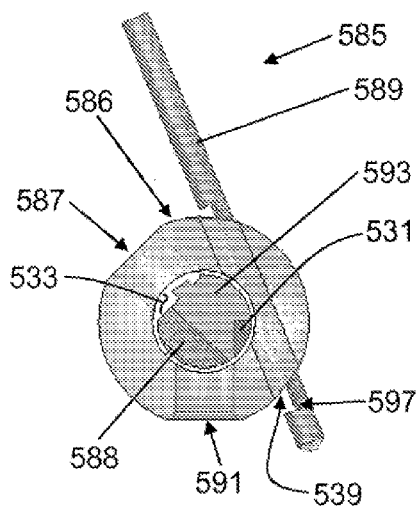
Figure 5S:
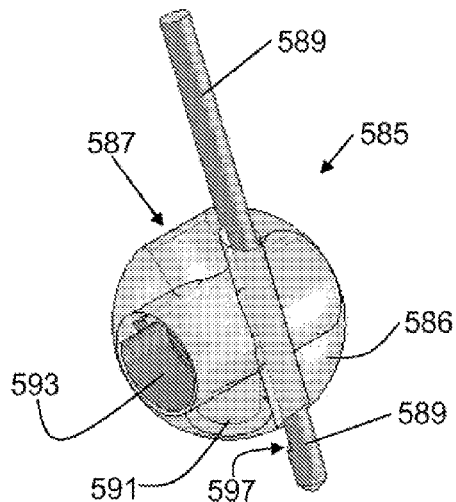
Figure 5T:
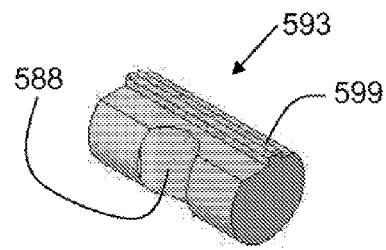
Figure 5U:
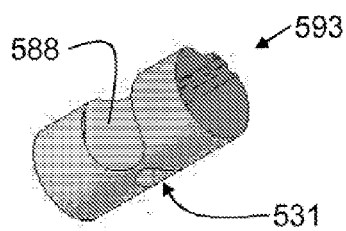
Figure 5V:
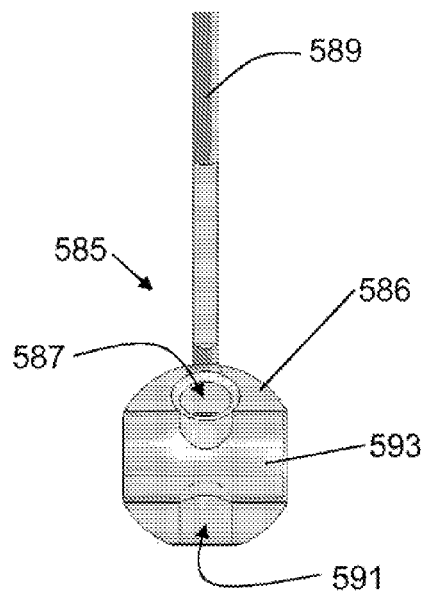
Figure 5W:
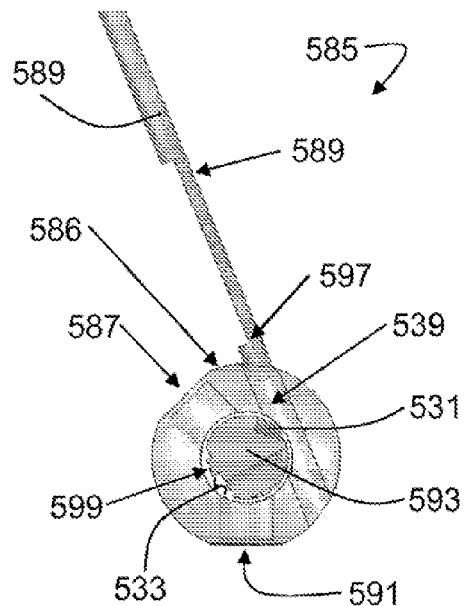
Figure 5X:
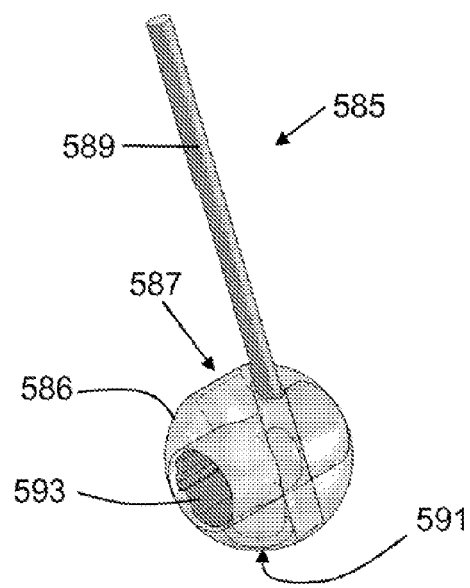

For example, FIGS. 5Q-5X show a variation of a locking device comprising a rotatable plug, where the locking device uses a pullwire mechanism to lock a tether. As shown there, a locking device (585) comprises a generally spherical locking member (586), a rotatable plug or cam (593) disposed within a lumen (533) of locking member (586), and a pullwire (589) passing through a channel (539) in locking member (586) (FIG. 5R). FIGS. 5Q-5S depict locking device (585) in its unlocked or open position, and FIGS. 5V-5X depict locking device (585) in its locked or closed position.

In use, plug (593) may be advanced into lumen (533) of locking member (586), and a tether (not shown) may be routed through the locking member when the locking member is in its unlocked position. It should be noted that in some variations, a locking device may comprise a locking member and a rotatable plug that are preassembled. Locking member (586) includes two apertures (587) and (591) configured for passage of a tether therethrough, and plug (593) also has a slot (588) configured for passage of a tether when the locking device is in its unlocked position.

After a tether has been routed through locking device (585), pullwire (589) may be actuated (e.g., by pulling on the pullwire) to transition locking device (585) into its locked position. Plug (593) includes a notch (531) (FIG. 5U) configured to interface with a notch (597) (FIGS. 5R, 5S, and 5W) on pullwire (589). More specifically, when pullwire (589) is actuated, notch (597) on pullwire (589) engages notch (531) on plug (593), thereby causing plug (593) to rotate. The rotation of the plug helps to secure the tether. Additionally, plug (593) includes steps (599) configured to engage the tether as the plug is rotated, thereby helping to lock the tether in place. Other suitable devices and methods for locking a tether using a rotatable plug may also be employed, as appropriate.

Figure 6:
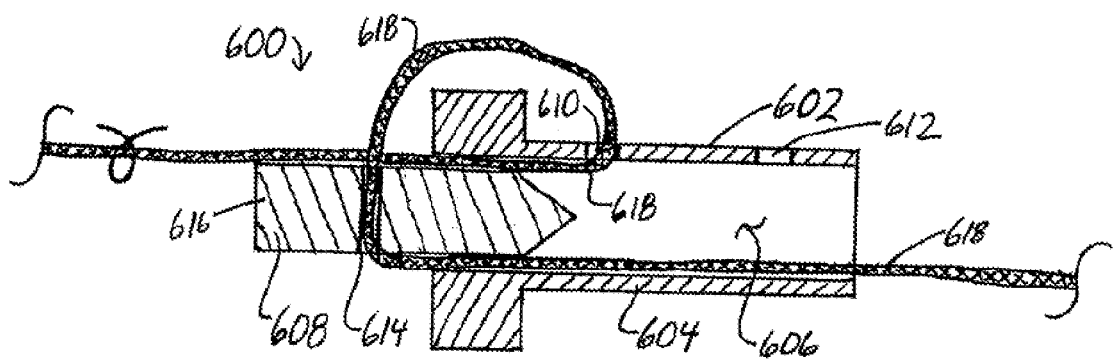
FIGS. 6 and 7 are side cross-sectional views of variations of devices for locking a tether.

As discussed above, in certain variations, a locking device may comprise a plug having one or more grooves, apertures, etc. configured for passage of a tether therethrough. As an example, FIG. 6 shows a locking device (600) comprising a tubular member (602) having a wall portion (604) and a lumen (606), and a plug (608) configured to fit within the lumen of the tubular member. As shown, wall portion (604) has two apertures (610) and (612) therethrough, and plug (608) itself also has a channel (614) extending through its body (616). A tether (618) is routed through aperture (610) of wall portion (604), as well as through channel (614) of plug (608). When the plug is further advanced into the lumen of the tubular member (e.g., by pushing on the plug with a pushing member), it secures the tether between the body of the plug and the wall portion of the tubular member. The routing of the tether through a hole in the wall portion, as well as through a channel in the plug body, may help to further secure the tether.

Figure 7:
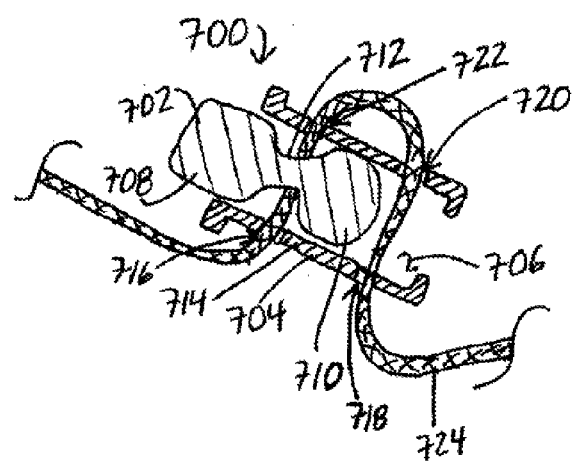

Plugs may comprise any of a number of different features suitable for routing of a tether around, through, and/or against the features. As an example, FIG. 7 shows a locking device (700) comprising a plug (702) and a tubular member (704) configured to receive the plug within a lumen (706) of the tubular member. Plug (702) is somewhat barbell-shaped, such that it has two larger portions (708) and (710) separated by a smaller neck portion (712). Tubular member (704) comprises a wall portion (714) having four apertures (716), (718), (720), and (722) in it. As shown in FIG. 7, a tether (724) may be routed through apertures (716), (718), (720), and (722), passing between the larger portions of the plug, and against smaller neck portion (712). As the plug is further fitted into the lumen of the tubular member, the tether may become secured between the plug body and the wall portion of the tubular member. Additionally, the routing of the tether along the smaller neck portion of the plug may further help to trap the tether between the two larger portions of the plug. While not shown, in some variations, plug (702) may have one or more apertures (e.g., channels, etc.) therethrough, and the tether may also be passed through one or more of those apertures.

Figure 8:
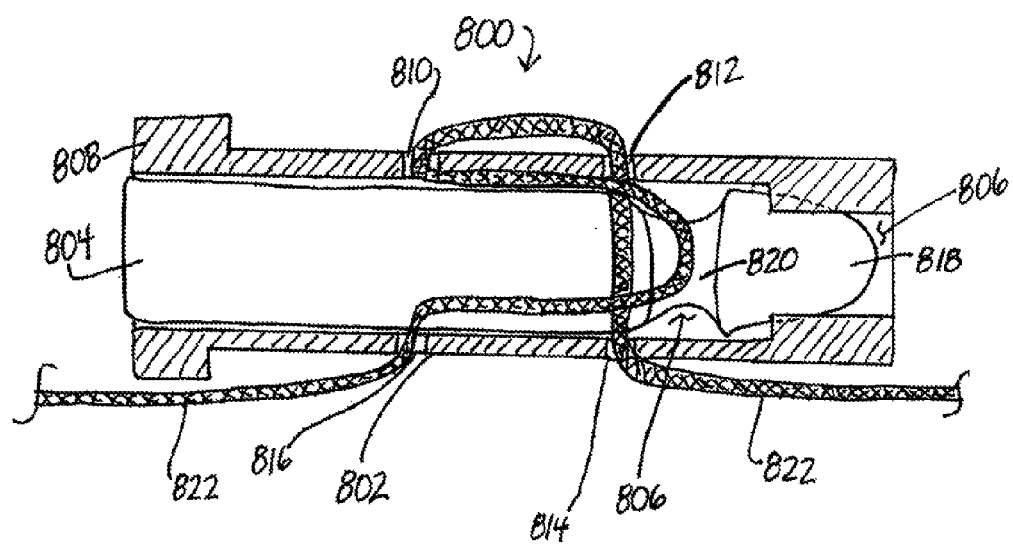
FIG. 8 is a side view in partial cross-section of an additional variation of a device for locking a tether.

FIG. 8 shows an additional variation of a locking device comprising a plug. As shown there, a locking device (800) comprises a tubular member (802) and a plug (804) configured to fit within a lumen (806) of the tubular member. Tubular member (802) comprises a wall portion (808) having four apertures (810), (812), (814), and (816) therethrough, and plug (804) comprises a body (818) including a grooved neck portion (820). As shown, a tether (822) may be routed through apertures (810), (812), (814), and (816), and within grooved neck portion (820). While one tether routing configuration is depicted, any appropriate tether routing configuration may be used.

Figure 9A:
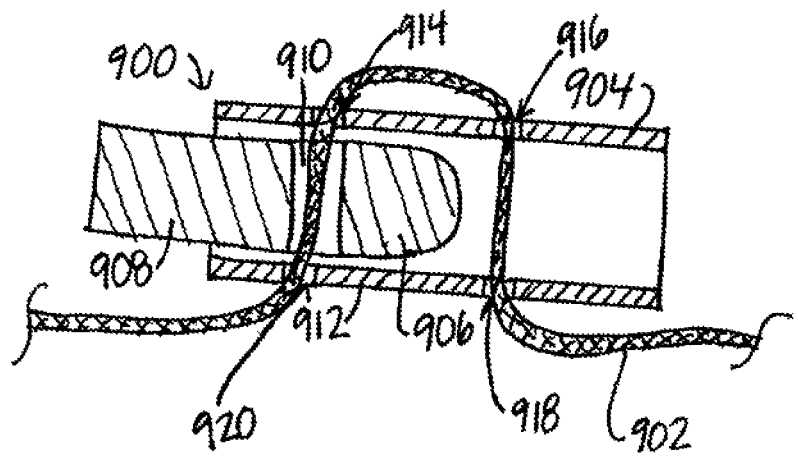
FIGS. 9A and 9B depict variations of a device and a method for locking a tether.
Figure 9B:
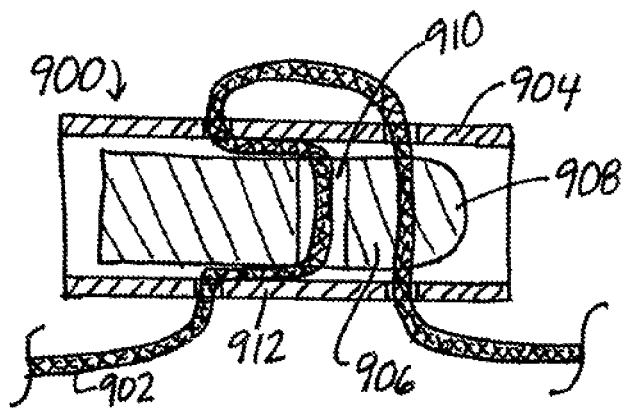

FIGS. 9A and 9B show another variation of a locking device (900) and a tether (902) routed through the locking device in a particular routing configuration. As shown in FIG. 9A, locking device (900) comprises a tubular member (904) and a plug (906). Plug (906) comprises a body (908) having a channel (910) therethrough. Tubular member (904) has a wall portion (912) with four apertures (914), (916), (918), and (920) therethrough. Tether (902) is routed through the apertures in the wall portion and through the channel in the body of the plug. As shown in FIG. 9B, as the plug is advanced into the tubular member, the tether becomes secured between the body of the plug and the wall portion of the tubular member. The additional routing of the tether through the channel in the body of the plug may, for example, enhance the securing of the tether within the locking device.

Figure 10:
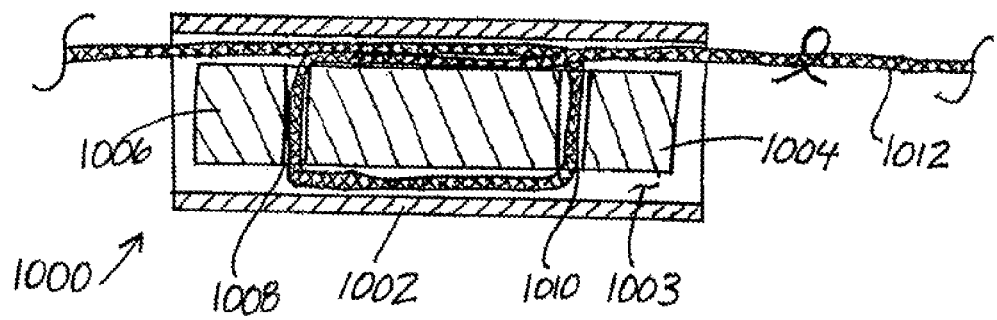
FIGS. 10 and 11 are side cross-sectional views of variations of devices for locking a tether.

While a plug having one channel therethrough has been shown, plugs may have any suitable number and combination of apertures (e.g., holes, channels), grooves, etc. For example, FIG. 10 shows a locking device (1000) comprising a tubular member (1002) having a lumen (1003), and a plug (1004) configured to fit within the lumen of the tubular member. Plug (1004) has a body (1006) and two channels (1008) and (1010) through body (1006). A tether (1012) has been routed into the lumen of the tubular member, past channel (1010), and through channel (1008). The tether has then been routed through channel (1010), and back out of the lumen of the tubular member. This looped routing configuration may provide an especially secure tether lock (e.g., by providing a relatively long section of the tether that is in engagement with the plug). Tethers may be routed through apertures, grooves, etc. in a plug while the plug is not disposed within a locking member, and/or while the plug is disposed within a locking member.

Figure 11:
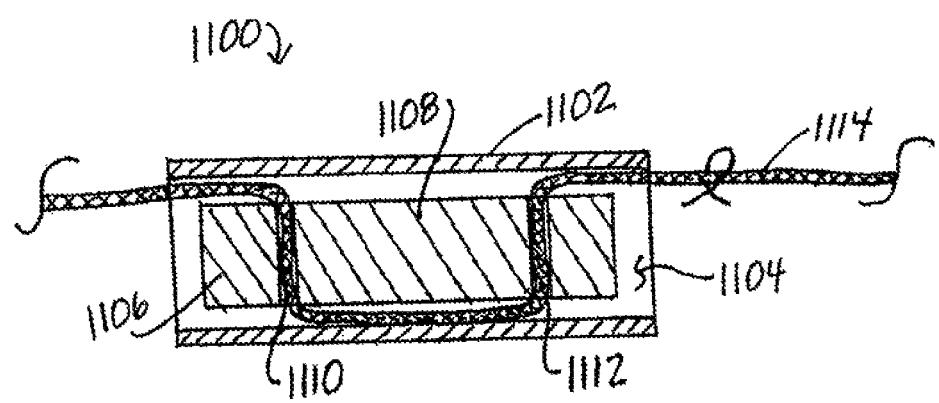

FIG. 11 shows a locking device (1100) similar to device (1000), but having a tether routed therethrough in a different routing configuration. As shown there, locking device (1100) comprises a tubular member (1102) having a lumen (1104), and a plug (1106) comprising a body (1108) with two channels (1110) and (1112) formed therein. A tether (1114) has been routed into lumen (1104), through channel (1112), back out into lumen (1104), through channel (1110), and out into lumen (1104), eventually exiting the tubular member. The tether routing configurations that have been shown are only exemplary, and other tether routing configurations may also be used, as described in further detail below. Moreover, in some variations, a tether that has been routed through a device may not be routed through one or more apertures, etc. in one or more components of the device. The number of apertures or other features through which a tether is routed may depend, for example, on the desired length of the procedure and/or the desired degree of the security of the tether.

Figure 12:
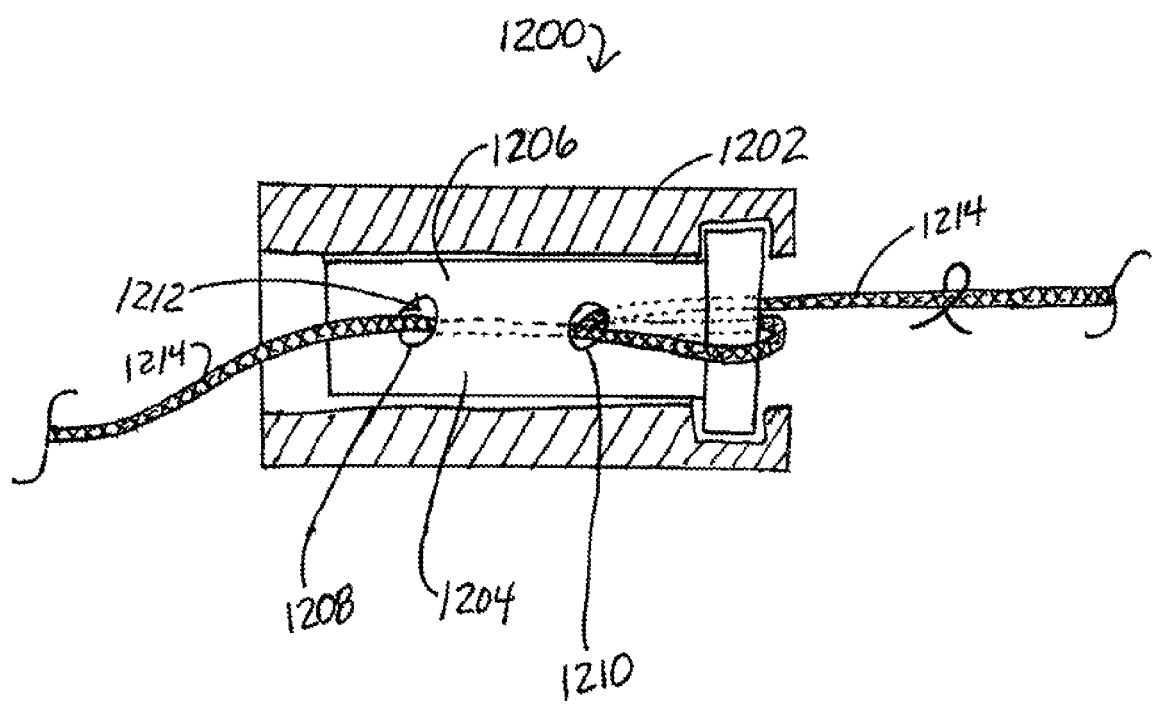
FIG. 12 is a side view in partial cross-section of another variation of a device for locking a tether.

FIG. 12 depicts yet another routing configuration, although the routing configuration shown in FIG. 12 is of a tether through a locking tube disposed within a removable outer sheath. As shown in FIG. 12, a locking device (1200) comprises a sheath (1202), a locking tube (1204) comprising a wall portion (1206) having two apertures (1208) and (1210) and defining a lumen (1212), and a plug (not shown) configured to fit within the lumen of the locking tube to secure a tether against the wall portion of the locking tube. In FIG. 12, locking tube (1204) is disposed within sheath (1202). A tether (1214) has been routed through the lumen of the locking tube, as well as through the two apertures in the wall portion of the locking tube. While one particular routing configuration is shown, other appropriate routing configurations may also be used.

Figure 13:
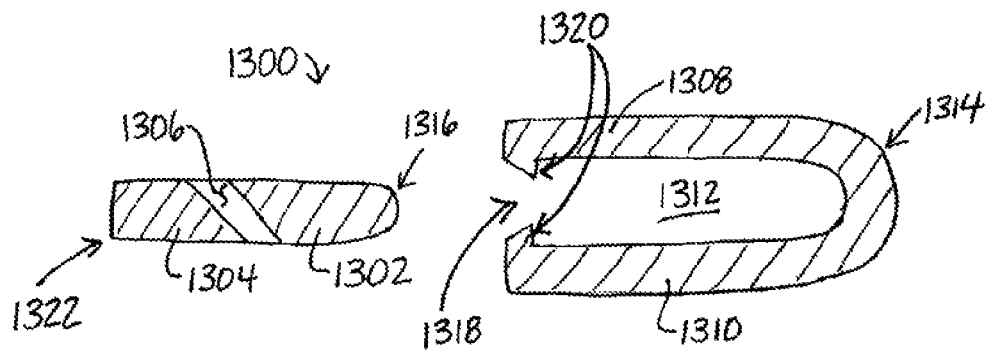
FIGS. 13 and 14 are side cross-sectional views of variations of devices for locking a tether.

Locking tubes, plugs, and other locking device components may have any appropriate size, shape, and/or configuration. For example, FIG. 13 shows a locking device (1300) comprising a plug (1302) having a body (1304) and a channel (1306) through the body. Locking device (1300) also comprises a locking member (1308) including a wall portion (1310) and having a lumen (1312) configured to receive the plug. Locking member (1308) has a closed rounded end (1314) that may be an atraumatic tip with respect to tissue and/or other devices. Additionally, plug (1302) has a rounded end (1316) that may aid in guiding the plug into an opening (1318) in the locking member. In use, a tether (not shown) may be routed through channel (1306), and plug (1302) may be advanced into locking member (1308) to secure the tether. The proximal end (1322) of plug (1302) helps to secure the plug and prevent it from backing out of the locking member by forming a snap-fit with a lip (1320) at the inner diameter of opening (1318).

Figure 14:
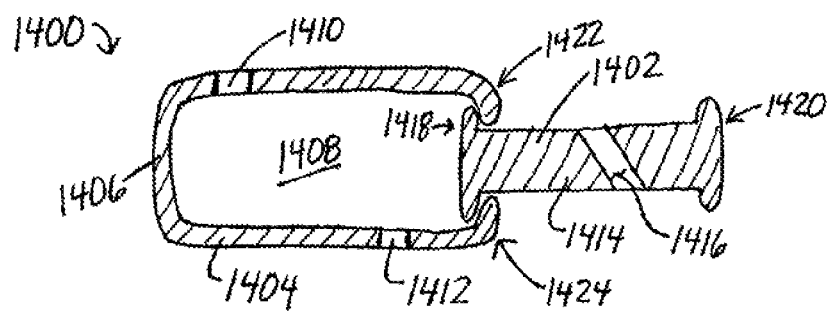

FIG. 14 shows a locking device (1400) comprising a plug (1402) and a locking member (1404). Locking member (1404) comprises a wall portion (1406) defining a lumen (1408) and having two apertures (1410) and (1412) for routing of a tether therethrough. Plug (1402) comprises a body (1414) having a channel (1416) therethrough. Plug (1402) has protruding end portions (1418) and (1420) (e.g., in the form of flanges) which can, for example, engage with end portions (1422) and (1424) on locking member (1404). During use, plug (1402) may be advanced further into locking member (1404) (e.g., using a pushing member), and a tether (not shown) may be routed through apertures (1410) and (1412) and/or channel (1416). In some cases, the plug may then be partially withdrawn out of the locking member, thereby converting the linear path of the tether to a convoluted path, which may further secure the tether between the plug and the locking member. The plug may be partially withdrawn out of the locking member using, for example, a clamping member that clamps onto the plug and that is pulled proximally to withdraw the plug.

In some variations, plug (1402) and locking member (1404) may be preassembled to avoid having loose parts. In other words, the plug and the locking member may be preassembled as a single unit having components that can slide with respect to each other, via engagement between protruding end portion (1418) on plug (1402) and corresponding snap-fit end portions (1422) and (1424) on locking member (1404). In certain variations, a ratcheting feature or additional snap-fits may be implemented to ensure that the plug and the locking member are secured in the final configuration.

Additional variations of methods that include routing a tether through an aperture in a plug may be employed. As an example, in some variations, a tether may be routed through a lumen or channel within a body of a plug, and a sheath or sleeve may then be pushed over the plug to compress the tether, thereby securing the tether.

Figure 15:
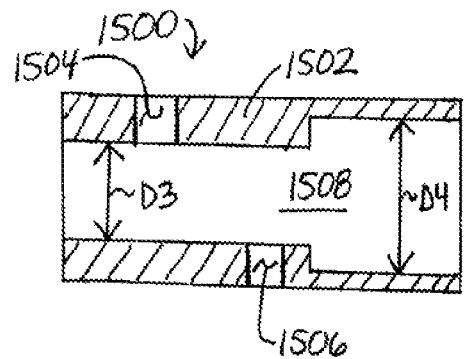
FIG. 15 is a side cross-sectional view of a variation of a component of a device for locking a tether.

Other locking member configurations may also be used. For example, FIG. 15 shows a locking tube (1500) comprising a wall portion (1502) having two apertures (1504) and (1506) therethrough. Locking tube (1500) has a lumen (1508) configured to receive a plug for securing a tether. As shown, lumen (1508) has a first diameter (D3) and a second diameter (D4) that is larger than the first diameter. A plug that is designed to fit within lumen (1508) may have a corresponding shape (i.e., a smaller diameter portion and a larger diameter portion), or may have a different shape. As an example, the plug may have one uniform cross-sectional diameter, but may be compressible such that the plug may be compressed to at least partially fit within the smaller diameter portion of the lumen. In some variations, the plug may not have a circular cross-section. For example, the plug may have an oval cross-section or an irregular cross-section. Moreover, in certain variations, the plug may not have rounded edges. For example, the plug may have a polygonal cross-section, such as a hexagonal cross-section, along its entire length.

Figure 16A:
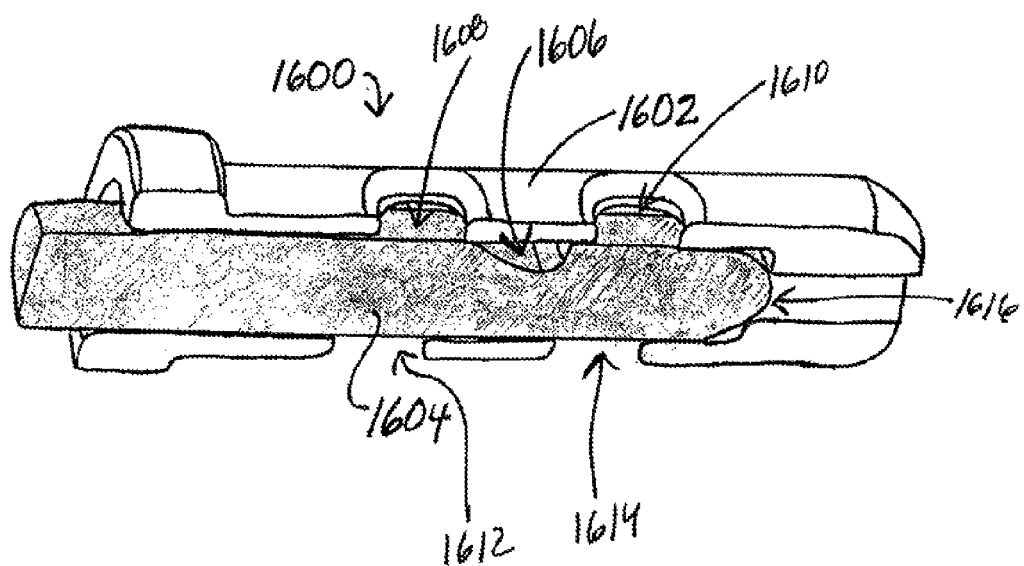
FIGS. 16A and 16B are perspective views of a variation of a device for locking a tether.
Figure 16B:
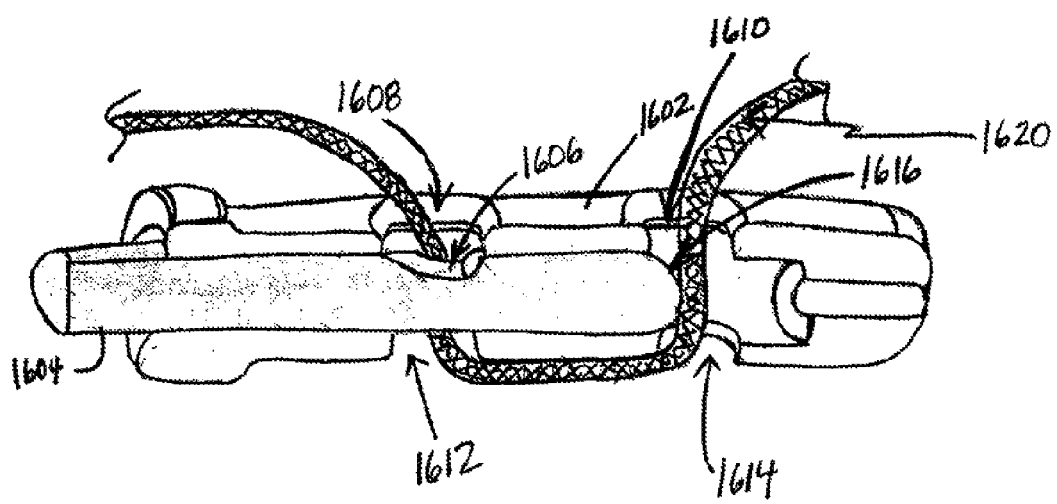

FIGS. 16A and 16B show a locking device (1600) comprising a semi-tubular locking member (1602) and a plug (1604) that is configured to be fitted into the semi-tubular locking member. Plug (1604) includes a groove (1606) configured for routing of a tether therethrough. For example, and as shown in FIG. 16B, a tether (1620) may be routed through apertures (1608), (1610), (1612), and (1614) in locking member (1602), as well as through groove (1606). The tether may be locked by advancing the plug into the semi-tubular locking member.

During the initial advancement of plug (1604) into semi-tubular locking member (1602), groove (1606) aligns with apertures (1608) and (1612), and the tip (1616) of plug (1604) aligns with apertures (1610) and (1614). At this time, plug (1604) may be prevented from being loose within the body of the subject (i.e., the plug may be secured within locking member (1602)). At the same time, tether (1620) is allowed to move freely within the locking device because there is sufficient room for the tether to be pulled through the space between plug (1604) and locking member (1602) and through apertures (1608), (1610), (1612), and (1614). The tether fills the circumferential space formed between groove (1606) and locking member (1602) sufficiently to still allow tether movement while not allowing the plug to disengage from the locking member. To lock tether (1620), the plug may be further advanced into the semi-tubular locking member. While a semi-tubular locking member is shown, in certain variations, a plug may engage with a tubular locking member (as shown above, for example), or a locking member having any other appropriate shape or configuration.

Figure 17A:
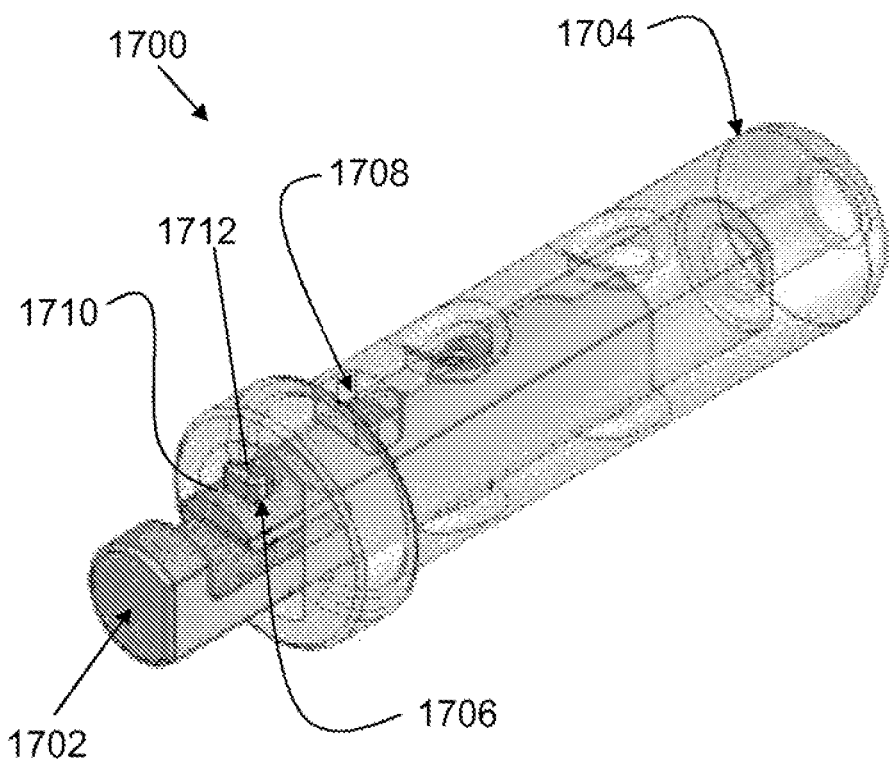
FIGS. 17A and 17B are perspective views of a variation of a device for locking a tether.
Figure 17B:
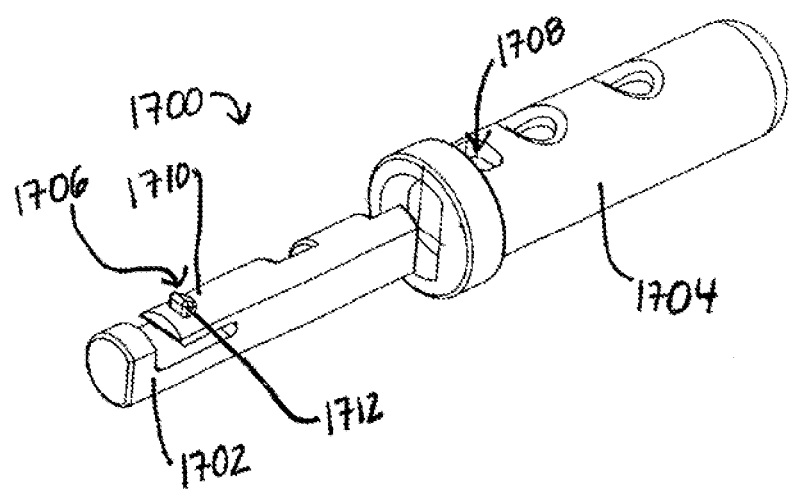
Figure 17C:
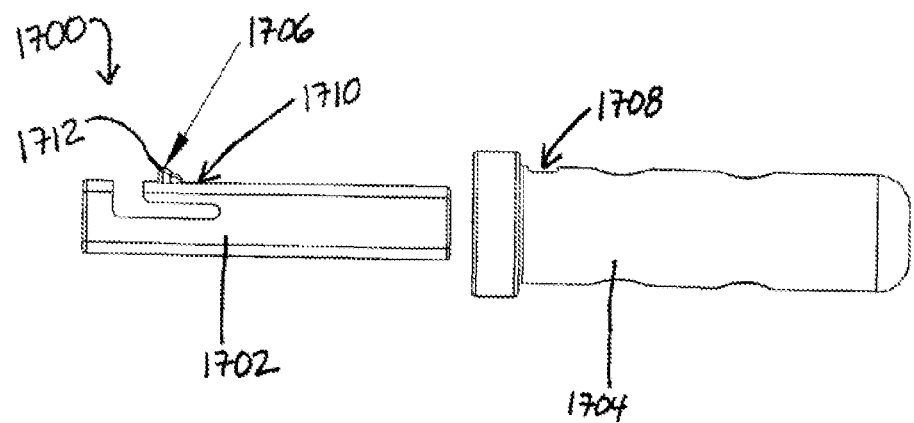
FIG. 17C is a side view of the device of FIGS. 17A and 17B.
Figure 17D:
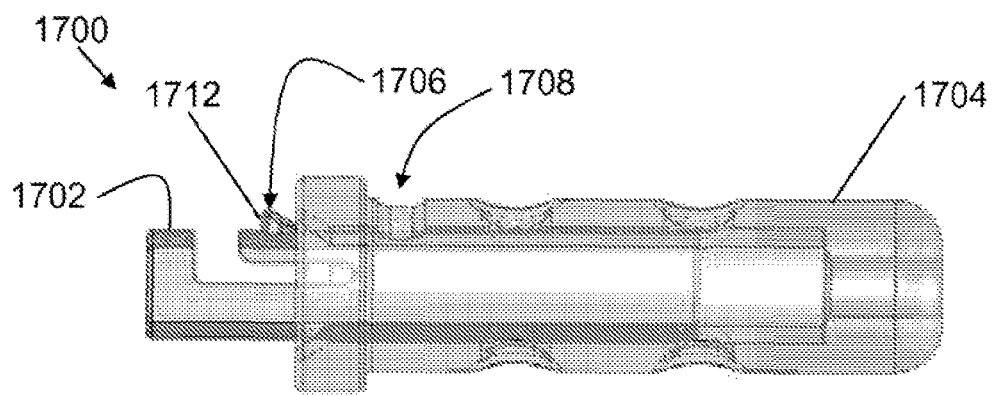
FIG. 17D is a side perspective view of the device of FIGS. 17A-17C, FIGS. 17E and 17F are front views of the device of FIG. 17D.
Figure 17E:
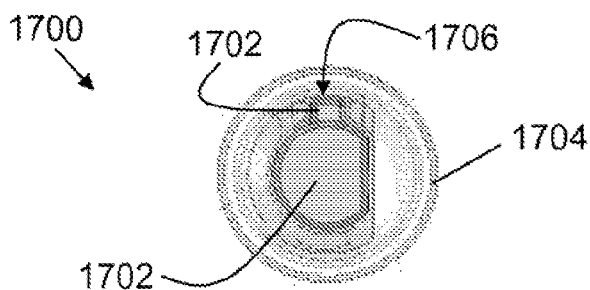
FIG. 17G is a side cross-sectional view of the device of FIGS. 17A-17F.
Figure 17F:
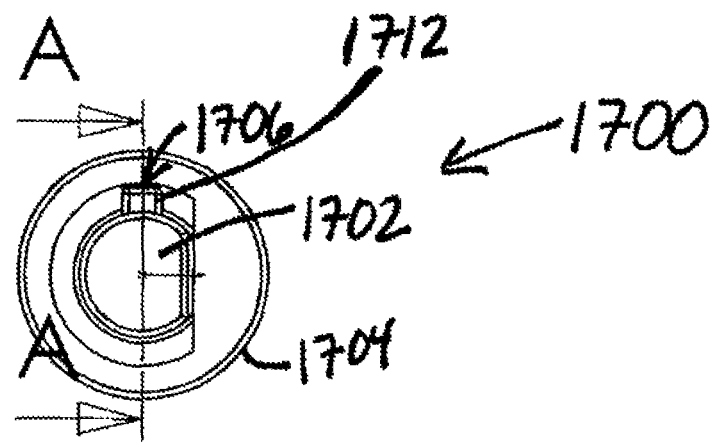
Figure 17G:
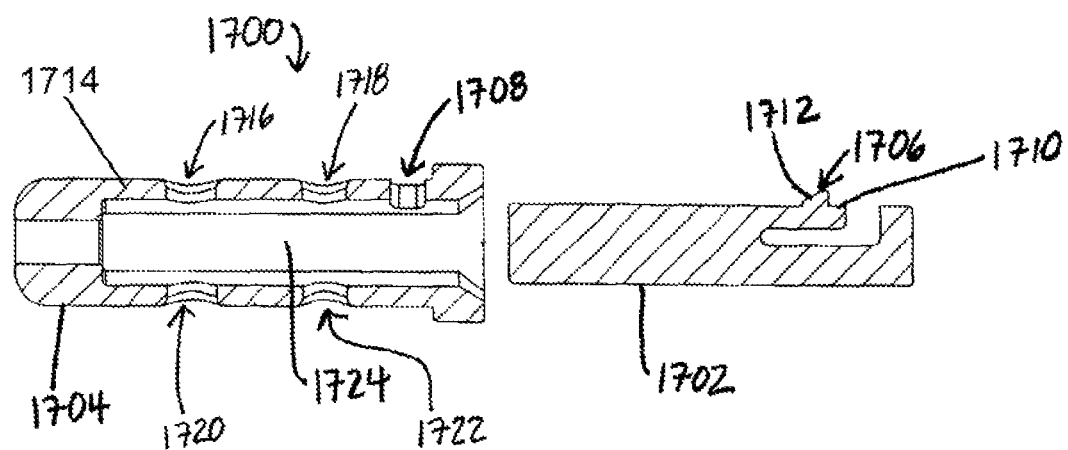

As described above, in some cases, a locking device may comprise at least two components that engage with each other by forming a snap-fit to lock a tether. As an example, FIGS. 17A-17G show a locking device (1700) including a locking tube (1704) and a plug (1702) that forms a snap-fit into the locking tube. More specifically, plug (1702) includes a snap-fit feature (1706) that engages with a corresponding feature (1708) on locking tube (1704). Snap-fit feature (1706) comprises a cantilever arm (1710) and a protrusion (1712) on the cantilever arm. The cantilever arm is compressed as the plug is fit into locking tube (1704), and then snaps back into place once placed in the locking tube (i.e., protrusion (1712) engages with feature (1708) on the locking tube). Locking tube (1704) comprises a wall portion (1714) having four apertures (1716), (1718), (1720), and (1722) therethrough (FIG. 17G). As described above with respect to FIGS. 16A and 16B, plug (1702) is constrained from coming loose from locking tube (1704). During use of locking device (1700), a tether (not shown) may be routed through one or more of the apertures, such that the tether enters a lumen (1724) (FIG. 17G) of locking tube (1704). The tether may then be secured between the plug and the wall portion of the locking tube when the plug is snap-fit into the locking tube.

Figure 18A:
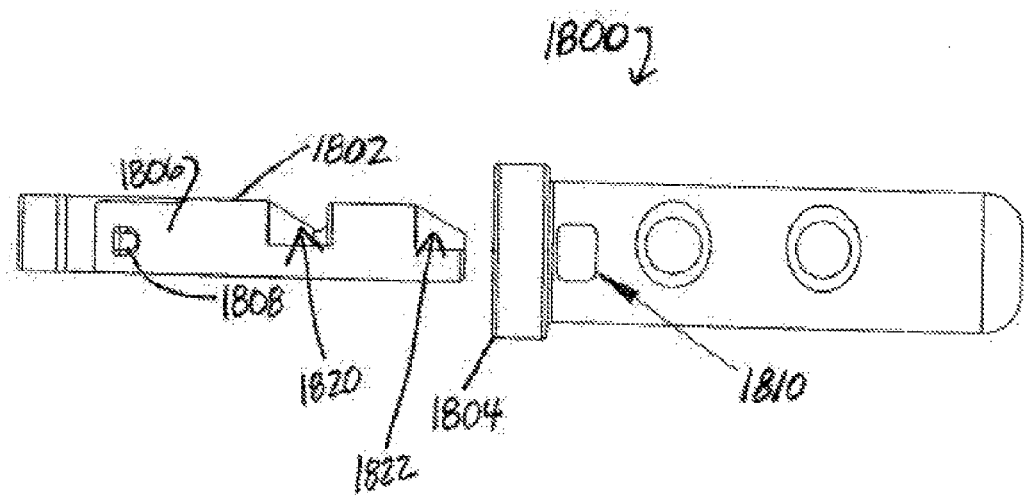
FIGS. 18A and 18B are top views of a variation of a device for locking a tether.
Figure 18B:
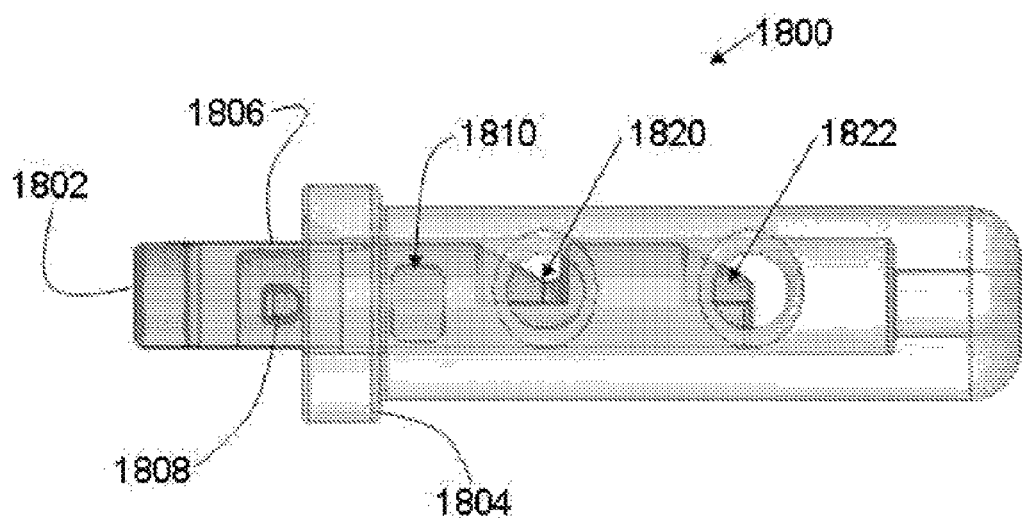
Figure 19A:
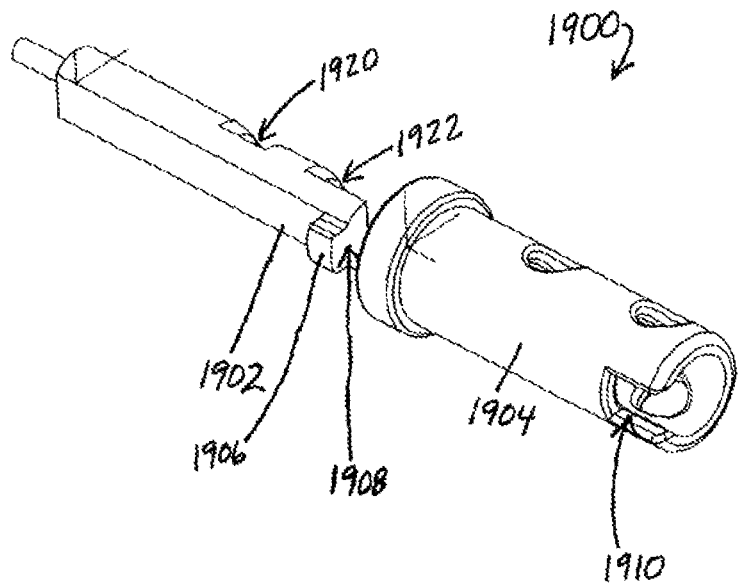
FIG. 19A is a perspective view of a variation of a device for locking a tether.
Figure 19B:
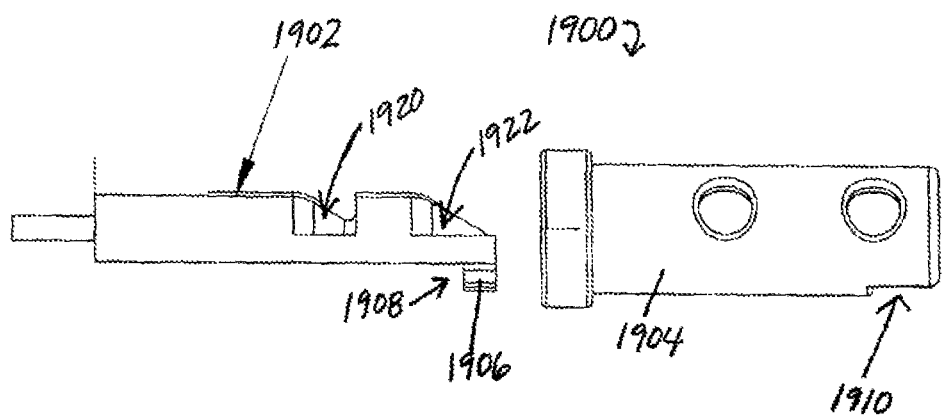
FIG. 19B is a side view of the device of FIG. 19A.
Figure 19C:
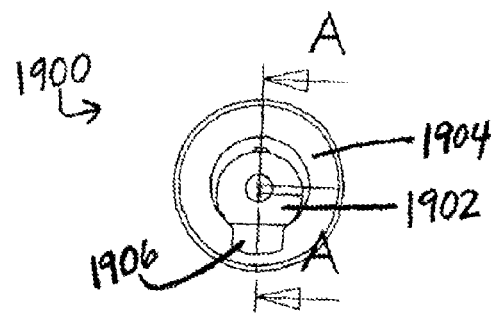
FIG. 19C is a front view of the device of FIGS. 19A and 19B when the components of the device are coupled to each other.
Figure 19D:
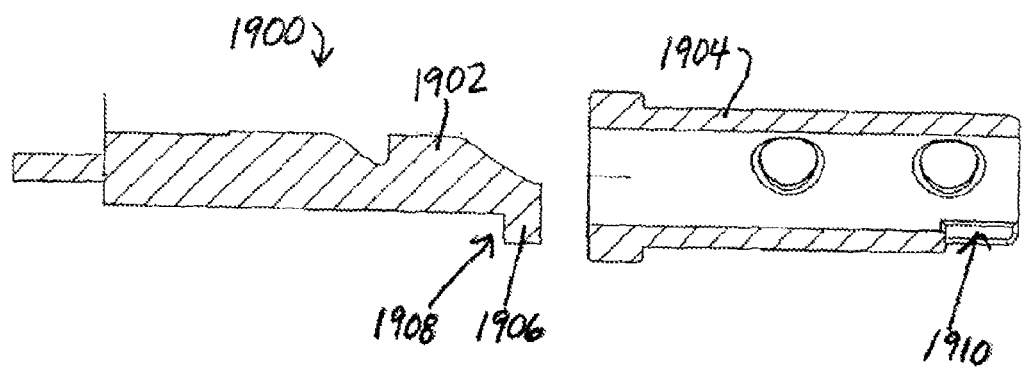
FIG. 19D is a side cross-sectional view of the device of FIGS. 19A-19C.
Figure 19E:
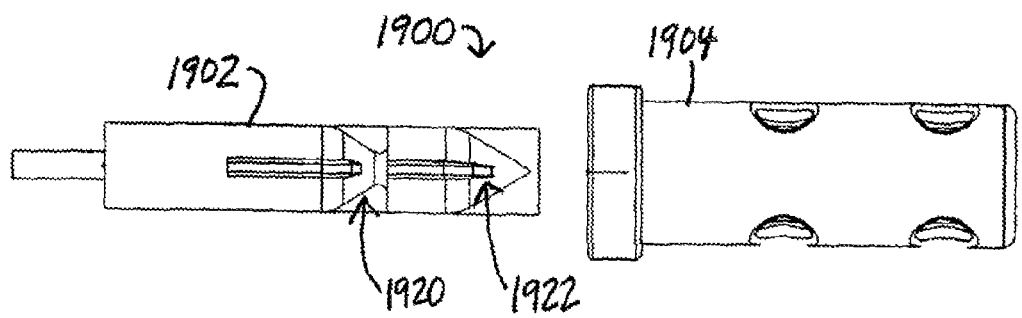
FIG. 19E is a top view of the device of FIGS. 19A-19D.

FIGS. 18A and 18B show another variation of a locking device (1800) comprising a plug (1802) that forms a snap-fit with a locking tube (1804). Plug (1802) has a somewhat different configuration and shape from plug (1702) of FIGS. 17A-17G. However, plug (1802), like plug (1702), also comprises a cantilever arm (1806) and a protrusion (1808) on the cantilever arm that is configured to snap-fit into a corresponding feature (1810) on locking tube (1804). Plug (1802) further comprises two regions (1820) and (1822) that may be used for tether routing. Plug (1802) may be advanced into locking tube (1804) using, for example, any suitable device that provides an axial force to plug (1802) while providing a counteracting force to locking tube (1804).

FIGS. 19A-19E show a locking device (1900) comprising a plug (1902) and a locking tube (1904) configured to receive the plug. The plug has a protrusion (1906) on its distal portion (1908) that is configured to form a snap-fit with a corresponding feature (1910) on locking tube (1904) (e.g., when the plug is pushed into the locking tube). Plug (1902) also comprises tether-routing regions (1920) and (1922). These tether-routing regions may be used, for example, to position one or more tethers for locking by locking device (1900).

While certain variations of snap-fitting plugs have been shown and described, other suitable configurations may also be used. Additionally, other suitable configurations of locking devices in general may be used.

For example, different types of locking tubes may be used in tether-locking devices. Locking tubes may have any suitable number of apertures along the locking tube body. Moreover, the apertures may be in any appropriate location, including but not limited to being located within a wall portion of the locking tube body, and/or on either end or both ends of the locking tube body. The apertures may be sized and shaped for the passage of one or more tethers therethrough. The location, size, and number of apertures in a locking tube may vary depending, for example, on the size of the tether to be threaded through, the anticipated level of tension that may be sustained by the tether, the geometry of the corresponding plug, and other related factors. In some variations, the location, size, and number of apertures may be selected to withstand the forces that may result from tensioning the tether (e.g., pressure, tensional, shear), so that the locking tube is unlikely to collapse under stress.

Figure 20A:
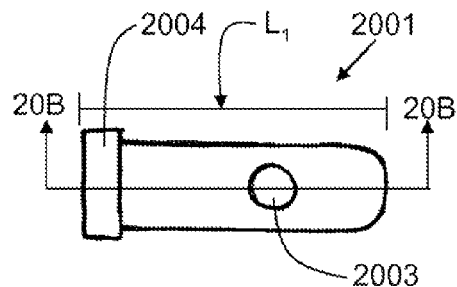
FIG. 20A is a side view of a variation of a device that may be used to cut a tether.
Figure 20B:
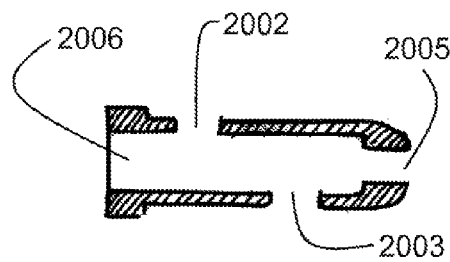
FIG. 20B is a cross-sectional view of the device of FIG. 20A, taken along line 20B-20B.

FIGS. 20A-20H depict different variations of locking tubes that are configured to receive a plug. FIGS. 20A and 20B depict a locking tube (2001) that may, for example, secure a plug by friction fit only, or by both friction fit and snap-fit. Locking tube (2001) comprises a shoulder (2004) that may be used, for example, to help temporarily couple the locking tube to one or more other components of a locking device. Locking tube (2001) also has two offset apertures (2002) and (2003) in a wall portion of the tube, along the tube body, as well as an aperture (2005) located at its distal end. All of the apertures are in fluid communication with a lumen (2006) of locking tube (2001). Apertures (2002), (2003), and/or (2005) may have the same or different diameters. In some variations, one or more of the apertures may have a diameter of about 0.01 inch to about 0.07 inch, for example, about 0.015 inch to about 0.06 inch, or about 0.04 inch. For example, apertures (2002) and (2003) may have a diameter of about 0.04 inch, and/or aperture (2005) may have a diameter of about 0.032 inch. Other appropriate diameters or other dimensions may also be used. The length $L_1$ of locking tube (2001) may be from about 0.2 inch to 0.4 inch, for example, 0.264 inch. Apertures such as apertures (2002), (2003), and (2005) may be formed at the same time the tube body is formed, or may be formed after tube body formation.

Figure 20C:
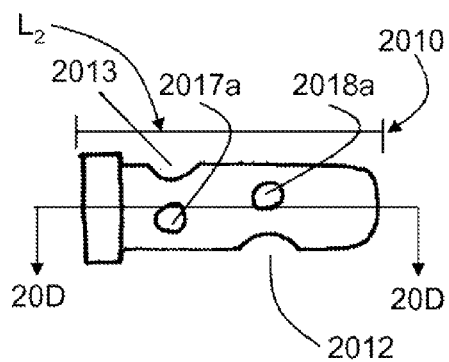
FIG. 20C is a side view of a variation of a device that may be used to cut a tether.
Figure 20D:
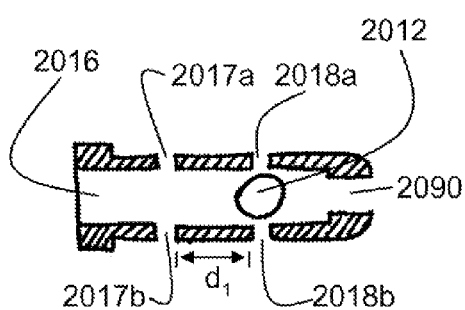
FIG. 20D is a cross-sectional view of the device of FIG. 20C, taken along line 20D-20D.

FIGS. 20C and 20D depict another variation of a locking tube (2010). As shown there, locking tube (2010) comprises offset apertures (2012) and (2013), as well as pairs of apertures (i.e., apertures (2017a) and (2017b), and apertures (2018a) and (2018b)) that are aligned with each other. Locking tube (2010) also has an aperture (2090) located at its distal end. In some variations, one or more of the apertures may have a diameter of about 0.01 inch to about 0.07 inch, for example, about 0.015 inch to about 0.06 inch, or about 0.04 inch. For example, apertures (2017a) and (2017b), and apertures (2018a) and (2018b) may be about 0.028 inch, and/or aperture (2090) may be about 0.032 inch. One or more of the apertures may be in fluid communication with a lumen (2016) of locking tube (2010). In some variations, offset apertures (2012) and (2013) may be molded into locking tube (2010), and/or apertures (2017a), (2017b), (2018a), and (2018b) may be formed after the tube body has been formed (e.g., by drilling in the tube body).

Apertures may have any appropriate diameter, such as 0.028 inch. Referring again to FIGS. 20C and 20D, apertures (2017a) and (2017b) are directly across from each other (i.e., aligned), and apertures (2018a) and (2018b) are also directly across from each other (i.e., aligned). These apertures may be located a certain distance from a center line indicated by line 20D-20D (i.e., along the longitudinal axis of a locking tube), such as 0.01 inch away from the center line. Additionally, apertures (2017a) and (2017b) are located at a distance ($d_1$) apart from apertures (2018a) and (2018b), where ($d_1$) may be, for example, 0.085 inch. The length $L_2$ of locking tube (2010) may be from about 0.2 inch to 0.4 inch, for example, 0.264 inch.

Figure 20E:
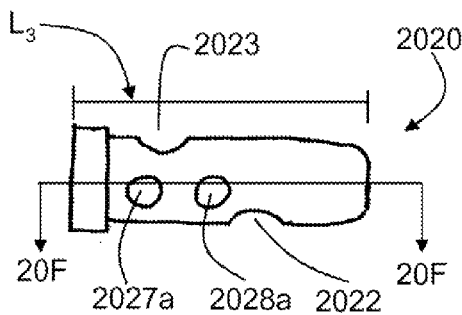
FIG. 20E is a side view of a variation of a device that may be used to cut a tether.
Figure 20F:
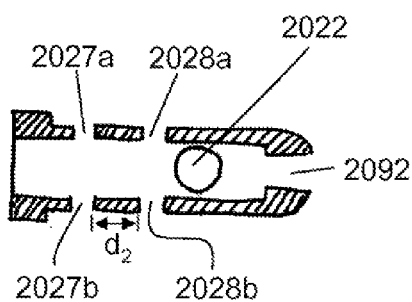
FIG. 20F is a cross-sectional view of the device of FIG. 20E, taken along line 20E-20F.

Other variations of locking tubes may include apertures in other locations, which may be aligned in different configurations. For example, FIGS. 20E and 20F show a locking tube (2020) including aligned apertures (2027a) and (2027b), as well as aligned apertures (2028a) and (2028b). Locking tube (2010) also includes offset apertures (2022) and (2023). The pairs of aligned apertures are closer to each other than the apertures shown in FIGS. 20C and 20D. As shown here, the pairs of aligned apertures are separated by a distance ($d_2$), where ($d_2$) may be, for example, 0.06 inch. Distance ($d_2$) may be chosen, for example, according to the expected pressure on the locking tube during routine use (e.g., when a tether threaded therethrough is tensioned). Distance ($d_2$) may be any appropriate distance, such as from 0.06 inch to 0.085 inch, or greater than 0.085 inch (e.g., if a large pressure is expected when a tether threaded therethrough is tensioned). Locking tube (2020) also has an aperture (2092) located at its distal end. In some variations, one or more of the apertures may have a diameter of about 0.01 inch to about 0.07 inch (e.g., about 0.015 inch to about 0.06 inch, or about 0.04 inch). For example, apertures (2027a), (2027b), (2028a) and/or (2028b) may be about 0.026 inch, apertures (2022) and/or (2023) may be about 0.04 inch, and/or aperture (2092) may be about 0.032 inch. Alternatively or additionally, in certain variations the length $L_3$ of locking tube (2020) may be from about 0.2 inch to 0.4 inch, for example, 0.264 inch.

FIGS. 20G and 20H depict another variation of a locking tube (2030), in which an aperture (2037) is aligned with offset apertures (2032) and (2033). Locking tube (2030) also has an aperture (2094) located at its distal end. In some variations, one or more of the apertures may have a diameter of about 0.01 inch to about 0.07 inch (e.g., about 0.015 inch to about 0.06 inch, or about 0.04 inch). For example, apertures (2032) and (2033) may be about 0.04 inch, aperture (2037) may be about 0.028 inch, and aperture (2094) may be about 0.032 inch. Alternatively or additionally, in certain variations, the length of locking tube $L_4$ (2030) may be from about 0.2 inch to 0.4 inch, for example, 0.264 inch.

The characteristics of a locking tube's apertures, such as their diameters, relative locations, and/or methods of formation, may be modified as desired (e.g., to ensure that the locking tube is able to sustain the pressure of a particular tensioned tether during use). While certain variations of locking tubes have been shown and described, other suitable configurations may also be used.

In some variations, a locking device plug may comprise one or more one-way features that help to engage the plug with one or more other locking device components. As an example, FIG. 21A shows a locking device (2100) comprising a plug (2102) and a locking tube (2104) configured to receive the plug within a lumen (2106). Plug (2102) comprises a body (2108) and a locking portion (2110) at the distal end of body (2108). Locking portion (2110) comprises an elongated member (2112) having a bulbous tip (2114). When plug (2102) is pushed into lumen (2106), bulbous tip (2114) passes through an engagement feature (2116) within lumen (2106). Because of its shape, bulbous tip (2114) is not able to disengage from the engagement feature. Thus, plug (2102) may be coupled to locking tube (2104) (e.g., prior to or in conjunction with tether locking). Other variations of plugs having such one-way features may be used. For example, FIG. 21B shows a locking device (2150) comprising a locking tube (2152) and a plug (2154). Locking tube (2152) has a lumen (2156) and an inner rim (2158). Plug (2154) has a bulbous head (2160) that is configured to pass through inner rim (2158) when the plug is advanced into the locking tube, thereby engaging the plug with the locking tube. Once this engagement occurs, the bulbous head functions as a one-way feature, such that the plug generally will not move in the proximal direction and disengage from the locking tube.

Figure 22:
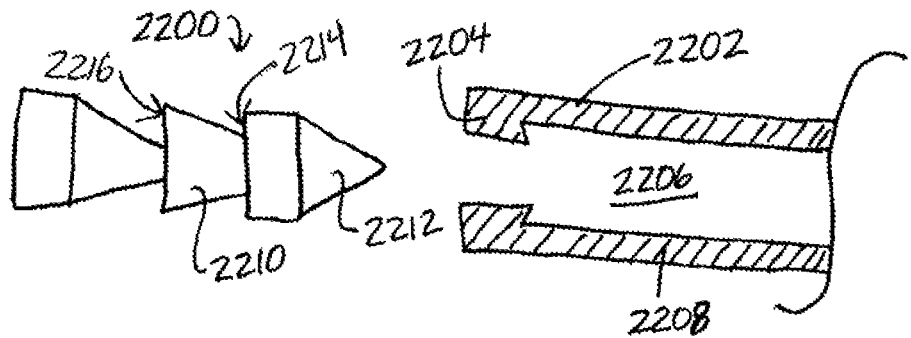

Other plug and locking member configurations are possible. As an example, FIG. 22 shows a locking device (2200) comprising a locking tube (2202) having a rim (2204) and a lumen (2206) defined by a wall portion (2208). Locking device (2200) further comprises a plug (2210) configured to fit within the lumen of the locking tube. Plug (2210) comprises engagement portions (2214) and (2216), and a pointed head (2212). The engagement portions function as one-way features that engage with rim (2204) when plug (2210) is advanced into lumen (2206). Plug (2210) may be advanced just far enough to cause engagement portion (2214) to engage with rim (2204), or may be advanced further to cause engagement portion (2216) to engage with rim (2204).

Figure 23:
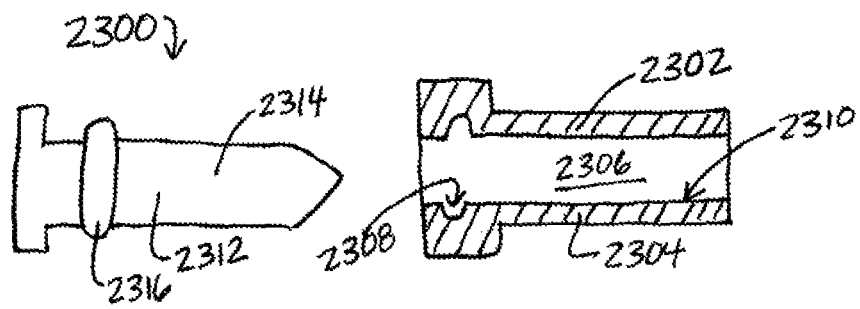
Figure 24:
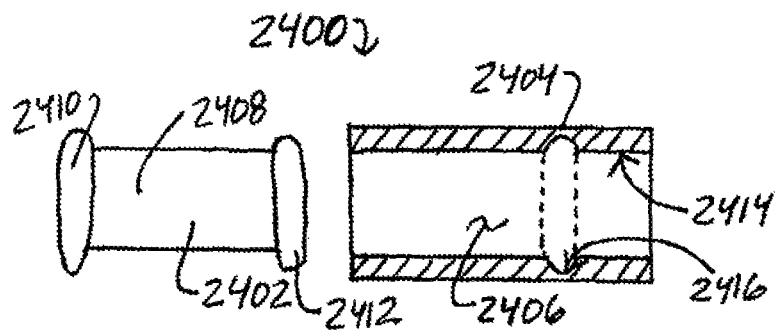

As another example, FIG. 23 shows a locking device (2300) comprising a locking tube (2302) having a wall portion (2304) defining a lumen (2306) and including an annular groove (2308) on its interior surface (2310). Locking device (2300) further comprises a plug (2312) comprising a body (2314) and a rim (2316) around the body. When plug (2312) is advanced into lumen (2306) of locking tube (2302), rim (2316) engages with annular groove (2308), thereby securing the plug to the locking tube. Similarly, FIG. 24 shows a locking device (2400) comprising a plug (2402) and a locking tube (2404) configured to receive the plug within a lumen (2406). Plug (2402) comprises a body (2408) having annular protrusions (2410) and (2412) at each of its ends. Locking tube (2404) has an interior surface (2414) including a groove (2416) configured to form a snap-fit with annular protrusion (2410) or (2412), thereby coupling the plug to the locking tube (and, e.g., securing a tether therebetween).

Figure 25:
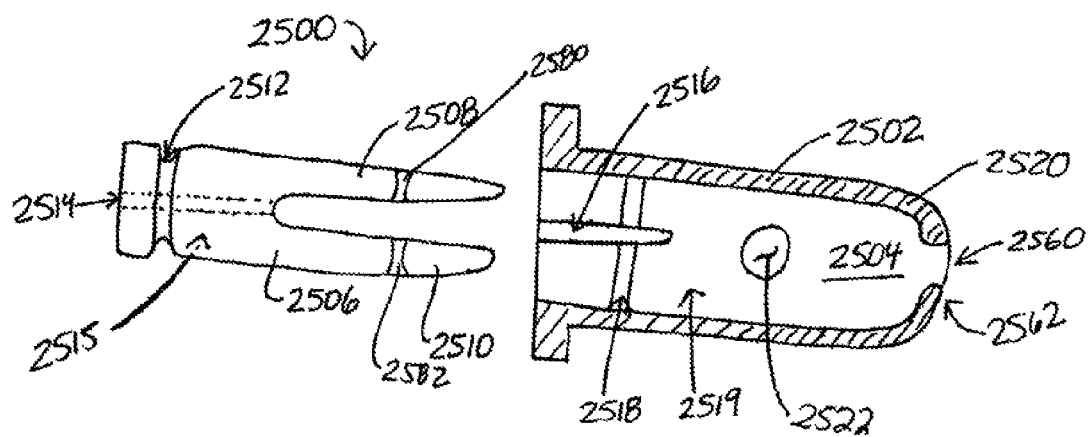

As noted above, locking device plugs may have any suitable size, shape, and/or configuration. For example, FIG. 25 shows a locking device (2500) comprising a locking member (2502) having a hollow portion (2504), and a plug (2506) configured to at least partially fit within the hollow portion of the locking member. Plug (2506) comprises two flexible legs (2508) and (2510) capable of being compressed toward each other (e.g., as the plug is being fitted into the hollow portion of the locking member). Plug (2506) also comprises ridges (2512) and (2514) on its back surface (2515), as well as ridges (2580) and (2582). The ridges are configured to engage with corresponding grooves (2516) and (2518) on an interior surface (2519) of locking member (2502) as the plug is being advanced into the locking member. Initially, ridges (2580) and (2582) engage groove (2518) to secure the plug to the locking member (thereby preventing the plug from being loose in the body). Then, as the plug is advanced, ridge (2512) engages groove (2518) and ridge (2514) engages groove (2516). Thus, plug (2506) may form a secure fit with locking member (2502), and may thereby securely lock a tether therebetween.

Locking member (2502) comprises a wall portion (2520) having an aperture (2522) therethrough suitable for passage of such a tether. Wall portion (2520) also comprises an aperture (2560) at the distal end (2562) of locking member (2502). In certain variations, aperture (2560) may be sized and shaped for routing of a tether therethrough. In some cases, locking device (2500) may be pre-assembled, such that plug (2506) is coupled to locking member (2502) prior to use. During use, the plug may, for example, be further advanced into the locking member to secure a tether. The pre-assembling of the plug and the locking member may, for example, prevent the plug from becoming displaced from the target site when the locking device is in use.

Additional different configurations of plugs are shown in FIGS. 26A-29B. As shown in FIGS. 26A and 26B, a plug (2600) has a generally cylindrical shape with a rounded end (2602). The rounded end may be the distal end of the plug or, in some variations, may be the proximal end of the plug. FIGS. 27A and 27B show another variation of a plug (2700). As shown there, plug (2700) is generally arrow-shaped in side view (FIG. 27A), and comprises an elongated portion (2702) and a pointed head portion (2704). FIGS. 28A and 28B depict a plug (2800) that is mushroom-shaped, with an elongated portion (2802) and a bulbous head (2804). Finally, FIGS. 29A and 29B show a plug (2900) comprising an elongated portion (2902) and a head portion (2904) having a pointed tip (2906) and multiple one-way features (2908), (2910), and (2912). Plug (2900) may be formed by, for example, cutting into the exterior surface of a polyethylene tube and thereby causing strips to peel up from the exterior surface of the tube (e.g., skiving the tube). The one-way features may, for example, allow the plug to be translated in one direction within a hollow portion (e.g., a lumen) of a locking member, while not allowing the plug to be translated in another direction (e.g., the opposite direction) within the hollow portion of the locking member.

The head portions of the plugs shown in FIGS. 27A, 27B, 28A and 28B may serve a similar function. For example, they may be compressible, such that they may be squeezed into a hollow portion of a locking member. However, once within the hollow portion, they may return to their original size and shape, which may prevent them from moving back out of the hollow portion. As a result, the plugs may form a relatively secure coupling with a locking member.

While certain plug configurations have been shown, others are possible. For example, in some variations, a plug may have a pointed tip that is off-center with respect to a longitudinal axis of the plug. The off-center location of the tip may, for example, help prevent the plug from inadvertently spearing a tether crossing the center of a locking tube lumen.

Plugs may be formed of any suitable material, and in some cases, a plug may be formed of a swellable and/or otherwise expandable material. For example, a plug may be formed of a hydrogel that absorbs water over time to provide enhanced locking. In some variations, a nylon plug may be employed (e.g., with a Nitinol locking tube).

Figure 30A:
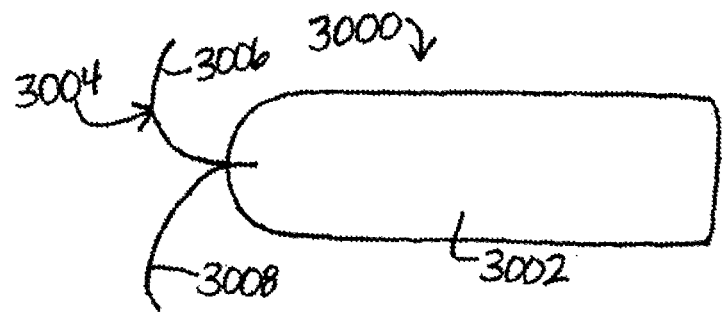
FIG. 30A is a side view of a variation of a component of a device for locking a tether.
Figure 30B:
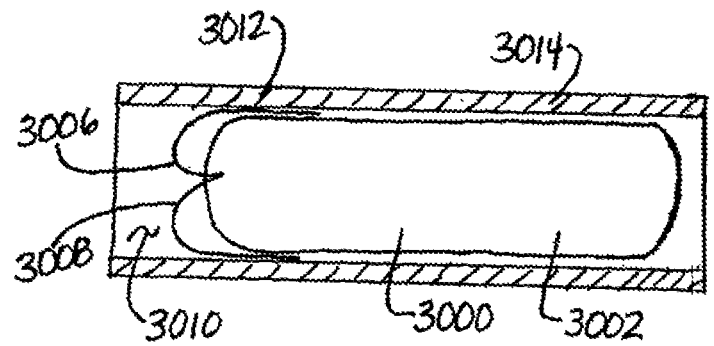
FIGS. 30B and 30C are side views in partial cross-section of a device for locking a tether that comprises the component of FIG. 30A.
Figure 30C:
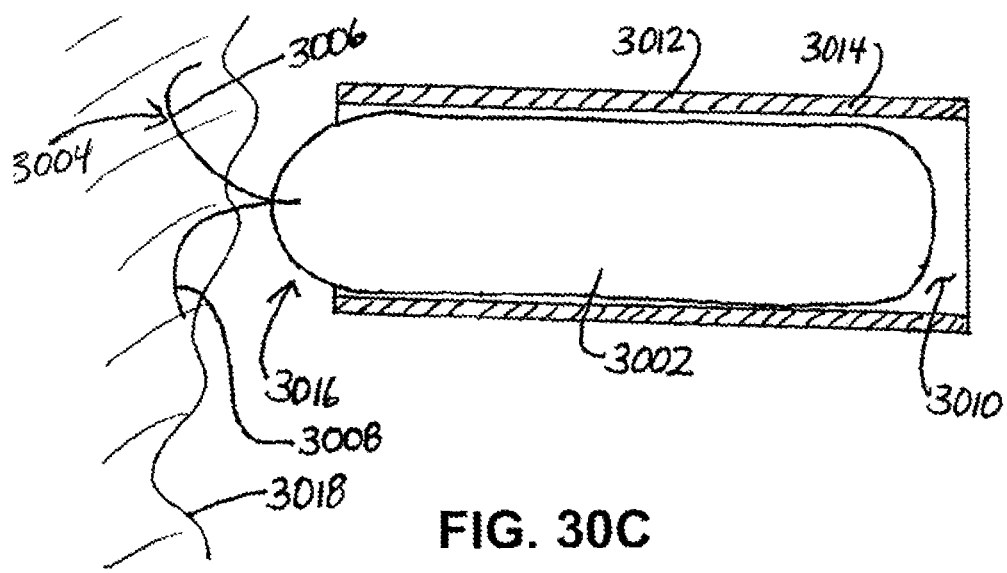

In certain variations, a plug may comprise one or more anchor portions. The anchor portions may, for example, help to anchor the plug to body tissue during use. As an example, the plug may be used to lock a tether that is coupled to multiple anchors. The anchors may be embedded in tissue, and the anchor portion of the plug may also be embedded in tissue. This may, for example, limit the likelihood of the plug becoming displaced from the target site and traveling to a non-target area. As an example, FIG. 30A shows a plug (3000) comprising a body portion (3002) and an anchor portion (3004) extending from the body portion. Anchor portion (3004) may, for example, be molded into body portion (3002) or embedded in body portion (3002). Anchor portion (3004) comprises two hooked portions (3006) and (3008) extending in opposite directions. The hooked portions may, for example, have sharp tips suitable for engaging tissue. As shown in FIG. 30B, during use, plug (3000) may be advanced into a lumen (3010) of a locking member (3012) (e.g., to secure a tether between the body portion of the plug and a wall portion (3014) of the locking member). As shown in FIG. 30C, the plug may then be further advanced, such that a distal portion (3016) of the plug (including anchor portion (3004)) exits the lumen of the locking member. Anchor portion (3004) may then engage tissue (3018). Referring back to FIG. 30B, hooked portions (3006) and (3008) of anchor portion (3004) may be compressible, such that they may be compressed within a hollow portion of a locking member during advancement of the plug into the hollow portion. In certain variations, one or more rings (not shown) may be advanced over locking member (3012) to further secure the locking member to the plug.

Figure 31A:
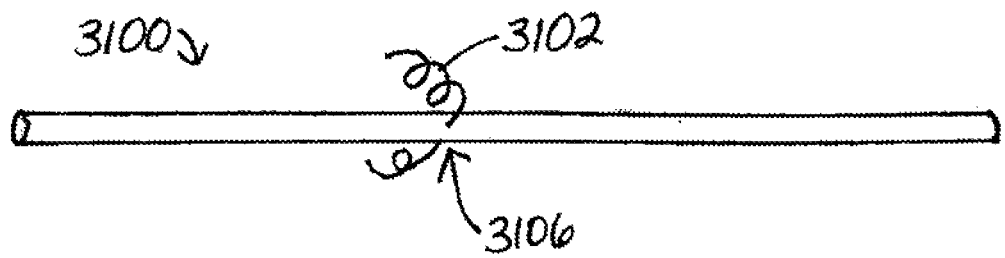
FIG. 31A and FIG. 31B are side perspective views of variations of a device for locking a tether.
Figure 31B:
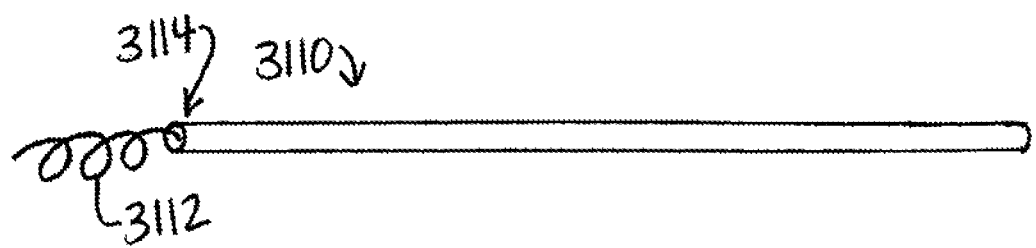
Figure 32:
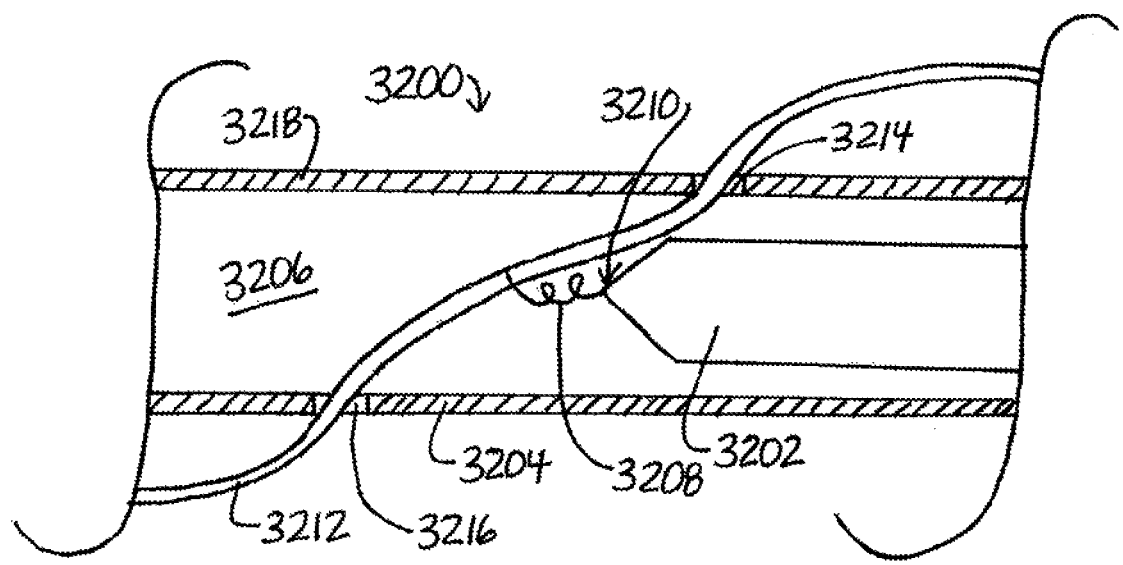
FIG. 32 depicts variations of a device and a method for locking a tether.

In some variations, a tether may comprise one or more features that help the tether to engage body tissue. For example. FIG. 31A shows a tether (3100) having a coil (3102) extending from a central region (3106) of the tether. The coil may engage tissue at a target site, thereby helping to secure the tether to the target site. Any number of coils or other engagement mechanisms or combinations thereof may be used. Non-limiting examples of other engagement mechanisms or features that may be used on a tether include bumps, ridges, etc. Additionally, the coils and/or other engagement mechanisms may be located at any suitable position along the tether. For example, FIG. 31B shows a tether (3110) having a coil (3112) extending from its distal end (3114). Of course, one or more other locking device components may alternatively or additionally include one or more coils and/or other engagement mechanisms. For example, FIG. 32 shows a locking device (3200) comprising a plug (3202) and a locking tube (3204) having a lumen (3206) configured to receive the plug. Plug (3202) comprises a coil (3208) at its distal end (3210). As shown in FIG. 32, the coil may engage a tether (3212) threaded through two apertures (3214) and (3216) in a wall portion (3218) of the locking tube. Thus, the coil may help to further lock the tether within the locking device.

Figure 33A:
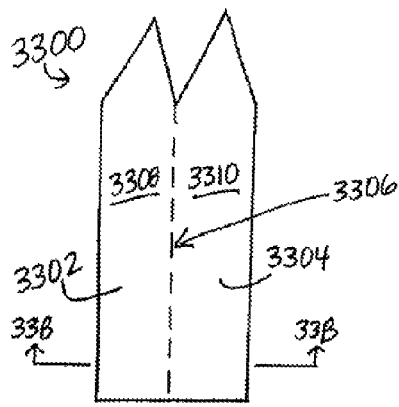
FIGS. 33A-33E illustrate variations of a device for locking a tether.
Figure 33B:
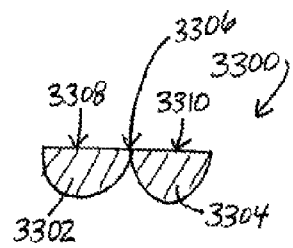

In certain variations, a plug may comprise two or more portions that are capable of being closed toward each other to engage one or more tethers therebetween. For example, FIGS. 33A and 33B show a plug (3300), with FIG. 33B being a cross-sectional view of the plug taken along line 33B-33B in FIG. 33A. Plug (3300) comprises two portions (3302) and (3304) that are connected to each other by a hinge (3306). While a hinge has been shown, other suitable connection mechanisms may alternatively or additionally be used. Portion (3302) has an interior surface (3308), and portion (3304) has an interior surface (3310). In use, one or more tethers (not shown) may be routed between surfaces (3308) and (3310) (e.g., contacting one or both of the surfaces). Then, portion (3302) may be folded toward portion (3304) around hinge (3306) so that interior surface (3308) contacts interior surface (3310). The tether or tethers may be trapped between the two portions when they are folded toward each other. In some variations, the plug may then be advanced into a locking member or another device component (e.g., to secure the tether).

Figure 33C:
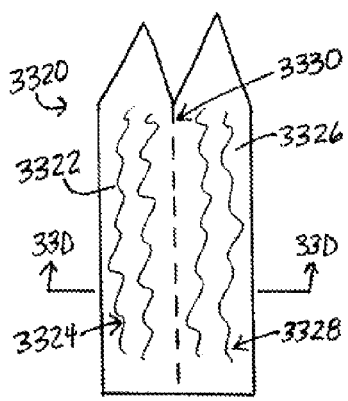
Figure 33D:
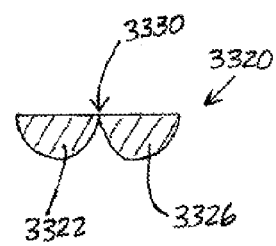
Figure 33E:
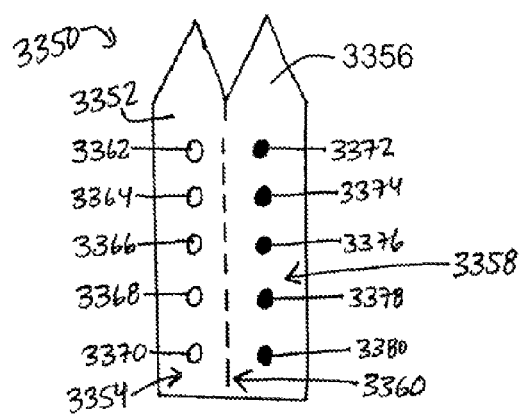

In certain variations, one or more of the portions may have a modified surface and/or one or more other features that help to maintain the coupling between the portions. For example, FIGS. 33C and 33D show a plug (3320), with FIG. 33D being a cross-sectional view of the plug taken along line 33D-33D in FIG. 33C. Plug (3320) has a first portion (3322) with an interior surface (3324) and a second portion (3326) with an interior surface (3328). The interior surfaces are textured to provide enhanced engagement between the interior surfaces when the two portions are folded toward each other around a hinge (3330). Other suitable engagement mechanisms may be used. As an example, FIG. 33E shows a plug (3350) comprising a first portion (3352) having an interior surface (3354) and a second portion (3356) having an interior surface (3358). The first and second portions may be folded toward each other around a hinge (3360), so that the surfaces contact each other and couple to each other, thereby entrapping one or more tethers (not shown) therebetween. Interior surface (3354) comprises holes (3362), (3364), (3366), (3368), and (3370), and interior surface (3358) comprises corresponding protrusions (3372), (3374), (3376), (3378), and (3380) sized to snap into the holes on interior surface (3354), thereby helping to secure second portion (3356) to first portion (3352).

While the first and second portions of the plugs shown in FIGS. 33A-33E are mirror images of each other, in some variations, a plug may comprise two or more portions that are not mirror images of each other. Moreover, the different portions of a plug may have different sizes.

Figure 34A:
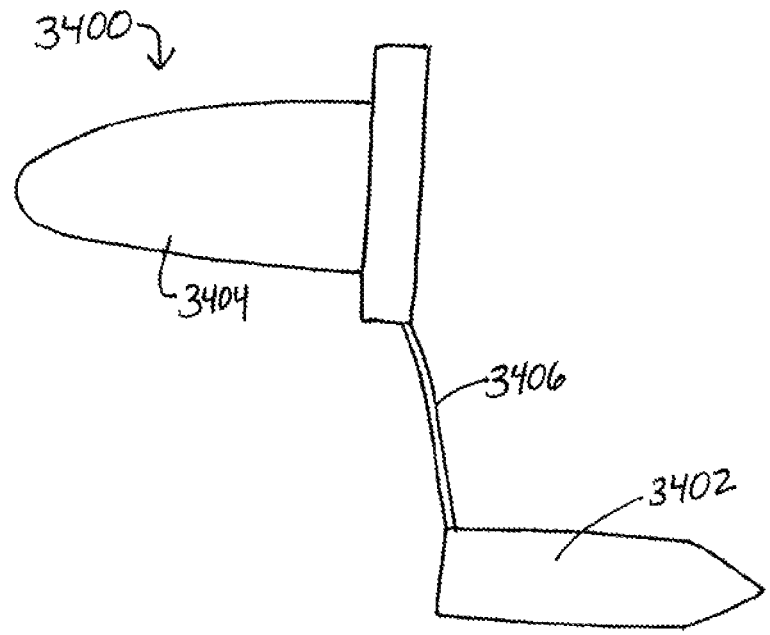
FIGS. 34A-34C depict variations of a device and a method for locking a tether.

In certain variations, a locking device may comprise a plug and a locking member that are coupled to each other. The locking member and the plug may be coupled in any of a number of different ways. As an example, FIG. 34A shows a locking device (3400) comprising a plug (3402) and a locking member (3404) configured to receive the plug. The locking member and the plug are coupled to each other by a coupling member (3406) (as shown, in the form of a tether, although other suitable coupling members may alternatively or additionally be used). While one coupling member is shown, in some variations, a locking member and a plug may be coupled by multiple coupling members. Coupling member (3406) may be attached to at least one of plug (3402) and locking member (3404), and/or may be integral with at least one of plug (3402) and locking member (3404). Locking device (3400) may be formed using, for example, injection molding.

Figure 34B:
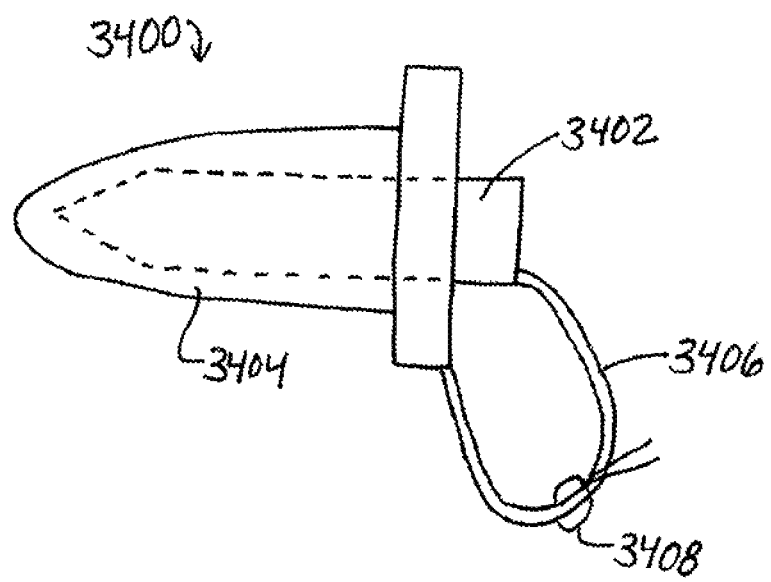

As shown in FIG. 34B, during use, plug (3402) may be fitted into locking member (3404) (e.g., to secure a tether therebetween). Should plug (3402) inadvertently become decoupled from locking member (3404), the coupling between the plug and the locking member may limit the likelihood of one or both of the components traveling to a non-target location. For example, the locking member may have one or more apertures in a wall portion through which a tether is threaded. If the plug becomes unplugged from the locking member, the plug may still remain at the target site because it is coupled to the locking member which, in turn, is coupled to the tether. In some variations, the coupled plug and locking member may be used in a procedure in which the plug and locking member are not contained within a device or device component, such as a catheter. In certain variations, and as shown in FIG. 34B, coupling member (3406) may be slidably or fixedly attached to an anchor (3408) which may, in turn, be affixed to tissue at a target site, thereby helping to retain locking device (3400) at the target site.

Figure 34C:
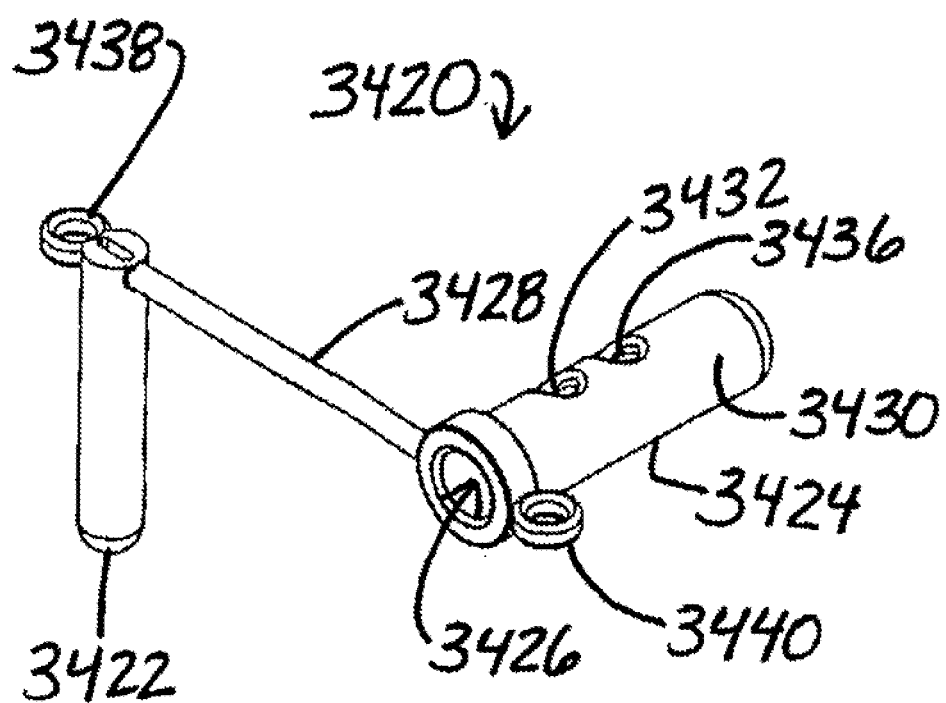

Locking devices comprising components that are coupled to each other by at least one coupling member may have any suitable configuration. For example, FIG. 34C shows a locking device (3420) comprising a plug (3422), a locking tube (3424) configured to receive plug (3422) within a lumen (3426), and a coupling member (3428) coupling plug (3422) to locking tube (3424). Locking tube (3424) comprises a wall portion (3430) having two apertures (3432) and (3436) for passage of a tether therethrough. Additionally, plug (3422) and locking tube (3424) each comprise a tether ring (3438) and (3440), respectively. A tether (not shown) may be passed through one or both of these tether rings, and may then be secured to a target site (e.g., by attaching the tether to tissue at the target site). This may help to retain locking device (3420) at the target site. Tether rings are discussed in further detail below.

Figure 35A:
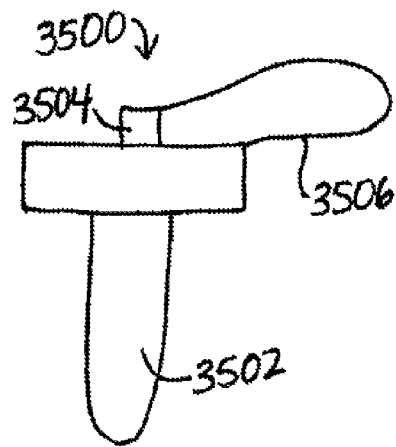
FIGS. 35A-35D show variations of a device for locking a tether.
Figure 35B:
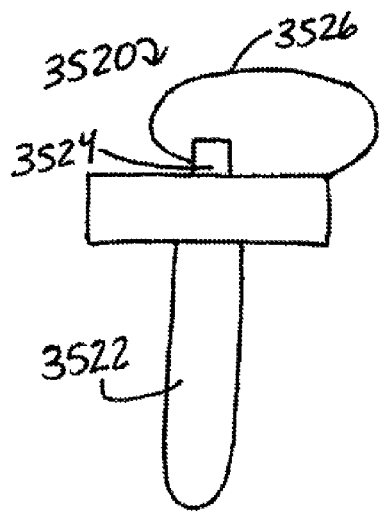
Figure 35C:
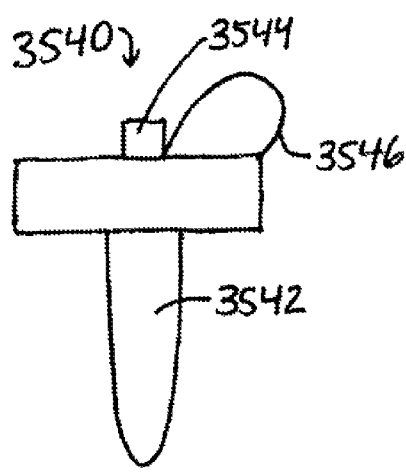
Figure 35D:
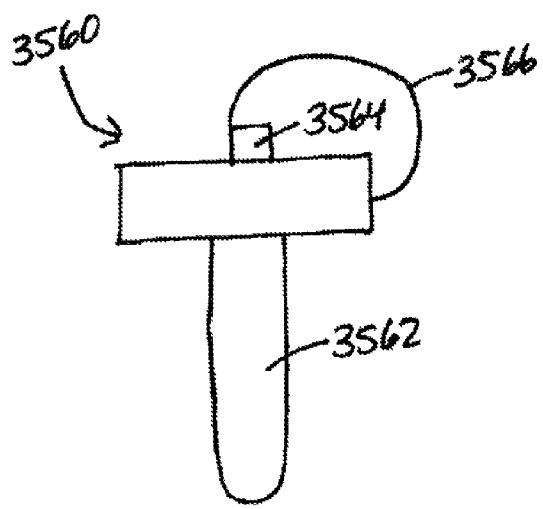

A coupling member may be attached to at least two components of a locking device at any appropriate location on the components. For example, FIG. 35A shows a variation of a locking device (3500) comprising a locking member (3502) coupled to a plug (3504) by a coupling member (3506). FIG. 35B shows another variation of a device (3520) comprising a locking member (3522) coupled to a plug (3524) by a coupling member (3526). FIG. 35C shows an additional variation of a device (3540) comprising a locking member (3542) coupled to a plug (3544) by a coupling member (3546). Finally, FIG. 35D shows a variation of a device (3560) comprising a locking member (3562) coupled to a plug (3564) by a coupling member (3566). Other coupling member configurations and attachment positions may also be used.

Figure 36:
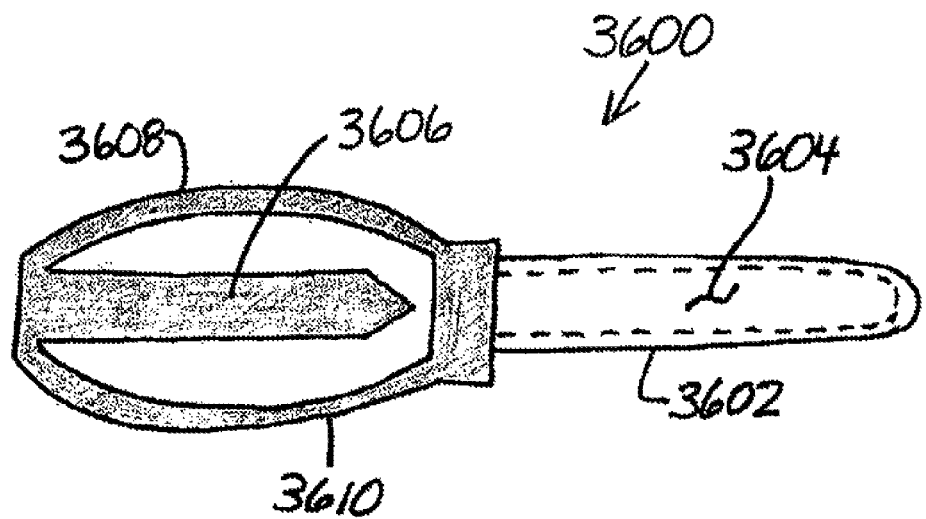
FIG. 36 shows a variation of a device for locking a tether.

FIG. 36 shows an additional variation of a locking device comprising a plug and a locking member that are coupled to each other. As shown there, a locking device (3600) comprises a locking member (3602) having a hollow portion (3604). Locking device (3600) also comprises a plug (3606) comprising two flexible coupling portions (3608) and (3610) configured to couple the plug to the locking member. More specifically, the coupling portions are configured to flexibly allow plug (3606) to slide into locking member (3602) (i.e., to advance plug (3606) into hollow portion (3604) of locking member (3602)). In some variations, locking device (3600) may be formed by molding hollow portion (3604) and plug (3606). In certain variations, the hollow portion and the plug may be molded on two different levels (e.g., so that the hollow portion may be formed using a mandrel that does not interfere with formation of the plug). Other configurations may be used. For example, a plug may be disposed in a sheath, and a tubular member may be advanced into the sheath to engage the plug.

Figure 37:
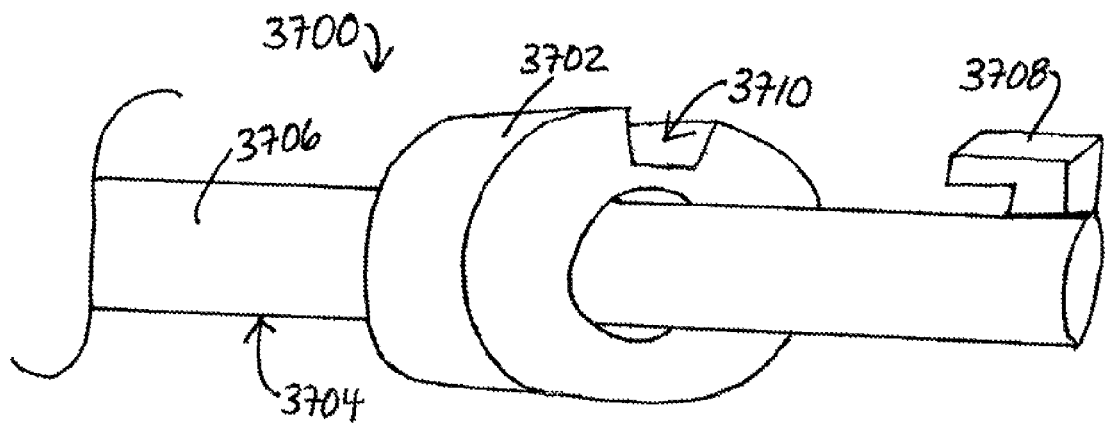
FIG. 37 is a perspective view of a variation of a device for locking a tether.

Another variation of a locking device (3700) is depicted in FIG. 37. As shown there, locking device (3700) comprises a ring-shaped locking member (3702) surrounding a plug member (3704) comprising an elongated portion (3706) and a plug portion (3708). Plug portion (3708) is configured to fit within a cut-out (3710) in ring-shaped locking member (3702) when plug portion (3708) is advanced toward ring-shaped locking member (3702) and/or ring-shaped locking member (3702) is advanced toward plug portion (3708). Ring-shaped locking member (3702) and plug portion (3708) are configured to secure a tether therebetween.

Figure 38:
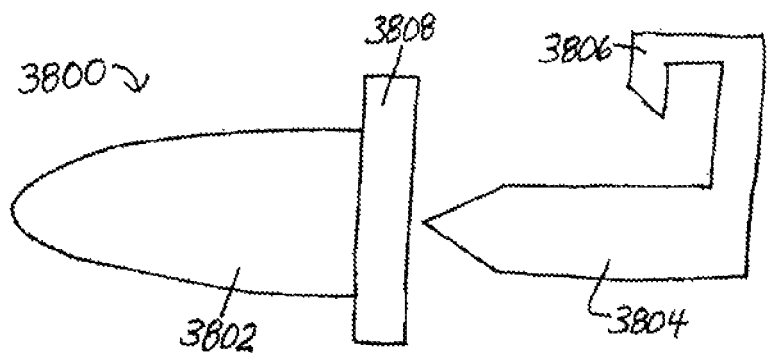
FIG. 38 is a side view of a variation of a device for locking a tether.

In certain variations, one or more components of a locking device may comprise at least one hook configured to engage one or more other components of the locking device. For example, FIG. 38 shows a locking device (3800) comprising a locking member (3802) having a hollow portion (not shown). Locking device (3800) also comprises a plug (3804) configured to at least partially fit within the hollow portion of the locking member. Plug (3804) has a hooked distal region (3806) that hooks onto a rim (3808) on locking member (3802) when the plug is advanced into the locking member. This hooked distal region may form a living hinge with the rest of the plug body that allows the hooked distal region to move to fit around rim (3808). While a rim is shown, in some variations, a locking member may include a notch, and the hooked distal region may couple to the notch. This may, for example, allow the locking device to maintain a relatively low profile.

Figure 39A:
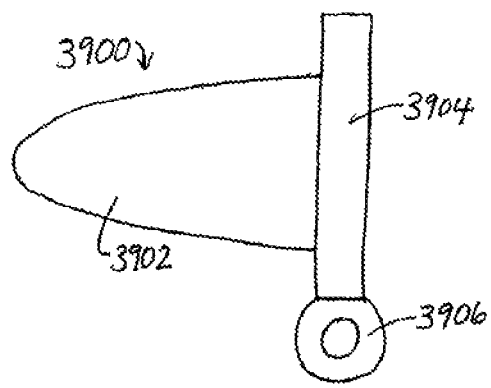
FIGS. 39A-39E are side views of variations of components of a device for locking a tether.
Figure 39B:
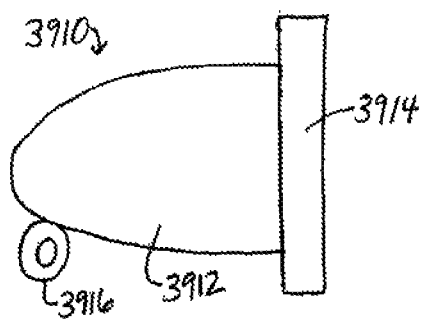
Figure 39C:
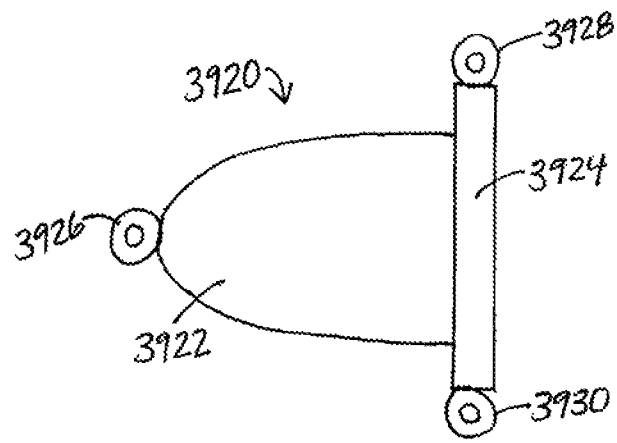

As described above, in certain variations, one or more components of a locking device may comprise at least one tether ring configured for passage of a tether therethrough. For example, FIG. 39A shows a locking member (3900) comprising a body portion (3902) and a rim (3904), as well as a tether ring (3906) coupled to or integral with rim (3904). FIG. 39B shows a locking member (3910) comprising a body portion (3912) and a rim (3914), as well as a tether ring (3916) coupled to or integral with body portion (3912). In some variations, a locking component may have multiple (e.g., two, three, four, five) tether rings. The tether rings may all be of the same size, or may have different sizes. For example, FIG. 39C shows a locking member (3920) comprising a body portion (3922) and a rim (3924), as well as a tether ring (3926) coupled to or integral with body portion (3922) and two tether rings (3928) and (3930) coupled to and/or integral with rim (3924). During use, one or more tethers (not shown) may be threaded through one or more of the tether rings and, for example, may be secured to tissue (e.g., a ventricle wall) at the target site.

Figure 39D:
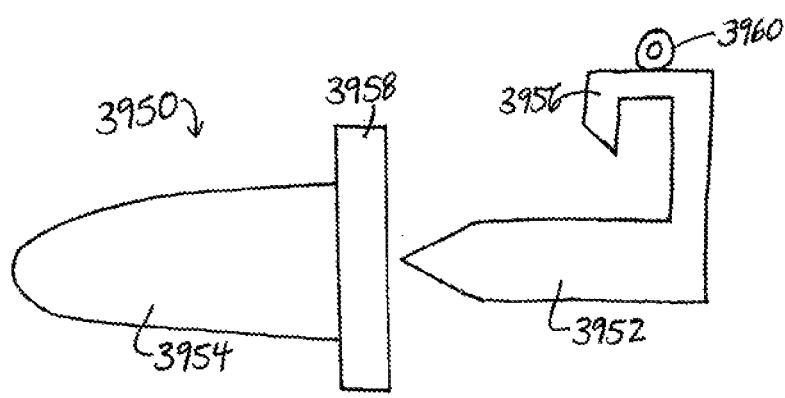
Figure 39E:
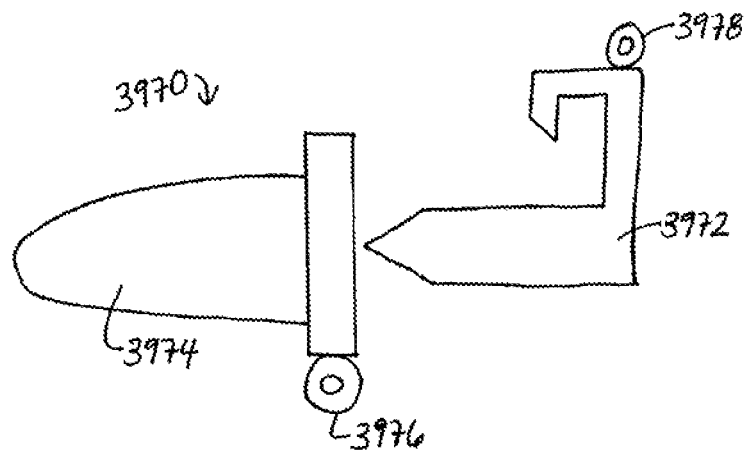

While locking members comprising tether rings have been shown, other components of locking devices may alternatively or additionally include one or more tether rings. For example, FIG. 39D shows a locking device (3950) comprising a plug (3952) and a locking member (3954) configured to receive the plug. Plug (3952) has a hooked distal region (3956) that hooks onto a rim (3958) on locking member (3954) when the plug is advanced into the locking member. Moreover, plug (3952) comprises a tether ring (3960) that may be used, for example, to secure plug (3952) to body tissue via a tether. In some variations, a tether ring may be used to help position one or more components of a locking device in the correct locking location. For example, a tether may be threaded through a tether ring on a plug, and the plug may be advanced along the tether to the target locking site. In certain variations, a locking device may comprise multiple components having tether rings. As an example, FIG. 39E shows a locking device (3970) comprising a plug (3972) and a locking member (3974) configured to receive the plug. Both the locking member and the plug comprise a tether ring. More specifically, locking member (3974) comprises a tether ring (3976), and plug (3972) comprises a tether ring (3978).

Figure 40A:
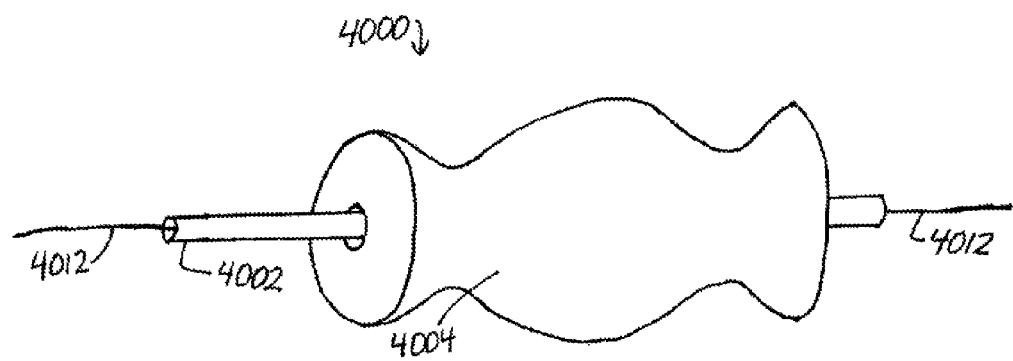
FIG. 40A is a side perspective view of a variation of a device for locking a tether.
Figure 40B:
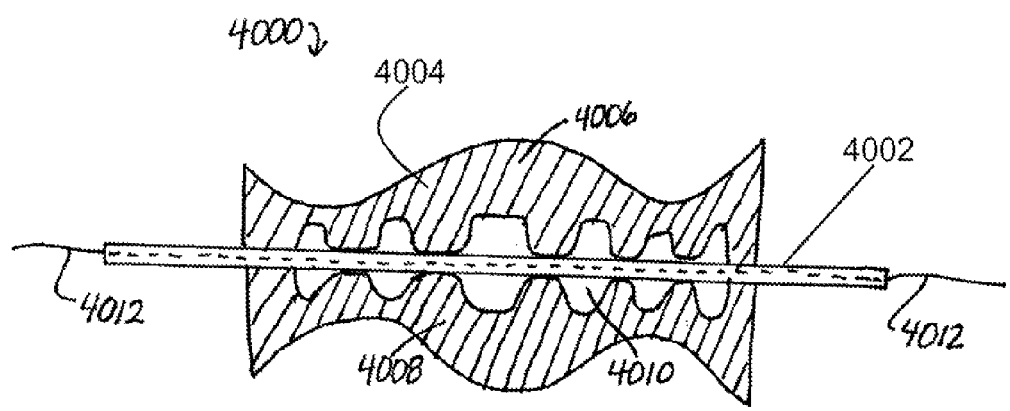
FIGS. 40B and 40C are side views in partial cross-section of the device of FIG. 40A.
Figure 40C:
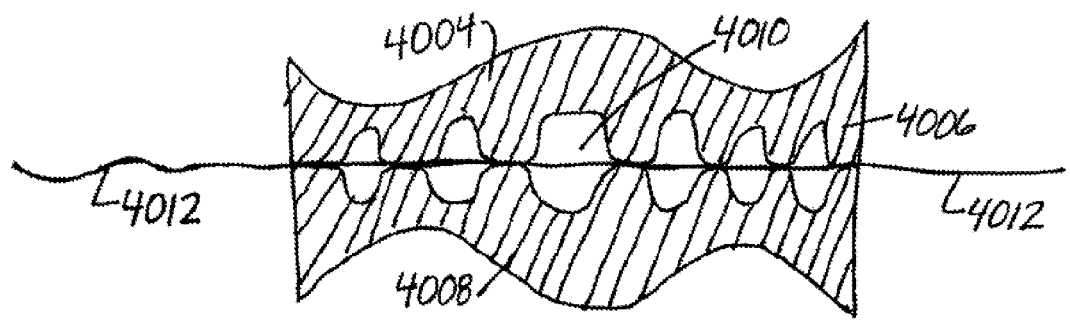

While locking devices comprising plugs and various locking member configurations have been shown, in some cases, other types of locking devices may be used to secure one or more tethers. For example, FIGS. 40A-40C illustrate variations of a locking device (4000) and a related method. As shown in FIGS. 40A and 40B, locking device (4000) comprises a tubular member (4002) and a locking member (4004). In FIGS. 40A and 40B, the locking member is in an open configuration. Locking member (4004) comprises a first clamping portion (4006), a second clamping portion (4008), and a hollow region (4010) therebetween. Hollow region (4010) is configured to receive at least a portion of tubular member (4002) when the locking member is in the open configuration. A tether (4012) is threaded through the tubular member.

Referring now to FIG. 40C, locking member (4004) can be changed from an open configuration to a closed configuration by withdrawing tubular member (4002) from hollow region (4010). As shown, the tubular member has been withdrawn without also withdrawing the tether. This may be achieved, for example, by temporarily holding the tether in place (e.g., with a clamp) while withdrawing the tubular member over the tether. In the closed configuration, first clamping portion (4006) clamps against second clamping portion (4008), thereby securing tether (4012) therebetween.

Locking device (4000) may be deployed using, for example, a catheter comprising an outer sheath, a pushing member, and a tubular member that is a slidable element within a lumen of the pushing member. The locking device may initially be constrained within the catheter. When the tubular member is retracted, the frictional forces between the tubular member and the locking device may pull the locking device proximally up against the pushing member. This may prevent further movement of the locking device, and the tubular member may slide proximally, thereby causing locking device (4000) to clamp down on a tether. Subsequently, the pushing member may be pushed distally to release the locking device from the catheter.

Figure 41:
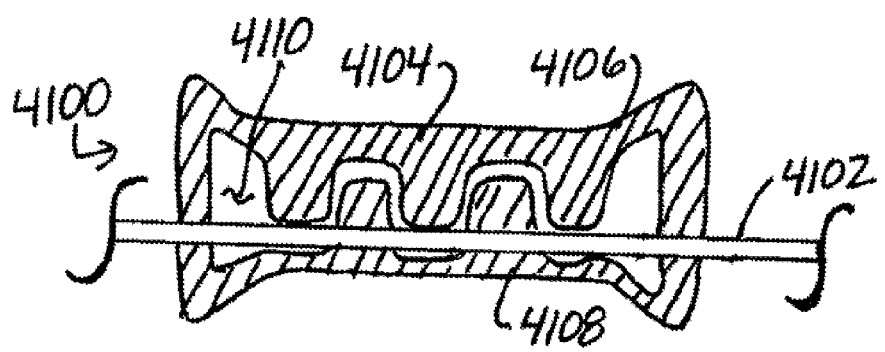
FIG. 41 is a side view in partial cross-section of another variation of a device for locking a tether.

While locking member (4004) comprises clamping portions (4006) and (4008) having a particular configuration, locking members comprising clamping portions with different configurations may also be used. For example, FIG. 41 shows a locking device (4100) comprising a tubular member (4102) and a locking member (4104) having two clamping portions (4106) and (4108) and a hollow region (4110) therebetween. In its open configuration (shown in FIG. 41), locking member (4104) is configured to hold at least a portion of tubular member (4102) in hollow region (4110). However, when tubular member (4102) is withdrawn or otherwise removed from locking member (4104), locking member (4104) assumes its closed configuration, in which the clamping portions of the locking member clamp together (e.g., thereby securing a tether (not shown) therebetween).

FIGS. 42A-42G show another variation of a locking device (4200), this variation comprising a collet (4201) and a sleeve (4203) configured to surround at least a portion of the collet to clamp a tether within the collet. Collet (4201) and/or sleeve (4203) may be formed of, for example, one or more metals (e.g., titanium), metal alloys (e.g., Nitinol, stainless steel), and/or one or more polymers (e.g., PEEK). The collet and sleeve may be formed of the same materials, or different materials. They may be formed using, for example, conventional machining methods, electrical discharge machining (EDM), laser cutting, metal injection molding, and/or phase injection molding. Collet (4201) is a single-slit design with a proximal feature (4220) that allows for attachment to the rest of device (4200), as well as a radiused distal end (4222), and a collet body (4221) therebetween. While a single-slit configuration is shown, other collet configurations may also be used, as discussed in further detail below. Sleeve (4203) comprises a rigid or semi-rigid tube with an internal diameter that closely matches the outer diameter of collet body (4221). Sleeve (4203) is coupled to an elongated tubular portion (4204). During use of locking device (4200), sleeve (4203) may slide over collet body (4221), thereby forcing the collet body to compress. This may cause the collet body to secure a tether (4208) routed through slit (4230).

Figure 42A:
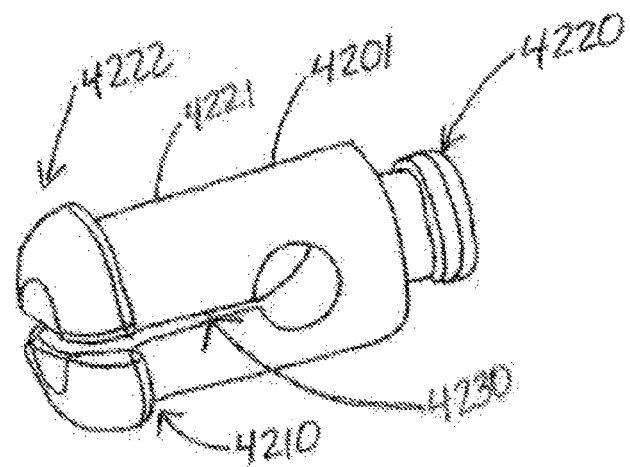
FIG. 42A is a perspective view of a variation of a component of a device for locking a tether.
Figure 42B:
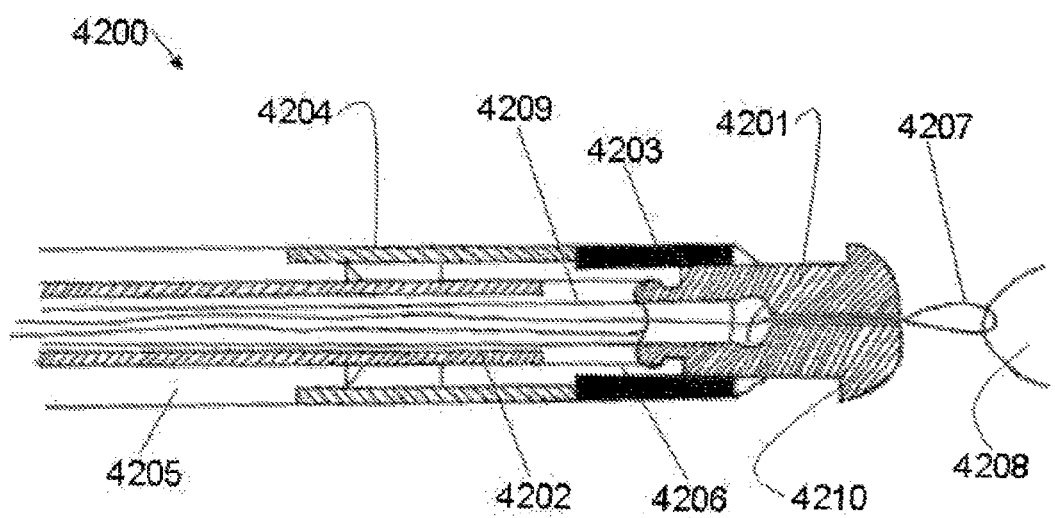
FIG. 42B depicts a device comprising the component of FIG. 42A, and FIGS. 42C-42G illustrate a variation of a method for locking a tether using a device comprising the component of FIG. 42A.

Referring to FIG. 42B specifically, the tether may be routed into the locking device using, for example, a lasso or snare (described in further detail below). Locking device (4200) comprises a series of concentric shafts that slide relative to each other to decouple the collet from the rest of the locking device, after the collet has been used to lock a tether. A release tube (4209) provides a lumen for the passage of a tether snare (4207) and tether (4208). Release tube (4209) may also be used to decouple collet (4201) from the rest of locking device (4200) by pushing the collet away from the rest of the locking device.

During use, tether (4208) is drawn into locking device (4200) through release tube (4209) using snare (4207). The locking device is then advanced over tether (4208) until collet (4201) reaches the desired locking location. At the desired locking location, tether (4208) may be tensioned to provide a cinching effect, and sleeve (4203) may be pushed over collet (4201) using a pushing member (4205). When sleeve (4203) comes into contact with a stop (4210) on collet (4201), pushing member (4205) retracts to expose an interlocking collet feature (4206) and the distal end of a pull tube (4202). Release tube (4209) may then be advanced distally, causing collet (4201) to decouple from the rest of locking device (4200).

Figure 42C:
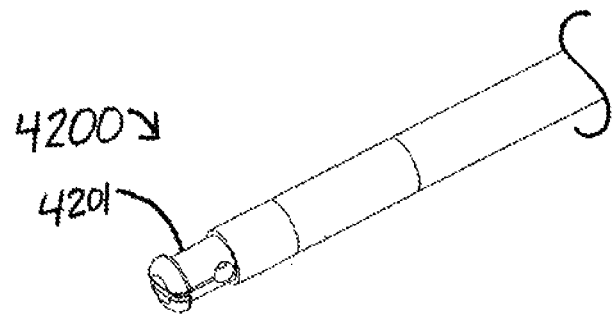
Figure 42D:
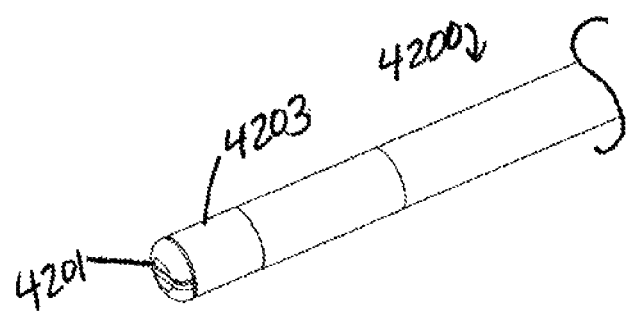
Figure 42E:
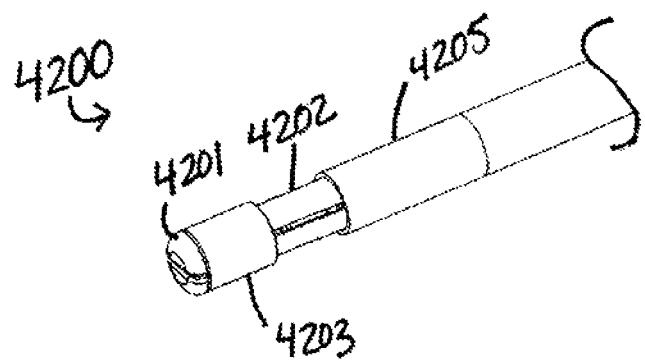
Figure 42F:
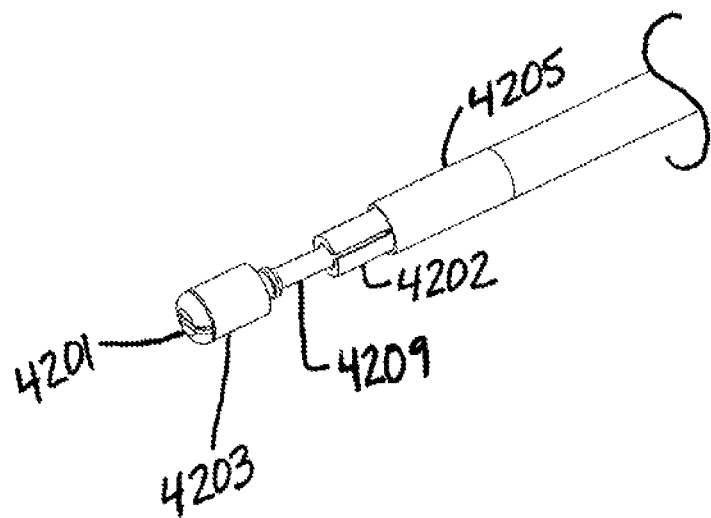
Figure 42G:
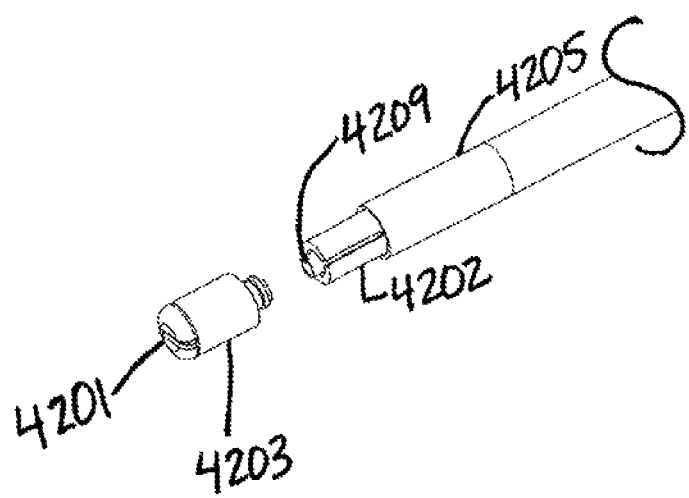

A method of using locking device (4200) to lock a tether is shown more in more detail in FIGS. 42C-42G. First, FIG. 42C shows locking device (4200), including collet (4201), prior to deployment. FIG. 42D shows locking device (4200) after deployment, when sleeve (4203) has slid over collet (4201) and forced the collet to collapse, thereby securing tether (4208) (FIG. 42B). As shown in FIG. 42E, push tube (4205) may then be retracted to expose the distal end of pull tube (4202). Referring to FIG. 42F, release tube (4209) may then be used to release collet (4201). Finally, and referring now to FIG. 42G, release tube (4209) may be retracted after collet (4201) and sleeve (4203) have been released from the rest of locking device (4200).

Figure 43A:
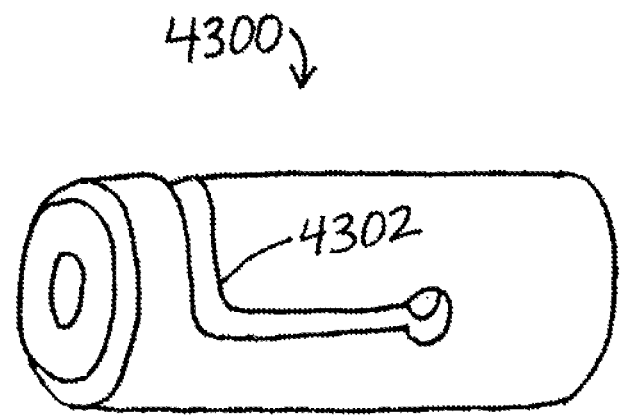
FIGS. 43A and 43B are perspective views of variations of devices for locking a tether.
Figure 43B:
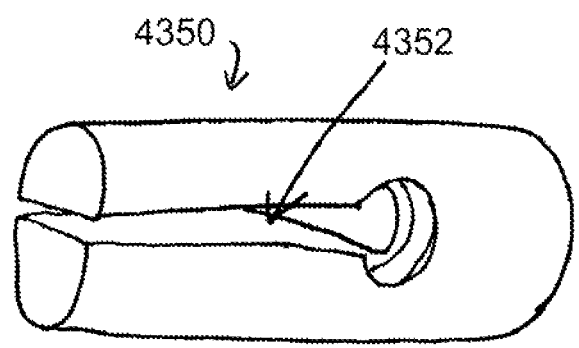

While a certain variation of a collet has been shown and described, any other suitable variations may be used. As an example, in some variations, a collet may be releasably coupled to a locking device by threading on the collet and/or one or more other components of the locking device. The number of threads on the collet and/or other component or components may be selected to minimize the amount of turning required to release the collet, and may be, for example, one to three threads. In variations in which threading is used, the collet may be decoupled from the locking device (e.g., after the collet has been used to lock a tether) by rotating the locking device to release the collet. In certain variations, a collet may have a slotted key feature that couples the collet to the rest of a locking device (e.g., in which a protrusion on the collet keys into a slot on one of the other components of the locking device, or vice versa). In some variations, and referring now to FIG. 43A, a collet (4300) may include a guide hole (4302) to control placement of a tether inside the collet. This guide hole may, for example, keep the tether centered in the collet. In certain variations, and referring now to FIG. 43B, a collet (4350) may include a clearance cut (4352) that allows the collet to receive a tether without having to open particularly wide. The edges of the clearance cut may, for example, be radiused (e.g., to limit tether abrasion).

Some variations of locking devices may comprise a collet deployment mechanism (e.g., the distal portion of locking device (4200)) comprising one or more relatively rigid components. Alternatively or additionally, a collet deployment mechanism may comprise one or more relatively flexible components. A relatively rigid collet deployment mechanism may, for example, exhibit high structural integrity, which may be particularly advantageous for pushing the collet components. In some cases in which a relatively rigid collet deployment mechanism is used, the collet deployment components may be relatively short in length. As the length of the components decreases, the flexibility of the locking device and the maneuverability of its distal portion may increase.

Figure 44A:
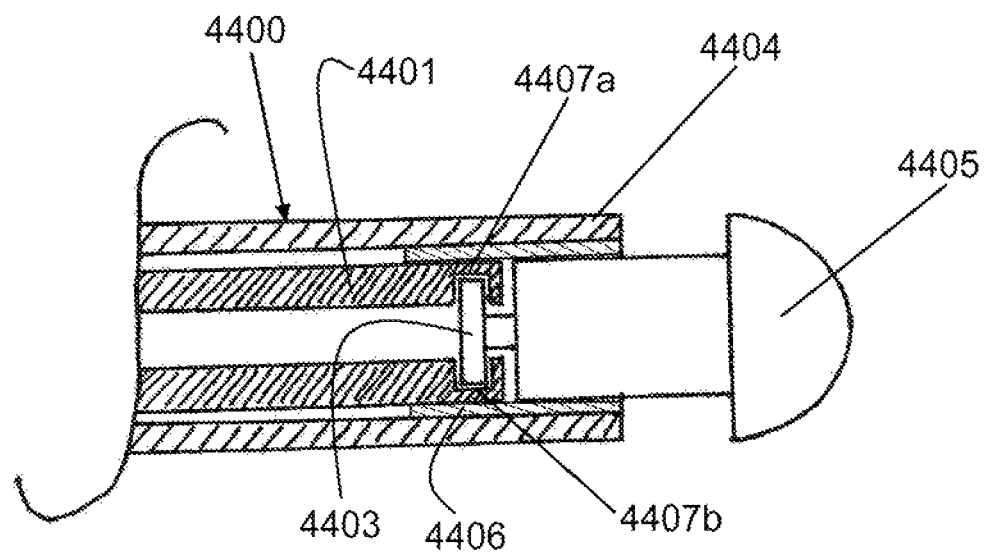
FIGS. 44A and 44B are side views in partial cross-section of different variations of devices that may be used to lock a tether.

One variation of a collet deployment mechanism is shown in FIG. 44A. As shown there, a locking device (4400) may be used to deploy a collet (4405) with a sleeve (4406). A tether may be secured, for example, by trapping it between collet (4405) and sleeve (4406), and/or within a slit in the collet, with the sleeve pressing down upon the slit to hold the tether in place. The proximal end (4403) of collet (4405) may be at least partially housed in a sheath (4404) of locking device (4400), and may be sized and shaped to be restrained by an interlocking collet feature (4401). Interlocking collet feature (4401), in turn is at least partially enclosed in sheath (4404). Interlocking collet feature (4401) includes two latches (4407a) and (4407b) that hook to the proximal end (4403) of collet (4405) and thereby retain the collet. When it is desired to release collet (4405), interlocking collet feature (4401) may be proximally withdrawn, drawing collet (4405) into sleeve (4406) (e.g., thereby securing and locking a tether). The interlocking collet feature may be further withdrawn in the proximal direction, so that latches (4407a) and (4407b) are no longer restrained and therefore separate from each other to release collet (4405). The combined collet and sleeve may then be deployed using, for example, a pushing member (not shown) of locking device (4400). Interlocking collet feature (4401) is also shown in FIG. 44C, where its collet coupling region (4408) is depicted as having a length (4402). In some variations, length (4402) may be, for example, from about 0.1 inch to about 0.75 inch.

Figure 44B:
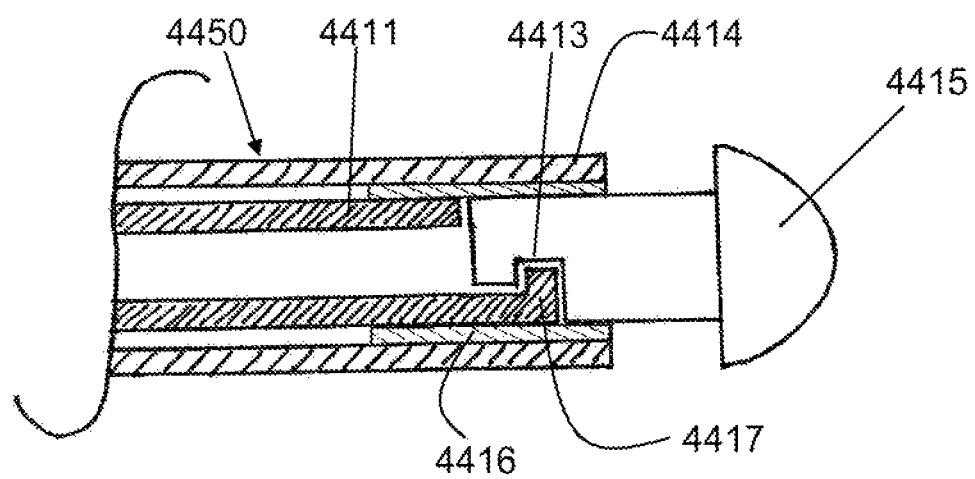
Figure 44C:
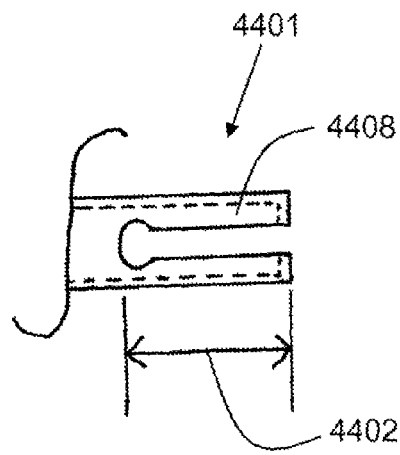
FIGS. 44C and 44D are side views of variations of components of devices that may be used to lock a tether.

Another variation of a collet deployment mechanism is depicted in FIG. 44B. FIG. 44B shows a locking device (4450) comprising a collet (4415) and a sleeve (4416). The proximal portion of collet (4415) has a groove (4413) configured to engage with an interlocking collet feature (4411) of device (4450). Interlocking collet feature (4411) is at least partially enclosed in a sheath (4414). Sheath (4414), as well as any other sheaths described here, may be formed of, for example, any suitably flexible material or materials, such as braided polyimide, or any similar braided material, or the like. Interlocking collet feature (4411) may retain collet (4415) via a single latch (4417) that fits into groove (4413).

Figure 44D:
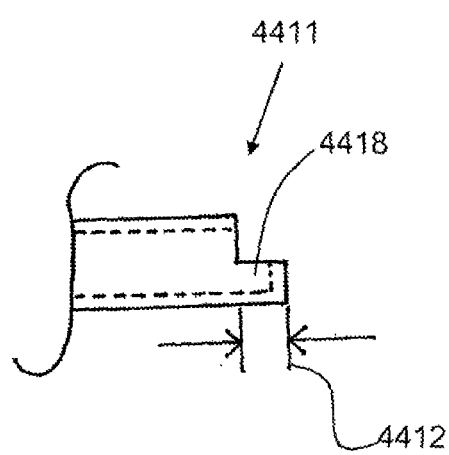

Interlocking collet feature (4411) is also shown in FIG. 44D, where its collet coupling region (4418) has a length (4412). In some cases, interlocking collet feature (4411), with its single latch (4417), may have a shorter collet coupling region than interlocking collet feature (4401), with its dual latches (4407a) and (4407b), as demonstrated by a comparison of length (4412) (FIG. 44D) to length (4402) (FIG. 44C). For example, length (4402) may be about 0.5 inch, while length (4412) may be about 0.25 inch. This difference in lengths may result from it being easier to deploy a collet by withdrawing a sheath over just one latch, in comparison to deploying a collet by withdrawing a sheath over two or more latches. As the number of latches in a collet coupling region increases, the length of the collet coupling region may also increase, in order to accommodate a greater outward expansion of the latches that may be required to effect collet release. While certain variations of interlocking collet features have been described, other variations of interlocking collet features may have other suitable configurations for releasably engaging a collet.

Other modifications to the collet geometry and/or interlocking collet feature may be made to reduce the length of the distal portion of the locking device. For example, some variations of collets may not have a distal cap (the dome-shaped structure in FIGS. 44A and 44B).

Figure 44E:
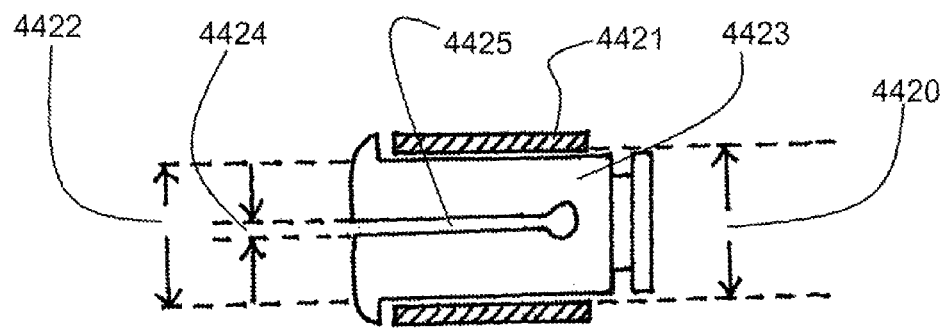
FIG. 44E is a side view in partial cross-section of a variation of a device that may be used to lock a tether.

Modifications to various collet and/or sheath dimensions may also be made to adjust the compressive force on a tether threaded through the collet. As an example, FIG. 44E shows a collet with a body (4423) restrained by a sheath (4421). Collet body (4423) has a slit (4425) having a dimension (4424), while collet body (4423) has a dimension (4422). Additionally, sheath (4421) has an inner diameter (4420). Modifying inner diameter (4420) of sheath (4421) with respect to dimension (4422) of collet body (4423) may alter the compressive force on a tether threaded through slit (4425) of collet (4423). In some variations, inner diameter (4420) and dimension (4422) may both be 0.085 inch, or dimension (4422) may be smaller than inner diameter (4420), which may reduce the compressive force on the tether. In certain variations, sheath (4421) may have first and second inner diameters, where the first inner diameter is a suitable size for receiving a collet, and the second inner diameter is a suitable size for retaining the collet with a desired compressive force. In some variations, the sheath may comprise one or more elastic materials. Modifying slit dimension (4424) may also alter the compressive force on the tether. Slit dimension (4424) may have any appropriate value (e.g., 0.006 inch), where a smaller width may result in a greater compressive force, while a larger width may result in a lesser compressive force.

Other features of the collet may alternatively or additionally be modified to effect different levels of compressive force on a tether threaded through the collet via slit (4425). Moreover, certain modifications may help to secure and lock a tether within slit (4425) of the collet. For example, a material with increased surface friction may be used to form the collet, the surface friction in the slit may be increased, the tether may be coated or otherwise modified to increase the surface friction on the tether, and/or the tether may have a relatively large diameter. Modifications such as these or other appropriate modifications may be made to the collet, sheath, and/or tether to ensure that the compressive force of the collet on the tether (or other force(s) relevant for retaining a tether in the collet) is sufficient to withstand the forces sustained during use, which may be, for example, approximately 2 lbs.

Figure 45A:
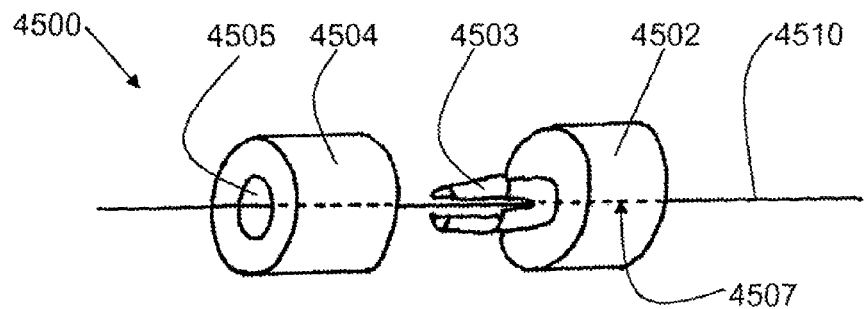
FIGS. 45A-45F illustrate variations of a device and method that may be used to lock a tether.

Collets that are used to clamp a tether may have any appropriate configuration. As shown above, in some variations, a sleeve may be used to essentially clamp a collet over a tether. For example, FIGS. 45A-45F depict a device (4500) comprising a collet (4502) comprising a pronged protrusion (4503) and a lumen (4507) therethrough. Lumen (4507) may be oriented along a longitudinal access of collet (4502) as illustrated, or may be oriented in any other suitable fashion. FIG. 45A depicts lumen (4507) extending through the entire length of collet (4502), however, in other variations, a lumen may extend through only a portion of the collet, and/or a collet may have multiple (e.g., two, three, four, five) lumens. Locking device (4500) also comprises a sleeve (4504) including an aperture (4505) sized and shaped to retain pronged protrusion (4503). As shown in FIGS. 45A and 45C, during use, a tether (4510) may be routed through aperture (4505) of sleeve (4504), and through lumen (4507) of collet (4502).

Figure 45B:
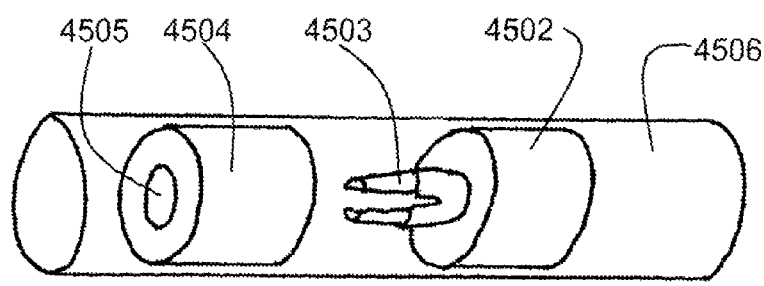
Figure 45C:
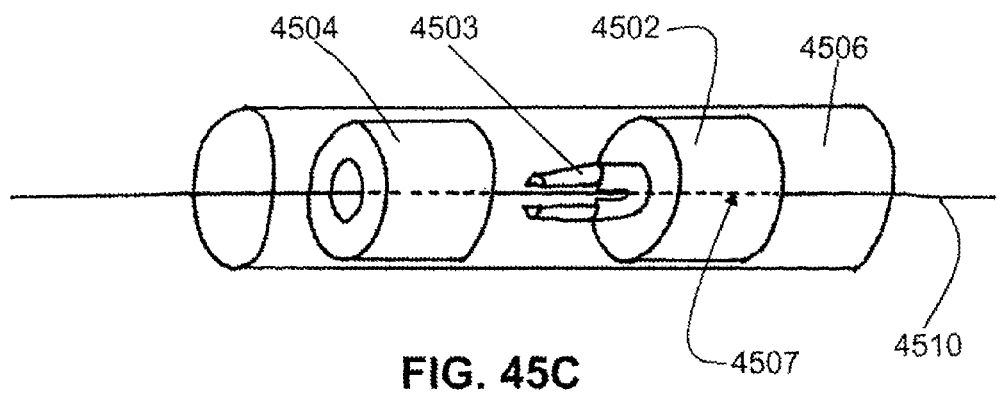
Figure 45D:
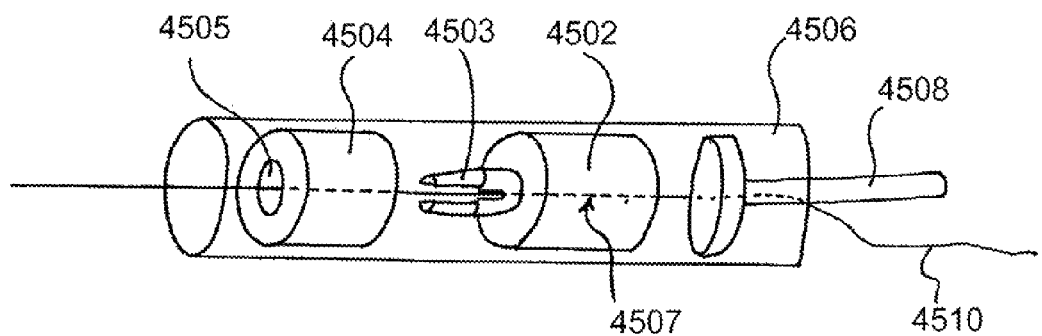
Figure 45E:
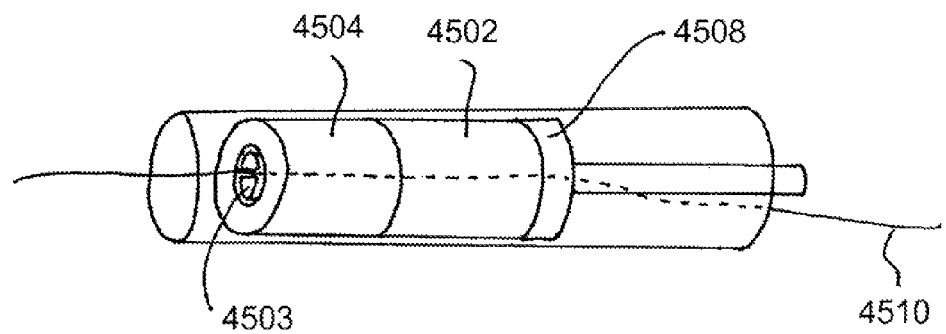
Figure 45F:
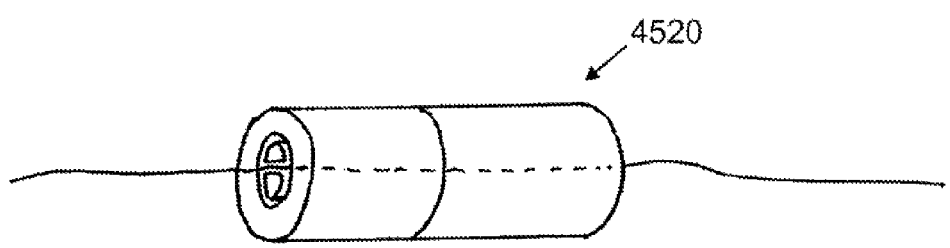

In some variations, locking device (4500) may also comprise an elongated tubular member (4506), and both collet (4502) and sleeve (4504) may be contained within the elongated tubular member, as shown in FIGS. 45B and 45C. FIGS. 45B and 45C depict a potential arrangement of collet (4502), sleeve (4504), and elongated tubular member (4506) prior to the deployment of collet (4502). Referring now to FIG. 45D, according to one method of deployment, collet (4502), sleeve (4504), and a rod (4508) may be arranged at least partially within elongated tubular member (4506). Tether (4510) may be threaded through sleeve (4504) and collet (4502), such that a portion of the tether passes through pronged protrusion (4503). The tether may be tensioned before it is threaded through the sleeve and collet, and/or may be tensioned after such threading. To secure tether (4510), rod (4508) may be actuated in the distal direction to push collet (4502) toward sleeve (4504), thereby engaging pronged protrusion (4503) with aperture (4505) of sleeve (4504). As a result, tether (4510) may become clamped, as shown in FIG. 45E. Pronged protrusion (4503) may be secured within aperture (4505) of sleeve (4504) by any suitable mechanism. For example, pronged protrusion (4503) may form a snap-fit or a friction fit with aperture (4505). As depicted in FIG. 45F, once the resulting collet-sleeve assembly (4520) has fixedly secured tether (4510), elongated tubular member (4506) may be withdrawn, and/or collet-sleeve assembly (4520) may be pushed out of elongated tubular member (4506) by advancing rod (4508) further distally.

Figure 45G:
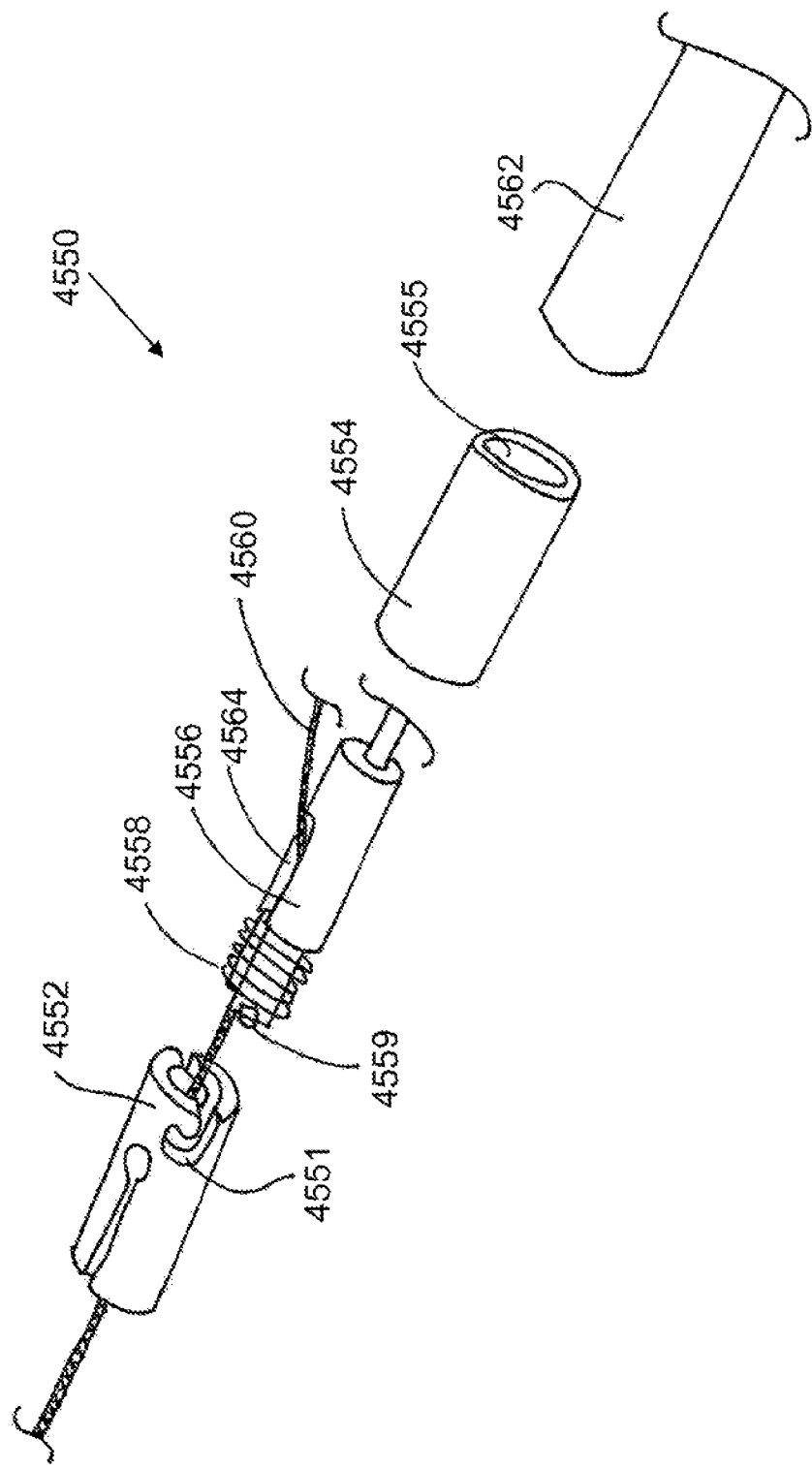
FIG. 45G is an exploded view of another variation of a device that may be used to lock a tether.

As shown in FIG. 45G, in some variations, a locking device comprising a collet may also comprise a collet coupler that may facilitate the interaction between the collet and a collet sleeve of the locking device. FIG. 45G shows a locking device (4550) comprising a collet coupler (4556) (as shown, comprising a protrusion (4559), although other appropriate configurations may be used). Collet (4552) comprises curved grooves (4551) shaped to mechanically interlock with a protrusion (4559) of collet coupler (4556). Collet coupler (4556) further comprises a slit (4564) and a spring (4558) that may function to engage protrusion (4559) and grooves (4551), thereby causing collet (4552) to be retained by the collet coupler (4556). Spring (4558) may help to engage collet (4552) onto collet coupler (4556) by applying a force that wedges protrusion (4559) within curved grooves (4551) (e.g., a spring-loaded compressive force may retain protrusion (4559) within curved grooves (4551)).

During use, a tether (4560) may be threaded through collet (4552), into collet coupler (4556), and through slit (4564). After the tether has been threaded through the collet and the collet coupler, the collet and collet coupler may be slid distally (e.g., toward a terminal anchor in a mitral valve repair procedure). Locking device (4550) also comprises a pushing member (4562) and a sleeve (4554). Pushing member (4562) may be used to push sleeve (4554) distally so that collet (4552) is seated in aperture (4555). In some variations, the diameter of collet (4552) may be slightly larger than the diameter of aperture (4555), such that when collet (4552) is retained in sleeve (4554), it is compressed. The compression of the collet may act to pinch tether (4560) and thereby secure it in the collet. During and/or after securement of the tether, pushing member (4562) may be retracted proximally. Collet (4552) may then be disengaged from collet coupler (4556) by, for example, compressing spring (4558) while sliding protrusion (4559) out from curved grooves (4551). This may allow for controlled and reversible engagement between collet (4552) and collet coupler (4556). For example, when the spring is compressed, collet (4552) may be moved with respect to collet coupler (4556) and when the spring is expanded, collet (4552) may be retained by collet coupler (4556) via protrusion (4559). While one variation of a retractable spring system is shown, in some cases, other suitable variations of retractable spring systems may be used to control the engagement between collet (4552) and collet coupler (4556).

Figure 46A:
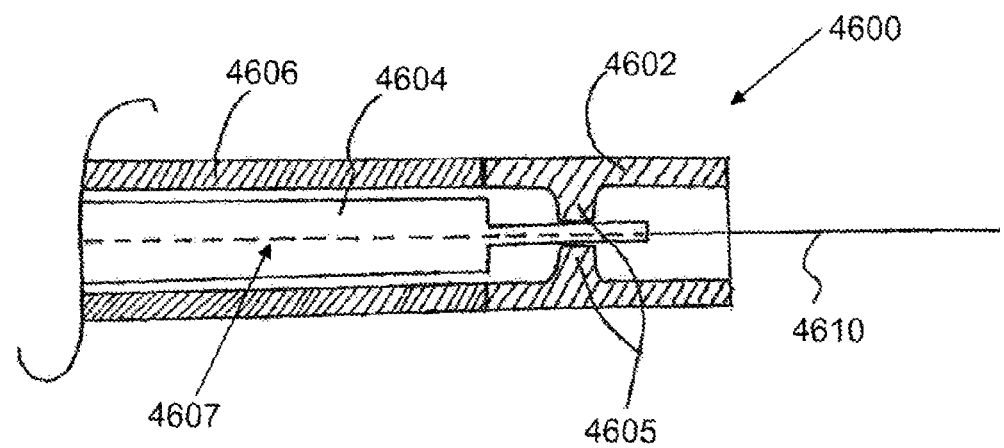
FIGS. 46A and 46B are partial cross-sectional views of a variation of a device that may be used to lock a tether.
Figure 46B:
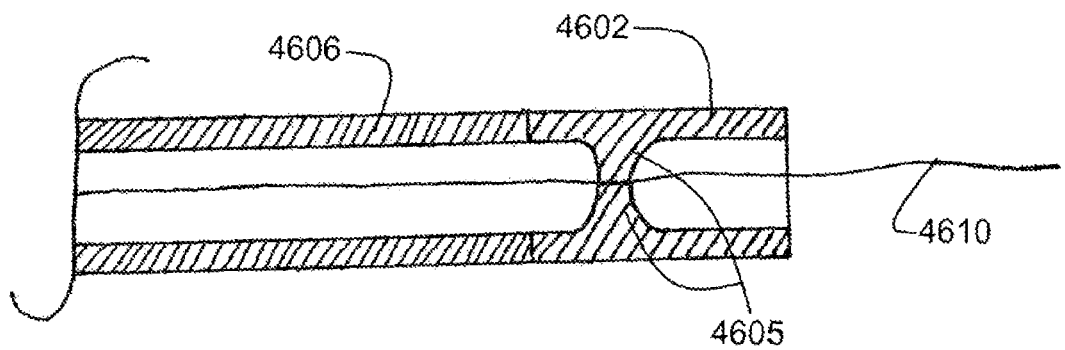

While sleeves have been shown and described, in some variations, a collet may be used to lock a tether without the use of a sleeve. Such a collet may, for example, be temporarily expanded to receive a tether, and then allowed to collapse back onto the tether to lock the tether. As an example, FIGS. 46A and 46B show a locking device (4600) comprising an elongated tubular member (4606), a mandrel (4604), and a collet (4602). Mandrel (4604) is disposed within elongated tubular member (4606), and also is inserted between protrusions (4605) of collet (4602). As shown, mandrel (4604) may have a longitudinal lumen (4607) therethrough that is sized and shaped for the passage of a tether. Mandrel may be generally cylindrical as shown in FIG. 46A (in which the mandrel actually comprises two cylindrical portions), or may have any other suitable geometry (e.g., rectangular, triangular, or the like).

Collet (4602) has an open configuration (FIG. 46A), and a closed configuration (FIG. 46B). In the open configuration, protrusions (4605) are not in contact with each other, and tether (4610) may slide through collet (4602). By contrast, in the closed configuration, protrusions (4605) contact each other, thereby locking tether (4610) in place. Any suitable mechanism may be used to convert collet (4602) from its open configuration to its closed configuration. According to one mechanism, collet (4602) may be formed of an elastic or shape-memory material, e.g., nickel titanium alloys, such as Nitinol, such that collet (4602) has a relaxed state in which protrusions (4605) fully contact each other (i.e., a closed configuration), as shown in FIG. 46B. The collet may be converted to an open configuration, as shown in FIG. 46A, by wedging mandrel (4604) between protrusions (4605). In the open configuration, tether (4610) may be slidable through collet (4602). To secure tether (4610) within collet (4602), mandrel (4604) may be withdrawn proximally, so that it is no longer located between protrusions (4605). During such withdrawal, the tether may, for example, be held in place (e.g., clamped), so that it is not also withdrawn. As depicted in FIG. 46B, in the absence of the mandrel, the protrusions (4605) may close so that they contact each other and thereby clamp tether (4610).

Figure 46C:
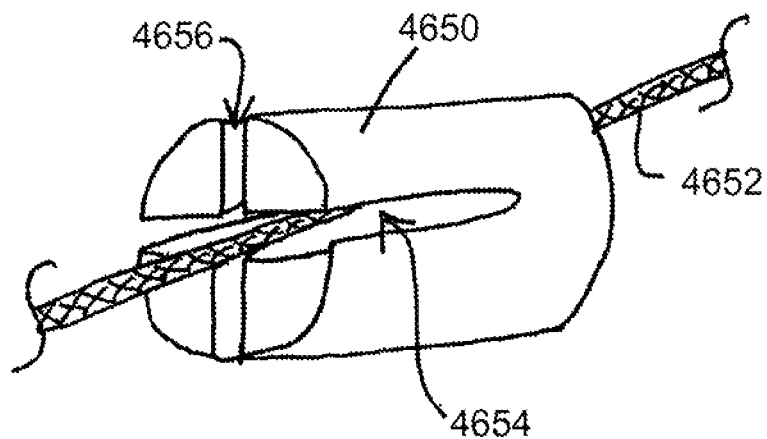
FIGS. 46C and 46D are perspective views of variations of devices for locking a tether.
Figure 46D:
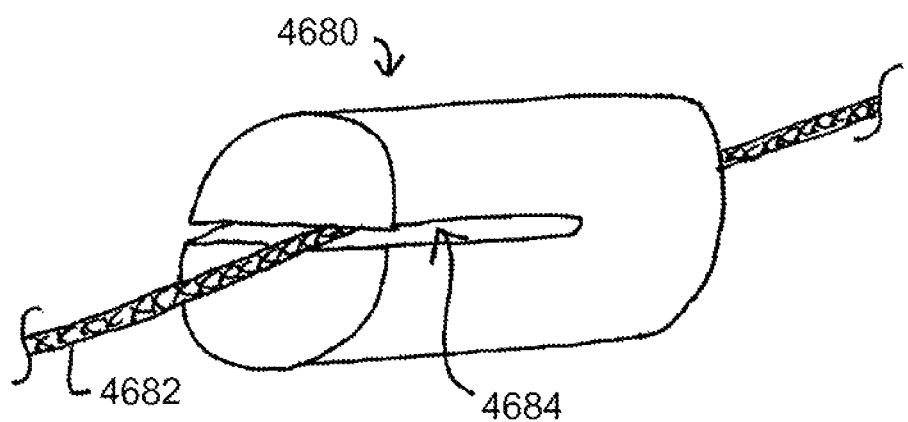

FIGS. 46C and 46D each show additional variations of sleeveless collets (4650) and (4680), respectively. Sleeveless collet (4650) has a horizontal slot (4654) and a vertical slot (4656) sized and shaped for the passage of a tether (4652) therethrough, and sleeveless collet (4680) has a horizontal slot (4684) sized and shaped for the passage of a tether (4682) therethrough. The collets may be temporarily expanded by, for example, pushing a spreading mandrel into their horizontal slots, and/or by loading the collets over a spreading mandrel. Sleeveless collets may, for example, be formed of spring steel and/or one or more other suitable materials.

Still other variations of tether locking devices may be used. In some variations, a locking device may comprise a one-piece locking component that is slid over a tether and then crimped into place with the tether trapped inside. The locking component may be formed of, for example, a malleable metal, such that the locking component may be collapsed by drawing the locking component into a catheter with a smaller inner diameter. As another example, a polymer locking component may be configured to snap together and lock when it is drawn into a catheter. In certain variations, a locking component may be formed of a shape-memory alloy (e.g., Nitinol), such that the locking component may be held open during delivery and then allowed to collapse onto a tether to lock the tether.

In some variations, a locking component may be in the form of a self-collapsing tube that is propped open by a catheter shaft. In use, the tube may be pushed off the catheter shaft to allow the tube to collapse and clamp on a tether. The tube may be made of, for example, a spring-like material (e.g., Nitinol) or any other suitable material. In some variations, the tube may initially have an elliptical cross-section. In certain variations, the tube may comprise a liner made of one or more polymers (e.g., polyurethane) that fill up any gaps inside the tube. The tube may be propped open into a more circular shape by the catheter shaft. A tether may run through the inner lumen of the catheter shaft freely so that the tube may be advanced over the tether to the target locking site by advancing the catheter shaft over the tether. At the target locking site, tension may be applied to the tether to provide a cinching effect, and the tube may then be pushed off the delivery catheter shaft, leading to its collapse onto the tether.

In some variations, a tether-locking effect may be achieved by deploying a spring element that expands outward to clamp a tether against an outer tube. For example, a locking device may comprise an inner spring element disposed within an outer tube, with a catheter shaft propping up a space between the inner spring element and the outer tube. During use, a tether may be routed through the inner lumen of the catheter shaft, and the tube-spring combination may be pushed off the end of the catheter shaft to remove the compressive effect of the catheter shaft and allow the spring to expand outward, thereby clamping the tether against the outer tube.

While certain variations of tether-locking tubular members have been shown, additional variations of tubular members may be used to lock a tether. As an example, FIGS. 47A and 47B show a locking tube (4700). Locking tube (4700) comprises a wall portion (4702) and a lumen (4704). Four apertures (4706), (4708), (4710), and (4712) are formed in wall portion (4702). Two of the apertures (4706) and (4710) are generally circular, while the other two apertures (4708) and (4712) are horseshoe-shaped. In use, a tether may be threaded through at least one of the apertures. Threading the tether through one or more of the horseshoe-shaped apertures may help to secure the tether, at least because the tether may become somewhat compressed by the walls of the aperture or apertures. Additionally, in some variations, a locking effect may be enhanced by, for example, threading a tether through one of the horseshoe-shaped apertures in one direction (e.g., the direction of arrow (4703) in FIG. 47A), and then pulling the tether in the opposite direction to cause the horseshoe shape to effectively dig into the tether and secure it. While not shown, in certain variations, a plug may be advanced into the lumen of the locking tube to provide an additional locking effect on the tether.

While FIGS. 47A and 47B show one variation of a locking tube, other variations may be used. For example, FIG. 48 shows a locking tube (4800) having only horseshoe-shaped apertures (4802) and (4804), while FIG. 49 shows a locking tube (4900) having only elongated slits (4902), (4904), (4906), and (4908). A locking tube may have any suitable number, combination, size, shape, and configuration of apertures (e.g., holes, slits, etc.).

Figure 50A:
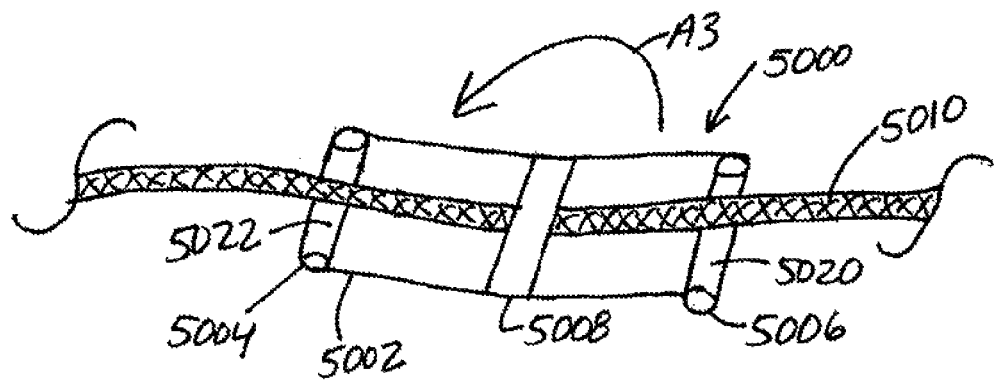
FIGS. 50A and 50B depict further variations of a device and a method for locking a tether.
Figure 50B:
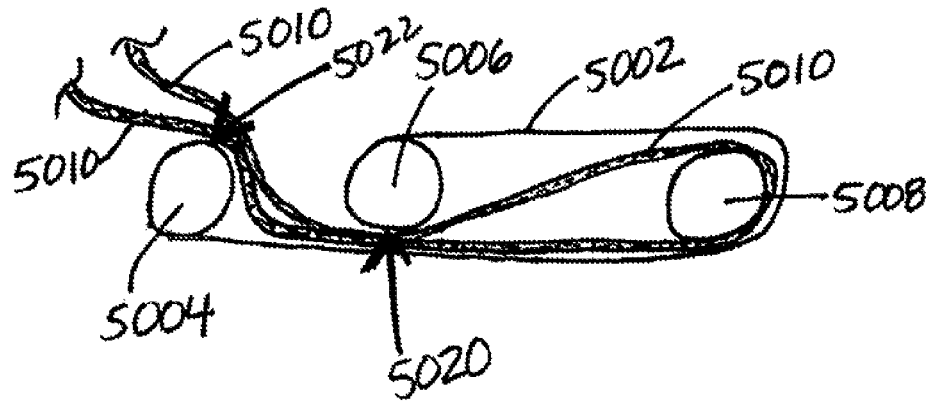
Figure 50C:
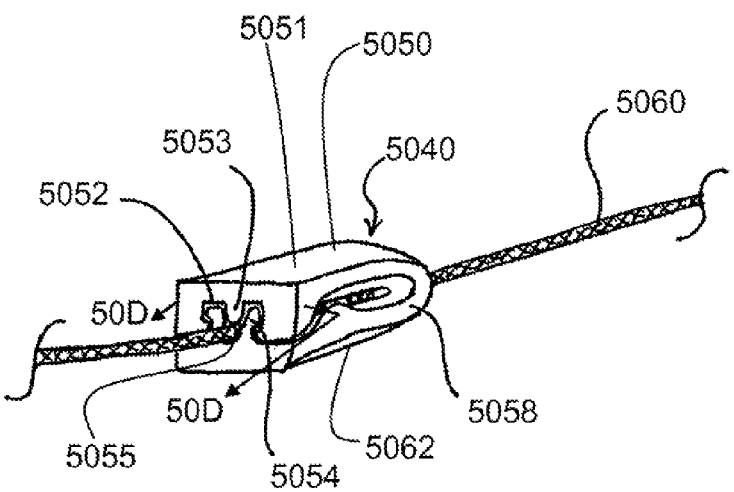
FIG. 50C is a perspective view of a tether and a variation of a tether-locking device.
Figure 50D:
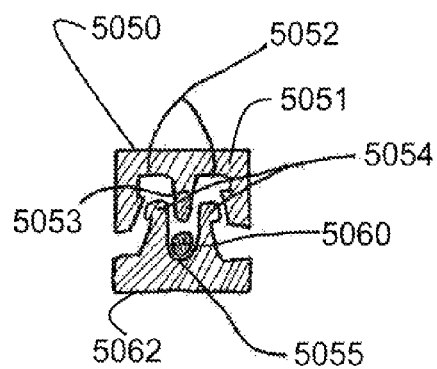
FIG. 50D is a front cross-sectional view of the tether and device of FIG. 50C, taken along line 50D-50D.
Figure 50E:
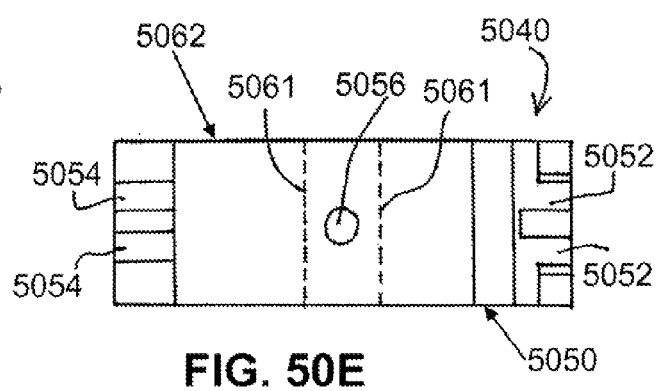
FIG. 50E is a schematic view of the device of FIG. 50C when flattened.

FIGS. 50A and 50B show an additional variation of a locking device. As shown there, a locking device (5000) has a buckle configuration comprising a strip (5002) having a first end (5004) and a second end (5006), and a strap (5008) therebetween. A tether (5010) has been routed over surfaces (5020) and (5022) of strip (5002), and underneath strap (5008). Second end (5006) is preferentially sprung to move in the direction of arrow (A3) toward first end (5004) (FIG. 50A), to close the strip on itself and thereby secure tether (5010) (FIG. 50B). The tether may be secured because as the strip closes on itself, it converts the tether from a linear configuration to a convoluted configuration that is less likely to slide freely. In some variations, first end (5004) and/or second end (5006) may comprise one or more features that help to secure the first end to the second end, and thereby enhance the locking of the tether. In certain variations, second end (5006) may be configured to move toward first end (5004) when locking device (5000) is deployed from a delivery device, such as a catheter.

Other variations of locking devices comprising different portions that close toward each other to lock a tether may be used. For example, FIGS. 50C-50F depict a locking device (5040) comprising a body (5051) having grooves (5052), teeth (5054), a hinge (5058) including an aperture (5056), and a tether-receiving area (5055). As shown, grooves (5052) and teeth (5054) are sized and shaped to form a snap-fit. However, in other variations, different portions of a locking device may interlock by friction-fit or any other suitable mechanism. Referring to both FIGS. 50C and 50D, a tether (5060) may be threaded such that it passes through tether-receiving area (5055), through the length of locking device (5040), and through aperture (5056). When in an open configuration, teeth (5054) may not be fully engaged in grooves (5052), or may not be in grooves (5052) at all, and the locking device may be slidable over the tether. In a closed configuration, tether (5060) may be secured by moving portions (5050) and (5062) toward each other, and positioning protrusion (5053) in tether-receiving area (5055), thereby clamping the tether. Locking device (5040) may assume a closed configuration by a variety of mechanisms. For example, in some variations, locking device (5040) may be disposed within a tubular member, and may be advanced against a wedge in the tubular member to close the device. The locking device may be retained in its closed configuration when teeth (5054) are inserted into grooves (5052) to form, for example, a snap-fit. Locking device (5040) may be manufactured using any appropriate method. For example, in some variations, locking device (5040) may be formed out of a single molded plastic or metal part, as shown in the flattened configuration in FIG. 50E. Hinge (5058) may be formed, for example, by bending the part along dotted lines (5061).

Figure 50F:
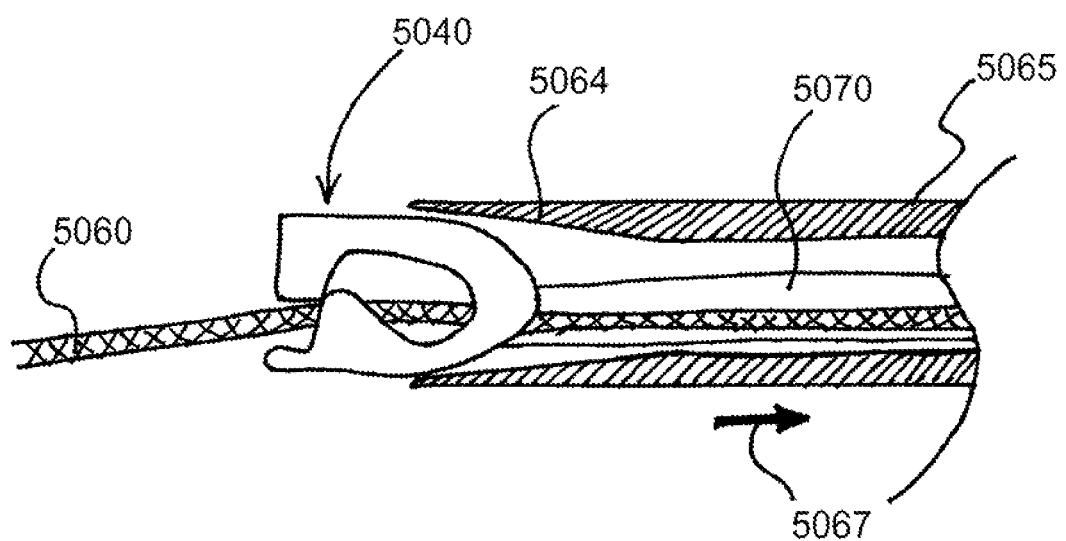
FIG. 50F is an illustrative depiction of the device of FIG. 50C when it is being used to lock a tether.

FIG. 50F depicts one variation of a method of using locking device (5040) to secure a tether (5060). As shown there, locking device (5040) may be at least partially disposed within a tubular member (5065) having angled walls (5064), such that the inner diameter of tubular member (5065) decreases in the direction of arrow (5067). A pulling feature (5070) may be releasably coupled to locking feature (5040). As pulling feature (5070) is withdrawn in the direction of arrow (5067) (e.g., proximally), locking device (5040) may be advanced along angled walls (5064) from a region of the tubular member with a larger diameter to a region with a smaller diameter. As the locking device is pushed into the region with a smaller diameter, the locking device becomes compressed, such that teeth (5054) and grooves (5052) become secured to each other. The engagement between the teeth and the grooves may fixedly secure the locking device on tether (5060). In some variations, actuating pulling feature (5070) in the direction of arrow (5067) (e.g., by pulling on the pulling feature) may then cause locking device (5040) to become decoupled from the pulling feature. However, other suitable mechanisms may alternatively or additionally be used to de-couple the locking device from the pulling feature and/or tubular member. As an example, in some variations, the pulling feature may be attached to the locking device by a frangible or perforated region which may break when sufficient force is applied. As another example, in certain variations, a cutting element may be used to sever the connection between the pulling feature and the locking device.

In some variations, and as shown schematically in FIGS. 51A and 51B, a locking device (5100) may comprise two or more members (here, plates (5102) and (5104)) that are capable of moving relative to each other to secure a tether routed through apertures in the members (here, apertures (5106) and (5108), respectively). When locking device (5100) is in its locked configuration (FIG. 51A), the plates are positioned such that their apertures are not directly aligned. As a result, a tether (5110) routed through the apertures may effectively become locked by the device. Locking device (5100) also has an open configuration (FIG. 51B) in which apertures (5106) and (5108) are directly aligned. This direct alignment may allow the tether to pass more freely through the apertures, thereby effectively unlocking the tether. Different configurations of devices may be used that incorporate this concept of aligning apertures and moving apertures out of alignment to lock and unlock a tether. The tether may function somewhat like a drawstring in such cases.

In certain cases, multiple (i.e., at least two) tethers may be wound together and effectively tangled to provide a locking effect. This may be achieved, for example, by temporarily coupling the tethers to a winding feature on a catheter, such as a Y-shaped rod with each tether coupled to a leg. The rod may then be rotated (e.g., on multiple axes) to wind the tethers together.

In some variations, a tether may have a feature that effectively locks the tether in place. As an example, FIG. 52 shows a tether (5200) having a bulbous member (5202) at one of its ends (5204). The bulbous member may, for example, prevent the tether from passing through one or more eyelets of an anchor to which the tether is coupled. In certain variations, the bulbous member may prevent the tether from becoming completely unlocked if, for example, a locking device locking the tether fails. Bulbous member (5202) may be formed, for example, by applying glue (e.g., fibrin, a hydrogel, etc.) to the end of tether (5200) (e.g., in vivo). While a bulbous member is shown, other appropriate configurations may alternatively or additionally be used. Moreover, in some variations, a tether may be frayed (e.g., using a cutting element in vivo) to help increase the friction between the tether and one or more of the locking device components, thereby enhancing the securing of the tether.

Figure 53A:
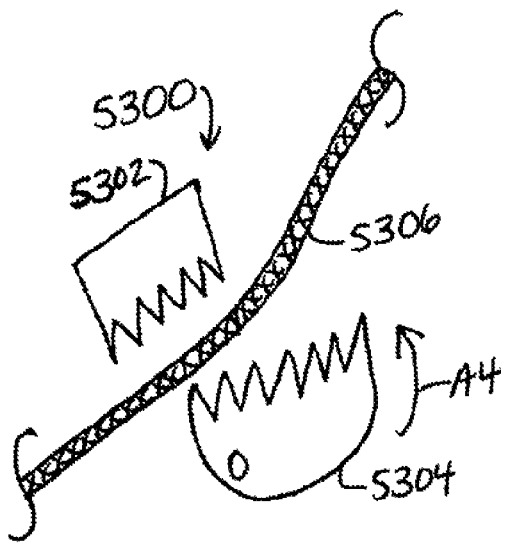
FIGS. 53A and 53B depict variations of a device and a method for locking a tether.
Figure 53B:
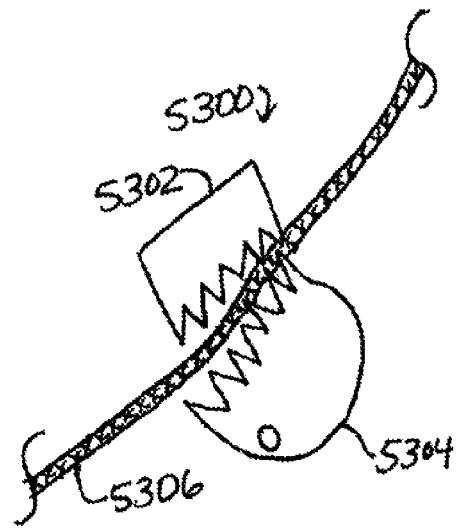

FIGS. 53A and 53B illustrate a cam-based locking mechanism that may be used to lock a tether. As shown there, a cam-based locking mechanism (5300) comprises a first component (5302) and a second component (5304). FIG. 53A shows the mechanism in its unlocked state, when a tether (5306) disposed between first component (5302) and second component (5304) can move freely between the components. However, when second component (5304) is rotated in the direction of arrow (A4), it engages tether (5306), and locks the tether against first component (5302), as shown in FIG. 53B. In some variations, second component (5304) may first be rotated in a direction opposite that of arrow (A4), and may then be released to secure the tether. While one cam-based locking mechanism is shown, in certain variations, a locking device may comprise two or more cam-based locking mechanisms, or at least one cam-based locking mechanism in combination with one or more other types of locking mechanisms.

Figure 54:
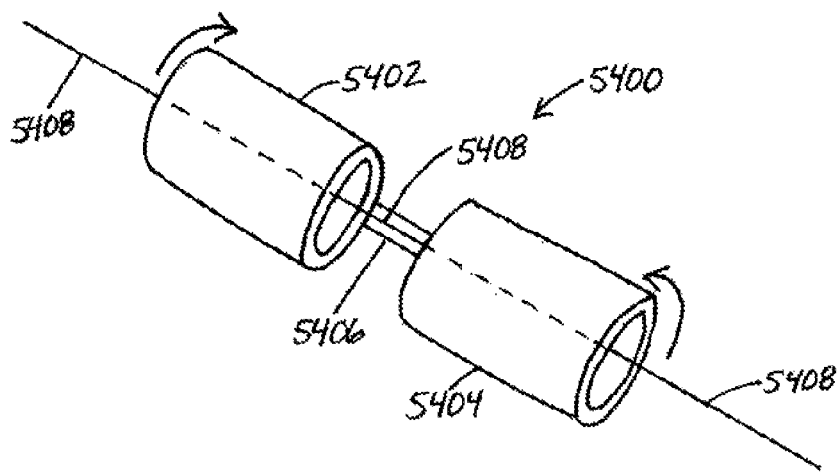
FIG. 54 depicts variations of a device and a method for locking a tether.

FIG. 54 shows another variation of a locking device (5400). Locking device (5400) comprises a first tubular member (5402) connected to a second tubular member (5404) by a flexible strip (5406). When one of the tubular members is rotated clockwise, while the other tubular member is rotated counter-clockwise (as indicated by the arrows), a tether (5408) that is threaded through the tubular members may become locked. The rotation of the tubular members may cause the tubular members to become off-axis with respect to each other. In some variations, flexible strip (5406) may be made of, for example, Nitinol, and may be shape-set to create the rotation. Initially, locking device (5400) may be constrained within a catheter, with the axes of tubular members (5402) and (5404) aligned. This may be achieved, for example, by using an alignment rod internal to the tubular members, an alignment sleeve external to the tubular members, and/or one or more alignment features within the catheter that maintain the ends of the tubular members in an aligned configuration. After locking device (5400) has been released from the catheter, flexible strip (5406) may spring to its unconstrained position, such that tubular members (5402) and (5404) are off-axis with respect to each other. The same effect could be achieved by using a polymer flexible strip. The polymer flexible strip may be molded or shape-set such that in the unconstrained state, the tubular members are off-axis with respect to each other.

Figure 55:
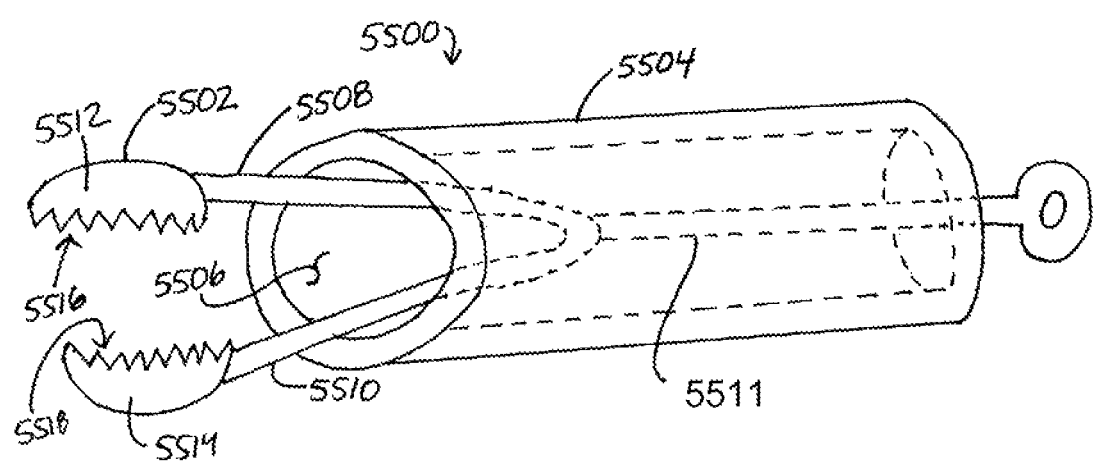
FIG. 55 illustrates another variation of a device for locking a tether.

Some methods may include clamping a tether to lock the tether. As an example, FIG. 55 shows a locking device (5500) comprising a clamping member (5502) and a tubular member (5504) configured to receive the clamping member in a lumen (5506). Clamping member (5502) comprises jaws (5508) and (5510) connected to an elongated manipulating member (5511). Jaws (5508) and (5510) have portions (5512) and (5514) comprising teeth (5516) and (5518). While jaws (5508) and (5510) each have teeth in only one portion, in some variations, jaws may have teeth along their entire length, or may have teeth in multiple different portions. The elongated manipulating member may be pushed to push the jaws out of the lumen of the tubular member, or pulled to pull the clamping arms into the lumen of the tubular member. The jaws may be used to clamp down on a tether (not shown) outside of the tubular member, and then may be retracted into the lumen of the tubular member to maintain the clamp on the tether. More specifically, the tubular member may help maintain the tether in a locked position by pushing down on the jaws and keeping them clamped toward each other. Locking device (5500) may, for example, provide relatively easily controlled locking of one or more tethers.

Figure 56A:
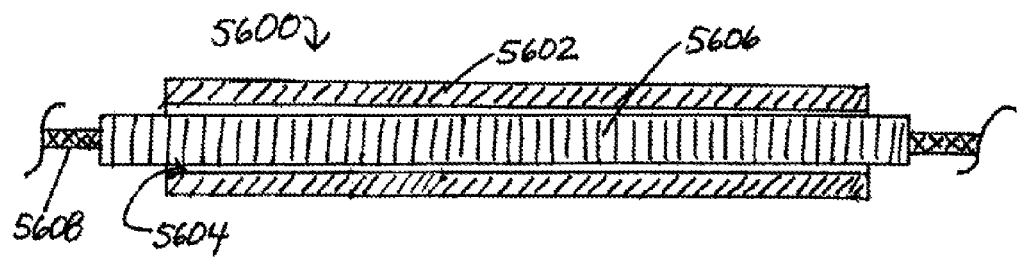
FIGS. 56A and 56B depict variations of a device and a method for locking a tether.
Figure 56B:
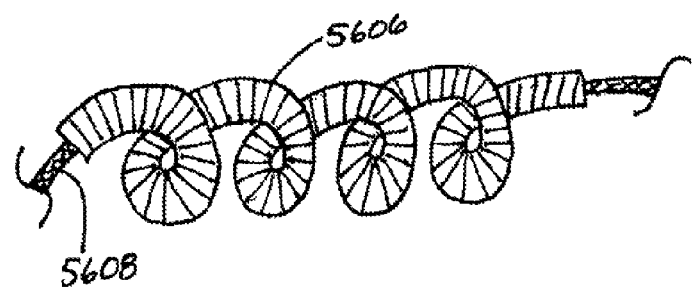
Figure 57:
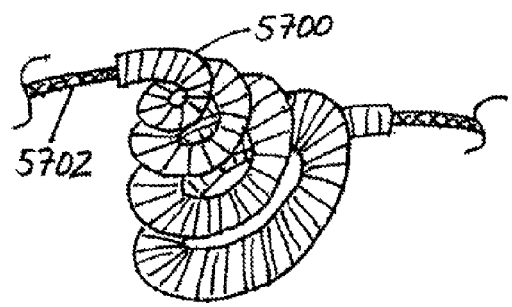
FIG. 57 illustrates variations of a device and a method for locking a tether.

Still other locking devices may be employed. For example, FIG. 56A shows a locking device (5600) comprising a tubular member (5602) comprising a lumen (5604), and a coil (5606) disposed within the lumen of the tubular member. The coil itself has a lumen (not shown), through which a tether (5608) has been threaded. The coil is in its primary configuration when it is disposed within the lumen of the tubular member (FIG. 56A). As shown in FIG. 56B, the coil assumes a secondary configuration when it is no longer disposed within the lumen of the tubular member (e.g., after the tubular member has been withdrawn from the coil and/or the coil has been pushed out of the lumen of the tubular member). Coils having primary and secondary configurations may be formed, for example, by heat-shaping the coils first on a primary mandrel, and then on a secondary mandrel or shaping block. The secondary configuration shown in FIG. 56B is helical, and it causes the tether to wind up such that movement of the tether may be limited. Accordingly, the tether may become locked by the coil. Coils may have different secondary configurations. For example, FIG. 57 shows a coil (5700) having a conical secondary configuration that locks a tether (5702) routed through a lumen (not shown) of the coil. In some variations, a tether may be configured to coil on its own. For example, the tether may be pre-formed using heat-forming, and a mandrel may be routed through the center of the tether to temporarily keep the tether straight. The mandrel may later be removed when it is desired for the tether to coil.

In some methods, it may be necessary to load a tether into a device, such as a locking device, a cutting device, or a combination locking and cutting device. Various methods and/or devices may be used to accomplish this loading.

Figure 58A:
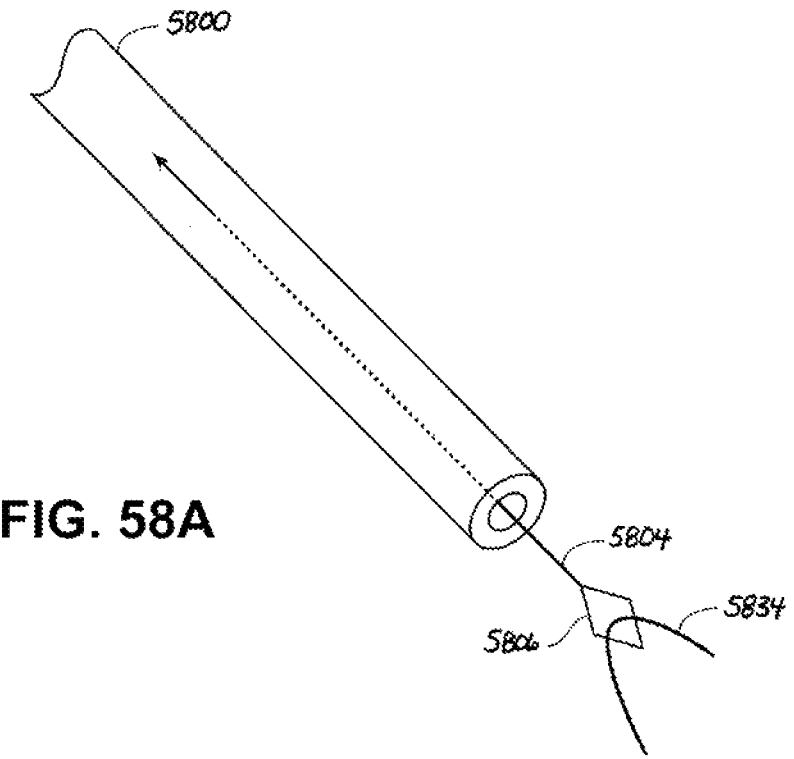
FIGS. 58A and 58B are illustrative variations of devices for loading tethers into catheters.
Figure 58B:
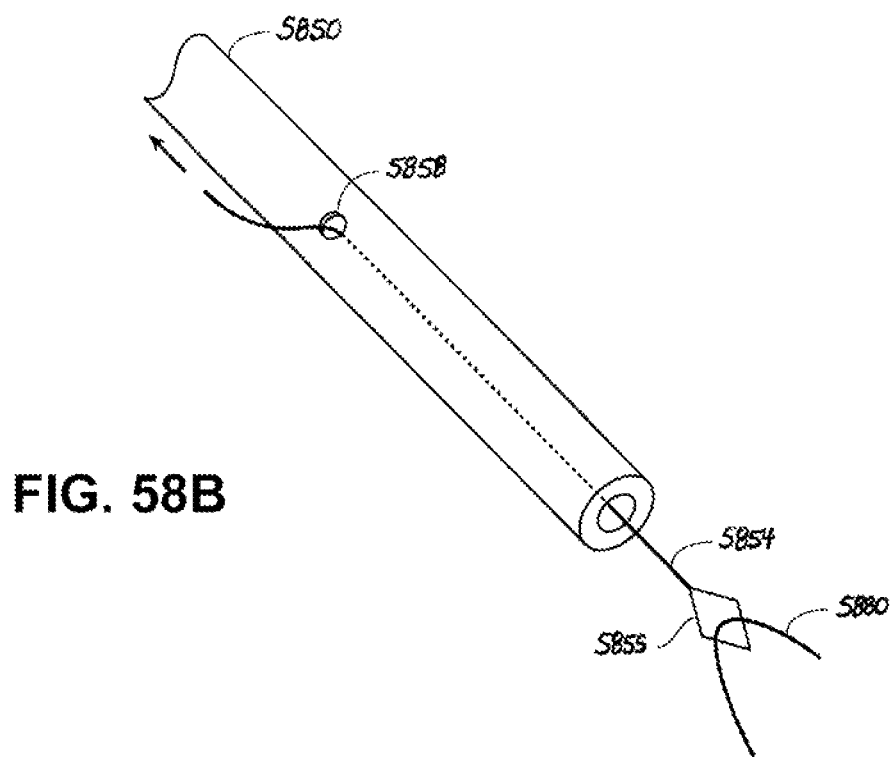

As an example, and referring now to FIGS. 58A and 58B, in some variations, a tether (5834) may be loaded into a device (5800) using a lasso (5804) which comprises a loop (5806) at one end. One end of tether (5834) is threaded through loop (5806) of lasso (5804). Lasso (5804) may then be pulled along the longitudinal axis of device (5800) (FIG. 58A), to load tether (5834) into device (5800). In alternative implementations, shown in FIG. 58B, a lasso (5854) having a loop (5855) may be pulled through a side hole (5858) in a device (5850) to load a tether (5880) into the device. Device (5800) or device (5850) may be used to perform one or more functions, such as locking and/or cutting (described in further detail below). Lassos may be made from, for example, conventional materials such as wire, suture, cable, string, or a monofilament. A lasso may comprise a loop (as show in FIGS. 58A and 58B), a hook, a coil, a tube, an elongate element with a hole, or any other structure or material that can "grab" a tether.

While the use of tether-loading devices to load tethers into locking devices has been described, such tether-loading devices may have other uses, such as to load tethers into cutting devices or combination locking and cutting devices (described in further detail below). Other uses may also apply. Moreover, any of the features described herein with respect to a locking device may also be used, as appropriate, in a cutting device, or in a combined locking and cutting device.

Figure 58C:
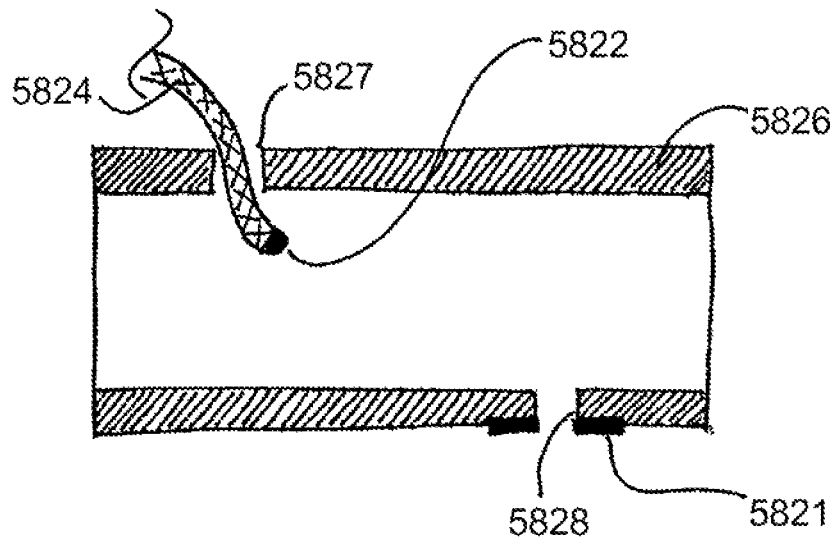
FIGS. 58C and 58D are cross-sectional views of exemplary variations of tether-threading devices.

Additionally, while certain variations of tether-loading devices have been described, other variations of devices may be used to load tethers into locking devices and/or other types of devices. For example, in some variations, a tether may be loaded into a device, such as locking device or a cutting device, using magnetic components. As an example, FIG. 58C shows one variation of a locking device (5826) including two apertures (5827) and (5828) sized and shaped for passage of a tether (5824) therethrough. Tether (5824) comprises a first magnetic component (5822) at its tip. First magnetic component (5822) may comprise a magnet (of a first polarity), or one or more magnetic materials (e.g., metals such as nickel or cobalt, metallic alloys, combinations thereof, or the like). A second magnetic component may be located in the proximity of an aperture in the locking device. For example, in FIG. 58C, a second magnetic component (5821) is located on the external surface of locking device (5826), near aperture (5828). Second magnetic component (5821) may, for example, be a magnet of the opposite polarity of first magnetic component (5822), or may comprise any magnetic material or materials that substantially attract first magnetic component (5822). In some variations, second magnetic component (5821) may be directly attached to locking device (5826), as shown in FIG. 58C. Magnetic components (5822) and (5821) may be radiopaque, which may allow the location of locking device (5826) to be tracked using X-ray fluoroscopy. Other appropriate imaging modalities may alternatively or additionally be used.

During use, tether (5824) may, for example, be threaded through locking device (5826) by inserting the tether through aperture (5827) and advancing the tether, which may be guided by the attraction between first and second magnetic components (5822) and (5821). While tether (5824) and locking device (5826) are shown as each having one magnetic component in a particular position, other variations of locking devices and tethers may have different numbers and/or arrangements of magnetic components. In some variations, the magnetic components and their configurations may be selected based on the desired routing of a tether through a locking device. Moreover, the path of a tether through a locking device may be determined using both attractive and repulsive magnetic forces.

Figure 58D:
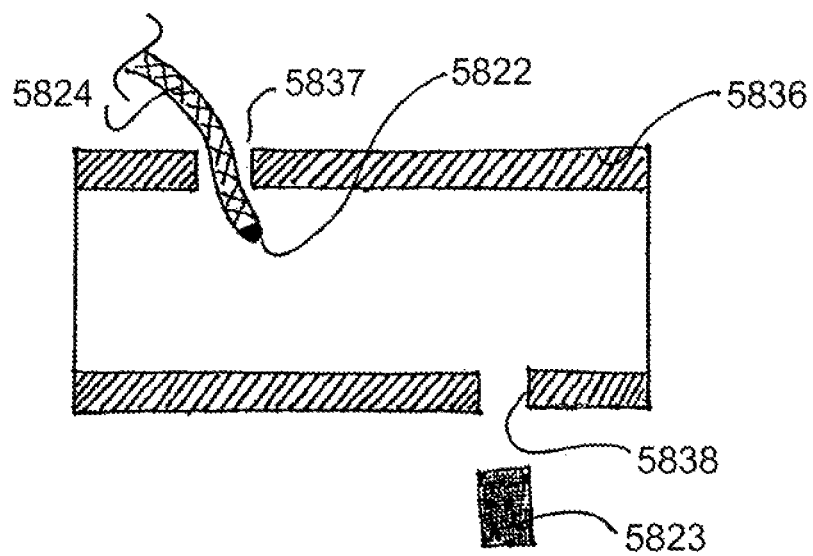

In some circumstances, it may be inappropriate or undesirable to introduce a magnetic material into a patient. In some such cases, and as shown in FIG. 58D, a locking device (5836) may comprise a removable magnetic component (5823) that is only intended to be a part of the locking device when the locking device is outside of the body of the subject (i.e., such that the removable magnetic component is not implanted into the body of the subject). Prior to locking device (5836) being inserted into a patient, removable magnetic component (5823) may be used to thread a tether (5824) from aperture (5837) to aperture (5838). Once the desired tether path has been attained, removable magnetic component (5823) may be removed from locking device (5836), and the locking device may then be used in a body of a subject. While one variation of a locking device with a removable magnetic component has been described, it should be understood that other suitable variations may also be used. In some variations, a magnetic "wand" (e.g., comprising an elongated member with a magnet at its distal end) may be used to thread a tether through a locking device, when the tether also comprises one or more magnets.

Figure 59A:
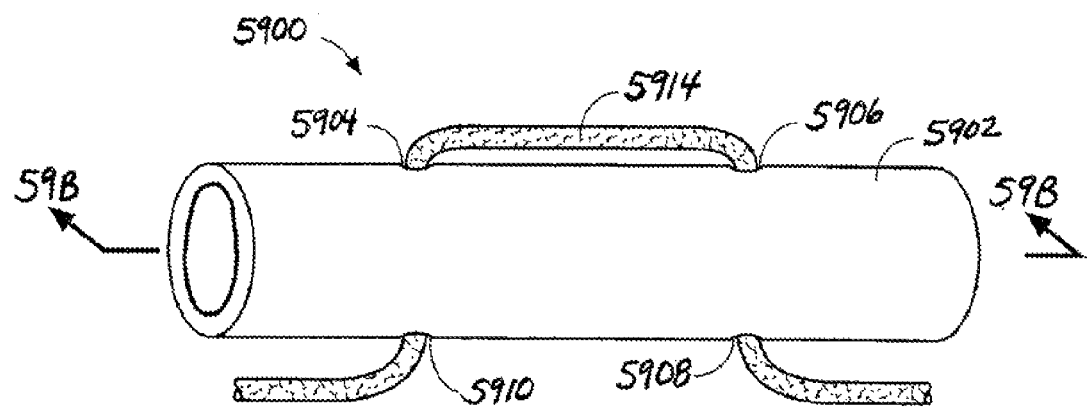
FIG. 59A is a perspective view of a variation of a device that may be used to lock a tether.
Figure 59B:
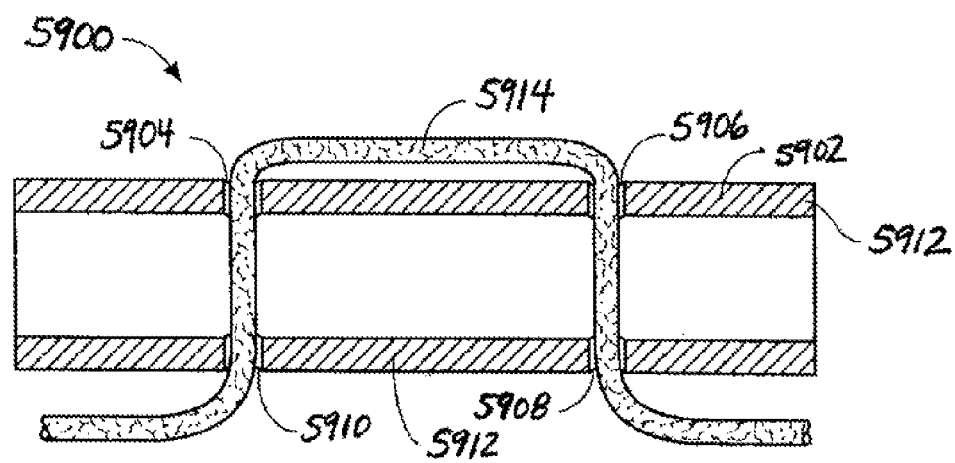
FIG. 59B is a cross-sectional view of the device of FIG. 59A, taken along line 59B-59B.

Tethers may be routed through a device, such as a locking device or a cutting device, in any of a number of different configurations. For example, FIGS. 59A and 59B show a variation of a locking device (as shown, a locking catheter (5900)). Locking catheter (5900) includes a tubular member (5902) having a wall (5912) with four apertures (5904), (5906), (5908), and (5910) formed in it. A locking catheter such as locking catheter (5900) may be used, for example, to maintain tension in a tether, and to stabilize the tether for cutting. In FIGS. 59A and 59B, a tether (5914) has been threaded into locking catheter (5900), through apertures (5904), (5906), (5908), and (5910). The tether may be threaded into the locking catheter using, for example, a lasso, such as one of the lassos described above. The lasso may have a relatively flexible loop which may enhance the maneuverability of the lasso through the apertures in the locking catheter.

While locking catheter (5900) is shown as including four apertures through which tether (5914) is threaded, locking catheters can include other numbers of apertures. For example, some variations of locking catheters may include fewer apertures (e.g., two apertures), while other variations of locking catheters may include more apertures (e.g., six apertures, eight apertures, etc.). As the number of apertures in a locking catheter increases, the likelihood of movement by a tether that is threaded through the apertures may decrease.

As noted above, tethers may be routed through tubular members or other elongated members in any appropriate tether routing configuration. Different non-limiting examples of tether-routing configurations are shown, for example, in FIGS. 60A-60R. As shown there, the proximal end of each tether is located at the left-hand side of the figures, with the exception of FIG. 60R, in which the proximal end of the tether is located at the right-hand side of the figure.

Figure 60A:
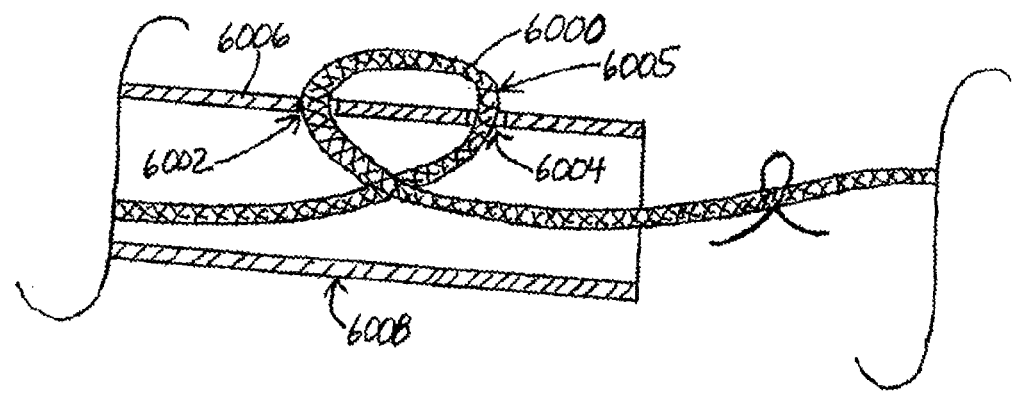
FIGS. 60A-60R show various tether-routing configurations through variations of components of tether-locking devices.
Figure 60B:
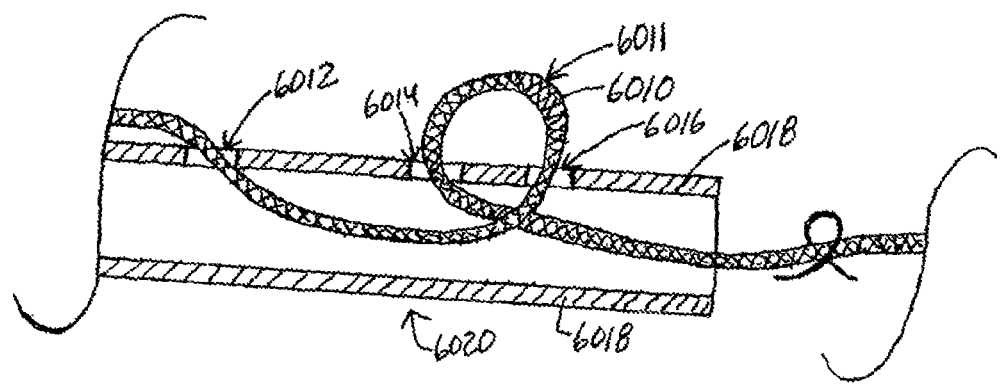
Figure 60C:
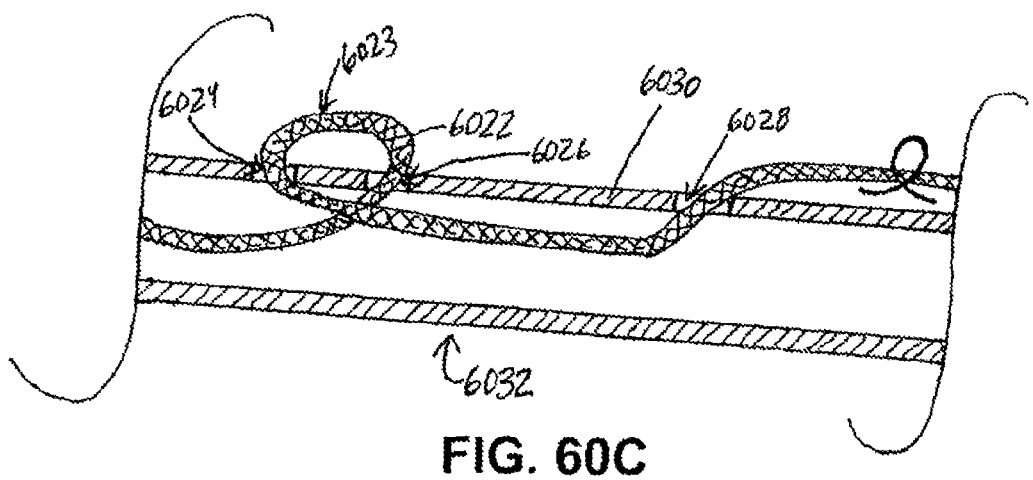

FIG. 60A shows a tether (6000) routed through two apertures (6002) and (6004) in a wall portion (6006) of a tubular member (6008) to form a loop (6005). Tether (6010) in FIG. 60B also forms a loop (6011), but is routed through three apertures (6012), (6014), and (6016) in a wall portion (6018) of a tubular member (6020). FIG. 60C similarly shows a tether (6022) that forms a loop (6023), and that also is routed through three apertures (6024), (6026), and (6028) in a wall portion (6030) of a tubular member (6032).

Figure 60D:
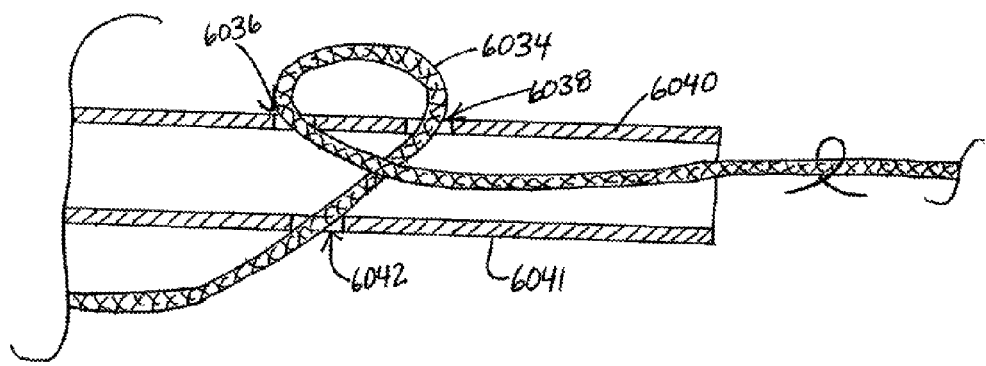
Figure 60E:
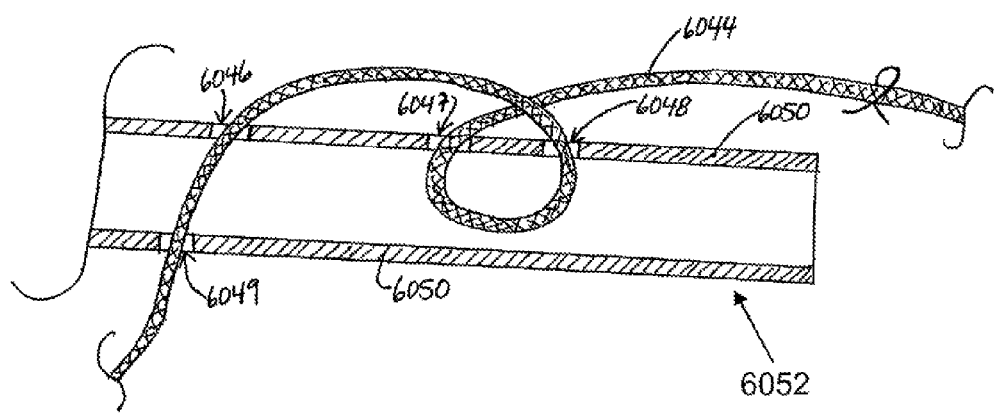

FIG. 60D shows a tether (6034) that is routed through two apertures (6036) and (6038) in a wall portion (6040) of a tubular member (6041), and also through a third aperture (6042) across from apertures (6036) and (6038). In FIG. 60E, a tether (6044) is routed through four apertures (6046), (6047), (6048), and (6049) in a wall portion (6050) of a tubular member (6052). Tethers may be routed through any number of apertures having any suitable size and/or shape. The number, size, and/or shape of the aperture or apertures through which a tether is routed may be selected, for example, based on the desired level of security of the tether lock.

Figure 60F:
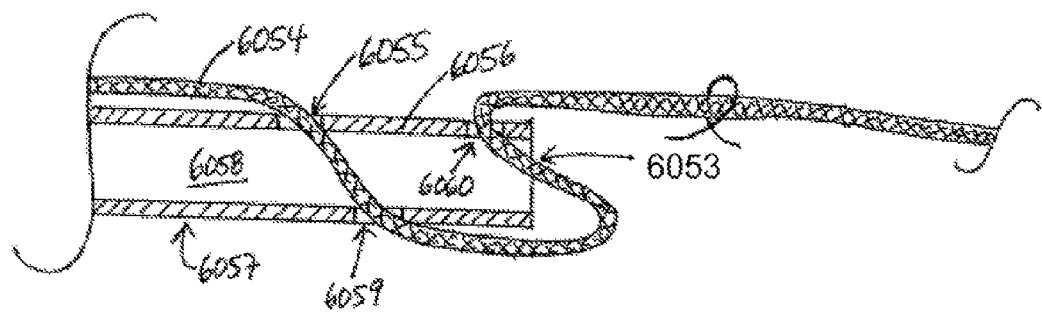

In some cases, a tether may be routed into and out of a lumen of a tubular member multiple times. For example, FIG. 60F shows a tether (6054) routed through a first aperture (6055) in a wall portion (6056) of a tubular member (6057), such that the tether enters a lumen (6058) of the tubular member. Tether (6054) then exits the lumen via a second aperture (6059) in wall portion (6056), and loops back around to re-enter the lumen via the distal end (6053) of the tubular member. The tether then exits the lumen once again via a third aperture (6060) in wall portion (6056).

Figure 60G:
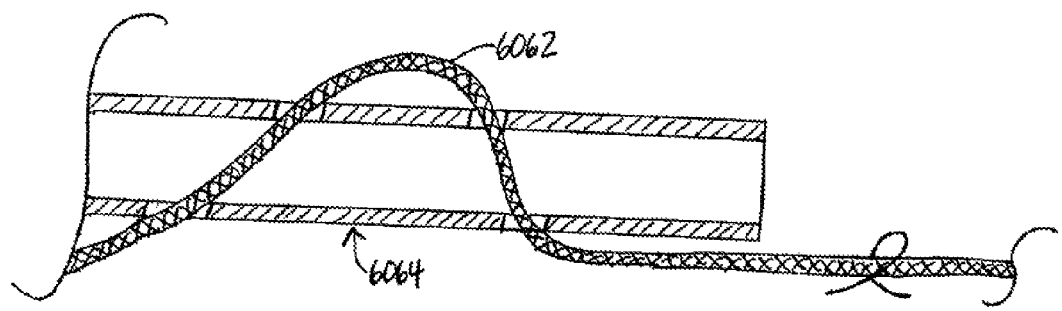
Figure 60H:
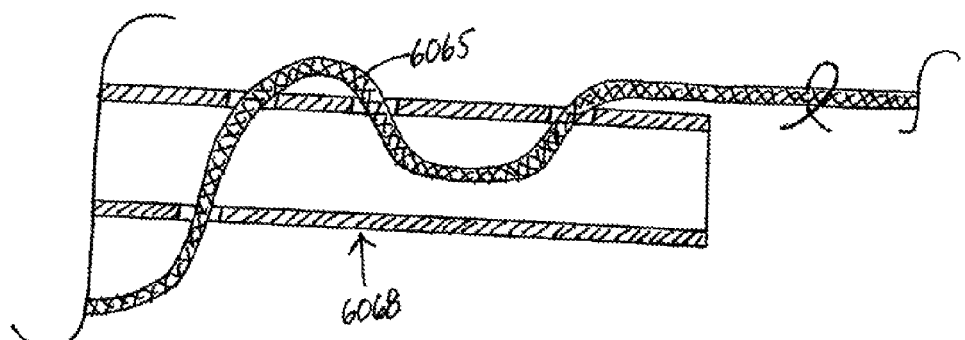
Figure 60I:
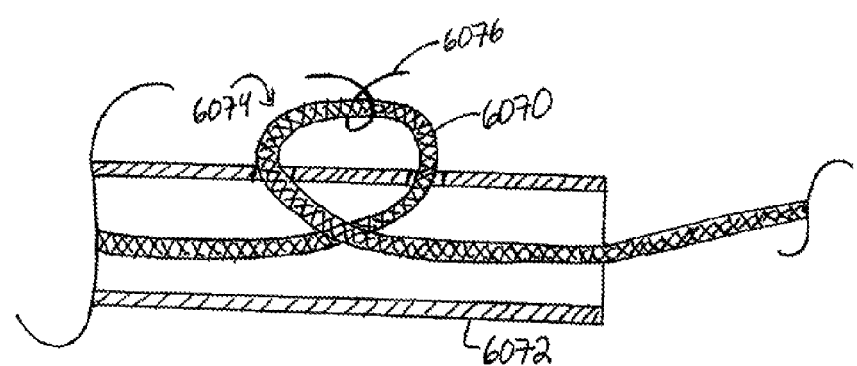
Figure 60J:
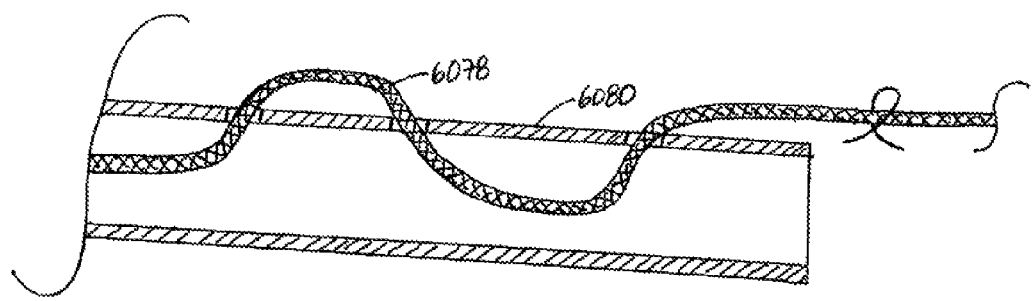
Figure 60K:
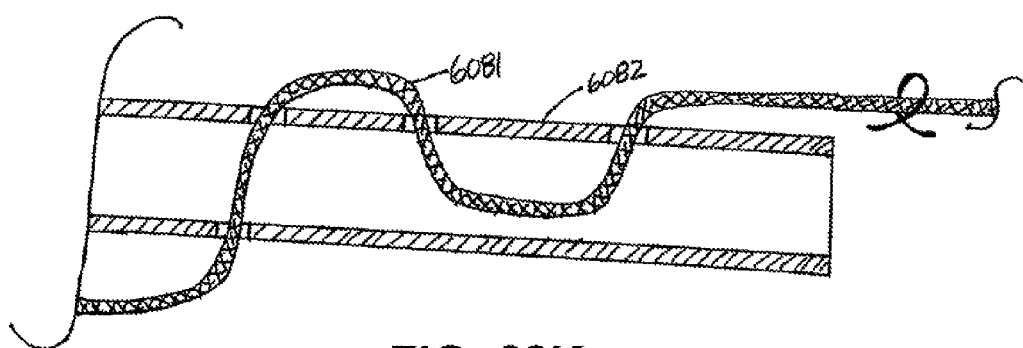

Still further tether routing configurations are possible. For example, FIG. 60G shows a tether (6062) routed through a tubular member (6064), FIG. 60H shows a tether (6065) routed through a tubular member (6068), FIG. 60I shows a tether (6070) routed through a tubular member (6072) such that the tether forms a loop (6074) with an anchor (6076) slidably engaged along its center portion, FIG. 60J shows a tether (6078) routed through a tubular member (6080), and FIG. 60K shows a tether (6081) routed through a tubular member (6082).

Figure 60L:
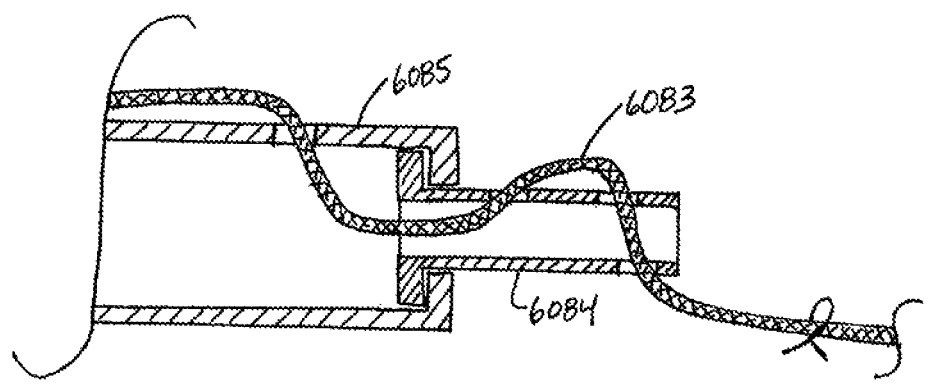
Figure 60M:
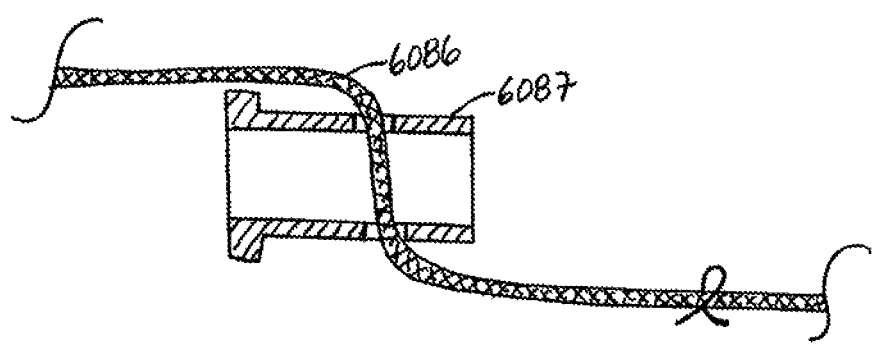
Figure 60N:
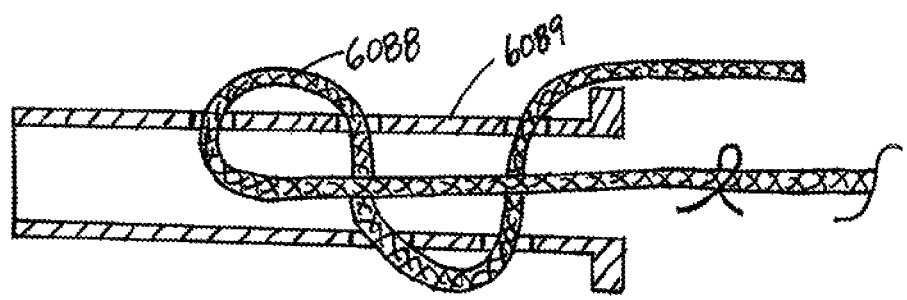
Figure 60O:
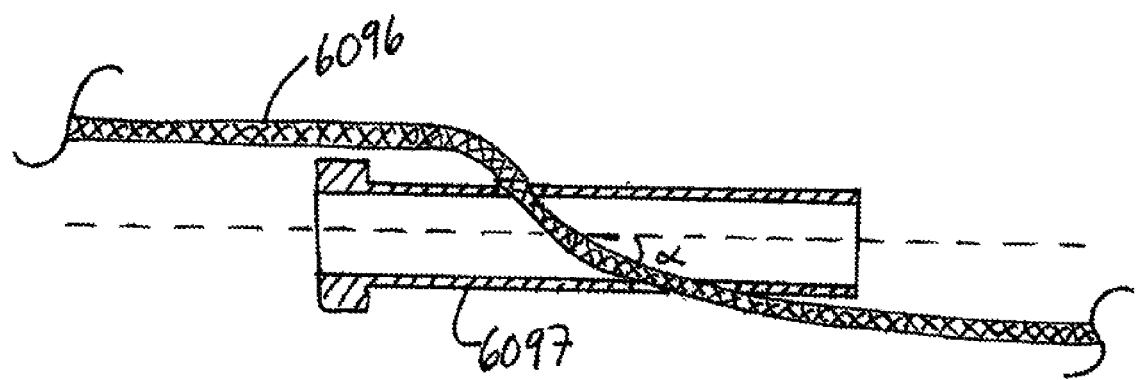

Additional tether routing configurations through various different locking device components may be employed. For example, FIG. 60L shows a tether (6083) routed through a locking tube (6084) and through a sheath (6085) engaged with the locking tube, FIG. 60M shows a tether (6086) routed through a locking tube (6087), and FIG. 60N shows a tether (6088) routed through a locking tube (6089). FIG.

Figure 60P:
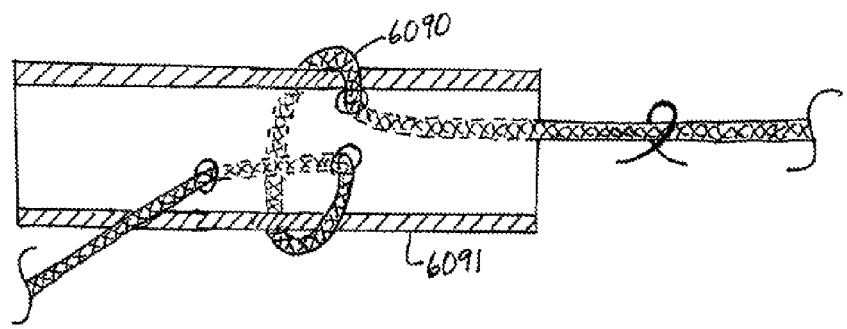
Figure 60Q:
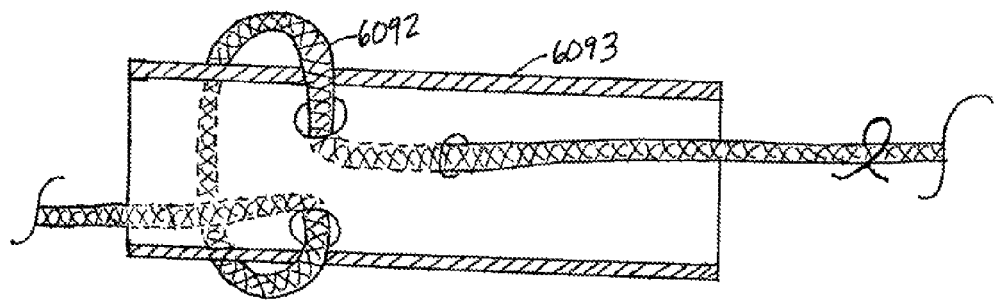
Figure 60R:
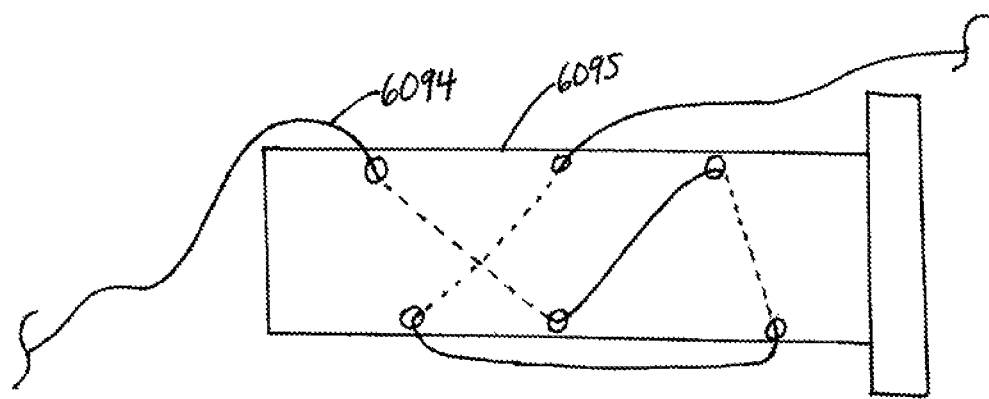

60O shows a tether (6096) routed through a locking tube (6097) such that the tether path forms an angle (α) with respect to the longitudinal axis of the locking tube. Angle (α) may be, for example, from about 5° to about 70° (e.g., from about 10° to about 45°, or about 45°). This routing configuration may, for example, allow for a relatively low passing force, and/or may allow for tension in the tether to be released relatively easily. FIG. 60P shows a tether (6090) routed through and around a locking tube (6091), FIG. 60Q similarly shows a tether (6092) routed through and around a locking tube (6093), and FIG. 60R shows a tether (6094) routed through and around a locking tube (6095).

Tethers may be routed through the center of a lumen or hollow portion of a locking tube or other locking member, or may be routed so that they do not cross the center of the lumen or hollow portion (e.g., to limit the likelihood of being pierced by a plug tip).

In some variations, a tether may be routed along an outer surface of a locking member (e.g., a locking tube). The tether may, for example, be routed into or through one or more apertures and/or grooves on the outer surface. In certain variations, a tether may be wound around an outer surface of a locking member (e.g., a locking tube). An outer surface of a locking member may include one or more features (e.g., barbs, texturing, etc.) that help to retain the tether. For example, the outer surface may be bead-blasted. In some variations, a tether may be melted to an outer surface of a locking member (e.g., by applying RF energy to the tether). Alternatively, if it is desired for the tether not to engage with the outer surface of a locking member, the outer surface may, for example, be super polished.

In some cases, one or more components of a locking device may be configured to couple with a tethered anchor. As an example, a locking tube may comprise a slot configured to receive and couple to an anchor. This may, for example, help to securely situate the locking device component at a target site.

While methods using one locking device have been described, it should be understood that multiple locking devices may be employed to lock one or more tethers. The locking devices may be the same as each other, or different from each other.

As described above, in operation, a locking device may be used to secure a tether to fix the length of the tether and/or to prevent the tether from moving. After the tether has been locked, any excess length of the tether may be cut and removed. In some variations in which a detachable locking member is used, a tether may be cut to remove excess material either before or after detaching the locking member from the rest of the device. Generally, the tether may be cut proximal to the locking mechanism. In many cases, it may be desirable to cut the tether as closely as possible to the locking mechanism, while leaving enough excess length to allow for any slippage that may occur. Examples of various methods and devices that may be used to cut tethers are described in more detail below.

FIG. 61A shows a cutting device (6101) that may be used to cut a tether (6100) extending through anchors (6126). Cutting device (6101) comprises a catheter (6105) and a tubular cutter (6107) disposed within catheter (6105). As shown in FIG. 61A, tether (6100) has been fixed by a locking element (6104), and has been threaded into catheter (6105) such that it exits through a side aperture (6106) in the catheter. Tether (6100) may be threaded into catheter (6105) by any suitable method including, for example, one or more of the methods described above. Tubular cutter (6107) has an edge (6108) that is sufficiently sharp to cut a tether. For example, tubular cutter (6107) may be in the form of a metal tube having a sharpened edge. During use, tubular cutter (6107), which may be attached to a flexible tube or a rod, may be advanced within catheter (6105) such that the tubular cutter passes over side aperture (6106). As tubular cutter (6107) is advanced over tether (6100), tubular cutter (6107) shears off the excess portion of the tether. While tubular cutter (6107) is tubular in shape, other configurations of cutters may be used. For example, a cutter may be semitubular (e.g., having a shape similar to a half-pipe), or may have any other suitable configuration. In some variations, a cutter may not be tubular or semitubular. As an example, a cutter may be in the form of a flat blade.

In some variations, and as shown in FIG. 61B, a cutting device (6143) comprises a catheter (6145), a base (6149) positioned on an interior surface of the catheter, and a tubular cutter (6147) concentrically disposed within the catheter. Tubular cutter (6147) has an edge (6148) that is sufficiently sharp to cut a tether. While cutter (6147) is tubular, other configurations of cutters may be used. Base (6149) may, for example, be in the form of a block that is attached to the interior surface of catheter (6145), or that is integral with the interior surface of catheter (6145). Base (6149) may be formed of any suitable material or materials, such as any elastomeric or rigid material. FIG. 61B shows cutting device (6143) being used to cut a tether (6134) extending through anchors (6190), into catheter (6145), and through a side aperture (6146) in catheter (6145). Prior to being cut, tether (6134) is fixed in place by a locking element (6144). Then, tubular cutter (6147) is advanced to cut tether (6134). Tubular cutter (6147) is advanced against base (6149), which assists tubular cutter (6147) in cutting tether (6134). In some variations, tubular cutter (6147) may be spun or rotated to improve cutting.

Tubular cutters may have any suitable cutting edge configuration. For example, a tubular cutter may have a beveled cutting edge, as exemplified by tubular cutter (6155) of FIG. 61C, a sharpened outer cutting edge, as exemplified by tubular cutter (6156) of FIG. 61D, or a sharpened inner cutting edge, as exemplified by tubular cutter (6157) of FIG. 61E. In addition, a tubular cutter may have a serrated or saw-tooth pattern of sharp protrusions around its perimeter to aid in cutting. Such variations may be used, for example, when the tubular cutter is spun or rotated during the cutting process.

In some variations, and as shown in FIG. 61F, a tubular cutter (6160) may be positioned distal to a side aperture (6162) in a catheter (6164). Tubular cutter (6160) may then be pulled in a proximal direction toward side aperture (6162) (indicated by solid arrow) to cut a tether (6170) extending through side aperture (6162), which has been fixed by a locking element (6174). Pulling a cutter proximally may provide for a relatively easy and/or efficient way of cutting a tether, and/or for relatively controlled tether-cutting.

Figure 62:
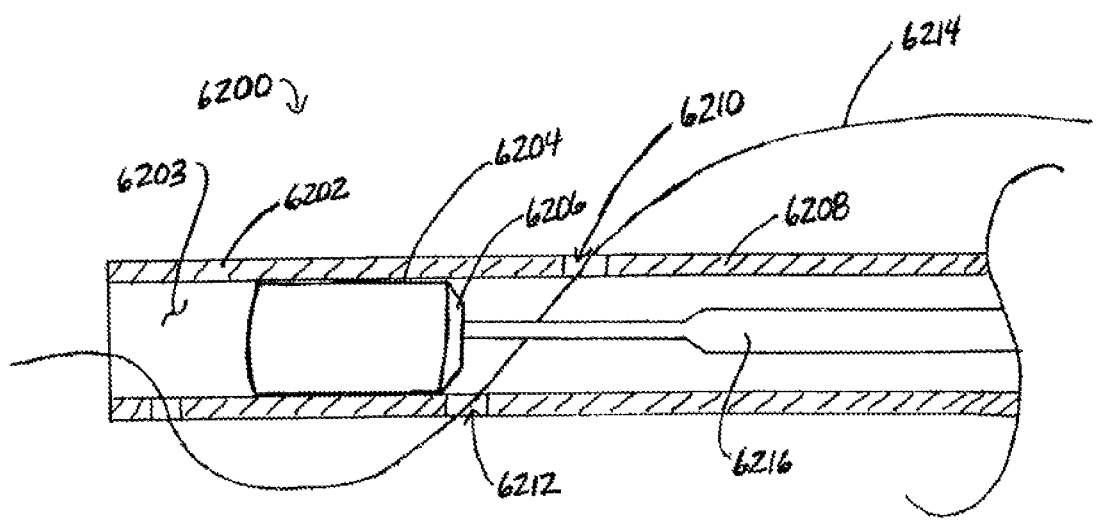
FIG. 62 is a side view in partial cross-section of a variation of a device for cutting a tether.

FIG. 62 shows another variation of a cutting device. As shown there, a cutting device (6200) comprises a tubular elongated member (6202) having a lumen (6203), and a cutter (6204) disposed within the lumen of the elongated member. Cutter (6204) has a cutting blade (6206) that faces in a proximal direction. Elongated member (6202) comprises a side wall (6208) having two apertures (6210) and (6212) through which a tether (6214) may be threaded, such that the tether crosses the lumen of the elongated member. While two side wall apertures are shown, other variations of devices may include a different number of side wall apertures, such as three or four side wall apertures. When it is desired to sever tether (6214), cutter (6204) may be pulled proximally using a pulling member (6216) that is attached to cutter (6204). This causes cutting blade (6206) to contact and sever tether (6214). While cutter (6204) may be pulled proximally using pulling member (6216), in some variations, a cutter disposed within the lumen of an elongated member may alternatively or additionally be pushed in a proximal direction. For example, a pushing member may be placed into the elongated member at its distal end, and used to push the cutter toward the proximal end of the elongated member.

Figure 63A:
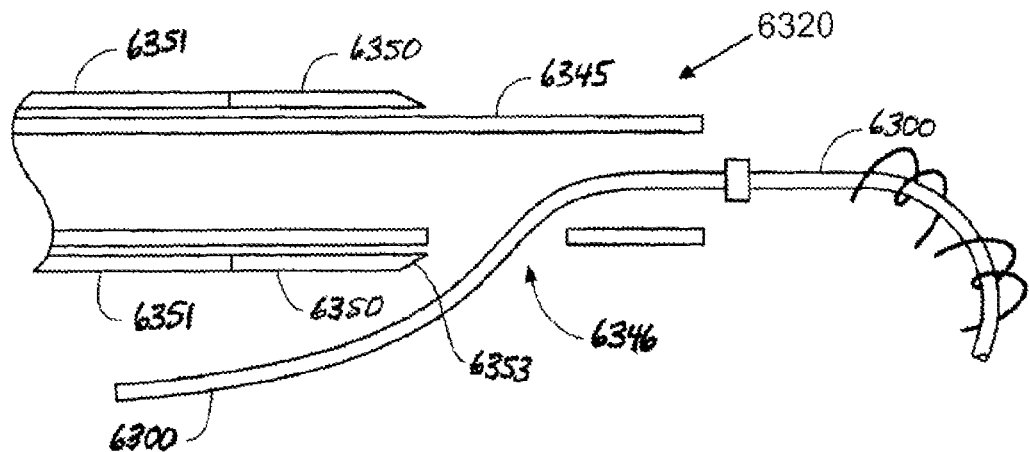
FIGS. 63A and 63B depict examples of devices that may be used to cut a tether.

The cutting devices shown above in FIGS. 61A-61F and 62 comprise cutters that are located internally of their catheters. However, some variations of cutting devices include a catheter and one or more cutters that are located externally of the catheter. For example, as shown in FIG. 63A, a cutting device (6320) includes a catheter (6345) and a tubular cutter (6350) that is configured to slide along the exterior of catheter (6345). Tubular cutter (6350) can, for example, be in the form of a sharpened metal tube (e.g., having a beveled edge). In some variations, and as shown, tubular cutter (6350) is attached to a second tube (6351) which also is configured to slide along the exterior of catheter (6345). In certain variations, second tube (6351) can be flexible.

During use of cutting device (6320), a tether (6300) may be threaded into catheter (6345), and may exit catheter (6345) through a side aperture (6346). Tether (6300) may be threaded into catheter (6345) using any suitable method, including methods described herein. As tubular cutter (6350) is advanced in a distal direction toward side aperture (6346), end (6353) of tubular cutter (6350) severs tether (6300).

Figure 63B:
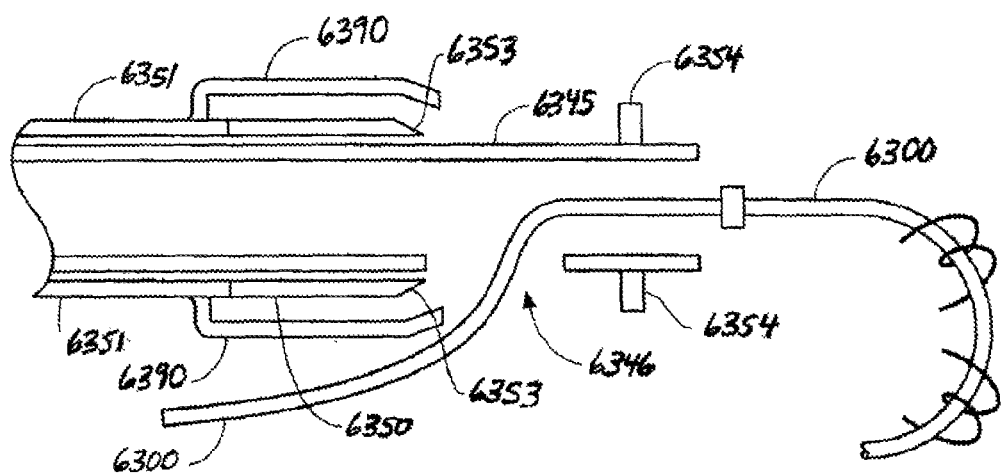

As shown in FIG. 63B, in some variations, a base (6354) may be positioned along catheter (6345), to assist in the tether-cutting process. During use, tether (6300) may be pushed against base (6354) as tubular cutter (6350) is advanced toward side aperture (6346). In certain variations, and as also shown in FIG. 63B, a cover or shroud (6390) may be provided around tubular cutter (6350) to limit the likelihood of sharpened end (6353) catching on tissue or the like. In some variations, cover (6390) is attached to second tube (6351).

Figure 64A:
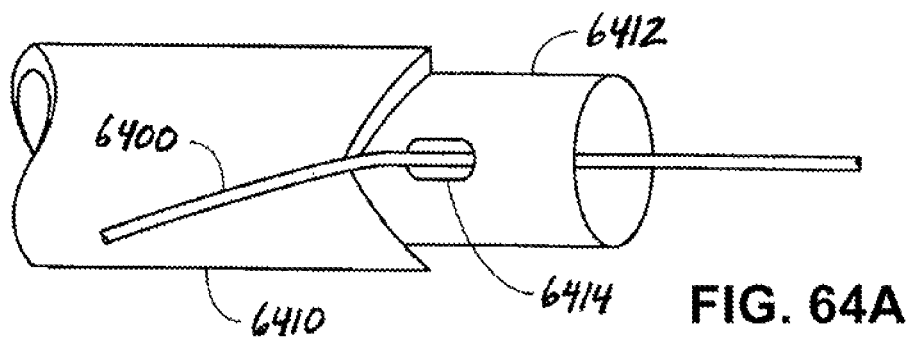
FIGS. 64A-64D illustrate variations of devices that may be used to cut a tether.

While tubular cutters having certain configurations have been shown, a tubular cutter may have any suitable configuration. For example, as shown in FIG. 64A, a tubular cutter (6410) may have a V-shaped cutting edge designed to channel a tether, such as tether (6400). Tubular cutter (6410) is externally disposed relative to a catheter (6412) having a side aperture (6414). During use of tubular cutter (6410), tether (6400) is threaded through side aperture (6414), so that it is positioned to be cut by tubular cutter (6410).

Figure 64B:
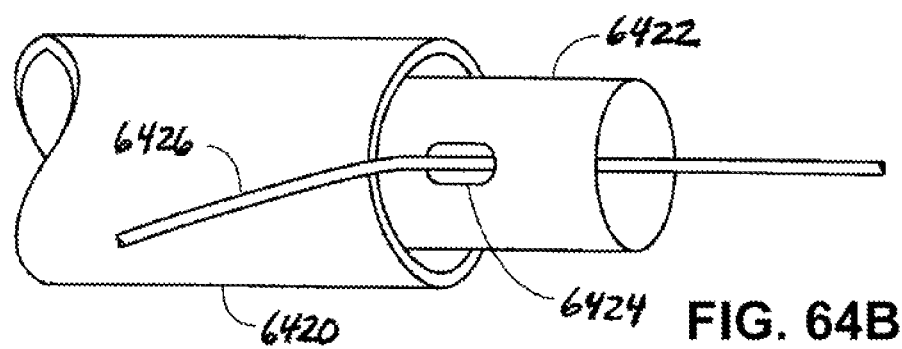
Figure 64C:
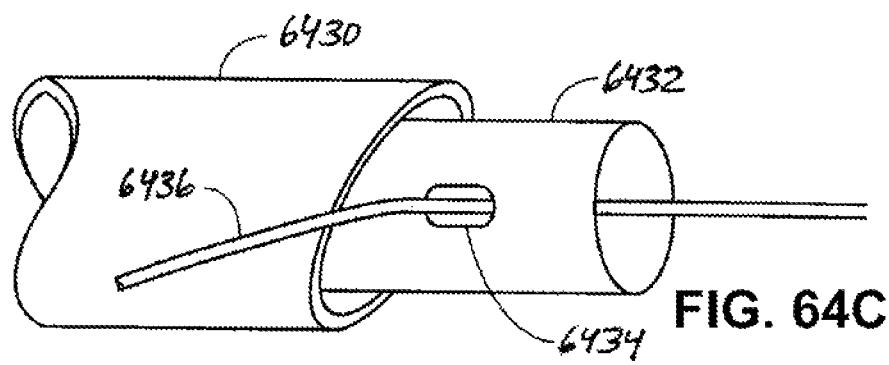
Figure 64D:
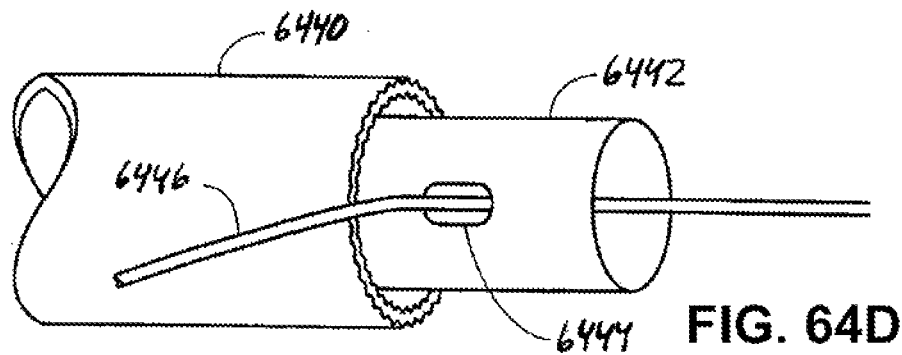

While tubular cutter (6410) has a V-shaped cutting edge, any other appropriate notched feature may be used on a cutter, and other cutting edge configurations may also be used. As an example, FIG. 64B shows a tubular cutter (6420) having a curved cutting edge. Tubular cutter (6420) is externally disposed relative to a catheter (6422) having a side aperture (6424). During use, a tether (6426) may be threaded through side aperture (6424), so that it may be severed by tubular cutter (6420). As another example, FIG. 64C shows a tubular cutter (6430) having an angled cutting edge. Tubular cutter (6430) is external to a catheter (6432) having a side aperture (6434) through which a tether (6436) is threaded. As an additional example, FIG. 64D shows a tubular cutter (6440) having a serrated cutting edge. Tubular cutter (6440) is external to a catheter (6442) having a side aperture (6444) through which a tether (6446) is threaded. Additional cutting edge configurations may be used, such as a saw-tooth cutting edge (not shown). The latter two variations may be useful, for example, when the tubular cutter is rotated or spun during the cutting process. In some variations, the perimeter of a side aperture in a cutting member may be sharpened to help cut the tether. Tubular cutters, as well as other types of cutters, may be configured such that they operate either externally or internally to a catheter.

Figure 65A:
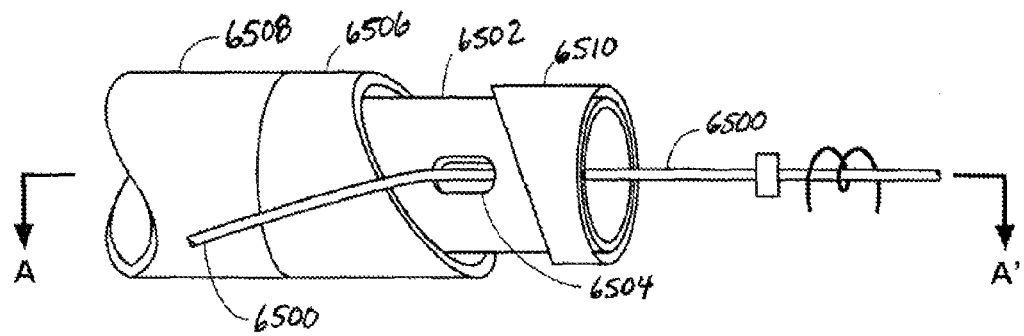
FIGS. 65A and 65B show additional variations of devices that may be used to cut a tether.

In some variations, tubular cutters may be used to sever a tether by cutting in a direction roughly perpendicular to the longitudinal axis of a catheter. For example, one concentric tube may be rotated relative to a second concentric tube to cut a tether. As an example, in FIG. 65A, a tether (6500) enters a catheter (6502) and exits through a side aperture (6504) in the catheter. A tubular cutter (6506) is configured such that when it is rotated about the longitudinal axis A-A' of catheter (6502), it can slice tether (6500). For example, tubular cutter (6506) may have an angled shape such that when it rotates about longitudinal axis A-A', it cuts tether (6500). In some variations, tubular cutter (6506) may be attached to a flexible tube (6508), as shown in FIG. 65A. In certain variations (also shown in FIG. 65A), a blocking structure (6510) may be disposed on catheter (6502). Blocking structure (6510) may have any suitable shape, and may serve as a base against which tether (6500) may be pushed during the cutting process. Blocking structure (6510) may be attached to, part of, or integral with, catheter (6502).

Figure 65B:
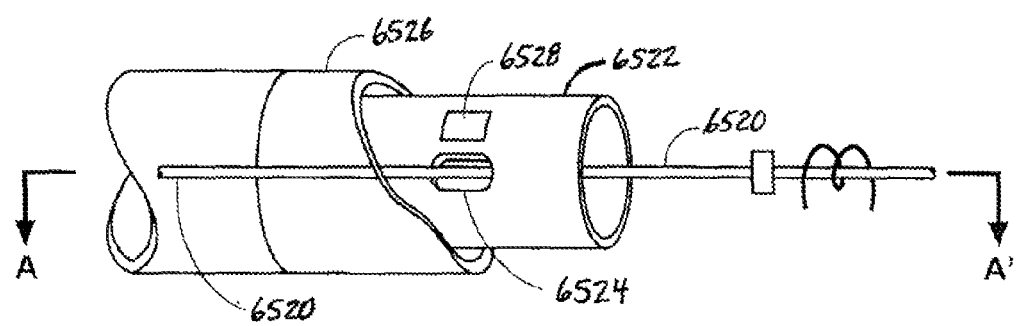

Other variations may also be used. As an example, FIG. 65B shows a tether (6520) that is threaded through a catheter (6522) and that exits through a side aperture (6524) in the catheter. A tubular cutter (6526) is disposed around catheter (6522). Tubular cutter (6526) has a cutting edge that is shaped to cut tether (6520) in a direction generally orthogonal to longitudinal axis A-A' of catheter (6522) as it is rotated around longitudinal axis A-A'. Optionally, a blocking structure (6528) can be provided on catheter (6522) such that tether (6520) is pushed against blocking structure (6528) during the cutting process. Blocking structure (6528) may be any suitable shape or have any suitable configuration and may be attached to, part of, or integral with, catheter (6522). While not shown, in some variations, tubular cutters such as those illustrated in FIGS. 65A and 65B may be configured such that they are internal to the catheter.

Figure 65C:
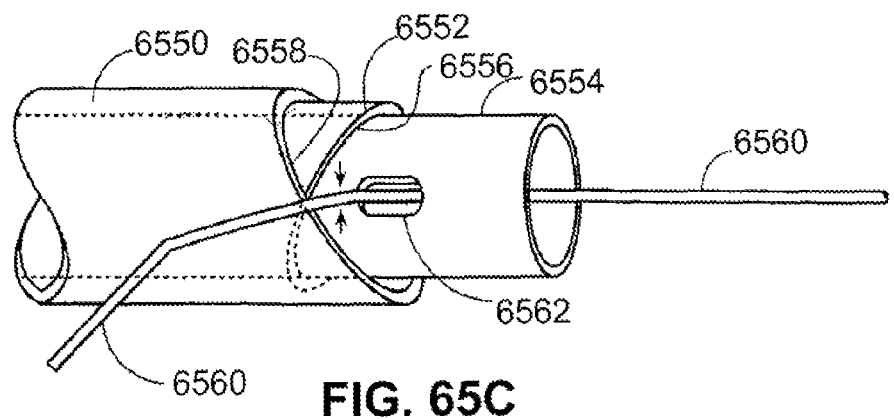
FIG. 65C illustrates a variation of a device that may be used to cut a tether.

In some variations, a pair of concentric tubular cutters may be used to cut a tether. The concentric tubular cutters may be either internal or external to a catheter. For example, as illustrated in FIG. 65C, two concentric tubular cutters (6550) and (6552) are externally disposed relative to a catheter (6554). Tubular cutters (6550) and (6552) may be rotated about the longitudinal axis of catheter (6554) in opposite directions (indicated by solid arrows). Thus, the cutting edges (6556) and (6558) of the tubular cutters may cut a tether (6560) that is routed through a side aperture (6562) in catheter (6554) in a scissor-like fashion. Cutting edges (6556) and (6558) may be sharpened in such a way to enable cutting edges (6556) and (6558) to pass each other as closely as possible.

Figure 66A:
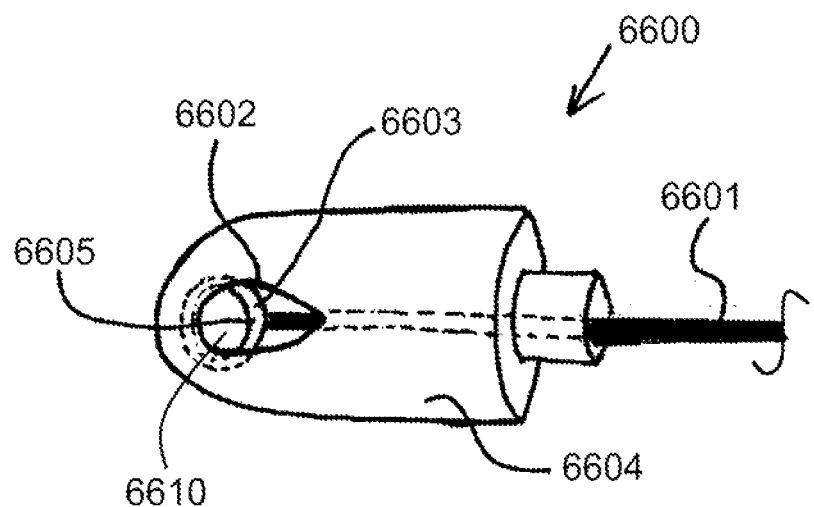
FIGS. 66A and 66B are perspective views of a variation of a device that may be used to cut a tether.
Figure 66B:
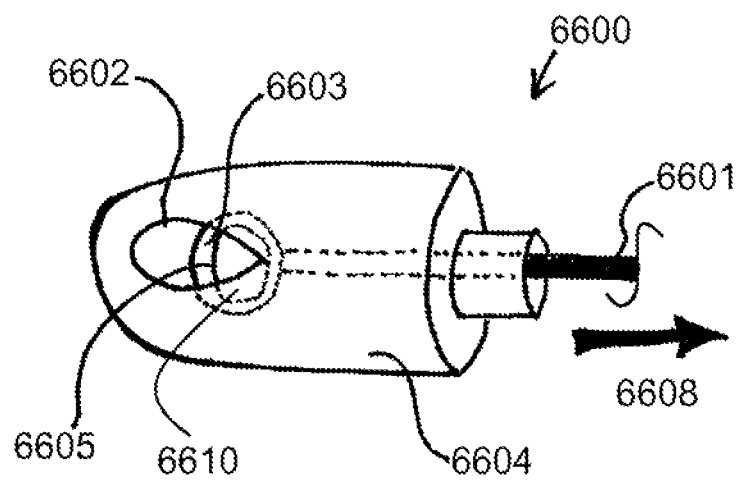

Tubular tether cutters have been described. However, in some variations, a tether-cutting device may alternatively or additionally comprise one or more non-tubular tether cutters. For example, FIGS. 66A and 66B show a tether-cutting device (6600) comprising a housing (6604), an aperture (6602) in the housing, a mandrel (6601), and a blade (6603) having an aperture (6610). The inner perimeter (6605) of blade aperture (6610) may serve as a cutting edge. Housing (6604) may shield and/or stabilize blade (6603). In the variation shown, blade (6603) is ring-shaped; however, in other variations, a blade may have any other suitable shape or size. Mandrel (6601) is coupled to blade (6603), and is slidable within housing (6604).

Tether-cutting device (6600) may have at least two configurations. The first configuration is shown in FIG. 66A. In this configuration, inner perimeter (6605) of blade (6603) is positioned so that it is substantially aligned with housing aperture (6602). A tether may be threaded through aperture (6602), as well as through inner perimeter (6605) of blade (6603). To cut the tether, tether-cutting device (6600) may be converted into the second configuration, shown in FIG. 66B, where mandrel (6601) may be actuated in the direction of arrow (6608), which in turn may actuate blade (6603) in the direction of arrow (6608). The tether may be cut when inner perimeter (6605) of blade (6603) contacts or crosses the edge of aperture (6602).

Figure 66C:
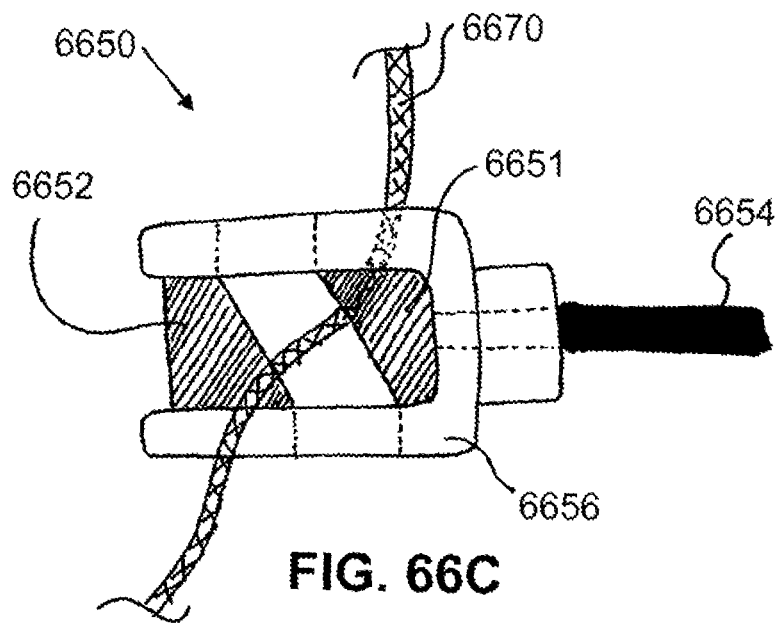
FIGS. 66C and 66D are side views of additional variations of devices that may be used to cut a tether.

Alternate blade geometries may be used in other variations of tether-cutting devices. For example, FIG. 66C shows a tether-cutting device (6650) comprising blades (6651) and (6652), which are angled such that they may substantially contact each other to cut a tether therebetween. Tether-cutting device (6650) comprises a housing (6656) that may stabilize blades (6651) and (6652) and/or prevent the blades from inadvertently cutting tissue during use, as well as a mandrel (6654) coupled to blade (6651). While a mandrel is shown, any other appropriate actuating mechanisms may alternatively or additionally be used. As shown, during use a tether (6670) may be positioned between blades (6651) and (6652), and mandrel (6654) may be used to actuate blade (6651), such that blade (6651) contacts blade (6652) to cut tether (6670).

Figure 66D:
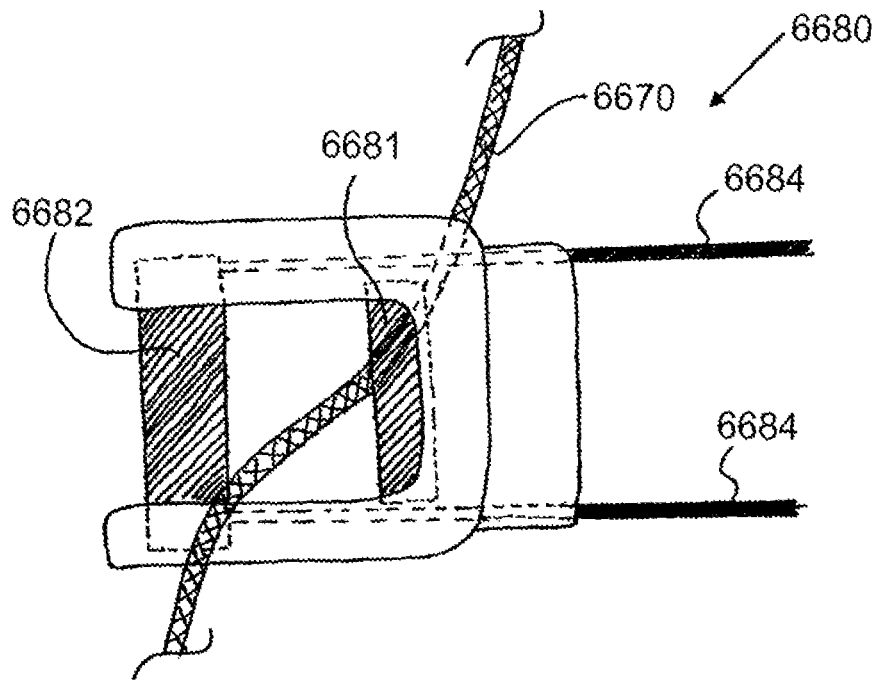

Another variation of a tether-cutting device (6680) is shown in FIG. 66D. As shown there, tether-cutting device (6680) comprises blades (6681) and (6682), as well as a pair of mandrels (6684) that actuate blade (6682) so that it contacts blade (6681), and thereby cuts tether (6670). Other arrangements of dual-blade tether-cutting devices, with different blade geometries, angles, and/or configurations, may also be used to cut a tether. Moreover, while single- and dual-blade tether-cutting devices have been described, some variations of tether-cutting devices may comprise more than two blades, such as three, four, or five blades.

As described above, a tether-cutting device may comprise any appropriate structure or material. Additionally, tether-cutting devices may comprise one or more tubular cutters, as described above, and/or one or more tether cutters that cut by heat, electricity, chemical reaction, or the like. For example, in some variations, a tether-cutting device may comprise an electrode or filament through which electrical energy is applied to cut a tether.

In some variations, multiple cutting devices may be used together to cut one or more tethers. The cutting devices may be the same as each other or different from each other. Moreover, while tether cutting has been described, in some variations, a tether may not be cut, or the tether may be cut, but may still maintain some length. The extra tether length may, for example, help to maintain the tether in a locked state.

While locking devices and cutting devices have been described, in some variations, a single device may provide both locking and cutting functions.

Figure 67A:
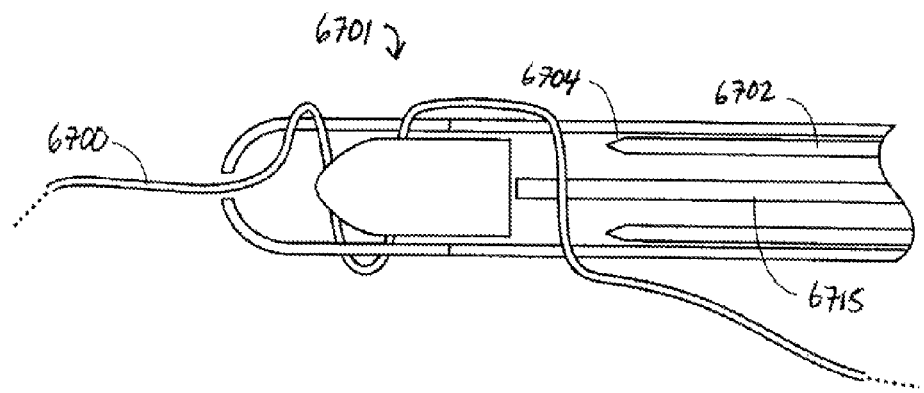
FIGS. 67A and 67B show different variations of devices that may be used to lock and cut a tether.

For example, FIG. 67A shows a device (6701) that is in the form of a catheter and that comprises a detachable locking element. The device also includes a tubular tether cutter (6702) having a sharpened outer edge (6704), and a pushing member (6715) that passes through cutter (6702). Device (6701) further includes guides which may guide a tether (6700) through the device and position the tether for cutting. As shown in FIG. 67A, tether (6700) is positioned through the device so that it can be readily cut by cutter (6702) when the cutter is brought forward (e.g., by moving the cutter distally). In FIG. 67A, cutter (6702) has at least one edge (e.g., over half of the cutter's circumference) so that at least one end of the tether (e.g., the end contacting the more proximal end of the tether) is cut by the cutter.

Figure 67B:
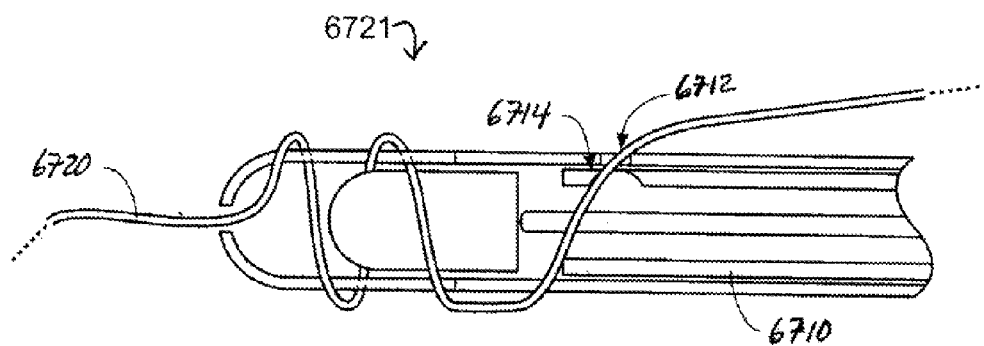

As described above, other types of tether cutters may be used as well. For example, FIG. 67B shows a device (6721) comprising a similar tubular tether cutter (6710) that is configured to cut the tether when the cutter is retracted proximally. In FIG. 67B, cutter (6710) has a passage (6712) through which a tether (6720) passes, and where at least a portion (6714) of the cutter is sharp. Tether (6720) also passes through the wall of the device (configured as a catheter in FIG. 67B, although other suitable configurations may be used). The end of the tether may be cut by drawing the tether taut after securing the locking element of the device and then moving the cutter against the tether so that it is cut.

In some variations, a locking and cutting device may comprise a tether cutter located on the outer surface of a plug. For example, FIGS. 68A-68J show an exemplary combined tether-locking and -cutting device (6800). As shown there, device (6800) comprises a tubular locking member (6801) and a plug (6803) configured to fit within locking member (6801). Tubular locking member (6801) includes several apertures (6802a) and (6802b) that are sized and shaped for the passage of a tether (6820) therethrough. In some variations, aperture (6802c) may also be sized and shaped for the passage of a tether therethrough. However, any number of apertures positioned in any way may be used, as previously described (see, e.g., FIGS. 59A, 59B, and 60A-60R). Plug (6803) comprises a plug body (6804) and a blade (6805) in a distal portion (6806) of plug body (6804). It should be noted, though, that other appropriate variations of plugs may alternatively or additionally be used. During use, plug (6803) may be advanced into locking member (6801) to secure tether (6820) between plug (6803) and an inner wall of locking member (6801). Plug (6803) may be advanced by pushing at the proximal portion (6807) using any suitable mechanism. Additionally, as plug (6803) is advanced into locking member (6801), blade (6805) may come into contact with tether (6820), and may thereby cut the tether. Plug (6803) may be advanced into locking member (6801) using any of the mechanisms and methods previously described, or any other suitable mechanisms and methods.

Figure 68D:
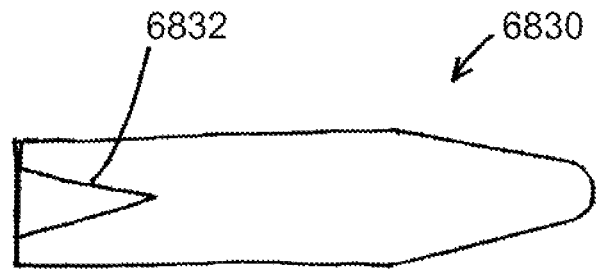
FIGS. 68D-68G are side views of different variations of devices that may be used to lock and cut a tether.
Figure 68E:
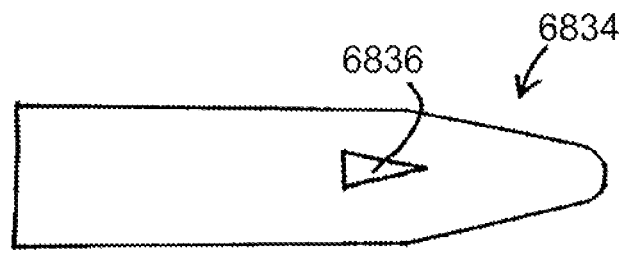
Figure 68F:
Figure 68G:
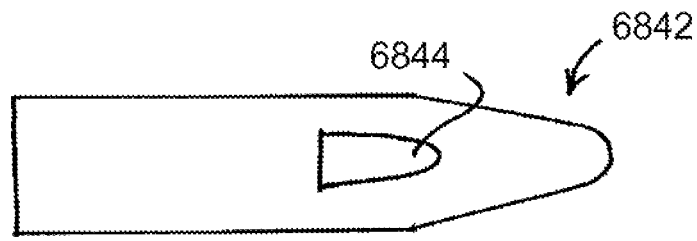
Figure 68H:
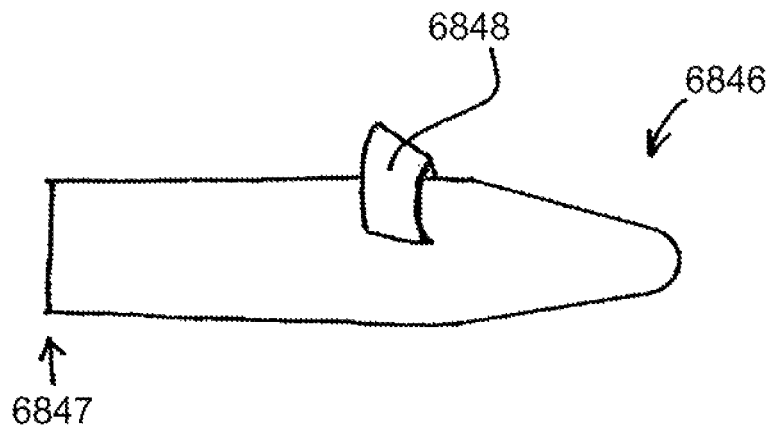
FIGS. 68H-68J are side perspective views of additional variations of devices that may be used to lock and cut a tether.
Figure 68I:
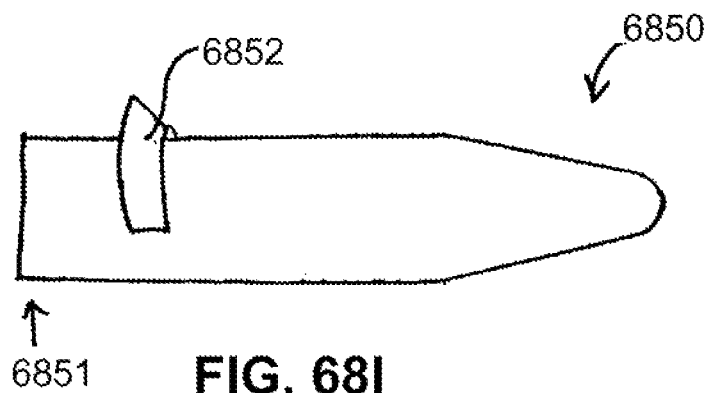
Figure 68J:
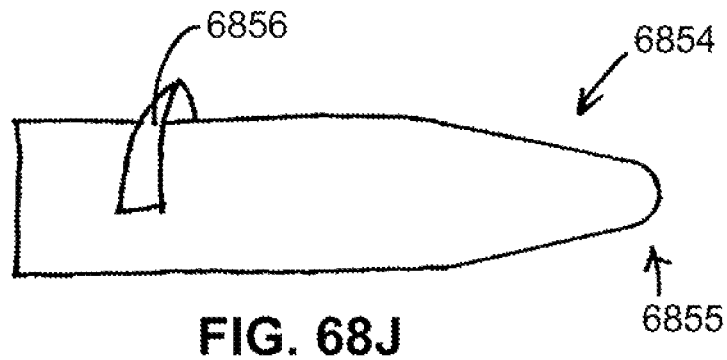

A tether cutter may be situated in any location on a plug. Several non-limiting examples of tether cutters are illustrated in FIGS. 68B-68J. First, FIG. 68B shows a plug (6822) comprising a cutting member (6824) that outlines an outer perimeter of the plug. While cutting member (6824) is located at one end of plug (6822), a plug may optionally have a cutting member in either or both of its proximal and distal portions. FIGS. 68C and 68J depict plugs (6826) and (6854) having tether cutting members (6828) and (6856), respectively, that are angled toward the distal portions (6827) and (6855), respectively, of the plugs. FIGS. 68H and 68I depict plugs (6846) and (6850) having tether cutting members (6848) and (6852), respectively, that are angled toward the proximal portions (6847) and (6851), respectively, of the plugs. FIGS. 68D-68G illustrate variations of plugs having cutting members of different shapes and locations. For example, cutting members may comprise sharp angles, such as cutting members (6832) and (6836) in FIGS. 68D and 68E, or may comprise rounded edges, such as cutting members (6840) and (6844) in FIGS. 68F and 68G. Cutting members may also be located toward one end of a plug, such as shown for plugs (6830) and (6838) in FIGS. 68D and 68F, or located toward the opposite end of the plug, such as shown for plugs (6834) and (6842) in FIGS. 68E and 68G. The above-described figures simply provide examples of plugs that comprise a cutting member, and other appropriate variations and configurations may also be used.

Figure 69A:
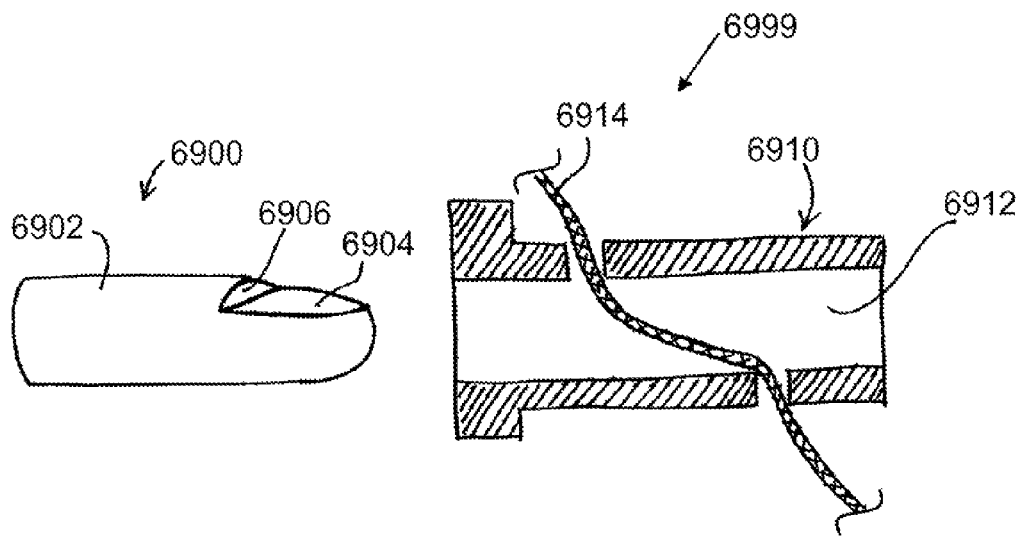
FIG. 69A is a side perspective view in partial cross-section of a variation of a device that may be used to lock and cut a tether.

In some variations in which a plug comprises one or more cutting members, the cutting members may be formed into the body of the plug, and/or may be integral with the body of the plug. For example, FIG. 69A shows a device (6999) comprising a plug (6900) and a locking member (6910) configured to receive the plug. Plug (6900) comprises a body (6902) having an edge (6904) with a sharpened portion (6906). When plug (6900) is advanced into lumen (6912) of locking member (6910), a tether (6914) may be secured between plug (6900) and the wall of lumen (6912). When plug (6900) is advanced further, sharpened portion (6906) of edge (6904) may contact and cut tether (6914). The location of sharpened portion (6906) within plug body (6902) may provide for a relatively streamlined plug body. This, in turn, may provide for good surface contact between the plug and the lumen, which may further secure a tether passing therebetween.

Figures 69B, 69C:
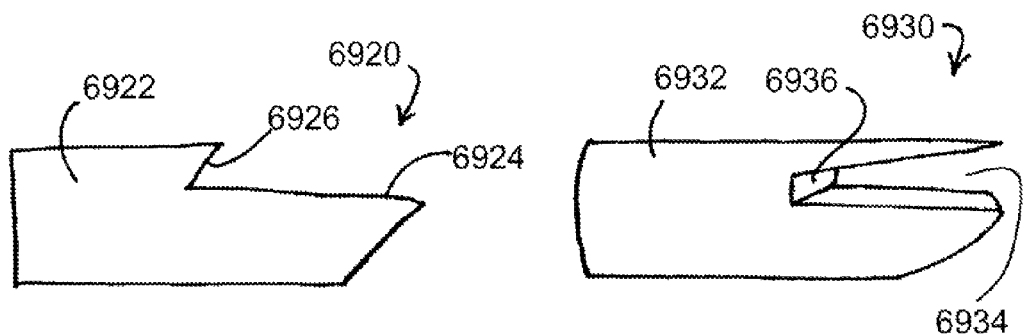
FIG. 69B is a side view of a variation of a component of a device that may be used to lock and cut a tether.
FIG. 69C is a side perspective view of a variation of a component of a device that may be used to lock and cut a tether.

While device (6999) has been described, other variations of locking and cutting devices may be used, as appropriate. As an example, FIG. 69B shows a plug (6920) comprising a plug body (6922) having an edge (6924) with an angled sharpened portion (6926). The angle of sharpened portion (6926) may be any suitable angle, for example, from about 1° to about 180° (e.g., from about 30° to about 150°, from about 45° to about 135°, from about 60° to about 120°, from about 75° to about 105°, etc.). As another example, FIG. 69C shows a plug (6930) comprising a plug body (6932) including a notch (6934) with a sharpened portion (6936). Other variations of plugs may have notches of different shapes and/or positions, where the sharpened portion may be located anywhere along or in the notch. Moreover, some variations of plugs may have multiple different sharpened portions. Both plug (6920) and (6930) may be advanced into a locking member to first secure a tether, and to then contact and cut the tether with the cutting member.

Figure 70A:
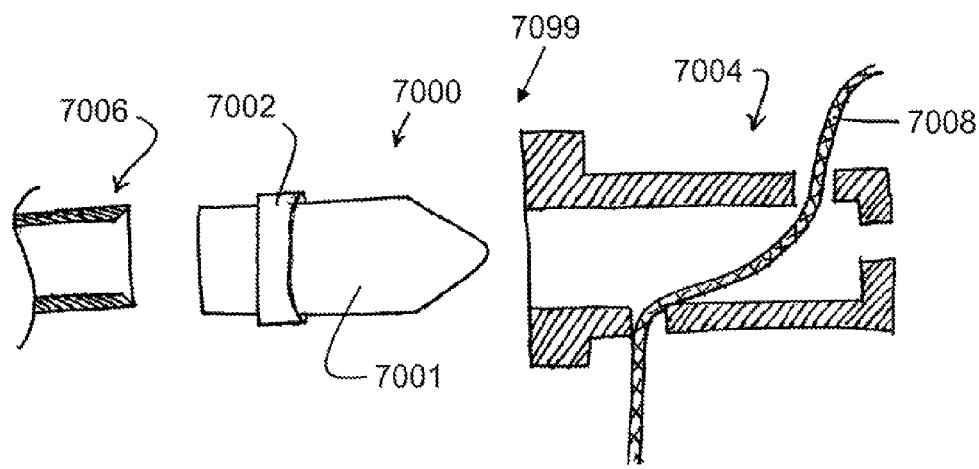
FIG. 70A is a side perspective view in partial cross-section of a variation of a device that may be used to lock and cut a tether.
Figure 70B:
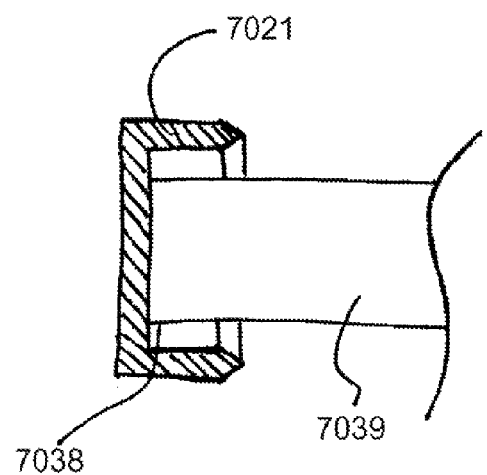
FIG. 70B is a side view in partial cross-section of a variation of a component of a device that may be used to lock and cut a tether.

Other variations of plugs may comprise a cutting member that encircles the perimeter of a plug. For example, FIG. 70A shows a locking device (7099) comprising a plug (7000) and a locking member (7004) configured to received the plug. As shown in FIG. 70A, plug (7000) comprises a plug body (7001) and a cutting member (7002) circumscribing the perimeter of plug body (7001). Plug (7000) may be advanced into locking member (7004) by a pushing element (7006) to first secure, and then cut, a tether (7008). While plug (7000) is cylindrical, other variations of plugs with cutting members may have any of a variety of different shapes, such as square, polyhedral, etc., and the cutting members may be sized and shaped to surround the outer perimeters of the plugs. Another variation of a plug comprising a cutting member that traces the perimeter of the plug is shown in FIG. 70B. As shown there, plug (7039) comprises a cutting member (7021) located in a proximal portion (7038) of the plug. A cutting member may have any sharpened edge that may be suitable for cutting a tether. For example, a cutting member may have angled sharpened edges as depicted in FIG. 70B, and/or may have beveled, straight, or serrated sharpened edges, or the like.

Figure 71:
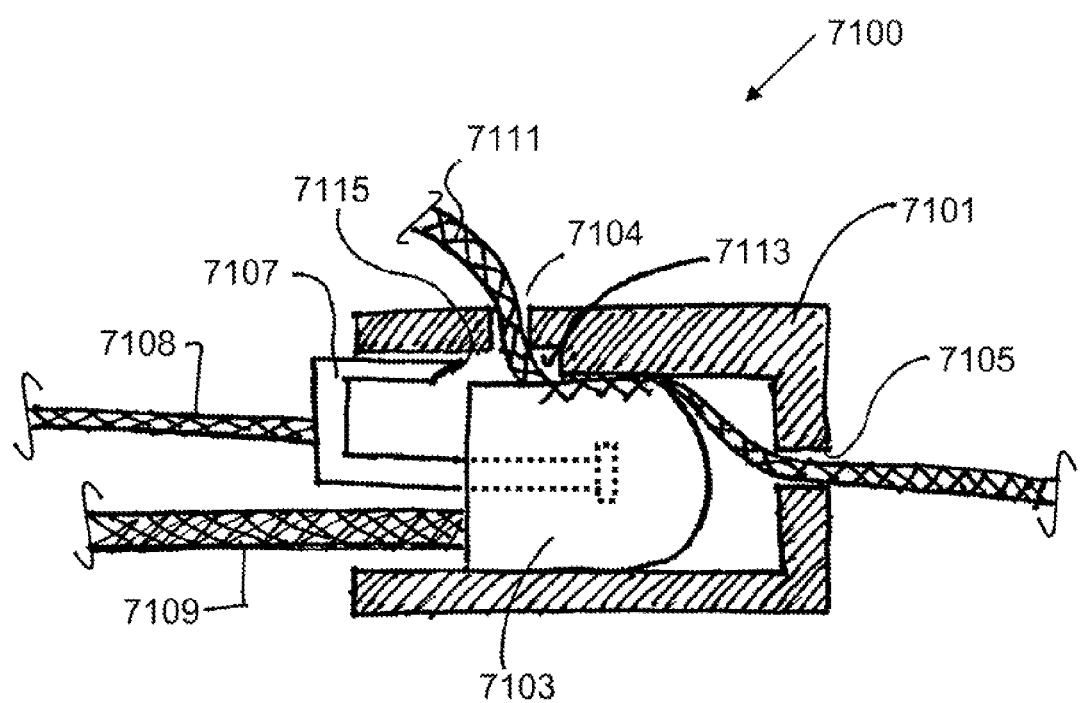
FIG. 71 is a side view in partial cross-section of variations of a device and method that may be used to lock and cut a tether.

In some variations, a plug may comprise a cutting element comprising a sharpened edge, where the cutting element is coupled to the plug, but is actuated separately from the plug. An example of such a plug is shown in FIG. 71. As shown there, a tether-cutting and -locking device (7100) comprises a plug (7103) and a locking member (7101) configured to receive plug (7103). Locking member (7101) comprises two apertures (7104) and (7105) through which a tether (7111) may be threaded. A lumen of locking member (7101) may also comprise a notch (7113). Plug (7103) is coupled to a cutting element (7107), such that a sharpened edge (7115) of cutting element (7107) may be moved toward or away from the plug. For example, cutting element (7107) may be slidable within a channel in plug (7103), as shown in FIG. 71.

In some variations, plug (7103) may be actuated by a first pushing member (7109), and cutting element (7107) may be actuated by a second pushing member (7108). To lock and cut tether (7111) that is threaded through locking member (7101), plug (7103) may first be advanced into locking member (7101) by pushing on plug (7103) with pushing member (7109). Cutting element (7107) may be advanced in the direction of the plug (7103), but in some cases, may not be advanced as far into locking member (7101) as the plug is. Once tether (7111) has been secured between the plug and the wall of the locking member, the tether, which is threaded such that it crosses notch (7113), may be cut by pushing cutting element (7107) further into locking member (7101), so that sharpened edge (7115) contacts and cuts the tether against the notch. After tether (7111) has been locked and cut, both pushing members (7108) and (7109) may be withdrawn. In some variations, cutting element (7107) may also be withdrawn. Such a variation of a locking and cutting device may, for example, permit specific control of each of the lock and cut functions, thereby limiting the likelihood of a tether being cut prior to being fully secured.

Figure 72A:
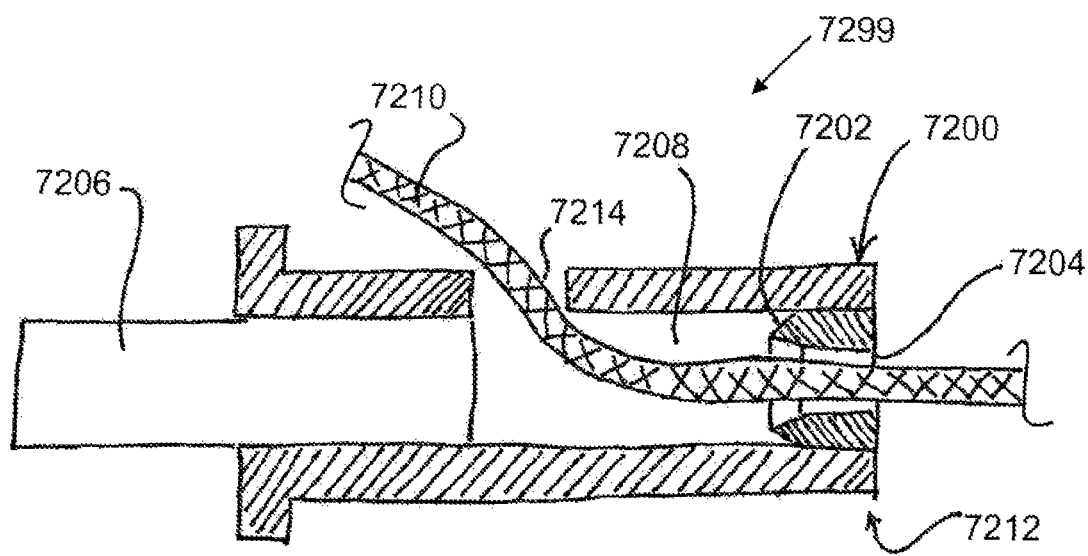
FIGS. 72A and 72B are side views in partial cross-section of different variations of devices that may be used to lock and cut a tether.
Figure 72B:
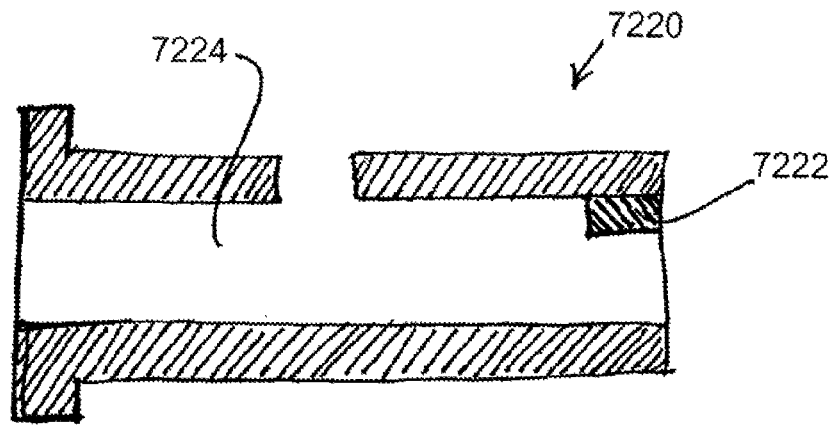

In some combination locking and cutting devices, a locking member may comprise a cutting member. One example of such a device is depicted in FIGS. 72A and 72B. As shown there, a combination locking and cutting device (7299) comprises a plug (7206) and a locking member (7200) configured to receive the plug. Locking member (7200) comprises a lumen (7208), an aperture (7214), and a cutting member (7202). As shown, cutting member (7202) is located within lumen (7208), at its distal end (7212). Cutting member (7202) has an aperture (7204) sized and shaped for the passage of at least one tether therethrough, as shown with reference to tether (7210) in FIG. 72A. During use, plug (7206) may be advanced into lumen (7208) to secure a tether (7210) between the walls of the plug and the locking member. Advancing plug (7206) into locking member (7200) may first secure the tether, and may then cut it by causing the tether to contact cutting member (7202). As shown in FIG. 72A, cutting member (7202) occupies a substantial portion of lumen (7208); however, other variations of cutting members may occupy a smaller portion of a lumen.

Referring now to FIG. 72B, another variation of a locking member (7220) comprises a lumen (7224) and a cutting member (7222) disposed within lumen (7224), where the cutting member only occupies an upper portion of the lumen. This may, for example, provide for enhanced contact between the plug, the tether, and the locking member lumen wall, so that the tether may be secured more readily. Of course, other shapes, locations, and configurations of a cutting member within a locking member may also be used.

Figure 73A:
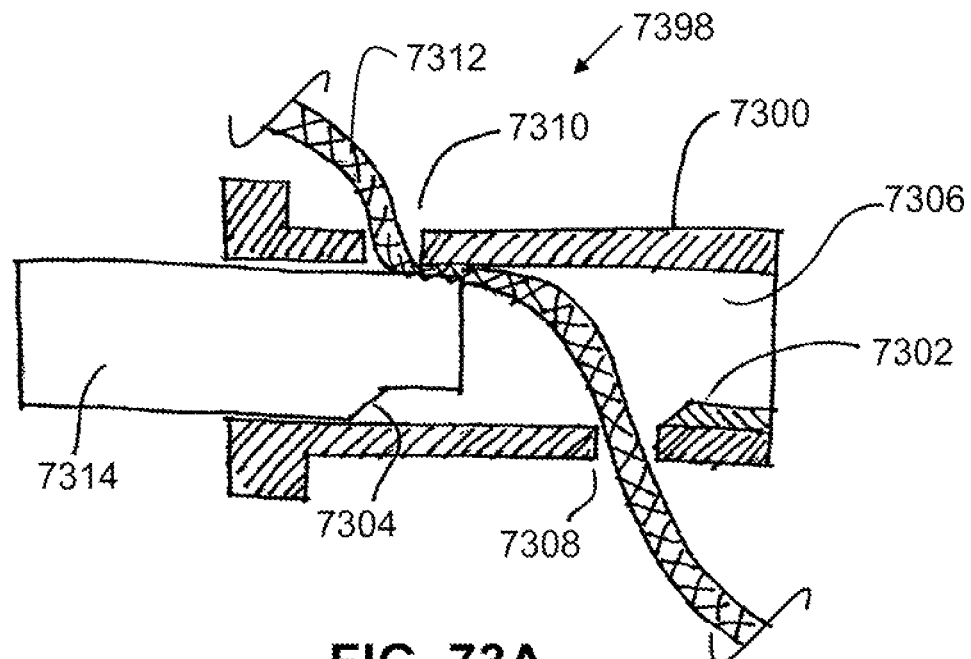
FIGS. 73A and 73B are illustrative side views in partial cross-section of variations of a device and method that may be used to lock and cut a tether.
Figure 73B:
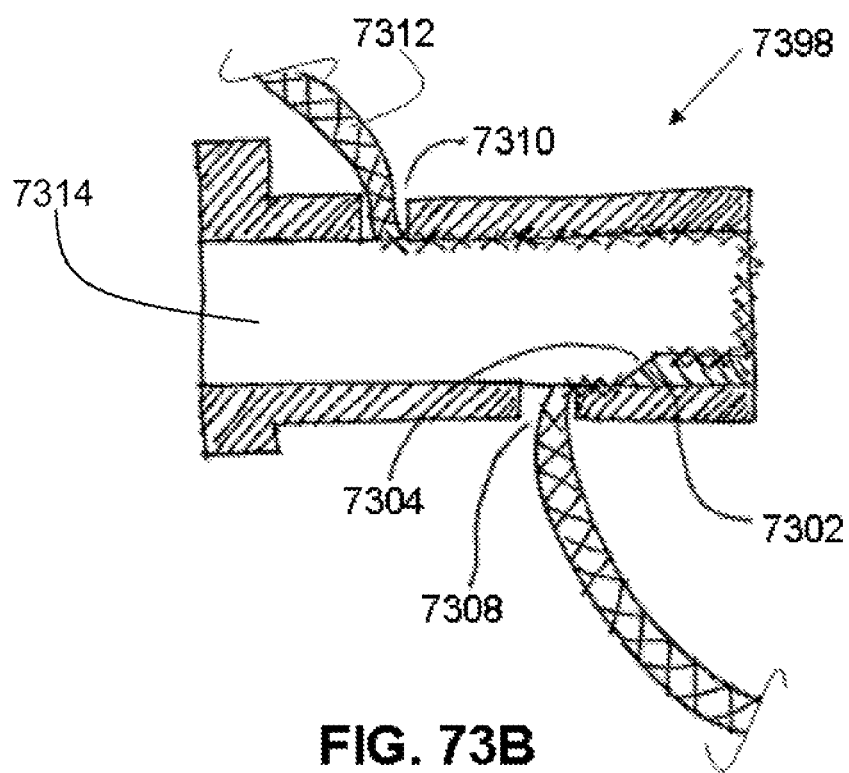

In some variations of combined locking and cutting devices comprising a locking member and a plug, the locking member and the plug may each comprise a cutting member. For example, FIGS. 73A and 73B show a combination locking and cutting device (7398) comprising a plug (7314) and a locking member (7300) configured to receive plug (7314). Locking member (7300) comprises a lumen (7306), two apertures (7308) and (7310), and a first cutting member (7302). Plug (7314) comprises a second cutting member (7304), in the form of a sharpened edge. First and second cutting members (7302) and (7304) are sized and shaped such that the sharpened portions of each cutting member may substantially contact each other when plug (7314) has been advanced into locking member (7300) (i.e., the plug and locking member may have complementary shapes that interfit together). For example, the angles of first and second cutting members (7302) and (7304) may align with each other, as depicted in FIGS. 73A and 73B. A tether (7312) may be threaded through locking member (7300) in any suitable manner (such as described previously), for example, from aperture (7310), through lumen (7306), and out of aperture (7308). During use, plug (7314) may be pushed into lumen (7306) to secure the tether against the wall of the lumen (see the hatched portions shown in FIG. 73B). Additionally, as plug (7314) is advanced, first and second cutting members (7302) and (7304) may be brought together with tether (7312) therebetween, and tether (7312) may be severed (e.g., when the first and second cutting members contact each other as shown in FIG. 73B, the tether may be cut).

Figure 73C:
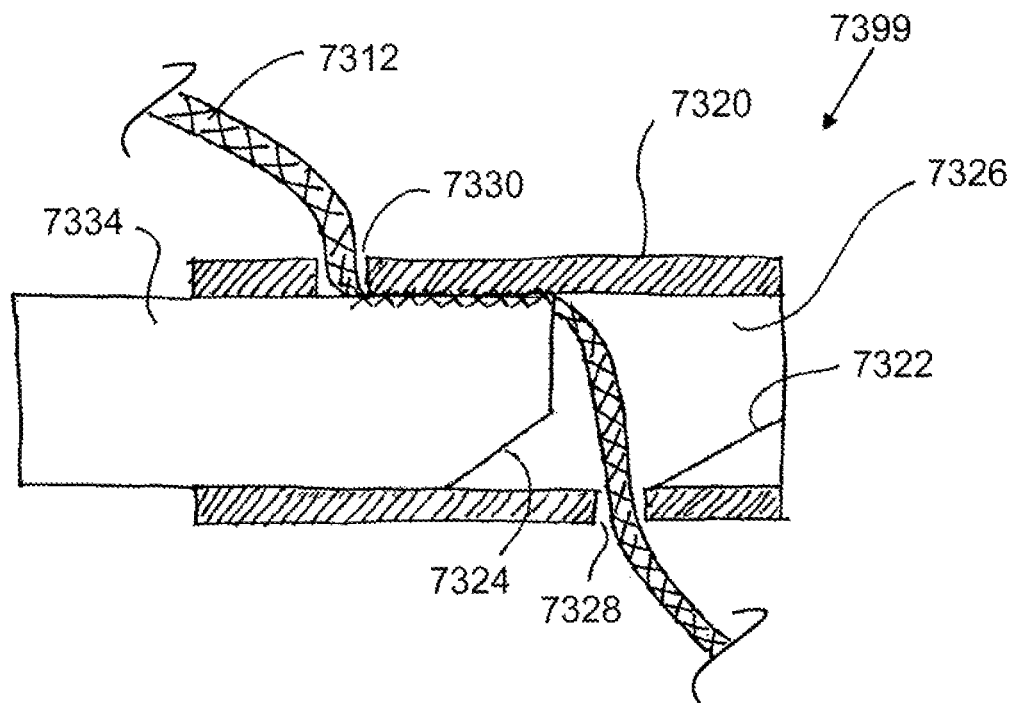
FIGS. 73C and 73D are illustrative side views in partial cross-section of additional variations of a device and method that may be used to lock and cut a tether.
Figure 73D:
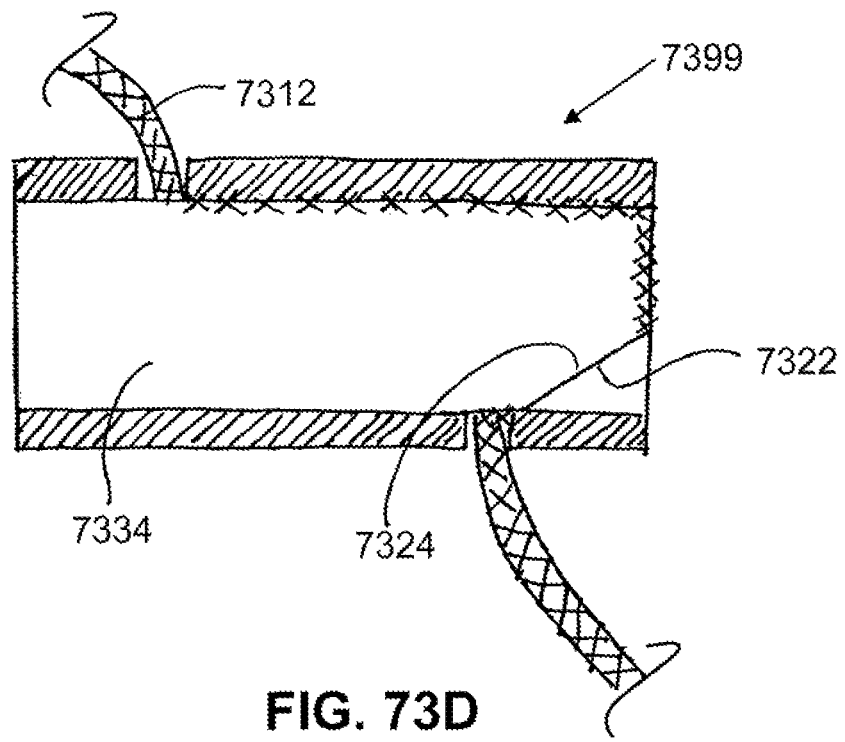

Another variation of a combined locking and cutting device comprising a locking member and a plug that each comprise a cutting member is shown in FIGS. 73C and 73D. As depicted there, a combined locking and cutting device (7399) comprises a plug (7334) and a locking member (7320) configured to receive the plug. Locking member (7320) comprises a lumen (7326), two apertures (7328) and (7330), and a first cutting member (7322). In this variation, first cutting member (7322) occupies a substantial portion of the cross-section of lumen (7326), for example, cutting member (7322) may be sized such that its cross-section is one-third or more of the cross-section of lumen (7326). A cutting member with a relatively large cross-section may, for example, help to ensure that a tether secured between plug (7334) and locking member (7320) is cut. Plug (7334) comprises a second cutting member (7324) that is angled similarly to first cutting member (7322). This arrangement of cutting members (7322) and (7324) may provide increased contact with a tether (7312), so that the tether may be fully severed. Other variations of combined locking and cutting devices may comprise other cutting members having any suitable configuration.

Figure 74A:
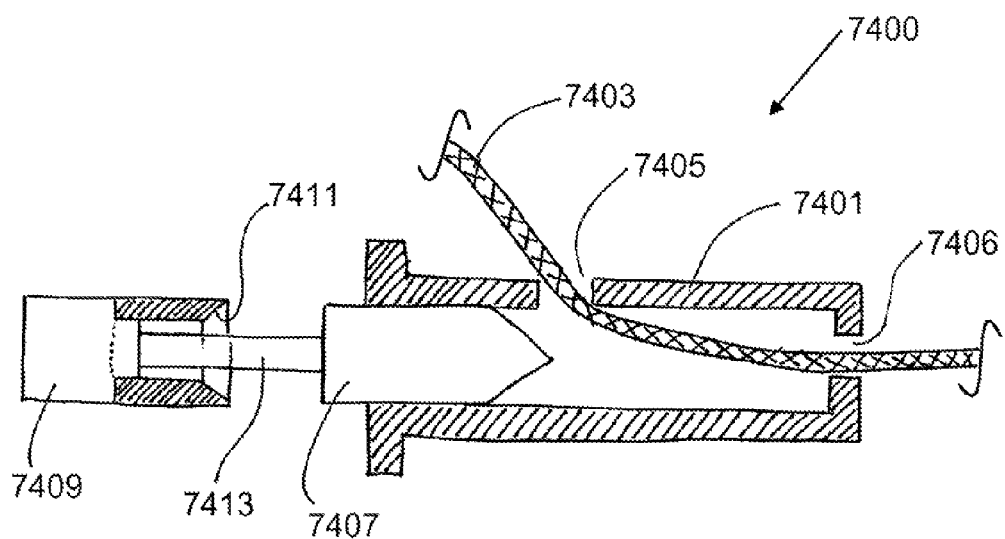
FIGS. 74A and 74B are cross-sectional views of different variations of devices and methods that may be used to lock and cut a tether.
Figure 74B:
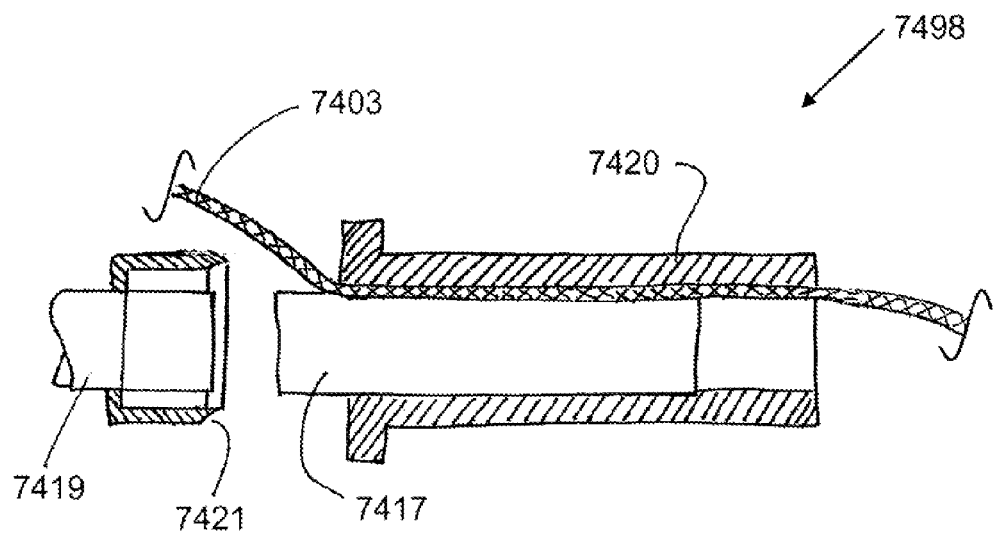

As described above, in some variations of combined locking and cutting devices, a plug may be advanced by a pushing member into the lumen of a locking member to secure a tether that is threaded through the locking member. In certain variations, the pushing member may comprise a cutting member that may cut the tether (e.g., after it has been locked). Some variations of pushing members comprising a cutting member are shown in FIGS. 74A and 74B. First, FIG. 74A shows a combined locking and cutting device (7400) comprising a plug (7407) and a locking member (7401) configured to receive plug (7407). Locking member (7401) comprises two apertures (7405) and (7406), which may be sized and shaped for threading a tether (7403) therethrough, as depicted in FIG. 74A. Plug (7407) may be engaged with locking member (7401), and advanced into the locking member using a pushing member (7409). Pushing member (7409), in turn, may comprise a rod (7413) and a cutting member (7411). As plug (7407) is pushed into the locking member, the plug may trap/wedge a tether (7403) against the wall of the locking member lumen. As the plug continues to be advanced, cutting member (7411) may contact and cut the portion of tether (7403) exiting side aperture (7405). The length of rod (7413) may be adjusted, for example, according to the location of side aperture (7405), so that the tether may be sufficiently wedged/trapped before it is cut. After tether (7403) has been secured in locking member (7401), and cut by element (7411), pushing member (7409) may be withdrawn from locking member (7401).

FIG. 74B shows another variation of a combined locking and cutting device (7498) comprising a plug (7417) and a locking member (7420) configured to receive the plug. As shown there, locking member (7420) has a lumen therethrough, but no side aperture. Plug (7417) may be pushed into the lumen of locking member (7420) by a pushing member (7419) comprising a cutting element (7421). Pushing the plug into the locking member may wedge and secure tether (7403) along the entire length of plug (7417). After the tether has been secured in the locking member, the portion of the tether exiting the locking member (7420) may be contacted and cut by cutting element (7421). Cutting element (7421) may be situated in any appropriate location along pushing member (7419). As illustrated in FIG. 74B, cutting element (7421) is located on the body of pushing member (7419). However, in some variations, it may be located on the proximal portion of pushing member (7419). This arrangement may, for example, permit a longer length of the tether to be secured to the locking member prior to cutting, thereby securing the tether relatively tightly, while also allowing for tether (7403) to be cut against pushing member (7419). In some variations, such as some variations described previously, the locking member and plug may be arranged so that tether (7403) is sheared.

Figure 75A:
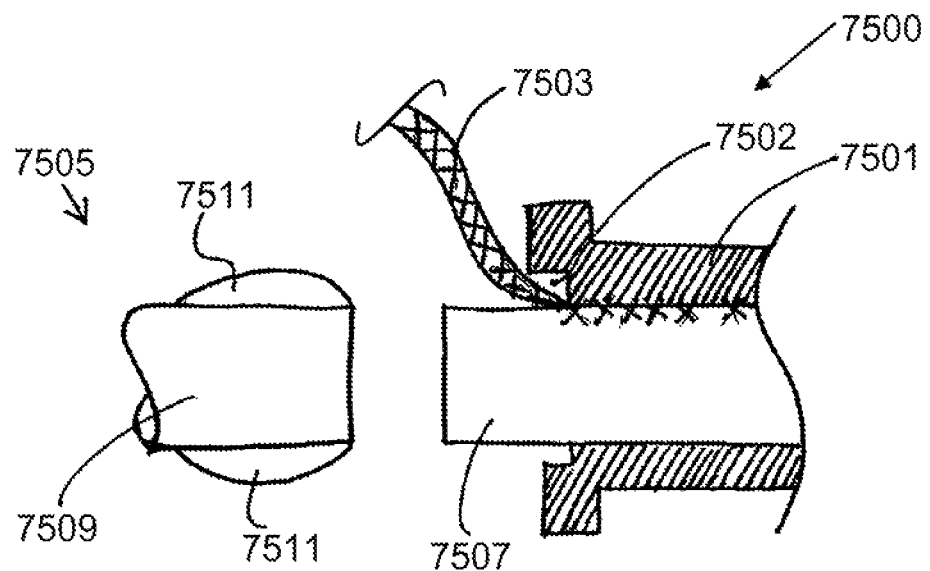
FIGS. 75A and 75B are side views in partial cross-section of variations of a device and method that may be used to lock and cut a tether.
Figure 75B:
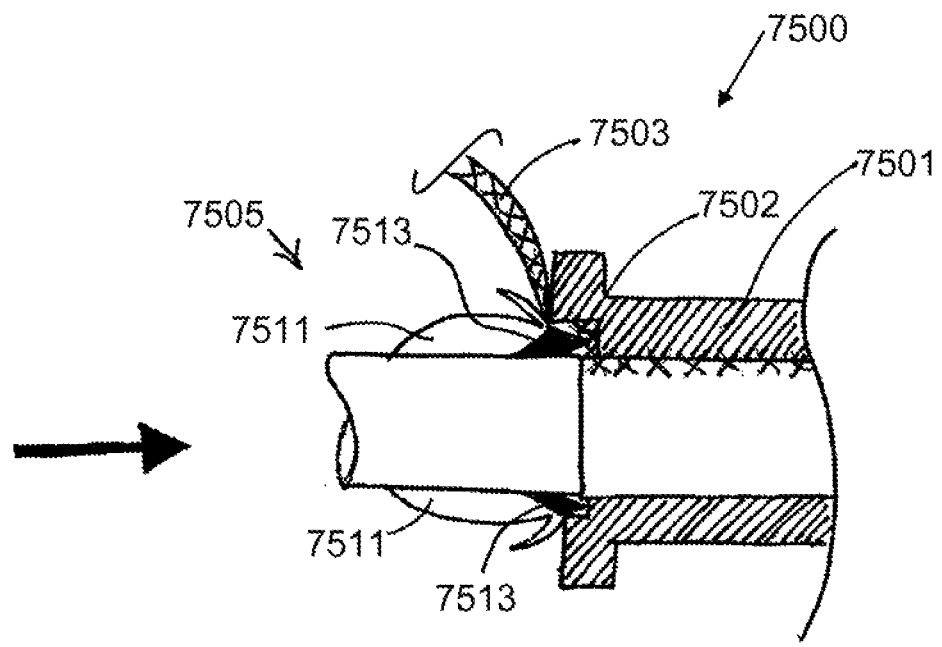

Another variation of a pushing member comprising a cutting element is shown in FIGS. 75A and 75B. As shown there, a combined locking and cutting device (7500) comprises a plug (7507), a locking member (7501) configured to receive plug (7507), and a pushing member (7509). Pushing member (7509) comprises flexible flaps (7511) in its distal portion (7505) that may cover cutting elements (7513). Cutting elements (7513) may be covered by flaps (7511) until pushing member (7509) has been advanced to the point at which flaps (7511) contact a notch (7502) in locking member (7501). This may cause flaps (7511) to peel back, thereby exposing cutting elements (7513). Tether (7503) may also exit locking member (7501) at notch (7502). Exposed cutting elements (7513) may contact and cut the tether at notch (7502). Flaps (7511) may, for example, function to prevent accidental contact with cutting elements (7513), as well as to preserve the sharpness of the cutting elements. The flaps may be made of any appropriate material, such as silicone, rubber, polymers, and the like. While certain variations of flaps have been shown, other variations of flaps may alternatively or additionally be used. For example, in some variations, flaps may be retracted to expose cutting elements by actuating a flap-retracting mechanism (e.g., using a proximal controller). This may relatively reliably ensure that cutting elements (7513) will be fully exposed and ready to cut a tether.

Figure 76:
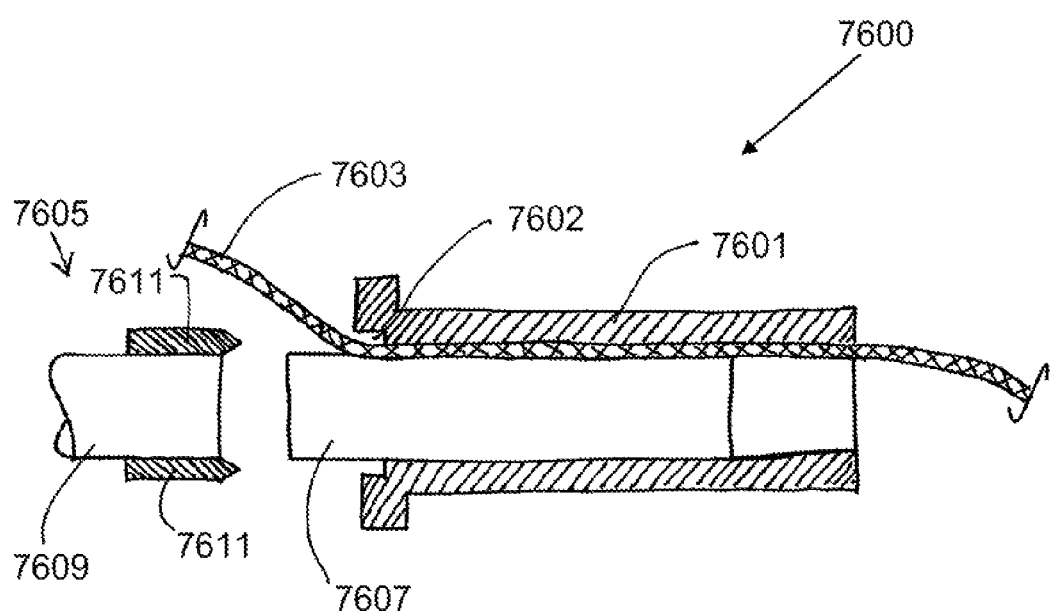
FIG. 76 is a side view in partial cross-section of variations of a device and method that may be used to lock and cut a tether.

Yet another variation of a pushing member comprising a cutting element is shown in FIG. 76. As shown there, a combined locking and cutting device (7600) comprises a plug (7607), a locking member (7601) configured to receive the plug, and a pushing member (7609). Pushing member (7609) comprises a distal portion (7605) comprising cutting members (7611) that may be sized and shaped to fit within a notch (7602) on locking member (7601). As pushing member (7609) urges plug (7607) into the lumen of locking member (7601), a tether (7603) that has been routed through the lumen may be wedged and secured between the plug and the lumen wall. Tether (7603) exits the locking member at notch (7602). As the pushing member is advanced, cutting elements (7611) may be inserted into notch (7602), where the cutting elements contact and cut the tether (7603). After the tether has been cut, pushing member (7609) may be withdrawn. Of course, while locking members with notches have been described, as shown previously, some variations of locking members may not have a notch (e.g., FIG. 74A), while other variations of locking members may have multiple notches.

Additional variations of devices that serve both a tether-locking function and a tether-cutting function may be used, as appropriate.

While certain variations of locking and/or cutting devices and methods have been described above, other variations may be used. As an example, in some variations, one or more locking and/or cutting device components may include one or more radiopaque markers (e.g., platinum markers). The markers may enhance visualization of the components and identification of their location during a procedure (e.g., under X-ray fluoroscopy). As another example, in certain variations, a locking device may comprise a tubular locking member and a plug, where the plug may be advanced within the tubular locking member by a wedge underneath the plug. A tether may be routed between the plug and an inner wall of the tubular locking member, and the wedge may be used to move the plug to secure the tether between the plug and the inner wall. As an additional example, in some variations, a cutting device may be used to cut a tether that is not under tension. In such variations, the tether may be cut, for example, by forcing the tether against a wall of the cutting device and using the wall as a backing for cutting the tether. Moreover, some variations of devices may be used to provide a cinching effect with a tether. These devices may be used for any procedure where these functions (or combinations thereof) are desired. Locking, cutting, and cinching devices are described, for example, in U.S. Patent Application Publication Nos. US 2006/0190030 A1 and US 2006/0122633 A1, and US 2008/0172035 A1, all of which were previously incorporated by reference in their entirety.

While methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A device for securing a tether comprising:
   a locking member configured to receive a plug and comprising a proximal end, a distal end, and a lumen extending between the proximal end and the distal end and having a lumen length therebetween; and
   a plug slidable within the lumen of the locking member to secure a portion of a tether within the lumen, the plug comprising an exterior surface and at least one protrusion, the plug having a length that is at least as long as the lumen length such that sliding the plug into the locking member frictionally secures the tether between the at least one protrusion and locking member,
   wherein the locking member comprises a wall portion comprising an interior surface, and wherein the plug is configured to rotate within the locking member in response to tension in the tether after the tether has been frictionally secured between the locking member and the plug, wherein the rotation of the plug further frictionally secures the tether against the exterior surface of the plug and the interior surface of the locking member.

2. The device of claim 1, further comprising an elongated member comprising a distal portion to which the locking member is releasably coupled.

3. The device of claim 1, wherein the wall portion of the locking member comprises first and second apertures alignable for passage of a tether therethrough.

4. The device of claim 3, wherein the first and second apertures are located such that a tether passing therethrough would not cross the center of the lumen of the locking member.

5. The device of claim 3, wherein the first and second apertures are located along a side wall portion of the locking member.

6. The device of claim 1, wherein the locking member comprises a tubular member.

7. The device of claim 1, wherein the plug is rotatable by at least about 1° to secure a portion of a tether within the lumen of the locking member.

8. The device of claim 7, wherein the plug is rotatable by at most about 180° to secure a portion of a tether within the lumen of the locking member.

9. The device of claim 1, wherein the plug is rotatable by at most about 180° to secure a portion of a tether within the lumen of the locking member.

10. The device of claim 1, further comprising a pullwire for rotating the plug within the lumen of the locking member.

11. The device of claim 1, further comprising a cutting member configured to cut a tether.

12. The device of claim 1, wherein the at least one protrusion is in the form of at least one ridge.

13. The device of claim 1, wherein the plug comprises multiple protrusions that form a stepped configuration.

14. The device of claim 1, wherein the plug comprises a gear-shaped portion.

15. The device of claim 14, wherein the gear-shaped portion comprises a plurality of teeth, each tooth being progressively longer than the previous tooth.

16. The device of claim 1, wherein the plug is slidable along a longitudinal axis of the locking member lumen and is rotatable along a direction that is perpendicular to the longitudinal axis of the lumen.

17. A device for securing a tether comprising:
   a locking member comprising a wall portion comprising an interior surface, a proximal end, a distal end, and a lumen extending between the proximal end and the distal end and having a lumen length therebetween; and
   a plug slidable within the lumen of the locking member and having a length that is at least as long as the lumen length, the plug comprising an exterior surface and at least one first protrusion configured to engage a groove or first aperture in the wall portion of the locking member when the plug is partially disposed within the lumen of the locking member and at least one second protrusion configured such that sliding the plug into the locking member frictionally secures a portion of a tether within the lumen of the locking member between the at least one second protrusion and locking member, and wherein the plug is configured to rotate within the locking member in response to tension in the tether after the tether has been frictionally secured between the locking member and the plug, wherein rotation of the plug further frictionally secures the tether against the exterior surface of the plug and the interior surface of the locking member.

18. The device of claim 17, wherein the at least one first protrusion of the plug is configured to form a snap-fit with the groove or first aperture in the wall portion of the locking member.

19. A device for securing a tether comprising:
a locking member comprising a wall portion comprising an interior surface, a proximal end, a distal end, and a lumen extending between the proximal end and the distal end and having a lumen length therebetween; and
a plug slidable within the lumen of the locking member, the plug comprising a body portion having a length that is at least as long as the lumen length and a head portion comprising a one-way feature allowing translation of the head portion in a first direction once within the lumen of the locking member, but not in a second direction opposite the first direction, and further comprising an exterior surface and at least one protrusion configured such that sliding the plug into the locking member frictionally secures the tether between the at least one protrusion and locking member, and wherein the plug is configured to rotate within the locking member in response to tension in the tether after the tether has been frictionally secured between the locking member and the plug, wherein rotation of the plug further secures the tether against the exterior surface of the plug and the interior surface of the locking member.

20. The device of claim 19, further comprising a pushing member configured to push the plug in the first direction.

* * * * *